United States Patent
Shaw et al.

(10) Patent No.: US 8,367,662 B2
(45) Date of Patent: Feb. 5, 2013

(54) ORGANIC COMPOUNDS

(75) Inventors: Duncan Shaw, Horsham (GB); Catherine Leblanc, Horsham (GB); Dimitrios Lizos, Basel (CH); Cathy Ritchie, Fareham (GB); Vikki Furminger, Horsham (GB); Sarah Lewis, Horsham (GB); Benoit Hornsperger, Altkirch (FR); Nikolaus Johannes Stiefl, Lorrach (DE); Sven Weiler, Lorrach (DE)

(73) Assignee: Novartis AG, Basel (CH)

( * ) Notice: Subject to any disclaimer, the term of this patent is extended or adjusted under 35 U.S.C. 154(b) by 210 days.

(21) Appl. No.: 12/679,549

(22) PCT Filed: Oct. 15, 2008

(86) PCT No.: PCT/EP2008/063841
§ 371 (c)(1),
(2), (4) Date: Mar. 23, 2010

(87) PCT Pub. No.: WO2009/050183
PCT Pub. Date: Apr. 23, 2009

(65) Prior Publication Data
US 2010/0210641 A1    Aug. 19, 2010

(30) Foreign Application Priority Data

Oct. 17, 2007 (EP) ..................... 07118726
Feb. 12, 2008 (EP) ..................... 08151336

(51) Int. Cl.
*A61K 31/5377* (2006.01)
*A61K 31/496* (2006.01)
*A61K 31/506* (2006.01)
*A61K 31/437* (2006.01)
*C07D 471/04* (2006.01)

(52) U.S. Cl. ............... 514/233.2; 514/253.04; 514/256; 514/300; 544/127; 544/333; 544/362; 546/121

(58) Field of Classification Search ............... 514/233.2, 514/300, 253.04, 256; 546/121; 544/127, 544/362, 333
See application file for complete search history.

(56) References Cited

FOREIGN PATENT DOCUMENTS

| EP | 1 382 603 | 7/2008 |
|---|---|---|
| WO | WO 01/38326 | 5/2001 |
| WO | WO 03/048132 | 6/2003 |
| WO | WO 2004/013138 | 2/2004 |
| WO | WO 2006/091671 | 8/2006 |
| WO | WO 2008/078091 | 7/2008 |

OTHER PUBLICATIONS

Cancer [online], [retrieved on Jul. 6, 2007] Retrieved from the Internet, URL: http://www.nlm.nih.gov/medlineplus/cancer.html.*
Lala et al., Role of nitric oxide in tumor progression: Lessons from experimental tumors, Cancer and Metastasis Reviews (1998), 17, 91-106.*
Golub et al., Molecular Classification of Cancer: Class Discovery and Class Prediction by Gene Expression Monitoring, Science (1999), vol. 286, 531-537.*
Jamal Koubachi et al., "Regioselective Palladium-Catalyzed Arylation and Heteroarylation of Imidazo[1,2-alpha]pyridines" Synlett 19:3237-3242, 2006.

* cited by examiner

*Primary Examiner* — Kristin Bianchi
(74) *Attorney, Agent, or Firm* — John B. Alexander

(57) ABSTRACT

Compounds of formula I: in free or salt or solvate form, where $R^1$, $R^2$, $R^3$ and $R^{20}$ have the meanings as indicated in the specification, are useful for treating diseases mediated by the ALK-5 and/or ALK-4 receptor. Pharmaceutical compositions that contain the compounds and processes for preparing the compounds are also described. These compounds are useful for the treatment of inflammatory or obstructive airways diseases such as pulmonary hypertension, pulmonary fibrosis, liver fibrosis, cancer, muscle diseases such as muscle atrophies and muscle dystrophies, and systemic skeletal disorders such as osteoporosis.

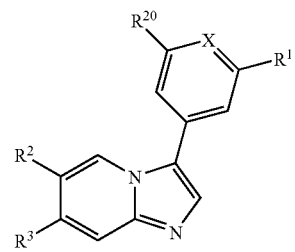

8 Claims, No Drawings

ORGANIC COMPOUNDS

This invention relates to organic compounds and their use as pharmaceuticals, in particular for the treatment of inflammatory or obstructive airways diseases such as pulmonary hypertension, pulmonary fibrosis, liver fibrosis; cancer; muscle diseases such as muscle atrophies and muscle dystrophies, and systemic skeletal disorders such as osteoporosis.

In one aspect, the invention provides a compound of Formula I:

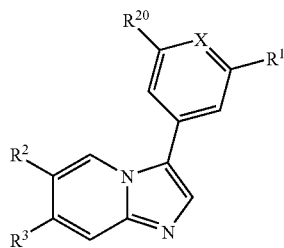

wherein

X is $CR^4$ or N;

$R^1$ is selected from aryl, heterocyclyl, $C_1$-$C_7$ alkyl, $C_3$-$C_{10}$-cycloalkyl, $C_5$-$C_{10}$ cycloalkenyl, $C(O)NR^5R^6$, halo, $C_1$-$C_7$ alkoxy, alkylthio, hydroxyl, $C_1$-$C_7$ alkylcarbonyl, carboxy, carbonyl, cyano and sulfonamide, wherein the alkyl, cycloalkyl, cycloalkenyl, aryl and heterocyclyl groups are optionally substituted by one or more substituents each independently selected from halogen, $C_1$-$C_6$ alkyl, $C_1$-$C_6$ haloalkyl, $C_1$-$C_6$ hydroxyalkyl, $C_3$-$C_8$ cycloalkyl and $C_1$-$C_6$ alkoxy;

$R^2$ is independently selected from H, halogen, OH, $C_1$-$C_6$ alkyl, $C_1$-$C_6$ hydroxyalkyl, $C_1$-$C_6$ alkoxy, $C_3$-$C_6$ cycloalkyl, $NR^7R^8$ and Z;

$R^3$ is independently selected from H, halogen, $C_2$-$C_7$ alkynyl, aryl and heterocyclyl, wherein the alkynyl group is optionally substituted by one or more groups independently selected from hydroxy, cyano, amino, $C_1$-$C_7$ alkylamino and halogen, and wherein the aryl and heterocyclyl groups are optionally substituted by one or more $R^x$ groups and each $R^x$ is independently selected from $C_1$-$C_7$ alkyl; hydroxyl; carbonyl; aminocarbonyl; $C_1$-$C_7$ alkylaminocarbonyl; amino; $C_1$-$C_7$ alkylamino; $C_1$-$C_7$ alkylthio; sulfonylamino; carbonylamino; $C_1$-$C_7$ alkylcarbonylamino; $C_1$-$C_7$ alkylaminocarbonyl; $C_1$-$C_7$ alkylcarbonyl; halogen; oxo; carboxyl; $C_1$-$C_7$ alkoxy; benzyloxy; $C_1$-$C_7$ alkoxycarbonyl; aminosulfonyl; cyano; sulfonyl; sulfanyl; sulfoxide; -L-$C_3$-$C_{10}$-cycloalkyl, -L-$C_5$-$C_{10}$ cycloalkenyl; -L-aryl; -L-het; carbonyloxy; $C_1$-$C_7$ aminoalkyl; $C_1$-$C_7$ alkylamino-$C_1$-$C_7$ alkyl; $C_1$-$C_7$ alkylamino-$C_1$-$C_7$ alkoxy; $C_1$-$C_7$ alkylamino-$C_1$-$C_7$ alkylcarbonyl; and a group of the formula: P-NH-Q-T, wherein each $R^x$ group itself is optionally substituted by one or more groups each independently selected from OH, COOH, halogen, $C_1$-$C_7$ alkyl, aryl, amino, $C_1$-$C_7$ alkylamino, het, cyano, sulfonyl, sulfanyl, sulfoxide, hydroxy-$C_1$-$C_7$ alkyl, $C_1$-$C_7$ alkoxy, $C_1$-$C_7$ alkoxycarbonyl and $C_1$-$C_7$ alkylamino-$C_1$-$C_7$ alkyl; or when two $R^x$ groups are present, they may be joined together to form a ring system fused to $R^3$, the ring system being optionally substituted by one or more groups each independently selected from hydroxyl, $C_1$-$C_7$ alkyl, aryl, amino, $C_1$-$C_7$ alkylamino, heterocyclyl, cyano, halo, sulfonyl, sulfanyl, sulfoxide, hydroxy-$C_1$-$C_7$ alkyl, $C_1$-$C_7$ alkoxy and $C_1$-$C_7$ alkylamino-$C_1$-$C_7$ alkyl;

each L is independently a bond, —C(O)—, —C(O)NH—, a $C_1$-$C_6$ alkylene linker, a $C_1$-$C_6$ alkylenecarbonyl linker or a $C_1$-$C_6$ alkyleneoxy linker;

P is —C(O)—, a $C_1$-$C_6$ alkylene linker, a $C_1$-$C_6$ alkylenecarbonyl linker or a $C_1$-$C_6$ alkyleneoxy linker;

Q is —C(O)—, a $C_1$-$C_6$ alkylene linker or a $C_1$-$C_6$ alkylenecarbonyl linker;

T is aryl, het, $NR^aR^b$ or $C_3$-$C_8$ cycloalkyl;

$R^a$ and $R^b$ are each independently selected from H and $C_1$-$C_6$ alkyl;

$R^4$ is selected from H, OH and $C_1$-$C_3$ alkoxy;

$R^5$, $R^6$ and $R^7$ are each independently selected from H and $C_1$-$C_6$ alkyl;

$R^8$ is selected from $C_5$-$C_7$ cycloalkyl and a 5- or 6-membered heterocyclic group, each optionally substituted by one or more groups independently selected from $C_1$-$C_6$ alkyl, $C_1$-$C_6$ alkoxy and OH;

Z is selected from 5- or 6-membered heteroaryl and aryl, each being optionally substituted by one or more groups independently selected from $C_1$-$C_6$ alkyl, $C_1$-$C_6$ alkoxy, $C_3$-$C_8$ cycloalkyl, OH, CN, halo, —C(O)H, —C(O)O$C_1$-$C_6$ alkyl, —C(O)$NR^9R^{10}$, —$(CH_2)_p NR^{11}R^{12}$, —$(CH_2)_n$het, —$NR^{13}C(O)C_1$-$C_6$ alkyl, —$S(O)_2 NHR^{14}$ and —$NR^{14}S(O)_2 C_1$-$C_6$ alkyl, wherein each alkyl group is optionally substituted by OH, $COOR^c$ and halogen;

each het is independently a 5- or 6-membered heterocyclic group optionally substituted by one or more groups each independently selected from OH, $C_1$-$C_6$ alkyl and $C_1$-$C_6$ alkoxy;

$R^c$ is H or $C_1$-$C_6$ alkyl;

n and p are each independently 0, 1 or 2;

$R^9$, $R^{11}$, $R^{13}$ and $R^{14}$ are each independently selected from H, $C_1$-$C_6$ alkyl, $C_1$-$C_6$ haloalkyl, $C_1$-$C_6$ hydroxyalkyl and $C_3$-$C_8$ cycloalkyl;

$R^{10}$ is selected from H, $C_1$-$C_6$ alkyl, $C_1$-$C_6$ hydroxyalkyl, —$(CH_2)_m NR^{15}R^{16}$, —$(CH_2)_t COOR^d$ and $C_5$-$C_7$ cycloalkyl optionally substituted by one or more groups independently selected from OH, $C_1$-$C_3$ alkyl and $C_1$-$C_3$ alkoxy; or $R^9$ and $R^{10}$, together with the nitrogen atom to which they are attached, form a 5- or 6-membered heterocyclic group which optionally contains one or more further heteroatoms selected from N, O and S, the heterocyclic group being optionally substituted by one or more groups independently selected from OH, $C_1$-$C_3$ alkyl and $C_1$-$C_3$ alkoxy;

m is 2 or 3;

t is 1, 2 or 3;

$R^d$ is H or $C_1$-$C_6$ alkyl;

$R^{12}$ is selected from H, $C_1$-$C_6$ alkyl and $(CH_2)_1 NR^{17}R^{18}$;

q is 2, 3 or 4;

$R^{15}$, $R^{16}$, $R^{17}$ and $R^{18}$ are each independently selected from H and $C_1$-$C_3$ alkyl; or $R^{15}$ and $R^{16}$, together with the nitrogen atom to which they are attached, form a 5- or 6-membered heterocyclic group which optionally contains one or more further heteroatoms selected from N, O and S, the heterocyclic group being optionally substituted by one or more groups independently selected from OH, $C_1$-$C_3$ alkyl and $C_1$-$C_3$ alkoxy; or $R^{17}$ and $R^{18}$, together with the nitrogen atom to which they are attached, form a 5- or 6-membered heterocyclic group which optionally contains one or more further heteroatoms selected from N, O and S, the heterocyclic group being optionally substituted by one or more groups independently selected from OH, $C_1$-$C_3$ alkyl and $C_1$-$C_3$ alkoxy;

$R^{20}$ is selected from H, halo, $NR^{21}R^{22}$ and $OR^{23}$; and $R^{21}$, $R^{22}$ and $R^{23}$ are each independently selected from H, $C_1$-$C_6$ alkyl and $C_3$-$C_6$ cyclolkyl; or $R^{21}$ and $R^{22}$, together with the nitrogen atom to which they are attached form a 4-, 5- or 6-membered N-containing heterocyclic group;

provided that when $R^3$ is other than H, $R^2$ is H, halo, OH, $C_1$-$C_6$ alkyl, $C_1$-$C_6$ alkoxy or $C_3$-$C_6$ cyclolkyl; and when $R^3$ is H, $R^2$ is halogen, $NR^7R^8$ or Z.

In an embodiment of the invention defined above, $R^1$ is selected from $C(O)NR^5R^6$, $C_1$-$C_6$ alkoxy, $C_5$-$C_6$ cycloalkenyl, halogen, 5- or 6-membered heteroaryl and aryl, wherein the cycloalkenyl, heteroaryl and aryl groups are optionally substituted by one or more groups independently selected from halogen, $C_1$-$C_6$ alkyl and $C_1$-$C_6$ alkoxy.

In a further embodiment of the invention as defined anywhere above, $R^3$ is H, optionally substituted phenyl or optionally substituted pyridinyl.

In a further embodiment of the invention as defined anywhere above, $R^3$ is H, phenyl or pyridinyl, wherein the phenyl and pyridinyl groups are optionally substituted by one or more groups independently selected from $C_1$-$C_6$ alkyl, $C_1$-$C_6$ alkoxy, OH, CN, halo, —C(O)H, —C(O)O$C_1$-$C_6$ alkyl, —C(O)$NR^9R^{10}$, —(CH$_2$)$_p$$NR^{11}R^{12}$, —(CH$_2$)$_n$het, —$NR^{13}$C(O)$C_1$-$C_6$ alkyl and —$NR^{14}$S(O)$_2$$C_1$-$C_6$ alkyl;

$R^9$, $R^{11}$, $R^{13}$ and $R^{14}$ are each independently selected from H and $C_1$-$C_3$ alkyl;

$R^{10}$ is selected from H, $C_1$-$C_6$ alkyl, $C_1$-$C_6$ hydroxyalkyl, —(CH$_2$)$_m$$NR^{15}R^{16}$ and $C_5$-$C_7$ cycloalkyl optionally substituted by one or more groups selected from OH, $C_1$-$C_3$ alkyl and $C_1$-$C_3$ alkoxy; or $R^9$ and $R^{10}$, together with the nitrogen atom to which they are attached, form a 5- or 6-membered heterocyclic group which optionally contains one or more further heteroatoms selected from N, O and S, the heterocyclic group being optionally substituted by one or more groups selected from OH, $C_1$-$C_3$ alkyl and $C_1$-$C_3$ alkoxy; and m is 2 or 3

In a still further embodiment of the invention as defined anywhere above, $R^4$ is H.

In a yet further embodiment of the invention, there is provided a compound of Formula I which is selected from:

3-(3-Pyrazol-1-yl-phenyl)-7-pyridin-3-yl-imidazo[1,2-a]pyridine;
3-[7-(3-Hydroxy-phenyl)-imidazo[1,2-a]pyridin-3-yl]benzamide;
7-(6-Morpholin-4-yl-pyridin-3-yl)-3-(3-pyrazol-1-yl-phenyl)-imidazo[1,2-a]pyridine;
3-[7-(6-Morpholin-4-yl-pyridin-3-yl)-imidazo[1,2-a]pyridin-3-yl]benzamide;
7-(6-Morpholin-4-yl-pyridin-3-yl)-3-(2-phenyl-pyridin-4-yl)-imidazo[1,2-a]pyridine;
7-[6-(4-Methyl-piperazin-1-yl)-pyridin-3-yl]-3-(3-pyrazol-1-yl-phenyl)-imidazo[1,2-a]pyridine;
7-[6-(4-Methyl-piperazin-1-yl)-pyridin-3-yl]-3-(2-phenyl-pyridin-4-yl)-imidazo[1,2-a]pyridine;
5-[3-(3-Pyrazol-1-yl-phenyl)-imidazo[1,2-a]pyridin-7-yl]nicotinonitrile;
3-[3-(3-Pyrazol-1-yl-phenyl)-imidazo[1,2-a]pyridin-7-yl]-benzaldehyde;
3-[3-(3-Pyrazol-1-yl-phenyl)-imidazo[1,2-a]pyridin-7-yl]-benzoic acid ethyl ester;
4-[3-(3-Pyrazol-1-yl-phenyl)-imidazo[1,2-a]pyridin-7-yl] benzoic acid ethyl ester;
4-[3-(2-Phenyl-pyridin-4-yl)-imidazo[1,2-a]pyridin-7-yl] benzoic acid ethyl ester;
3-{3-[2-(3-Fluoro-phenyl)-pyridin-4-yl]-imidazo[1,2-a]pyridin-7-yl}-N-methyl-benzamide;
N-Methyl-3-[3-(2-phenyl-pyridin-4-yl)-imidazo[1,2-a]pyridin-7-yl]-benzamide;
N-Methyl-3-[3-(2-m-tolyl-pyridin-4-yl)-imidazo[1,2-a]pyridin-7-yl]-benzamide;
3-{3-[2-(3-Fluoro-phenyl)-pyridin-4-yl]-imidazo[1,2-a]pyridin-7-yl}-phenylamine;
3-[2-(3-Fluoro-phenyl)-pyridin-4-yl]-7-pyridin-3-yl-imidazo[1,2-a]pyridine;
3-(2-Phenyl-pyridin-4-yl)-7-pyridin-3-yl-imidazo[1,2-a]pyridine;
4-[3-(2-Phenyl-pyridin-4-yl)-imidazo[1,2-a]pyridin-7-yl]-benzaldehyde;
3-[2-(3-Fluoro-phenyl)-pyridin-4-yl]-7-(6-methyl-pyridin-3-yl)-imidazo[1,2-a]pyridine;
7-(6-Methyl-pyridin-3-yl)-3-(2-phenyl-pyridin-4-yl)-imidazo[1,2-a]pyridine;
N-Methyl-3-[3-(3-pyrazol-1-yl-phenyl)-imidazo[1,2-a]pyridin-7-yl]benzamide;
3-(3-Pyrazol-1-yl-phenyl)-7-pyridin-4-yl-imidazo[1,2-a]pyridine;
3-(7-Pyridin-4-yl-imidazo[1,2-a]pyridin-3-yl)-benzamide;
2-Methoxy-4-(7-pyridin-4-yl-imidazo[1,2-a]pyridin-3-yl]-phenol;
3-(2-Phenyl-pyridin-4-yl)-7-pyridin-4-yl-imidazo[1,2-a]pyridine;
7-[3-(4-Methyl-piperazine-1-ylmethyl)-phenyl]-3-(3-pyrazol-1-yl-phenyl)-imidazo-[1,2-a]pyridine;
7-[4-(4-Methyl-piperazine-1-ylmethyl)-phenyl]-3-(3-pyrazol-1-yl-phenyl)-imidazo-[1,2-a]pyridine;
7-[3-(4-Methyl-piperazine-1-ylmethyl)-phenyl]-3-(2-phenyl-pyridin-4-yl)-imidazo-[1,2-a]pyridine;
7-(3-Morpholin-4-ylmethyl-phenyl)-3-(2-phenyl-pyridin-4-yl)-imidazo-[1,2-a]pyridine;
N,N-Dimethyl-N'-{3-[3-(2-phenyl-pyridin-4-yl)-imidazo-[1,2-a]pyridin-7-yl]benzyl}-propane-1,3-diamine;
N,N-Dimethyl-N'-{3-[3-(2-phenyl-pyridin-4-yl)-imidazo-[1,2-a]pyridin-7-yl]benzyl}-ethane-1,2-diamine;
7-(4-Morpholin-4-ylmethyl-phenyl)-3-(3-pyrazol-1-yl-phenyl)-imidazo-[1,2-a]pyridine;
N'-(4-{3-[2-(3-Fluoro-phenyl)-pyiridin-4-yl]-imidazo-[1,2-a]pyridin-7-yl}-N,N-dimethyl-propane-1,3-diamine;
N,N-Dimethyl-N'-{4-[3-(3-pyrazol-yl-phenyl)-imidazo-[1,2-a]pyridin-7-yl]benzyl}-propane-1,3-diamine;
N,N-Dimethyl-N'-{4-[3-(2-phenyl-pyiridin-4-yl)-imidazo-[1,2-a]pyridin-7-yl]-benzyl}-propane-1,3-diamine;
[2-(4-Methyl-piperazine-1-yl)-ethyl]-{3-[3-(2-phenyl-pyridin-4-yl)-imidazo-[1,2-a]pyridin-7-yl]-benzyl}-amine;
[2-(4-Methyl-piperazine-1-yl)-ethyl]-{4-[3-(3-pyrazol-1-yl-phenyl)-imidazo-[1,2-a]pyridin-7-yl]-benzyl}-amine;
{3-[3-(2-Cyclopent-1-enyl-pyridin-4-yl)-imidazo[1,2-a]pyridin-7-yl]-benzyl}-ethyl-amine;
N-(2-Hydroxy-ethyl)-3-[3-(3-pyrazol-1-yl-phenyl)-imidazo-[1,2-a]-pyridin-7-yl]-benzamide;
N-(2-Hydroxy-ethyl)-4-[3-(3-pyrazol-1-yl-phenyl)-imidazo-[1,2-a]-pyridin-7-yl]-benzamide;
N-(2-Dimethylamino-ethyl)-4-[3-(3-pyrazol-1-yl-phenyl)-imidazo-[1,2-a]-pyridin-7-yl]-benzamide;
(4-Methyl-piperazine-1-yl)-{4-[3-(2-phenyl-pyridin-4-yl)-imidazo-[1,2-a]-pyridin-7yl]-phenyl}-methanone;
N-(4-Hydroxy-cyclohexyl)-4-[3-(2-phenyl-pyridin-4-yl)-imidazo-[1,2-a]-pyridin-7-yl]-benzamide;
5-[3-(3-Pyrazol-1-yl-phenyl)-imidazo-[1,2-a]-pyridin-7-yl]-nicotinamide;
5-[3-(2-Phenyl-pyridin-4-yl)-imidazo-[1,2-a]-pyridin-7-yl]-nicotinamide;
[4-[3-(2-Chloro-pyridin-4-yl)-imidazo[1,2-a]pyridin-6-ylamino]-cyclohexanol;
[4-[3-(2-Methoxy-pyridin-4-yl)-imidazo[1,2-a]pyridin-6-ylamino]-cyclohexanol;

4-(3-(2-Furan-3-yl-pyridin-4-yl)-imidazo[1,2-a]pyridin-6-ylamino)-cyclohexanol;
4-(3-(2-Phenyl-pyridin-4-yl)-imidazo[1,2-a]pyridin-6-ylamino)-cyclohexanol;
4-(3-(2-Furanyl-pyridin-4-yl)-imidazo[1,2-a]pyridin-6-ylamino)-cyclohexanol;
4-{3-[2-(1H-Pyrazol-3-yl)-pyridin-4-yl]-imidazo[1,2-a]pyridin-6-ylamino}-cyclohexanol;
[4-[3-(2-Ethoxy-pyridin-4-yl)-imidazo[1,2-a]pyridin-6-ylamino]-cyclohexanol;
[2-[3-(2-Methoxy-pyridin-4-yl)-imidazo[1,2-a]pyridin-6-ylamino]-cyclohexanol;
3,6-Bis-(2-methoxy-pyridin-4-yl)-imidazo[1,2-a]pyridine;
3-[3-(2-Furan-3-yl-pyridin-4-yl)-imidazo[1,2-a]pyridine-6-yl-N-metylbenzamide;
3-(2-Furan-3-yl-pyridin-4-yl)-6-(2-methoxy-pyridin-4-yl)-imidazo[1,2-a]pyridine;
6-Furan-3-yl-3-(2-Furan-3-yl-pyridin-4-yl)-imidazo[1,2-a]pyridine;
3-(2-Furan-3-yl-pyridin-4-yl)-6-pyridin-3-yl)-imidazo[1,2-a]pyridine;
3-(2-Furan-3-yl-pyridin-4-yl)-6-pyridin-4-yl)-imidazo[1,2-a]pyridine;
3-(2-Furan-3-yl-pyridin-4-yl)-6-(3-methoxyphenyl)-imidazo[1,2-a]pyridine;
3-(2-Furan-3-yl-pyridin-4-yl)-6-(4-methoxyphenyl)-imidazo[1,2-a]pyridine;
N-{3-[3-(2-Furan-3-yl-pyridin-4-yl)-imidazo[1,2-a]pyridine-6-yl]-phenyl}-acetamide;
4-[3-(2-Furan-3-yl-pyridin-4-yl)-imidazo[1,2-a]pyridine-6-yl]-N-methyl-benzamide;
3-(2-Furan-3-yl-pyridin-4-yl)-6-(methyl-1H-pyrazole-4-yl)-imidazo[1,2-a]pyridine;
N-{3-[3-(2-Furan-3-yl-pyridin-4-yl)-imidazo[1,2-a]pyridine-6-yl]-phenyl}-methanesulfonamide;
(1RS,3RS-3-[3-(2-Chloro-6-furan-3-yl-pyridin-4-yl)-imidazo[1,2-a]pyridin-6-ylamino]-cyclohexanol; and
(1RS, 3RS)-3-[3-(2-tert-Butylamino-6-furan-3-yl-pyridinin-4-yl)-imidazo[1,2-a]pyridine-6-ylamino]-cyclohexanol.

In the embodiments mentioned herein, where only certain variables are defined, it is intended that the remainder of the variables are as defined in any embodiment herein. Thus, the invention provides for the combination of limited definitions of variables.

The following terms as used herein are intended to have the following meanings:

"Optionally substituted" as used herein means the group referred to can be unsubstituted, or substituted at one or two or three positions by any one or any combination of the radicals listed thereafter.

"Halo" or "halogen" as used herein means fluorine, chlorine, bromine or iodine.

"$C_1$-$C_3$ alkyl", "$C_1$-$C_6$ alkyl", "$C_1$-$C_7$ alkyl" and the like, as used herein, denotes straight chain, branched or cyclic alkyl that contains one to three, six or seven (or the relevant number) carbon atoms and which may be substituted by one or more radicals.

"Aryl", as used herein, represents carbocyclic aryl or biaryl. Preferably, it denotes an aromatic group having 6- to 15-ring carbon atoms. It can be monocyclic, bicyclic or tricyclic, and may be substituted by one or more radicals. Examples of $C_6$-$C_{15}$-aryl groups include but are not limited to phenyl, phenylene, benzenetriyl, indanyl, naphthyl, naphthylene, naphthalenetriyl and anthracenyl.

"Heterocyclyl", refers to a 4- to 14-membered heterocyclic ring containing at least one ring heteroatom selected from the group consisting of nitrogen, oxygen and sulphur, which may be saturated, partially saturated or unsaturated. Examples of 4- to 14-membered heterocyclic groups include but are not limited to furan, azetidine, pyrrole, pyrrolidine, pyrazole, imidazole, triazole, isotriazole, tetrazole, thiadiazole, isothiazole, oxadiazole, pyridine, piperidine, pyrazine, oxazole, isoxazole, pyrazine, pyridazine, pyrimidine, piperazine, pyrrolidine, pyrrolidinone, pyridinone, morpholine, triazine, oxazine, tetrahydrofuran, tetrahydrothiophene, tetrahydrothiopyran, tetrahydropyran, 1,4-dioxane, 1,4-oxathiane, indazole, quinoline, indole, thiazole, thiophene, isoquinoline, benzothiophene, benzoxazole, benzisoxazole, benzothiazole, benzisothiazole, benzofuran, dihydrobenzofuran, benzodioxole, benzimidazole or tetrahydronaphthyridine. The 4- to 14-membered heterocyclic group can be unsubstituted or substituted.

"Heterocyclyl" includes heteroaryl and heterocycloalkyl groups.

"Heteroaryl" is an aromatic monocyclic or bicyclic hydrocarbon containing from 5 to 18 ring atoms one or more of which are heteroatoms selected from O, N or S. Preferably there are one or two heteroatoms. Heteroaryl (heterocyclic aryl) represents, for example: pyridyl, indolyl, quinoxalinyl, quinolinyl, isoquinolinyl, benzothienyl, benzofuranyl, benzopyranyl, benzothiopyranyl, furanyl, pyrrolyl, thiazolyl, oxazolyl, isoxazolyl, triazolyl, tetrazolyl, pyrazolyl, imidazolyl, thienyl. The heteroaryl group can be substituted or unsubstituted.

"Heterocycloalkyl" represents a mono-, di- or tricyclic hydrocarbon which may be saturated or unsaturated and which contains one or more, preferably one to three heteroatoms selected from O, N or S. Preferably it contains between three and 18 ring atoms. The term heterocycloalkyl is intended also to include bridged heterocycloalkyl groups such as 3-hydroxy-8-aza-bicyclo[3.2.1]oct-8-yl and fused ring systems. The heterocycloalkyl group can be substituted or unsubstituted.

"$C_3$-$C_{10}$-cycloalkyl" denotes a fully saturated carbocyclic ring having 3 to 10 ring carbon atoms, for example a monocyclic group such as a cyclopropyl, cyclobutyl, cyclopentyl or cyclohexyl, cycloheptyl, cyclooctyl, cyclononyl or cyclodecyl, or a bicyclic group such as bicycloheptyl or bicyclooctyl. Different numbers of carbon atoms may be specified, with the definition being amended accordingly. The cycloalkyl group can be substituted or unsubstituted.

"$C_5$-$C_{10}$-cycloalkenyl" denotes a partially saturated carbocyclic ring having 5 to 10 ring carbon atoms, for example a monocyclic group such as a cyclopentenyl or cyclohexenyl, cycloheptenyl, cyclooctenyl or cyclononenyl, or a bicyclic group such as bicycloheptenyl or bicyclooctenyl. The ring or ring system may contain more than one carbon-carbon double bond. Different numbers of carbon atoms may be specified, with the definition being amended accordingly. The cycloalkenyl group can be substituted or unsubstituted.

"$C_1$-$C_7$-haloalkyl" as used herein denotes $C_1$-$C_7$-alkyl as hereinbefore defined substituted by one or more halogen atoms, preferably one, two or three halogen atoms. Different numbers of carbon atoms may be specified, with the definition being amended accordingly.

"$C_1$-$C_7$-alkylamino" as used herein denote amino substituted by one or two $C_1$-$C_7$-alkyl groups as hereinbefore defined, which may be the same or different. Different numbers of carbon atoms may be specified, with the definition being amended accordingly.

"$C_1$-$C_7$-alkoxy" as used herein denotes straight chain or branched alkoxy that contains 1 to 7 carbon atoms. Different numbers of carbon atoms may be specified, with the definition being amended accordingly.

Throughout this specification and in the claims that follow, unless the context requires otherwise, the word "comprise", or variations such as "comprises" or "comprising", should be understood to imply the inclusion of a stated integer or step or group of integers or steps but not the exclusion of any other integer or step or group of integers or steps.

Compounds of formula I that contain a basic centre are capable of forming acid addition salts, particularly pharmaceutically acceptable acid addition salts. Pharmaceutically acceptable acid addition salts of the compound of formula I include those of inorganic acids, for example, hydrohalic acids such as hydrofluoric acid, hydrochloric acid, hydrobromic acid, hydroiodic acid, nitric acid, sulfuric acid, phosphoric acid; and organic acids, for example aliphatic monocarboxylic acids such as formic acid, acetic acid, trifluoroacetic acid, propionic acid and butyric acid, caprylic acid, dichloroacetic acid, hippuric acid, aliphatic hydroxy acids such as lactic acid, citric acid, tartaric acid or malic acid, gluconic acid, mandelic acid, dicarboxylic acids such as maleic acid or succinic acid, adipic acid, aspartic acid, fumaric acid, glutamic acid, malonic acid, sebacic acid, aromatic carboxylic acids such as benzoic acid, p-chloro-benzoic acid, nicotinic acid, diphenylacetic acid or triphenylacetic acid, aromatic hydroxy acids such as o-hydroxybenzoic acid, p-hydroxybenzoic acid, 1-hydroxynaphthalene-2-carboxylic acid or 3-hydroxynaphthalene-2-carboxylic acid, and sulfonic acids such as methanesulfonic acid or benzenesulfonic acid, ethanesulfonic acid, ethane-1,2-disulfonic acid, 2-hydroxy-ethanesulfonic acid, (+) camphor-10-sulfonic acid, naphthalene-2-sulfonic acid, naphthalene-1,5-disulfonic acid or p-toluenesulfonic acid. These salts may be prepared from compounds of formula I by known salt-forming procedures. Pharmaceutically acceptable solvates are generally hydrates.

Compounds of formula I which contain acidic, e.g. carboxyl, groups, are also capable of forming salts with bases, in particular pharmaceutically acceptable bases such as those well known in the art; suitable such salts include metal salts, particularly alkali metal or alkaline earth metal salts such as sodium, potassium, magnesium or calcium salts, or salts with ammonia or pharmaceutically acceptable organic amines or heterocyclic bases such as ethanolamines, benzylamines or pyridine, arginine, benethamine, benzathine, diethanolamine, 4-(2-hydroxy-ethyl)morpholine,1-(2-hydroxyethyl) pyrrolidine, N-methyl glutamine, piperazine, triethanolamine or tromethamine. These salts may be prepared from compounds of formula I by known salt-forming procedures. Compounds of formula I that contain acidic, e.g. carboxyl, groups may also exist as zwitterions with the quaternary ammonium centre.

Compounds of formula I in free form may be converted into salt form, and vice versa, in a conventional manner. The compounds in free or salt form can be obtained in the form of hydrates or solvates containing a solvent used for crystallisation. Compounds of formula I can be recovered from reaction mixtures and purified in a conventional manner. Isomers, such as enantiomers, may be obtained in a conventional manner, e.g. by fractional crystallisation or asymmetric synthesis from correspondingly asymmetrically substituted, e.g. optically active, starting materials.

Some compounds of the invention contain at least one asymmetric carbon atom and thus they exist in individual optically active isomeric forms or as mixtures thereof, e.g. as racemic mixtures. In cases where additional asymmetric centres exist the present invention also embraces both individual optically active isomers as well as mixtures, e.g. diastereomeric mixtures, thereof.

The invention includes all such forms, in particular the pure isomeric forms. The different isomeric forms may be separated or resolved one from the other by conventional methods, or any given isomer may be obtained by conventional synthetic methods or; by stereospecific or asymmetric syntheses. Since the compounds of the invention are intended for use in pharmaceutical compositions it will readily be understood that they are each preferably provided in substantially pure form, for example at least 60% pure, more suitably at least 75% pure and preferably at least 85%, especially at least 98% pure (% are on a weight for weight basis). Impure preparations of the compounds may be used for preparing the more pure forms used in the pharmaceutical compositions; these less pure preparations of the compounds should contain at least 1%, more suitably at least 5% and preferably from 10 to 59% of a compound of the invention.

The invention includes all pharmaceutically acceptable isotopically-labelled compounds of formula I wherein one or more atoms are replaced by atoms having the same atomic number, but an atomic mass or mass number different from the atomic mass or mass number usually found in nature. Examples of isotopes suitable for inclusion in the compounds of the invention include isotopes of hydrogen e.g. $^2$H and $^3$H, carbon e.g. $^{11}$C, $^{13}$C and $^{14}$C, chlorine e.g. $^{36}$Cl, fluorine e.g. $^{18}$F, iodine e.g. $^{123}$I and $^{125}$I, nitrogen e.g. $^{13}$N and $^{15}$N, oxygen e.g. $^{15}$O, $^{17}$O and $^{18}$O, and sulfur e.g. $^{35}$S.

Certain isotopically-labelled compounds of formula I, for example those incorporating a radioactive isotope, are useful in drug and/or substrate tissue distribution studies. The radioactive isotopes tritium ($^3$H) and carbon-14 ($^{14}$C) are particularly useful for this purpose in view of their ease of incorporation and ready means of detection. Substitution with heavier isotopes such as deuterium ($^2$H) may afford certain therapeutic advantages that result from greater metabolic stability, for example increased in vivo half-life or reduced dosage requirements, and hence may be preferred in some circumstances. Substitution with positron emitting isotopes, such as $^{11}$C, $^{18}$F, $^{15}$O, and $^{13}$N can be useful in Positron Emission Topography (PET) studies for examining substrate receptor occupancy.

Isotopically-labelled compounds of formula I can generally be prepared by conventional techniques known to those skilled in the art or by processes analogous to those described in the accompanying examples using an appropriate isotopically-labelled reagent in place of the non-labelled reagent previously used.

Pharmaceutically acceptable solvates in accordance with the invention include those wherein the solvent of crystallisation may be isotopically substituted e.g. $D_2O$, $d_6$-acetone or d6-DMSO.

Synthesis

The compounds of the invention may be synthesized by the general synthetic routes below, specific examples of which are described in more detail in the Examples.

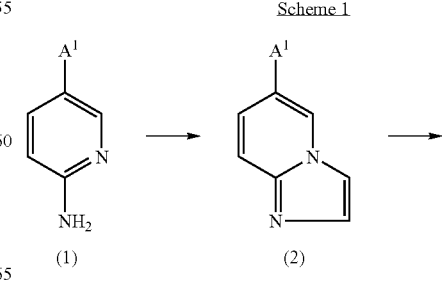

Scheme 1

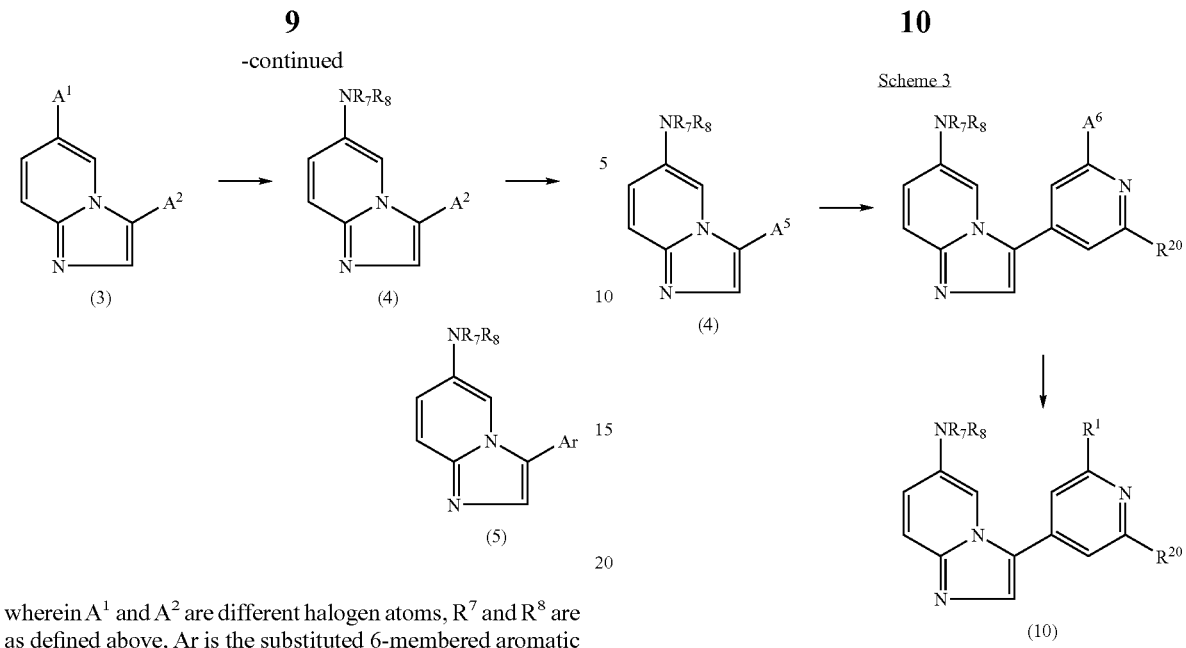

wherein $A^1$ and $A^2$ are different halogen atoms, $R^7$ and $R^8$ are as defined above, Ar is the substituted 6-membered aromatic ring according to Formula I and the compounds of Formula (5) are compounds of Formula I in which $R^2$ is $NR^7R^8$ and $R^3$ is H. The desired specific compounds can be prepared by selecting the appropriate starting materials, reactants and reaction conditions.

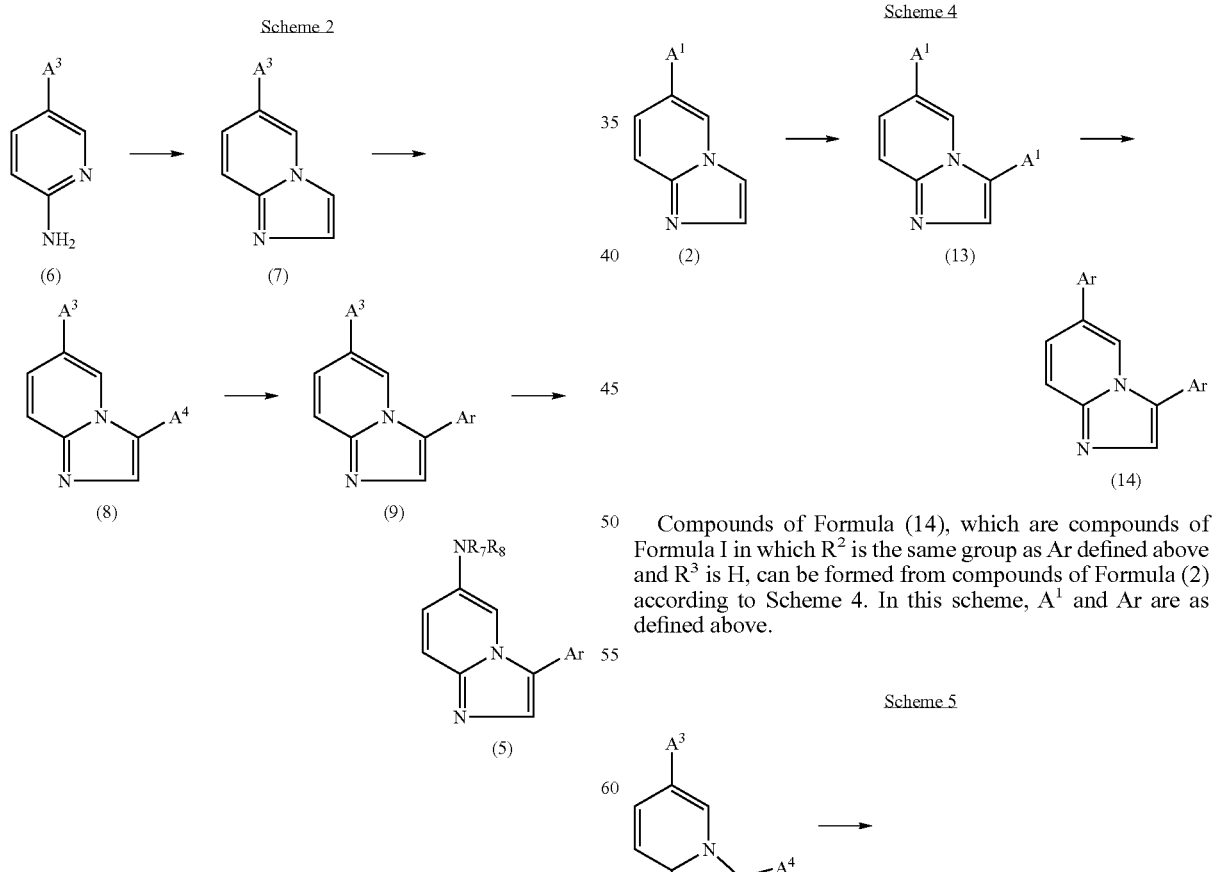

wherein $A^3$ and $A^4$ are different halogen atoms, and $R^7$, $R^8$ and Ar are as defined above. Again, the desired specific compounds can be prepared by selecting the appropriate starting materials, reactants and reaction conditions.

Compounds of Formula (10), which are compounds according to Formula I in which $R^2$ is $NR^7R^8$, $R^3$ is H and X is N, can be formed from compounds of Formula (4) according to Scheme 3. In this scheme, $A^5$ and $A^6$ are each independently halogen atoms which may be the same or different and $R^1$, $R^7$, $R^8$ and $R^{20}$ are as defined above.

Compounds of Formula (14), which are compounds of Formula I in which $R^2$ is the same group as Ar defined above and $R^3$ is H, can be formed from compounds of Formula (2) according to Scheme 4. In this scheme, $A^1$ and Ar are as defined above.

-continued

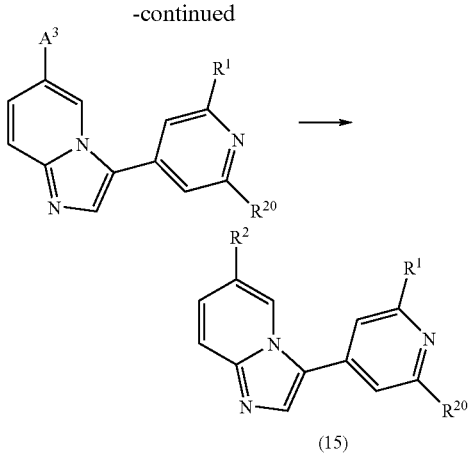

(15)

Compounds of Formula (15), which are compounds of Formula I in which X is N and $R^3$ is H, can be formed from compounds of Formula (8) according to Scheme 5. In this scheme, $A^3$, $A^4$, $R^1$, $R^2$ and $R^{20}$ are as defined above.

The above schemes show the synthesis of compounds of Formula I in which $R^2$ is other than H and $R^3$ is H. However, the skilled person will appreciate that compounds of Formula I where $R^3$ is other than H can be synthesized using analogous synthetic routes by use of the appropriate starting material, reactants and reaction conditions. Similarly, compounds of Formula I where X is $CR^4$ can be synthesized using analogous synthetic routes by use of the appropriate phenyl reactant in place of the pyridinyl reactant.

The compounds of formula (I) can be prepared, e.g., using the reactions and techniques described in detail in the Examples or modifications thereof. The reactions may be performed in a solvent appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

The various substituents on the synthetic intermediates and final products shown in the above reaction schemes can be present in their fully elaborated forms, with suitable protecting groups where required as understood by one skilled in the art, or in precursor forms which can later be elaborated into their final forms by methods familiar to one skilled in the art. The substituents can also be added at various stages throughout the synthetic sequence or after completion of the synthetic sequence. In many cases, commonly used functional group manipulations can be used to transform one intermediate into another intermediate, or one compound of formula (I) into another compound of formula (I). Examples of such manipulations are conversion of an ester or a ketone to an alcohol; conversion of an ester to a ketone; interconversions of esters, acids and amides; alkylation, acylation and sulfonylation of alcohols and amines; and many others. Substituents can also be added using common reactions, such as alkylation, acylation, halogenation or oxidation. Such manipulations are well-known in the art, and many reference works summarize procedures and methods for such manipulations. Some reference works which gives examples and references to the primary literature of organic synthesis for many functional group manipulations, as well as other transformations commonly used in the art of organic synthesis are *March's Organic Chemistry*, 5th Edition, Wiley and Chichester, Eds. (2001); *Comprehensive Organic Transformations*, Larock, Ed., VCH (1989); *Comprehensive Organic Functional Group Transformations*, Katritzky et al. (series editors), Pergamon (1995); and *Comprehensive Organic Synthesis*, Trost and Fleming (series editors), Pergamon (1991). It will also be recognized that another major consideration in the planning of any synthetic route in this field is the judicious choice of the protecting group used for protection of the reactive functional groups present in the compounds described in this invention. Multiple protecting groups within the same molecule can be chosen such that each of these protecting groups can either be removed without removal of other protecting groups in the same molecule, or several protecting groups can be removed using the same reaction step, depending upon the outcome desired. An authoritative account describing many alternatives to the trained practitioner is Greene and Wuts, *Protective Groups in Organic Synthesis*, Wiley and Sons (1999).

As a further aspect of the present invention there is also provided a process for the preparation of compounds of formula I in free or salt or solvate form.

According to a further aspect of the invention there is provided a process of preparing a compound of formula I comprising the step of:

(a) reacting a compound of Formula II

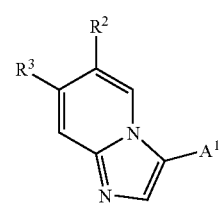

II where $R^2$ and $R^3$ are as defined anywhere above and $A^1$ is a halogen atom,

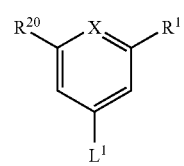

III with a compound of Formula III
where X, $R^1$ and $R^{20}$ are as defined anywhere above and $L^1$ is a boronic acid or boronic anhydride group; or (b) reacting a compound of Formula IV

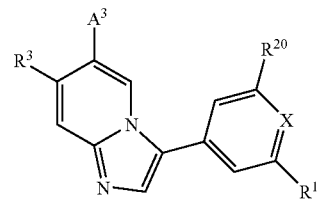

IV where X, $R^1$, $R^3$ and $R^{20}$ are as defined anywhere above and $A^3$ is a halogen atom, with a compound having the formula $R^2L^2$, where $R^2$ is as defined anywhere above and $L^2$ is a boronic acid or boronic anhydride group; or (c) reacting a compound of Formula V

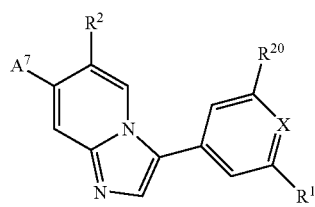

where X, R$^1$, R$^2$ and R$^{20}$ are as defined anywhere above and A$^7$ is a halogen atom, with a compound having the formula R$^3$L$^3$, where R$^3$ is as defined anywhere above and L$^3$ is a boronic acid or boronic anhydride group.

The agents of the invention act as activin-like kinase ("ALK")-5 inhibitors. At least many of these compounds also act as ALK-4 inhibitors too.

TGF-β1 is the prototypic member of a family of cytokines including the TGF-βs, activins, inhibins, bone morphogenetic proteins and Mullerian-inhibiting substance, that signal through a family of single transmembrane serine/threonine kinase receptors. These receptors can be divided into two classes, the type I or activin like kinase (ALK) receptors and type II receptors. The ALK receptors are distinguished from the type II receptors in that the ALK receptors (a) lack the serine/threonine rich intracellular tail, (b) possess serine/threonine kinase domains that are very homologous between type I receptors, and (c) share a common sequence motif called the GS domain, consisting of a region rich in glycine and serine residues. The GS domain is at the amino terminal end of the intracellular kinase domain and is critical for activation by the type II receptor. Several studies have shown that TGF-β signalling requires both the ALK and type II receptors. Specifically, the type II receptor phosphorylates the GS domain of the type I receptor for TGF-β, ALK5, in the presence of TGF-β. The ALK5, in turn, phosphorylates the cytoplasmic proteins smad2 and smad3 at two carboxy terminal serines. The phosphorylated smad proteins translocate into the nucleus and activate genes that contribute to the production of extracellular matrix. Therefore, preferred compounds of this invention are selective in that they inhibit the type I receptor.

Activins transduce signals in a manner similar to TGF-β. Activins bind to serine/thereonine kinase, the activin type II receptor (ActRIIB), and the activated type II receptor hyperphosphorylates serine/threonine residues in the GS region of the ALK4. The activated ALK4 in turn phosphorylates Smad2 and Smad3. The consequent formation of a hetero-Smad complex with Smad4 results in the activin-induced regulation of gene transcription.

Activation of the TGF-β1 axis and expansion of extracellular matrix are early and persistent contributors to the development and progression of chronic renal disease and vascular disease. Border W. A., et al, *N. Engl. J. Med.*, 1994; 331(19), 1286-92. Further, TGF-β1 plays a role in the formation of fibronectin and plasminogen activator inhibitor-1, components of sclerotic deposits, through the action of smad3 phosphorylation by the TGF-β1 receptor ALK5. Zhang Y., et al, *Nature*, 1998; 394(6696), 909-13; Usui T., et al, *Invest. Ophthalmol. Vis. Sci.*, 1998; 39(11), 1981-9.

Progressive fibrosis in the kidney and cardiovascular system is a major cause of suffering and death and an important contributor to the cost of health care. TGF-β1 has been implicated in many renal fibrotic disorders. Border W. A., et al, *N. Engl. J. Med.*, 1994; 331(19),1286-92. TGF-β1 is elevated in acute and chronic glomerulonephritis Yoshioka K., et al, *Lab. Invest.*, 1993; 68(2),154-63, diabetic nephropathy Yamamoto, T., et al, 1993, *PNAS* 90, 1814-1818., allograft rejection, HIV nephropathy and angiotensin-induced nephropathy Border W. A., et al, *N. Engl. 5 J. Med.*, 1994; 331(19), 1286-92. In these diseases the levels of TGF-β1 expression coincide with the production of extracellular matrix. Three lines of evidence suggest a causal relationship between TGF-β1 and the production of matrix. First, normal glomeruli, mesangial cells and non-renal cells can be induced to produce extracellular-matrix protein and inhibit protease activity by exogenous TGF-β1 in vitro. Second, neutralizing anti-bodies against TGF-β1 can prevent the accumulation of extracellular matrix in nephritic rats. Third, TGF-β1 transgenic mice or in vivo transfection of the TGF-β1 gene into normal rat kidneys resulted in the rapid development of glomerulosclerosis. Kopp J. B., et al, *Lab. Invest.*, 1996; 74(6),991 1003. Thus, inhibition of TGF-β1 activity is indicated as a therapeutic intervention in chronic renal disease.

TGF-β1 and its receptors are increased in injured blood vessels and are indicated in neointima formation following balloon angioplasty Saltis J., et al, *Clin. Exp. Pharmacol. Physiol.*, 1996; 23(3),193-200. In addition TGF-β1 is a potent stimulator of smooth muscle cell ("SMC") migration in vitro and migration of SMC in the arterial wall is a contributing factor in the pathogenesis of atherosclerosis and restenosis. Moreover, in multivariate analysis of the endothelial cell products against total cholesterol, TGF-β1 receptor ALK5 correlated with total cholesterol (P<0.001) Blann A. D., et al, *Atherosclerosis*, 1996; 120(1-2), 221-6. Furthermore, SMC derived from human atherosclerotic lesions have an increased ALK5/TGF-β1 type II receptor ratio. Because TGF-β1 is over-expressed in fibroproliferative vascular lesions, receptor-1 variant cells would be allowed to grow in a slow, but uncontrolled fashion, while overproducing extracellular matrix components McCaffrey T. A., et al, *Jr., J. Clin.; Invest.*, 1995; 96(6), 2667-75. TGF-β1 was immunolocalized to non-foamy macrophages in atherosclerotic lesions where active matrix synthesis occurs, suggesting that non-foamy macrophages may participate in modulating matrix gene expression in atherosclerotic remodelling via a TGF-β-dependent mechanism. Therefore, inhibiting the action of TGF-β1 on ALK5 is also indicated in atherosclerosis and restenosis.

Liver fibrosis is the result of unbalanced wound healing response to chronic liver injury trigged by a number of agents, such as hepatitis B and hepatitis C virus, alcohol or drugs, and autoimmune diseases. Ultimately, liver fibrosis could lead to life-threatening cirrhosis and liver cancer (see review article by Gressner et al (2006) *J. Cell. Mol. Med.* 2006, 10(1): 76-99).

Several cellular signaling pathways are known to be altered upon chronic liver injury. TGFβ signaling, its receptors and associated Smad-signaling proteins are well documented to be present in cell types involved in fibrogenesis. The circulating levels of TGFβ have been found to be elevated in a number of animal models of fibrotic diseases including liver fibrosis. Transgenic mice with overexpression of TGFβ1 develop fibrosis in multiple organs including liver, kidney, lungs and heart. It is apparent that an elevated TGFβ signaling is involved in all types of fibrotic diseases including liver fibrosis. This notion has been further validated in several studies using TGFβ inhibitors in fibrosis models. TGFβ mediates it signal by binding to two ser/thr kinase receptors, TGFβRII and ALK5. Expressing a dominant negative TGFβRII showed beneficial effects in a rat model of dimethylnitrosamine induced liver fibrosis (see Qi et al (1999) *Proc.*

Natl. Acad. Sci. 96: 2345-9 and Nakamura et al (2000) *Hepatology* 32: 247-55). Inhibiting TGFβ expression using an antisense approach also reduced liver fibrosis induced by bile duct ligation (see Arias et al (2003) BMC *Gastroenterol.* 3: 29). Recently, a small molecule inhibitor of ALK5, GW6604, when given therapeutically to rat, had significant effect in the treatment of dimethylnitrosamine induced liver fibrosis. It is quite remarkable that GW6604 prevented 40% of the death rate and inhibited extracellular matrix deposition by 60%, a key measurement for fibrosis. Importantly, no obvious side effects were noted during the 3 weeks treatment with GW6604 (see De Gouville et al (2005) *Br. J. Pharmacol.* 145: 166-77). Taken together these studies suggest that inhibiting TGFβ signaling could be an effective treatment for liver fibrotic diseases.

TGF-β1 is also indicated in wound repair. Neutralizing antibodies to TGF-β1 have been used in a number of models to illustrate that inhibition of TGF-β1 signalling is beneficial in restoring function after injury by limiting excessive scar formation during the healing process. For example, neutralizing antibodies to TGF-β1 and TGF-β2 reduced scar formation and improved the cytoarchitecture of the neodermis by reducing the number of monocytes and macrophages as well as decreasing dermal fibronectin and collagen deposition in rats Shah M., *J. Cell. Sci.,* 1995,108, 985-1002. Moreover, TGF-β antibodies also improve healing of corneal wounds in rabbits Moller-Pedersen T., *Curr. Eye Res.,* 1998,17, 736-747, and accelerate wound healing of gastric ulcers in the rat, Ernst H., *Gut,* 1996, 39, 172-175. These data strongly suggest that limiting the activity of TGF-β would be beneficial in many tissues and suggest that any disease with chronic elevation of TGF-β would benefit by inhibiting smad2 and smad3 signalling pathways.

TGF-β is also implicated in peritoneal adhesions Sand G. M., et al, *Wound Repair Regeneration,* 1999 November-December, 7(6), 504-510. Therefore, inhibitors of ALK5 would be beneficial in preventing peritoneal and sub-dermal fibrotic adhesions following surgical procedures.

TGF-β is also implicated in photoaging of the skin (see Fisher G J. Kang S W. Varani J. Bata-Csorgo Z. Wan Y S. Data S. Voorhees J J., Mechanisms of photoaging and chronological skin ageing, *Archives of Dermatology,* 138(11):1462-1470, 2002 November and Schwartz E. Sapadin A N. Kligman L H. "Ultraviolet B radiation increases steady state mRNA levels for cytokines and integrins in hairless mouse skin-modulation by 25 topical tretinoin", *Archives of Dermatological Research,* 290(3):137-144, 1998 March)

TGF-β signalling is also implicated in the development of pulmonary disorders, in particular pulmonary hypertension and pulmonary fibrosis (see Morrell N W, Yang X, Upton P D, Jourdan K B, Morgan N, Sheares K K, Trembath R C., Altered growth responses of pulmonary artery smooth muscle cells from patients with primary pulmonary hypertension to transforming growth factor-beta(1) and bone morphogenetic proteins. *Circulation.* 2001 Aug. 14;104(7):790-5. Bhatt N, Baran C P, Allen J, Magro C, Marsh C B., Promising pharmacologic innovations in treating pulmonary fibrosis. *Curr Opin Pharmacol.* 2006 Apr. 28).

TGF-β1 levels are increased in animal models of pulmonary hypertension (Mata-Greenwood E, Meyrick B, Steinhorn R H, Fineman J R, Black S M. Alterations in TGF-beta1 expression in lambs with increased pulmonary blood flow and pulmonary hypertension. *Am. J. Physiol. Lung Cell Mol. Physiol.* 2003 July; 285(1):L209-21). Other studies have suggested that pulmonary endothelial cell-derived TGF-β1 can stimulate the growth of pulmonary vascular smooth muscle cells which may underlie the enhanced muscularisation observed in the pulmonary vasculature of individuals with pulmonary hypertension (Sakao S, Taraseviciene-Stewart L, Wood K, Cool C D, Norbert V F. Apoptosis of pulmonary microvascular endothelial cells stimulates vascular smooth muscle cell growth. *Am. J. Physiol. Lung Cell Mol. Physiol.* 2006 Apr. 14). Therefore, inhibiting the action of TGF-β1 on ALK5 is indicated as a therapeutic intervention in pulmonary hypertension.

Additionally, dys-regulated TGF-β signalling has also been implicated in the development of idiopathic pulmonary fibrosis. Activation of ALK5 results in Smad3-activation and downstream modulation of the expression of genes involved in the fibrotic process such as plasminogen activator inhibitor-1, pro-collagen 3A1, and connective tissue growth factor. The levels of TGF-β1 and its downstream pro-fibrotic mediators have been demonstrated to be up-regulated in bronchoalveolar lavage taken from patients with idiopathic pulmonary fibrosis (Hiwatari N, Shimura S, Yamauchi K, Nara M, Hida W, Shirato K. Significance of elevated procollagen-III-peptide and transforming growth factor-beta levels of bronchoalveolar lavage fluids from idiopathic pulmonary fibrosis patients. *Tohoku J. Exp. Med.* 1997 February; 181(2): 285-95) and in animal models of idiopathic pulmonary fibrosis (Westergren-Thorsson G, Hernnas J, Sarnstrand B, Oldberg A, Heinegard D, Malmstrom A. Altered expression of small proteoglycans, collagen, and transforming growth factor-beta 1 in developing bleomycin-induced pulmonary fibrosis in rats. *J. Clin. Invest.* 1993 August;92(2):632-7).

Transient over-expression of active TGF-β1 in murine lungs, using adenoviral vector-mediated gene transfer, resulted in progressive pulmonary fibrosis in wild-type mice, whereas no fibrosis was seen in the lungs of Smad3 knockout mice up to 28 days following TGF-β1 challenge (Khalil N, Parekh T V, O'Connor R N, Gold L I. Differential expression of transforming growth factor-beta type I and II receptors by pulmonary cells in bleomycin-induced lung injury: correlation with repair and fibrosis. *Exp. Lung. Res.* 2002 April-May; 28(3):233-50. Thus, inhibition of TGF-β1 activation of ALK5 is also indicated for pulmonary fibrosis.

TGF-beta 1 may also be implicated in tumors and hence the agents of the invention may be useful in the treatment of cancer, including prostate cancer, breast cancer, gastric cancer, angiogenesis, metastasis, tumors, e.g. in the treatment and/or prevention of tumor progression.

Activin signalling and overexpression of activin is linked to pathological disorders that involve extracellular matrix accumulation and fibrosis (e.g., Matsuse, T. et al., *Am. J. Respir Cell Mol. Biol.* 13:17-24 (1995); Inoue, S. et al., *Biochem. Biophys. Res. Conn.* 205:441-448 (1994); Matsuse, T. et al., *Am. J. Pathol.* 148:707-713 (1996); De Bleser et al., *Hepatology* 26:905-912 (1997); Pawlowski, J. E., et al., *J. Clin. Invest.* 100:639-648 (1997); Sugiyama, M. et al., *Gastroenterology* 114:550-558 (1998); Munz, B. et al., EMBO J. 18:5205-5215 (1999)), inflammatory responses (e.g., Rosendahl, A. et al., *Am. J. Respir. Cell Mol. Biol.* 25:60-68 (2001), cachexia or wasting (Matzuk7 M. M. et al., *Proc. Natl. Acad. Sci. USA* 91:8817-8821 (1994); Coerver, K. A. et al., *Mol. Endocrinol.* 10:531 543 (1996); Cipriano, S. C. et al., *Endocrinology* 141:2319-2327 (2000)), diseases or pathological responses in the central nervous system (e.g., Logan, A. et al., *Eur. J. Neurosci.* 11:2367-2374 (1999); Logan, A. et al., *Exp. Neurol.* 159:504-510 (1999); Masliah, E. et al., *Neurochem. Int.* 39:393-400 (2001); De Groot, C. J. A. et al., *J. Neuropathol. Exp. Neural.* 58:174-187 (1999); John, G. R. et al., *Nat. Med.* 8:1115-1121 (2002)) and hypertension (e.g., Dahly, A. J. et al., *Am. J. Physiol. Regul. Integr Comp. Physiol.* 283: R757-767 (2002)). Studies have shown that TGF-β and activin can act synergistically to induce extracellular matrix production (e.g., Sugiyama, M. et al., *Gastroerterology* 114; 550-558 (1998)).

It follows, therefore, that inhibition of ALK5 and/or ALK4 phosphorylation of Smad2 and Smad3 by the agents of the invention can be useful to treat and prevent disorders that involve these signalling pathways.

Activin signalling is also implicated in the development of pulmonary disorders, in particular pulmonary hypertension and pulmonary fibrosis. For example, the expression of activin A in lung samples from patients with interstitial pulmonary fibrosis demonstrated strong expression of activin A on metaplastic epithelium, hyperplastic smooth muscle cells, desquamated cells, and alveolar macrophages. Pulmonary arteries from patients with primary or secondary pulmonary hypertension showed abundant immunoreactive activin A on smooth muscle cells. These findings suggest a potential role for this growth factor, activin A, in the pathogenesis of pulmonary tissue remodelling associated with interstitial pulmonary fibrosis and pulmonary hypertension (Matsuse T, Ikegami A, Ohga E, Hosoi T, Oka T, Kida K, Fukayama M, Inoue S, Nagase T, Ouchi Y, Fukuchi Y. Expression of immunoreactive activin A protein in remodelling lesions associated with interstitial pulmonary fibrosis. *Am. J. Pathol.* 1996 March;148(3):707-13). An increase in fibroblasts and associated connective tissue is a feature of pulmonary fibrosis and pulmonary hypertension. Activin A has been demonstrated to modulate human lung fibroblast (HFL1) activity, particularly with respect to proliferation and its differentiation into myofibroblast, thus activin A has potential effects on proliferation of lung fibroblast and its differentiation into myofibroblast, and may contribute to structural remodelling observed in pulmonary fibrosis and hypertension (Ohga E, Matsuse T, Teramoto S, Katayama H, Nagase T, Fukuchi Y, Ouchi Y. Effects of activin A on proliferation and differentiation of human lung fibroblasts. *Biochem. Biophys. Res. Commun.* 1996 Nov. 12;228(2):391-6). The induction of pulmonary fibrosis mediated by bleomycin challenge in rats results in the up-regulated expression of activin A in macrophages infiltrated in the lung, and was detected in fibroblasts accumulated in the fibrotic area. Administration of follistatin, an antagonist of activin signalling to bleomycin-treated rats significantly reduced the number of macrophages and neutrophils in bronchoalveolar lavage and reduced the protein content. Follistatin markedly reduced the number of infiltrating cells, ameliorated the destruction of lung architecture, and attenuated lung fibrosis (Aoki F, Kurabayashi M, Hasegawa Y, Kojima I. Attenuation of bleomycin-induced pulmonary fibrosis by follistatin. *Am. J. Respir. Crit. Care Med.* 2005 Sep. 15;172(6): 713-20).

Therefore, inhibiting activin signalling via ALK4 inhibition may also be beneficial for the treatment of pulmonary fibrosis and pulmonary hypertension.

It has been demonstrated recently that reduction in TGF-β signalling, through its effector Smad3, enhances the mechanical properties and mineral concentration of the bone matrix, as well as the bone mass, enabling the bone to better resist fracture. These results suggest that reduction of TGF-β signalling could be considered as a therapeutic target to treat bone disorders. (Balooch G, et al. *Proc. Natl. Acad. Sci. U S A*. 2005 Dec. 27;102(52):18813-8). Thus, inhibition of TGF-β1 activation of ALK5 is also indicated for increasing mineral density strength and content of bone and may be utilized to treat a wide variety of conditions, including for example, osteopenia, osteoporosis, fractures and other disorders in which low bone mineral density are a hallmark of the disease.

Having regard to their inhibition of ALK-5 and/or ALK-4 receptors, agents of the invention are useful in the treatment of conditions mediated by the ALK-5 and/or ALK-4 receptors. Treatment in accordance with the invention may be symptomatic or prophylactic.

Therefore according to a further aspect, the invention provides the use of agents of the invention in the preparation of a medicament for treating or preventing a disease or condition mediated by ALK-5 inhibition or ALK-4 inhibition.

Diseases or condition mediated by ALK-5 inhibition or ALK-4 inhibition include glomerulo-nephritis, diabetic nephropathy, lupus nephritis, hypertension-induced nephropathy, renal interstitial fibrosis, renal fibrosis resulting from complications of drug exposure, HIV-associated nephropathy, transplant necropathy, liver fibrosis due to all etiologies, hepatic dysfunction attributable to infections, alcohol-induced hepatitis, disorders of the biliary tree, pulmonary fibrosis, pulmonary hypertension, acute lung injury, adult respiratory distress syndrome, idiopathic pulmonary fibrosis, chronic obstructive pulmonary disease, pulmonary disease due to infectious or toxic agents, post-infarction cardiac fibrosis, congestive heart failure, dilated cardiomyopathy, myocarditis, vascular stenosis, restenosis, atherosclerosis, ocular scarring, corneal scarring, proliferative vitreoretinopathy, excessive or hypertrophic scar or keloid formation in the dermis occurring during wound healing resulting from trauma or surgical wounds, peritoneal and sub dermal adhesion, scleroderma, fibrosclerosis, progressive systemic sclerosis, dermatomyositis, polymyositis, arthritis, ulcers, impaired neurological function, male erectile dysfunction, Alzheimer's disease, Raynaud's syndrome, fibrotic cancers, tumor metastasis growth, radiation-induced fibrosis, thrombosis, and bone conditions such as osteopenia and osteoporosis, which are associated with increased calcium depletion or resorption or in which stimulation of bone formation and calcium fixation in the bone is desirable.

Diseases or conditions mediated by ALK-5 inhibition in particular include chronic renal disease, acute renal disease, wound healing, arthritis, osteoporosis, kidney disease, congestive heart failure, inflammatory or obstructive airways diseases, pulmonary hypertension, ulcers (including diabetic ulcers, chronic ulcers, gastric ulcers, and duodenal ulcers), ocular disorders, corneal wounds, diabetic nephropathy, impaired neuro-logical function, Alzheimer's disease, atherosclerosis, peritoneal and sub-dermal adhesion, any disease wherein fibrosis is a major component, including, but not limited to kidney fibrosis, lung fibrosis and liver fibrosis, for example, hepatitis B virus (HBV), hepatitis C virus (HCV), alcohol-induced hepatitis, haemochromatosis, primary biliary cirrhosis, restenosis, retroperitoneal fibrosis, mesenteric fibrosis, endometriosis, keloids, cancer, abnormal bone function, inflammatory disorders, scarring and photaging of the skin.

Inflammatory or obstructive airways diseases to which the present invention is applicable include asthma of whatever type or genesis including both intrinsic (non-allergic) asthma and extrinsic (allergic) asthma. Treatment of asthma is also to be understood as embracing treatment of subjects, e.g. of less than 4 or 5 years of age, exhibiting wheezing symptoms and diagnosed or diagnosable as "wheezy infants", an established patient category of major medical concern and now often identified as incipient or early-phase asthmatics. (For convenience this particular asthmatic condition is referred to as "wheezy-infant syndrome".)

Prophylactic efficacy in the treatment of asthma will be evidenced by reduced frequency or severity of symptomatic attack, e.g. of acute asthmatic or bronchoconstrictor attack, improvement in lung function or improved airways hyperreactivity. It may further be evidenced by reduced requirement for other, symptomatic therapy, i.e. therapy for or intended to restrict or abort symptomatic attack when it occurs, for example anti-inflammatory (e.g. corticosteroid) or bronchodilatory. Prophylactic benefit in asthma may in particular be apparent in subjects prone to "morning dipping". "Morning dipping" is a recognised asthmatic syndrome, common to a substantial percentage of asthmatics and characterised by asthma attack, e.g. between the hours of about 4 to 6 am, i.e. at a time normally substantially distant from any previously administered symptomatic asthma therapy.

Other inflammatory or obstructive airways diseases and conditions to which the present invention is applicable include adult/acute respiratory distress syndrome (ARDS), chronic obstructive pulmonary or airways disease (COPD or COAD), including chronic bronchitis, or dyspnea associated therewith, emphysema, as well as exacerbation of airways hyperreactivity consequent to other drug therapy, in particular other inhaled drug therapy. The invention is also applicable to the treatment of bronchitis of whatever type or genesis including, e.g., acute, arachidic, catarrhal, croupus, chronic or phthinoid bronchitis. Further inflammatory or obstructive airways diseases to which the present invention is applicable include pneumoconiosis (an inflammatory, commonly occupational, disease of the lungs, frequently accompanied by airways obstruction, whether chronic or acute, and occasioned by repeated inhalation of dusts) of whatever type or genesis, including, for example, aluminosis, anthracosis, asbestosis, chalicosis, ptilosis, siderosis, silicosis, tabacosis and byssinosis.

Preferably the disease or condition mediated by ALK-5 inhibition or ALK-4 inhibition is pulmonary hypertension, pulmonary fibrosis, liver fibrosis, muscular diseases, cancer or osteoporosis.

Pulmonary hypertension to be treated in accordance with the invention includes primary pulmonary hypertension (PPH); secondary pulmonary hypertension (SPH); familial PPH; sporadic PPH; precapillary pulmonary hypertension; pulmonary arterial hypertension (PAH); pulmonary artery hypertension; idiopathic pulmonary hypertension; thrombotic pulmonary arteriopathy (TPA); plexogenic pulmonary arteriopathy; functional classes I to IV pulmonary hypertension; and pulmonary hypertension associated with, related to, or secondary to, left ventricular dysfunction, mitral valvular disease, constrictive pericarditis, aortic stenosis, cardiomyopathy, mediastinal fibrosis, anomalous pulmonary venous drainage, pulmonary venoocclusive disease, collagen vascular disease, congenital heart disease, HIV virus infection, drugs and toxins such as fenfluramines, congenital heart disease, pulmonary venous hypertension, chronic obstructive pulmonary disease, interstitial lung disease, sleep-disordered breathing, alveolar hypoventilation disorder, chronic exposure to high altitude, neonatal lung disease, alveolar-capillary dysplasia, sickle cell disease, other coagulation disorder, chronic thromboemboli, connective tissue disease, lupus, schistosomiasis, sarcoidosis or pulmonary capillary hemangiomatosis.

Pulmonary hypertension to be treated in accordance with the invention is most particularly pulmonary hypertension associated with disorders of the respiratory system and/or hypoxemia, including chronic obstructive pulmonary disease, interstitial lung disease, sleep-disordered breathing, alveolar hypoventilation disorders, chronic exposure to high altitude, neonatal lung disease and alveolar-capillary dysplasia, but especially chronic obstructive pulmonary disease.

Lung fibrosis includes idiopathic pulmonary fibrosis in particular.

Compounds of the present may also be used to treat muscle diseases including muscular atrophies (e.g. disuse), muscular dystrophies (e.g. Duchenne's Muscle Dystrophy, Becker's Muscle Dystrophy, Limb-Girdle Muscle Dystrophy, Facioscapulohumeral Dystrophy), sarcopenia and cachexia.

Treatment of muscular diseases such as muscle atrophies and dystrophies is a largely unmet medical need. There are only few compounds approved for the use in assorted muscle disorders, mainly in the area of cancer-induced and HIV muscle wasting or cachexia, and a few more drugs are used off-label for these indications. In addition, most of these drugs only address the weight loss and do not specifically affect muscular growth and function. There is therefore a need for effective therapies to treat functional impairments associated with muscle diseases related to cachexia (e.g. in cancer, HIV and COPD), disuse atrophy, sarcopenia and dystrophy.

Myostatin, a member of the transforming growth factor β (TGFβ) family, is a key negative regulator of skeletal muscle mass. In double-muscle cattle and in a human body with skeletal muscle hypertrophy, different mutations in the myostatin gene were detected (McPherron et al (1997) *Nature* 387:83-90; Schuelke et al (2004) *N. Engl. J. Med.* 350:2682-2688). The important role of myostatin for skeletal muscle growth and disorders was confirmed in a wide variety of in vivo and in vitro studies. For example, muscle-specific overexpression of myostatin in mice causes loss of muscle mass (Reisz-Porszasz et al (2003) AJP-*Endo*. 285:876-888), whereas myostatin null mice have increased skeletal muscle mass and reduced body fat (Lin et al (2002) *Biochem. Biophys. Res. Comm.* 291: 701-706). In accordance systemic administration of myostatin induces cachexia (Zimmers et al (2002) *Science* 296:1486-1488), whereas inhibition of myostatin by, for example, the myostatin neutralizing antibody JA16 increases muscle mass and strength in wildtype and dystrophic mdx mice (Bogdanovich et al (2002) *Nature* 420: 418-421.2002; Wagner et al (2002) *Ann. Neurol.* 52: 832-836; Wolfman et al (2003) *Proc. Natl. Acad. Sci.* 100(26): 15842-15846). In addition, elevated myostatin levels have been observed in both experimental and clinical muscle atrophies such as in patients with Human Immunodeficiency Virus (HIV), cancer or liver cirrhosis as well as in sarcopenia of old age and under glucocorticoid-treatment (Ma et al (2003) *Am. J. Physiol. Endocrinol. Metab.* 285: E363-371; Gonzales-Cadavid et al (1998) *Proc. Natl. Acad. Sci.* 95: 14938-14943; see also Reisz-Porszasz et al (2003) AJP-*Endo*. 285:876-888 and Jespersen et al (2006) *Scand. J. Med. Sci. Sports.* 16: 74-82). These findings show the high potential of myostatin inhibitors as treatments for muscular atrophies and dystrophies.

The mode of action of myostatin is still under investigation. It is relatively well established that myostatin signals through Smad2/3 (Lee S. J. (2004) *Ann. Rev. Dev. Biol.* 20: 61-86). Moreover, mature myostatin has been shown to act via activin type IIb and activin receptor like kinase (ALK) receptors in adipocytes (Rebbarpragada et al (2003) *Mol. Cell. Biol.* 23: 7230-7242). However, respective findings in skeletal muscle cells are not described. Myostatin is believed to inhibit differentiation and cause atrophy via ALK signaling. Moreover, inhibition of ALK signaling promotes skMC differentiation and causes skMC hypertrophy.

Osteoporosis is a systemic skeletal disorder characterized by low bone mass and micro-architectural deterioration of bone tissue, with a consequent increase in bone fragility and susceptibility to fracture. The osteoporotic syndrome is multi faceted, encompassing primary disorders such as postmenopausal or age-related osteoporosis, and secondary conditions that accompany disease states or medications. The mechanical properties and composition of bone matrix, along with bone mass and architecture, are critical determinants of a bone's ability to resist fracture.

Thus in a further aspect the invention includes an agent of the invention for use as a pharmaceutical.

In a yet further aspect the invention includes a method for preventing or treating bone conditions which are associated with increased calcium depletion or resorption or in which stimulation of bone formation and calcium fixation in the bone is desirable in which an effective amount of an agent of the invention, or a pharmaceutically-acceptable and -cleavable ester, or acid addition salt thereof is administered to a patient in need of such treatment.

In a yet further aspect the invention includes a pharmaceutical composition for preventing or treating bone conditions which are associated with increased calcium depletion or resorption or in which stimulation of bone formation and calcium fixation in the bone is desirable comprising an agent of the invention, or a pharmaceutically-acceptable and -cleavable ester, or acid addition salt thereof, in admixture with a pharmaceutically acceptable excipient, diluent or carrier.

In a yet further aspect the invention includes the use of an agent of the invention in the manufacture of a medicament for the treatment or prevention of a bone condition.

The compounds of all of the Examples herein below have $IC_{50}$ values below 10 μM, typically below 1 μM. For instance, the following Examples have the stated $IC_{50}$ values.

| Example | $IC_{50}$ (μM) |
| --- | --- |
| 1.1 | 0.004 |
| 1.5 | 0.008 |
| 1.9 | 0.086 |
| 1.13 | 0.055 |
| 1.17 | 0.076 |
| 1.23 | 0.077 |
| 1.30 | 0.047 |
| 1.46 | 0.052 |
| 2.2 | 0.108 |
| 2.7 | 0.281 |
| 2.12 | 0.147 |
| 2.18 | 0.057 |
| 2.20 | 0.097 |

The kinase activity of ALK5 is assessed by measuring radiolabelled phosphate [33P] incorporation in to the generic substrate, casein. The kinase domain of human ALK5 (amino acids 200-503) is fused to an N-terminal histidine tag. The kinase activity of ALK5 is rendered constitutive via point mutation at amino acid 204 (threonine to aspartate modification, ALK5 T204D) and the kinase construct is engineered to be expressed from a baculovirus expression construct in insect cells. The purified, recombinantly-expressed histidine-tagged ALK5 T204D protein is dissolved at 5.4 mg/ml in 50 mM Tris-HCl pH 8.0, 150 mM NaCl, 5 mM DTT. ALK5 T204D is dissolved to 2.5 μg/ml in assay buffer (Assay buffer: 20 mM Tris-HCl pH 7.4, 10 mM $MgCl_2$, 2 mM $MnCl_2$) on the day of use.

Test compounds and reference compounds are dissolved in assay buffer without DTT containing 5% (v/v) DMSO. Stock solutions of test and reference compounds are diluted in assay buffer with DTT (1.25 mM) containing 4.5% (v/v) DMSO. 10 μl of test or reference compound are added to the appropriate wells of 96 well U-bottomed plate. Total enzyme activity is determined by measuring ALK5 T204D activity in the absence of ALK5 kinase inhibitor reference compounds. Non-specific binding (NSB) is determined by measuring the activity of ALK5 T204D in the presence of ALK5 kinase inhibitor reference compounds. 10 μl of dephosphorylated casein stock solution (dephosphorylated casein is dissolved in ddH2O at 20 mg/ml) is added per well (200 μg/well final assay concentration). 20 μl of ALK5 T204D (2.5 μg/ml solution) is added per well (50 ng/well final assay concentration). The plates are left to incubate at room temperature for 10 minutes.

10 μl of ATP mix is added to the well to initiate the reaction (0.66 nM [$^{33}$P]ATP/1 μM unlabelled ATP/well final assay concentration). The ATP mix is prepared as follows, unlabelled ATP (3 mM) is dissolved in ddH2O and pH adjusted to 7.4. The stock concentration of [$^{33}$P]ATP is 10 μCi/μl. The appropriate volume of [$^{33}$P]ATP is added to unlabelled ATP solution such that the final assay concentration per well is 0.1 μCi. Following addition of the ATP mix, the plates are incubated at room temperature for 50 minutes. The kinase reaction is terminated by the addition of 50 μL Stop Buffer (20 mM Tris-HCl pH 7.4, 10 mM EDTA).

75 μ/well from the reaction plate is transferred to a Multiscreen-IP plate (MultiScreen-IP plates are prepared by added 50 μL of 70% (v/v) ethanol per well and incubated for 5 minutes at room temperature. The ethanol is removed by aspiration via a MultiScreen HTS Vaccum Manifold unit (Millipore, Cat no: MSVMHT500). The plates are washed twice by adding 200 μl/well dd$H_2O$). The MultiScreen-IP plate is incubated at room temperature for 30 minutes to allowing binding of casein to the plate. The MultiScreen-IP plates are washed three times by adding 200 μl/well 100 mM phosphoric acid solution and the gasket is carefully removed from the back of the MultiScreen-IP plate and the plate dried in the oven for 30 minutes. The MultiScreen-IP plate is backsealed, 50 μL of Microscint®20 is added, then the plates are topsealed and radiolabelled casein detected and quantified on a TopCount™ plate-reader using the $^{33}$P scintillation protocol.

The agents of the invention are also useful as co-therapeutic agents for use in combination with other drug substances such as anti-inflammatory, bronchodilatory, antihistamine, decongestant or anti-tussive drug substances, particularly in the treatment of obstructive or inflammatory airways diseases such as those mentioned hereinbefore, for example as potentiators of therapeutic activity of such drugs or as a means of reducing required dosaging or potential side effects of such drugs. An agent of the invention may be mixed with one or more other drug substances in a fixed pharmaceutical composition or it may be administered separately, before, simultaneously with or after the other drug substance(s).

Such anti-inflammatory drugs include steroids, in particular glucocorticosteroids such as budesonide, beclamethasone dipropionate, fluticasone propionate, ciclesonide or mometasone furoate, or steroids described in WO 02/88167, WO 02/12266, WO 02/100879, WO 02/00679 [Novartis] (especially those of Examples 3, 11, 14, 17, 19, 26, 34, 37, 39, 51, 60, 67, 72, 73, 90, 99 and 101), WO 03/35668, WO 03/48181, WO 03/62259, WO 03/64445, WO 03/72592, WO 04/39827 and WO 04/66920; non-steroidal glucocorticoid receptor agonists, such as those described in DE 10261874, WO 00/00531, WO 02/10143, WO 03/82280, WO 03/82787, WO 03/86294, WO 03/104195, WO 03/101932, WO 04/05229, WO 04/18429, WO 04/19935, WO 04/26248 and WO 05/05452; LTB4 antagonists such as BIIL 284, CP-195543, DPC11870, LTB4 ethanolamine, LY 293111, LY 255283, CGS025019C, CP-195543, ONO-4057, SB 209247, SC-53228 and those described in U.S. Pat. No. 5,451,700 and WO 04/108720; LTD4 antagonists such as montelukast, pranlukast, zafirlukast, accolate, SR2640, Wy-48,252, ICI 198615, MK-571, LY-171883, Ro 24-5913 and L-648051; Dopamine receptor agonists such as cabergoline, bromocriptine, ropinirole and 4-hydroxy-7-[2-[[2-[[3-(2-phenylethoxy)-propyl]sulfonyl]ethyl]amino]ethyl]-2(3H)-benzothiazolone and pharmaceutically acceptable salts thereof (the hydrochloride being Viozan®—AstraZeneca); PDE4 inhibitors such as cilomilast (Ariflo® GlaxoSmithKline), Roflumilast (Byk Gulden), V-11294A (Napp), BAY19-8004 (Bayer), SCH-351591 (Schering-Plough), Arofylline (Almirall Prodesfarma), PD189659/PD168787 (Parke-Davis), AWD-12-281 (Asta Medica), CDC-801 (Celgene), SelCID (™) CC-10004 (Celgene), VM554/UM565 (Vernalis), T-440 (Tanabe), KW-4490 (Kyowa Hakko Kogyo), GRC 3886 (Oglemilast, Glenmark), WO 92/19594, WO 93/19749, WO 93/19750, WO 93/19751, WO 99/16766, WO 01/13953, WO 03/104204, WO 03/104205, WO 04/000814, WO 04/000839 and WO 04/005258 (Merck), WO 04018450, WO 04/018451, WO 04/018457, WO 04/018465, WO 04/018431, WO 04/018449, WO 04/018450, WO 04/018451, WO 04/018457, WO 04/018465, WO 04/019944, WO 04/019945, WO 04/045607, WO 04/037805, WO 04/063197, WO 04/103998, WO 04/111044, WO 05012252, WO 05012253, WO 05/013995, WO 05/030212, WO 05/030725, WO 05/087744, WO 05/087745, WO 05/087749 and WO 05/090345 as well as those described in WO 98/18796 and WO 03/39544. A2a agonists such as those described in EP 409595A2, EP 1052264, EP 1241176, WO 94/17090, WO 96/02543, WO 96/02553, WO 98/28319, WO 99/24449, WO 99/24450, WO 99/24451, WO 99/38877, WO 99/41267, WO 99/67263, WO 99/67264, WO 99/67265, WO 99/67266, WO 00/23457, WO 00/77018, WO 00/78774, WO 01/23399, WO 01/27130, WO 01/27131, WO 01/60835, WO 01/94368, WO 02/00676, WO 02/22630, WO 02/96462, WO 03/086408, WO 04/039762, WO 04/039766, WO 04/045618 and WO 04/046083; and A2b antagonists such as those described in WO 02/42298 and WO 03/042214.

Such bronchodilatory drugs include beta-2 adrenoceptor agonists. Suitable beta-2 adrenoceptor agonists include albuterol (salbutamol), metaproterenol, terbutaline, salmeterol, fenoterol, procaterol, and especially, formoterol, carmoterol, GSK159797 and pharmaceutically acceptable salts thereof, and compounds (in free or salt or solvate form) of formula I of WO 0075114, which document is incorporated herein by reference, preferably compounds of the Examples thereof, especially a compound of formula

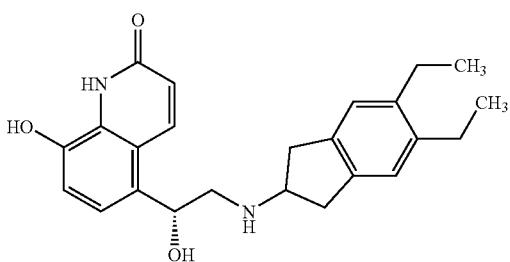 [SMILES: CCc1cc2c(cc1CC)CC(NC[C@H](O)c1ccc(O)c3[nH]c(=O)ccc13)C2]

and pharmaceutically acceptable salts thereof, as well as compounds (in free or salt or solvate form) of formula I of WO 04/16601 or of formula I of WO 04/087142. Further suitable β-2-adrenoreceptor agonists include compounds, such as those described in and also compounds of EP 147719, EP 1440966, EP 1460064, EP 1477167, EP 1574501, JP 05025045, JP 2005187357, US 2002/0055651, US 2004/0242622, US 2004/0229904, US 2005/0133417, US 2005/5159448, US 2005/5159448, US 2005/171147, US 2005/182091, US 2005/182092, US 2005/209227, US 2005/256115, US 2005/277632, US 2005/272769, US 2005/239778, US 2005/215542, US 2005/215590, US 2006/19991, US 2006/58530, WO 93/18007, WO 99/64035, WO 01/42193, WO 01/83462, WO 02/66422, WO 02/70490, WO 02/76933, WO 03/24439, WO 03/42160, WO 03/42164, WO 03/72539, WO 03/91204, WO 03/99764, WO 04/16578, WO 04/22547, WO 04/32921, WO 04/33412, WO 04/37768, WO 04/37773, WO 04/37807, WO 04/39762, WO 04/39766, WO 04/45618 WO 04/46083 , WO 04/80964, WO 04/087142, WO 04/89892, WO 04/108675, WO 04/108676, WO 05/33121, WO 05/40103, WO 05/44787, WO 05/58867, WO 05/65650, WO 05/66140, WO 05/70908, WO 05/74924, WO 05/77361, WO 05/90288, WO 05/92860, WO 05/92887, WO 05/90287, WO 05/95328, WO 05/102350, WO 06/56471, WO 06/74897 or WO 06/8173.

Such bronchodilatory drugs also include other anticholinergic or antimuscarinic agents, in particular ipratropium bromide, oxitropium bromide, tiotropium salts, glycopyrrolate, CHF 4226 (Chiesi) and SVT-40776, but also those described in EP 424021, U.S. Pat. No. 3,714,357, U.S. Pat. No. 5,171,744, US 2005/171147, US 2005/182091, WO 01/04118, WO 02/00652, WO 02/51841, WO 02/53564, WO 03/00840, WO 03/33495, WO 03/53966, WO 03/87094, WO 04/18422, WO 04/05285, WO 04/96800, WO 05/77361 and WO 06/48225.

Suitable dual anti-inflammatory and bronchodilatory drugs include dual beta-2 adrenoceptor agonist/muscarinic antagonists such as those disclosed in US 2004/0167167, US 2004/0242622, US 2005/182092, US 2005/256114, US 2006/35933, WO 04/74246, WO 04/74812, WO 04/89892 and WO 06/23475.

Suitable antihistamine drug substances include cetirizine hydrochloride, levocetirizine, acetaminophen, clemastine fumarate, promethazine, loratidine, desloratidine, diphenhydramine and fexofenadine hydrochloride, activastine, astemizole, azelastine, dimetinden, ebastine, epinastine, levocabastine, mizolastine and tefenadine as well as those disclosed in WO 03/099807, WO 04/026841 and JP 2004107299.

According to a further embodiment of the invention, the agents of the Invention may be employed as adjunct or adjuvant to other therapy, e.g. a therapy using a bone resorption inhibitor, for example as in osteoporosis therapy, in particular a therapy employing calcium, a ealeitonin or an analogue or derivative thereof, e.g. salmon, eel or human calcitonin, a steroid hormone, e.g. an estrogen, a partial estrogen agonist or estrogen-gestagen combination, a SERM (Selective Estrogen Receptor Modulator) e.g. raloxifene, lasofoxifene, TSE-424, FC1271, Tibolone (Livial A), vitamin D or an analog thereof or PTH, a PTH fragment or a PTH derivative e.g. PTH (1-84), PTH (1-34), PTH (1-36), PTH (1-38), PTH (1-31) NH2 or PTS 893.

In accordance with the foregoing, the present invention also provides a method for the treatment of an obstructive or inflammatory airways disease which comprises administering to a subject, particularly a human subject, in need thereof an agent of the invention, or a pharmaceutically acceptable salt or solvate thereof, as hereinbefore described. In another aspect, the invention provides an agent of the invention, or a pharmaceutically acceptable salt or solvate thereof, as hereinbefore described for use in the preparation of a medicament for the treatment of an obstructive or inflammatory airways disease.

The agents of the invention may be administered by any appropriate route, e.g. orally, for example in the form of a tablet or capsule; parenterally, for example intravenously; topically to the skin, for example in the treatment of psoriasis; intranasally, for example in the treatment of hay fever; or, preferably, by inhalation, particularly in the treatment of obstructive or inflammatory airways diseases. In particular, the agents of the invention may be delivered as an inhalable formulation for the treatment of COPD and asthma.

In a further aspect, the invention also provides a pharmaceutical composition comprising an agent of the invention in free form or in the form of a pharmaceutically acceptable salt or solvate thereof, optionally together with a pharmaceutically acceptable diluent or carrier therefor. Such compositions may be prepared using conventional diluents or excipients and techniques known in the galenic art. Thus oral dosage forms may include tablets and capsules. Formulations for topical administration may take the form of creams, ointments, gels or transdermal delivery systems, e.g. patches. Compositions for inhalation may comprise aerosol or other atomizable formulations or dry powder formulations.

Where the inhalable form of the active ingredient is an aerosol composition, the inhalation device may be an aerosol vial provided with a valve adapted to deliver a metered dose, such as 10 to 100 μl e.g. 25 to 50 μl of the composition, i.e. a device known as a metered dose inhaler. Suitable such aerosol vials and procedures for containing within them aerosol compositions under pressure are well known to those skilled in the art of inhalation therapy. For example, an aerosol composition may be administered from a coated can, for example as described in EP-A-0642992. Where the inhalable form of the active ingredient is a nebulizable aqueous, organic or aqueous/organic dispersion, the inhalation device may be a known nebulizer, for example a conventional pneumatic nebulizer such as an airjet nebulizer, or an ultrasonic nebulizer, which may contain, for example, from 1 to 50 ml, commonly 1 to 10 ml, of the dispersion; or a hand-held nebulizer, sometimes referred to as a soft mist or soft spray inhaler, for example an electronically controlled device such as an AERx (Aradigm, US) or Aerodose (Aerogen), or a mechanical device such as a RESPIMAT (Boehringer Ingelheim) nebulizer which allows much smaller nebulized volumes, e.g. 10 to 100 μl, than conventional nebulizers. Where the inhalable form of the active ingredient is the finely divided particulate form, the inhalation device may be, for example, a dry powder inhalation device adapted to deliver dry powder from a capsule or blister containing a dry powder comprising a dosage unit of (A) and/or (B) or a multidose dry powder inhalation (MDPI) device adapted to deliver, for example, 3-25 mg of dry powder comprising a dosage unit of (A) and/or (B) per actuation. The dry powder composition preferably contains a diluent or carrier, such as lactose, and a compound that helps to protect against product performance deterioration due to moisture e.g. magnesium stearate. Suitable such dry powder inhalation devices include devices disclosed in U.S. Pat. No. 3,991,761 (including the AEROLIZER™ device), WO 05/113042, WO 97/20589 (including the CERTIHALER™ device), WO 97/30743 (including the TWISTHALER™ device) and WO 05/37353 (including the GYROHALER™ device).

The invention also includes (A) an agent of the invention in free form, or a pharmaceutically acceptable salt or solvate thereof, in inhalable form; (B) an inhalable medicament comprising such a compound in inhalable form together with a pharmaceutically acceptable carrier in inhalable form; (C) a pharmaceutical product comprising such a compound in inhalable form in association with an inhalation device; and (D) an inhalation device containing such a compound in inhalable form.

Dosages of agents of the invention employed in practising the present invention will of course vary depending, for example, on the particular condition to be treated, the effect desired and the mode of administration. In general, suitable daily dosages for administration by inhalation are of the order of 0.0001 to 30 mg/kg, typically 0.01 to 10 mg per patient, while for oral administration suitable daily doses are of the order of 0.01 to 100 mg/kg.

The invention is illustrated by the following Examples.

EXAMPLES

Example compounds of the present invention include compounds of formula X

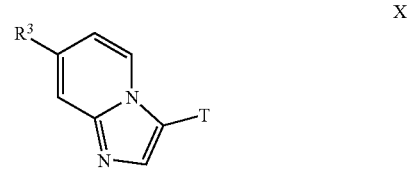

where $R^3$ and T are as shown in Table I below. The method of preparation being described hereinafter.

TABLE 1

| Ex. | $R^3$ | T | $[M + H]^+$ | Route |
|---|---|---|---|---|
| 1.1 | (3-methylpyridinyl) | (3-methylphenyl-pyrazolyl) | 338 | A |
| 1.2 | (3-methylphenol) | (3-methylbenzamide) | 330 | A |

TABLE 1-continued

| Ex. | R³ | T | [M + H]⁺ | Route |
|---|---|---|---|---|
| 1.3 | 5-methyl-2-morpholinopyridine | 3-(1H-pyrazol-1-yl)tolyl | 350 | A |
| 1.4 | 5-methyl-2-morpholinopyridine | 3-methylbenzamide | 400 | A |
| 1.5 | 5-methyl-2-morpholinopyridine | 4-methyl-2-phenylpyridine | 434 | A |
| 1.6 | 5-methyl-2-(4-methylpiperazin-1-yl)pyridine | 3-(1H-pyrazol-1-yl)tolyl | 436 | A |
| 1.7 | 5-methyl-2-(4-methylpiperazin-1-yl)pyridine | 4-methyl-2-phenylpyridine | 447 | A |
| 1.8 | 5-methylnicotinonitrile | 3-(1H-pyrazol-1-yl)tolyl | 362 | A |
| 1.9 | 3-methylbenzaldehyde | 3-(1H-pyrazol-1-yl)tolyl | 365 | A |
| 1.10 | ethyl 3-methylbenzoate | 3-(1H-pyrazol-1-yl)tolyl | 409 | A |

TABLE 1-continued
| Ex. | R³ | T | [M + H]⁺ | Route |
|---|---|---|---|---|
| 1.11 | 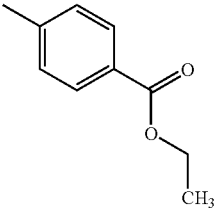 | 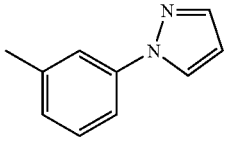 | 409 | A |
| 1.12 | 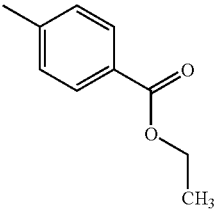 | 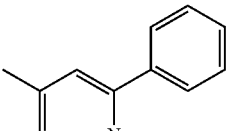 | 420 | A |
| 1.13 | 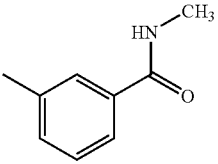 | 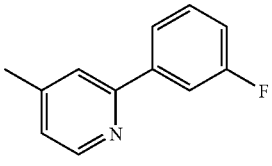 | 423 | A |
| 1.14 | 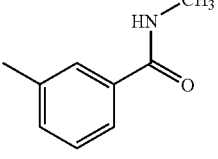 | 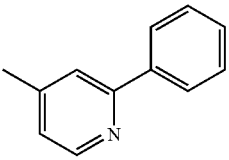 | 405 | A |
| 1.15 | 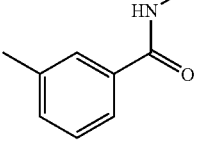 | 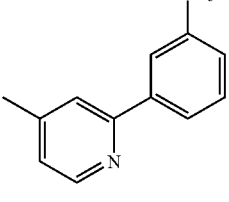 | 419 | A |
| 1.16 | 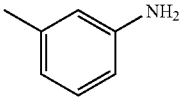 | 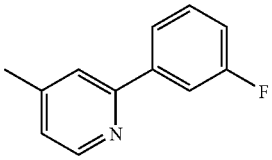 | 381 | A |
| 1.17 | 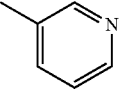 | 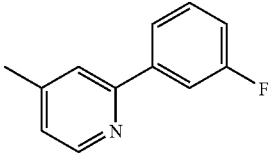 | 367 | A |
| 1.18 | 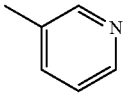 |  | 349 | A |

TABLE 1-continued

| Ex. | R³ | T | [M + H]⁺ | Route |
|---|---|---|---|---|
| 1.19 | 4-methylbenzaldehyde | 4-methyl-2-phenylpyridine | 376 | A |
| 1.20 | 2,5-dimethylpyridine | 3'-fluoro-4-methyl-2-phenylpyridine | 381 | A |
| 1.21 | 2,5-dimethylpyridine | 4-methyl-2-phenylpyridine | 363 | A |
| 1.22 | 1,4-dimethyl-1H-pyrazole | 2-(cyclopent-1-enyl)-4-methylpyridine | 342 | A |
| 1.23 | N-methyl-3-methylbenzamide | 4-methyl-2-(3-methyl-1H-pyrazol-1-yl)pyridine | 409 | A |
| 1.24 | 3-methylpyridine | 2-(4-fluorophenyl)-4-methylpyridine | 367 | A |
| 1.25 | 4-methylpyridine | 2-(4-fluorophenyl)-4-methylpyridine | 367 | A |

TABLE 1-continued

| Ex. | R³ | T | [M + H]⁺ | Route |
|---|---|---|---|---|
| 1.26 | 1-methyl-4-methylpyrazole | 4-methyl-2-(3-fluorophenyl)pyridine | 370 | A |
| 1.27 | 1-methyl-4-methylpyrazole | 4-methyl-2-(2,4-difluorophenyl)pyridine | 388 | A |
| 1.28 | 1-methyl-4-methylpyrazole | 4-methyl-2-(2-fluorophenyl)pyridine | 370 | A |
| 1.29 | 3-fluorotoluene | 4-methyl-2-(2-fluorophenyl)pyridine | 384 | A |
| 1.30 | 3-methylpyridazine | 4-methyl-2-(2-fluorophenyl)pyridine | 367 | A |
| 1.31 | 3-(N-methylcarboxamide)toluene | 4-methyl-2-(2-fluorophenyl)pyridine | 423 | A |

TABLE 1-continued

| Ex. | R³ | T | [M + H]⁺ | Route |
|---|---|---|---|---|
| 1.32 | 1-methyl-4-pyrazolyl | 4-methyl-2-phenylpyridine | 352 | A |
| 1.33 | 5-methyl-2-pyridone | 2-(4-fluorophenyl)-4-methylpyridine | 383 | A |
| 1.34 | 4-methyl-1H-pyrazolyl | 4-methyl-2-phenylpyridine | 338 | A |
| 1.35 | 3-(dimethylamino)-methylphenyl | 4-methyl-2-phenylpyridine | 391 | A |
| 1.36 | 3-fluorophenyl | 4-methyl-2-phenylpyridine | 366 | A |
| 1.37 | 5-methyl-2-pyridone | 4-methyl-2-phenylpyridine | 365 | A |
| 1.38 | phenyl | 4-methyl-2-phenylpyridine | 348 | A |
| 1.39 | 6-fluoro-3-methylpyridyl | 3-(1H-pyrazol-1-yl)-methylphenyl | 356 | A |

TABLE 1-continued
| Ex. | R³ | T | [M + H]⁺ | Route |
|---|---|---|---|---|
| 1.40 | 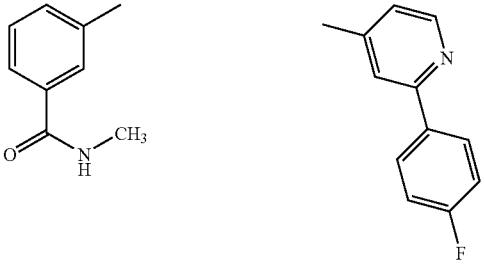 | 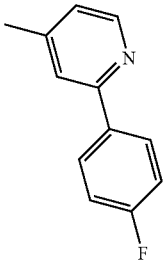 | 423 | A |
| 1.41 | 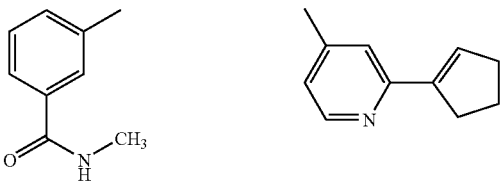 | 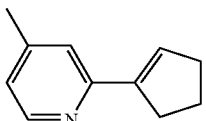 | 395 | A |
| 1.42 |  | 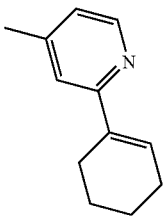 | 353 | A |
| 1.43 | 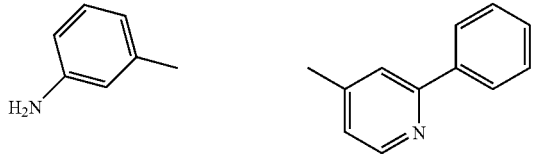 | 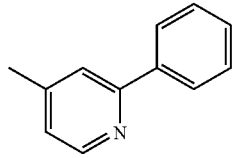 | 363 | A |
| 1.44 | 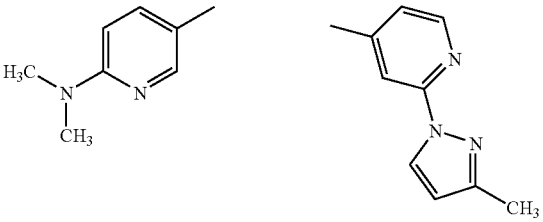 | 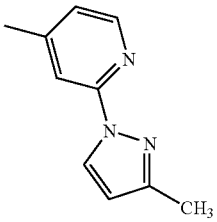 | 396 | A |
| 1.45 | 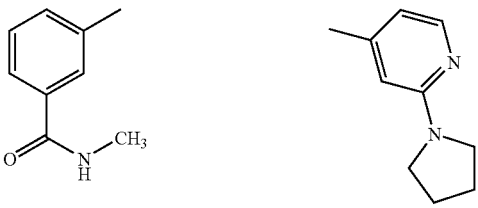 | 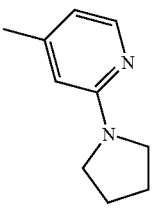 | 398 | A |
| 1.46 |  | 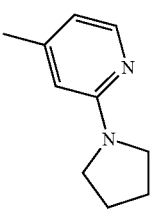 | 369 | A |

TABLE 1-continued

| Ex. | R³ | T | [M + H]⁺ | Route |
|---|---|---|---|---|
| 1.47 | 3-formylphenyl | 4-methyl-2-(3-methyl-1H-pyrazol-1-yl)pyridine | 380 | A |
| 1.48 | 6-methylpyridin-3-yl | 2-(4-fluorophenyl)-4-methylpyridine | 381 | A |
| 1.49 | 3,5-difluorophenyl | 4-methyl-2-phenylpyridine | 384 | A |
| 1.50 | 6-methylpyridin-3-yl | 4-methyl-2-(1H-pyrazol-1-yl)phenyl | 352 | A |
| 1.51 | 6-methoxypyridin-3-yl | 2-(cyclopent-1-en-1-yl)-4-methylpyridine | 369 | A |
| 1.52 | 6-(4-methylpiperazin-1-yl)pyridin-3-yl | 4-methyl-2-phenylpyridine | 447 | A |
| 1.53 | 6-morpholinopyridin-3-yl | 4-methyl-2-(1-methyl-1H-pyrazol-4-yl)pyridine | 438 | A |

TABLE 1-continued

| Ex. | R³ | T | [M + H]⁺ | Route |
|---|---|---|---|---|
| 1.54 | 3-formylphenyl (methyl-benzaldehyde) | 4-methyl-2-(cyclopentenyl)pyridine | 366 | A |
| 1.55 | 3-(piperidin-1-yl)phenyl methyl | 4-methyl-2-phenylpyridine | 431 | A |
| 1.56 | 6-morpholino-3-methylpyridine | 3-methylbenzamide | 400 | A |
| 1.57 | 3-fluoro-5-hydroxy-methylphenyl | 4-methyl-2-phenylpyridine | 382 | A |
| 1.58 | N-methyl-3-methylbenzamide | 4-methyl-2-(2,4-difluorophenyl)pyridine | 441 | A |
| 1.59 | 3-methylpyridine | 4-methyl-2-(2,4-difluorophenyl)pyridine | 385 | A |
| 1.60 | 3-methylpyridine | 4-methyl-2-(2-methylpyrrolidin-1-yl)pyridine | 356 | A |

TABLE 1-continued

| Ex. | R³ | T | [M + H]⁺ | Route |
|---|---|---|---|---|
| 1.61 | 3-methyl-N-methylbenzamide | 4-methyl-2-(2-methylpyrrolidin-1-yl)pyridine | 412 | A |
| 1.62 | 2,5-dimethylpyridine | 2-(2-fluorophenyl)-4-methylpyridine | 381 | A |
| 1.63 | N,N,5-trimethylpyridin-2-amine | 2-(2-fluorophenyl)-4-methylpyridine | 410 | A |
| 1.64 | N,N-dimethyl-1-(m-tolyl)methanamine | 2-(4-fluorophenyl)-4-methylpyridine | 423 | A |
| 1.65 | 2-methoxy-5-methylpyridine | 2-(4-fluorophenyl)-4-methylpyridine | 397 | A |
| 1.66 | N,N-dimethyl-1-(m-tolyl)methanamine | 2-(2-fluorophenyl)-4-methylpyridine | 423 | A |

TABLE 1-continued

| Ex. | R³ | T | [M + H]⁺ | Route |
|---|---|---|---|---|
| 1.67 | 3-(methylaminomethyl)phenyl | 4-methyl-2-phenylpyridin-2-yl | 391 | A |
| 1.68 | 3-(methylaminomethyl)phenyl | 2-(cyclopent-1-en-1-yl)-4-methylpyridin-2-yl | 381 | A |
| 1.69 | 4-(4-methylpiperazine-1-carbonyl)phenyl | 2-(4-fluorophenyl)-4-methylpyridin-2-yl | 492 | A |
| 1.70 | 4-(1-hydroxy-2-oxoethyl)phenyl | 4-methyl-2-phenylpyridin-2-yl | 406 | A |
| 1.71 | 4-(1-hydroxy-2-oxoethyl)phenyl | 2-(cyclopent-1-en-1-yl)-4-methylpyridin-2-yl | 396 | A |
| 1.72 | furan-3-yl | 2-(cyclopent-1-en-1-yl)-4-methylpyridin-2-yl | 328 | A |
| 1.73 | 1H-pyrazol-4-yl | 2-(cyclopent-1-en-1-yl)-4-methylpyridin-2-yl | 328 | A |
| 1.74 | thiophen-3-yl | 2-(cyclopent-1-en-1-yl)-4-methylpyridin-2-yl | 344 | A |
| 1.75 | 3-fluorophenyl | 2-(cyclopent-1-en-1-yl)-4-methylpyridin-2-yl | 356 | A |

TABLE 1-continued

| Ex. | R³ | T | [M + H]⁺ | Route |
|---|---|---|---|---|
| 1.76 | 3-fluoro-5-methyl-N-methylbenzamide | 4-methyl-2-phenylpyridine | 423 | A |
| 1.77 | 3-fluoro-5-methyl-N-methylbenzamide | 2-(4-fluorophenyl)-4-methylpyridine | 441 | A |
| 1.78 | 5-methylpyrimidine | 4-methyl-2-phenylpyridine | 350 | A |
| 1.79 | 1,3,4,5-tetramethylpyrazole | 2-(4-fluorophenyl)-4-methylpyridine | 398 | A |
| 1.80 | (3-fluoro-5-methylphenyl)methanol | 2-(4-fluorophenyl)-4-methylpyridine | 414 | A |
| 1.81 | N-methyl-(3-fluoro-5-methylphenyl)methylamine | 2-(4-fluorophenyl)-4-methylpyridine | 427 | A |

TABLE 1-continued

| Ex. | R³ | T | [M + H]⁺ | Route |
|---|---|---|---|---|
| 1.82 | 4-methyl-1-(piperidin-4-yl)-1H-pyrazole | 2-(4-fluorophenyl)-4-methylpyridine | 439 | A |
| 1.83 | N-methyl-1-(4-methylfuran-2-yl)methanamine | 4-methyl-2-phenylpyridine | 381 | A |
| 1.84 | 1-chloro-3-methylbenzene | 4-methyl-2-phenylpyridine | 382 | A |
| 1.85 | 2-fluoro-5-methylpyridine | 4-methyl-2-phenylpyridine | 367 | A |
| 1.86 | 3-fluoro-5-methylbenzoic acid | 4-methyl-2-phenylpyridine | 410 | A |
| 1.87 | 3,4-difluoro-1-methylbenzene | 4-methyl-2-phenylpyridine | 384 | A |
| 1.88 | 3-fluoro-4-methylpyridine | 4-methyl-2-phenylpyridine | 367 | A |
| 1.89 | 2-fluoro-3-methylpyridine | 4-methyl-2-phenylpyridine | 367 | A |

TABLE 1-continued

| Ex. | R³ | T | [M + H]⁺ | Route |
|---|---|---|---|---|
| 1.90 | 3,5-dimethyl-1H-pyrazol-4-yl | 4-methyl-2-phenylpyridin-2-yl | 366 | A |
| 1.91 | phenyl (tolyl) | 2-(cyclopent-1-en-1-yl)-4-methylpyridine | 338 | A |
| 1.92 | 2-(trifluoromethyl)pyridin-4-yl | 4-methyl-2-phenylpyridine | 417 | A |
| 1.93 | 2-methylpyridine | 4-methyl-2-phenylpyridine | 349 | A |
| 1.94 | 2,4-dimethylpyridine | 4-methyl-2-phenylpyridine | 363 | A |
| 1.95 | ethyl 2-(2-fluoro-4-methylphenyl)acetate | 4-methyl-2-phenylpyridine | 452 | A |
| 1.96 | N-methyl-3-methylbenzamide | 2-(3-methylcyclopent-1-en-1-yl)-4-methylpyridine | 409 | A |
| 1.97 | N-methyl-3-methylbenzamide | 2-(4,4-dimethylcyclopent-1-en-1-yl)-4-methylpyridine | 423 | A |

TABLE 1-continued
| Ex. | R³ | T | [M + H]⁺ | Route |
|---|---|---|---|---|
| 1.98 | 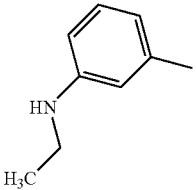 | 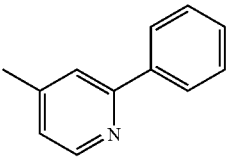 | 391 | A |
| 1.99 | 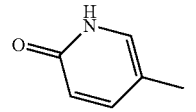 | 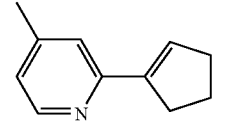 | 355 | A |
| 1.100 | 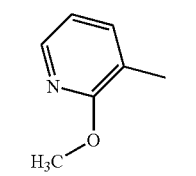 |  | 379 | A |
| 1.101 | 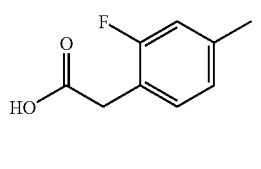 | 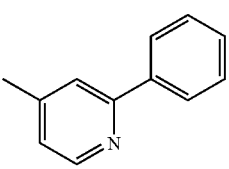 | 424 | A |
| 1.102 | 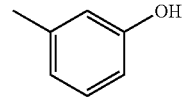 | 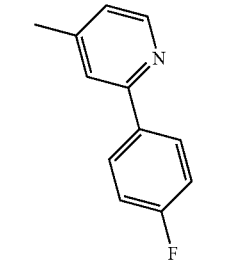 | 382 | A |
| 1.103 | 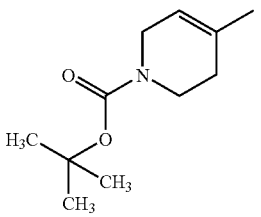 | 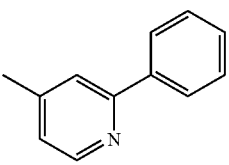 | 453 | A |
| 1.104 | 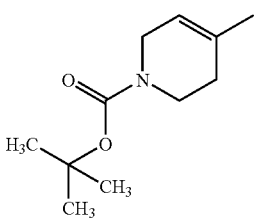 | 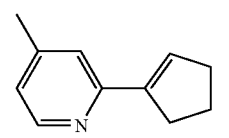 | 443 | A |
| 1.105 | 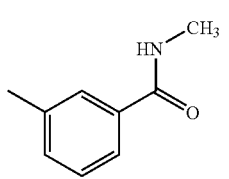 | 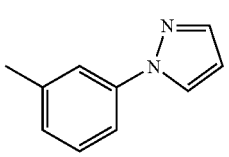 | 394 | B |

TABLE 1-continued
| Ex. | R³ | T | [M + H]⁺ | Route |
|---|---|---|---|---|
| 1.106 | 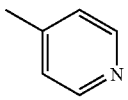 | 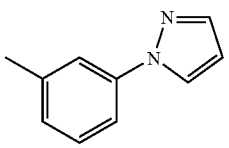 | 338 | B |
| 1.107 | 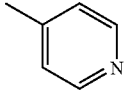 | 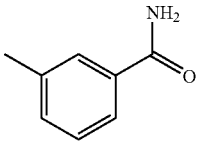 | 315 | B |
| 1.108 | 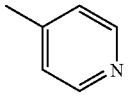 | 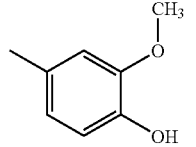 | 318 | B |
| 1.109 | 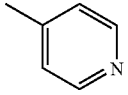 | 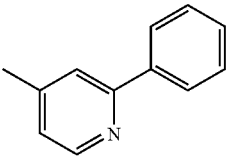 | 349 | B |
| 1.110 | 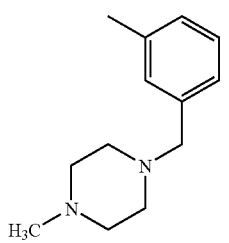 | 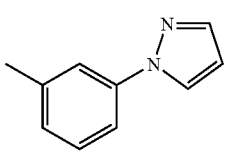 | 449 | C |
| 1.111 | 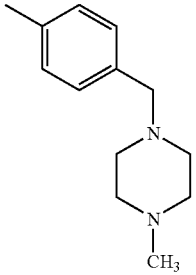 | 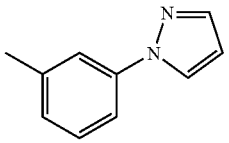 | 449 | C |
| 1.112 | 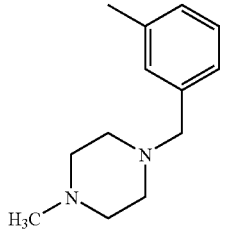 | 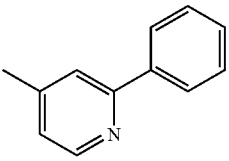 | 460 | C |

TABLE 1-continued

| Ex. | R³ | T | [M + H]⁺ | Route |
|---|---|---|---|---|
| 1.113 | 3-methylbenzyl-morpholine | 4-methyl-2-phenylpyridine | 447 | C |
| 1.114 | N,N-dimethyl-N'-(3-methylbenzyl)propane-1,3-diamine | 4-methyl-2-phenylpyridine | 462 | C |
| 1.115 | N,N-dimethyl-N'-(3-methylbenzyl)ethane-1,2-diamine | 4-methyl-2-phenylpyridine | 448 | C |
| 1.116 | 4-methylbenzyl-morpholine | 4-methyl-1-(1H-pyrazol-1-yl)benzene | 436 | C |
| 1.117 | N,N-dimethyl-N'-(4-methylbenzyl)propane-1,3-diamine | 4-methyl-2-(3-fluorophenyl)pyridine | 480 | C |
| 1.118 | N,N-dimethyl-N'-(4-methylbenzyl)propane-1,3-diamine | 4-methyl-1-(1H-pyrazol-1-yl)benzene | 451 | C |

TABLE 1-continued
| Ex. | R³ | T | [M + H]⁺ | Route |
|---|---|---|---|---|
| 1.119 | 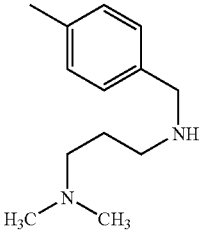 | 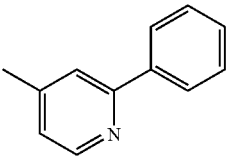 | 462 | C |
| 1.120 | 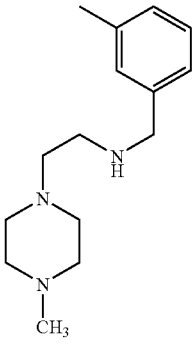 | 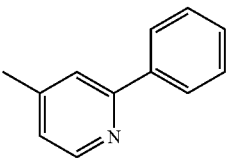 | 503 | C |
| 1.121 | 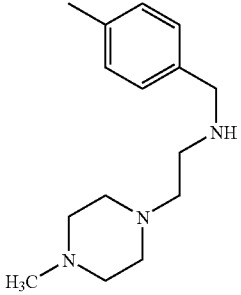 | 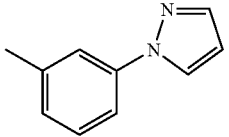 | 492 | C |
| 1.122 | 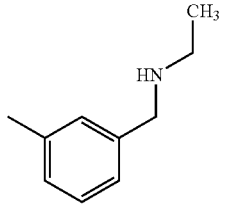 |  | 395 | C |
| 1.123 | 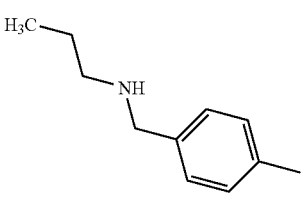 |  | 419 | C |
| 1.124 | 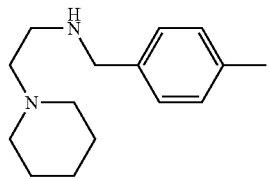 | 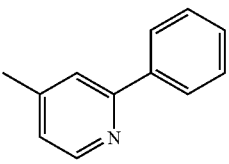 | 488 | C |

TABLE 1-continued
| Ex. | R³ | T | [M + H]⁺ | Route |
|---|---|---|---|---|
| 1.125 | 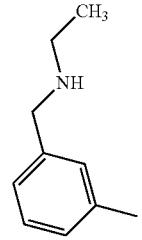 | 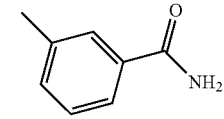 | 371 | C |
| 1.126 | 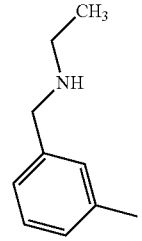 | 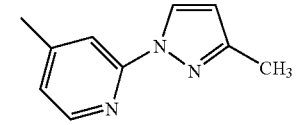 | 409 | C |
| 1.127 | 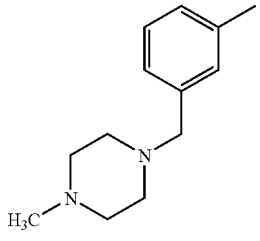 | 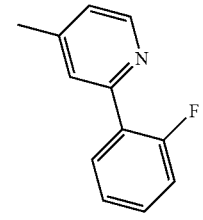 | 478 | C |
| 1.128 | 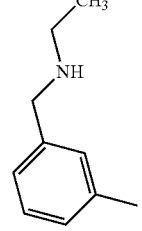 | 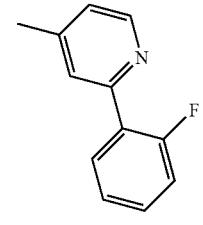 | 423 | C |
| 1.129 | 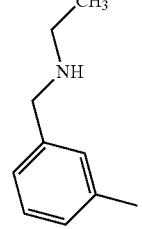 | 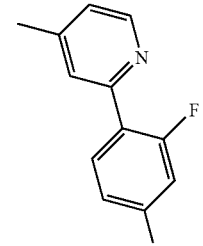 | 441 | C |
| 1.130 | 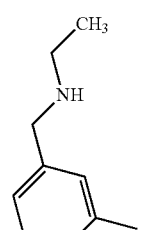 | 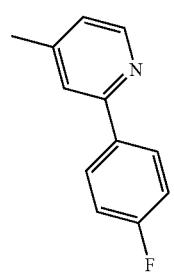 | 423 | C |

TABLE 1-continued
| Ex. | R³ | T | [M + H]⁺ | Route |
|---|---|---|---|---|
| 1.131 | 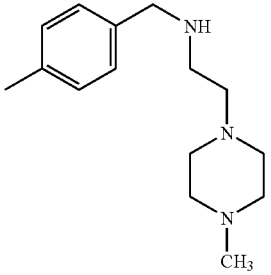 | 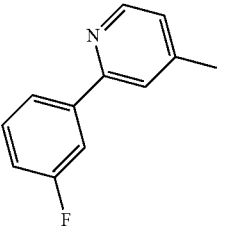 | 521 | C |
| 1.132 | 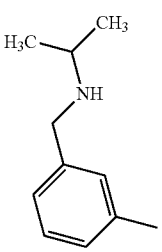 | 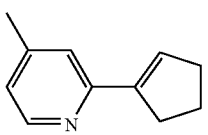 | 409 | C |
| 1.133 | 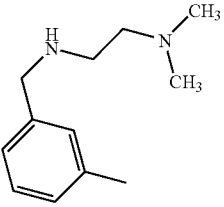 | 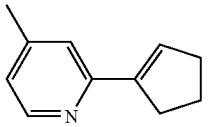 | 438 | C |
| 1.134 | 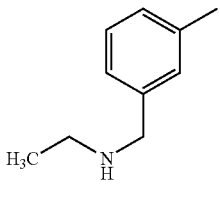 | 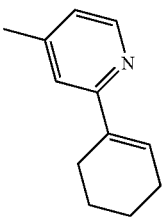 | 409 | C |
| 1.135 | 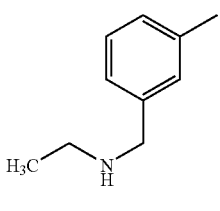 | 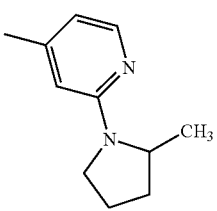 | 412 | C |
| 1.136 | 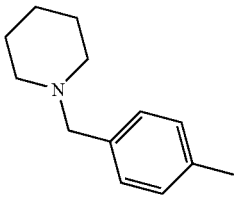 | 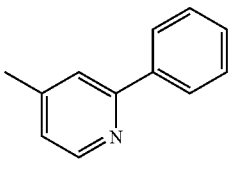 | 445 | C |
| 1.137 | 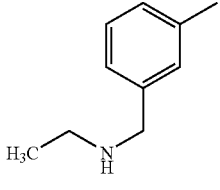 | 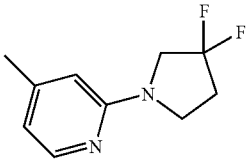 | 434 | C |

TABLE 1-continued

| Ex. | R³ | T | [M + H]⁺ | Route |
|---|---|---|---|---|
| 1.138 | 3-methylbenzyl-N(H)-CH(CH₃)₂ (N-isopropyl) | 4-methyl-2-(pyrrolidin-1-yl)pyridine | 412 | C |
| 1.139 | 3-methylbenzyl-NH-CH₂CH(CH₃)₂ (isobutyl) | 4-methyl-2-(pyrrolidin-1-yl)pyridine | 440 | C |
| 1.140 | 3-methylbenzyl-NH-CH₂CH(CH₃)₂ (isobutyl) | 3-methylbenzamide | 413 | C |
| 1.141 | 3-methylbenzyl-NH-CH₂CH(CH₃)₂ (isobutyl) | 4-methyl-2-(2-fluorophenyl)pyridine | 465 | C |
| 1.142 | 3-methylbenzyl-NH-CH₂CH(CH₃)₂ (isobutyl) | 4-methyl-2-(2,4-difluorophenyl)pyridine | 484 | C |
| 1.143 | 4-methylbenzyl-NH-CH₂CH₂CH₃ (N-propyl) | 3-methylbenzamide | 385 | C |
| 1.144 | 3-fluoro-5-methylbenzyl-NH-CH₃ | 4-methyl-2-phenylpyridine | 409 | C |

TABLE 1-continued
| Ex. | R³ | T | [M + H]⁺ | Route |
|---|---|---|---|---|
| 1.145 | 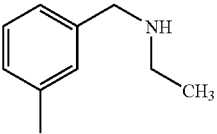 | 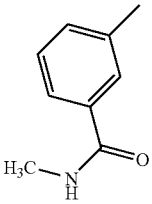 | 385 | C |
| 1.146 | 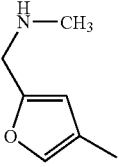 | 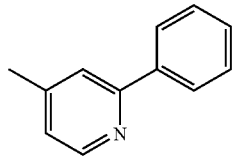 | 395 | C |
| 1.147 | 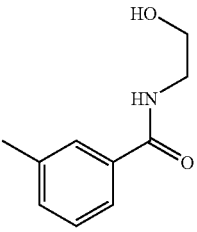 | 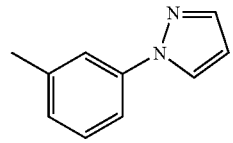 | 424 | D |
| 1.148 | 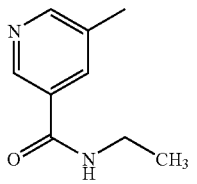 | 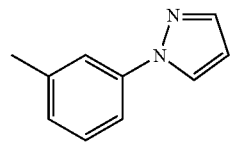 | 409 | D |
| 1.149 | 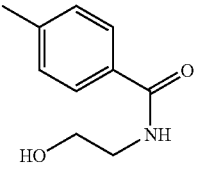 | 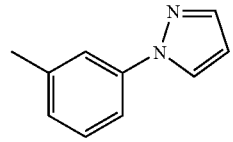 | 424 | E |
| 1.150 | 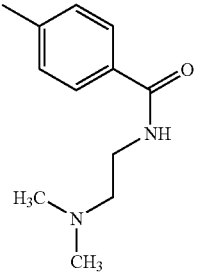 | 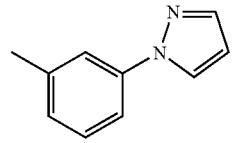 | 451 | E |
| 1.151 | 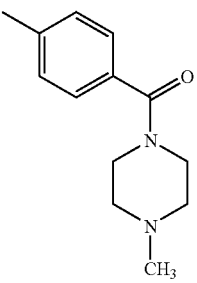 | 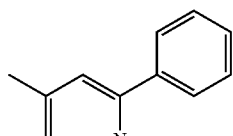 | 474 | E |

TABLE 1-continued

| Ex. | R³ | T | [M + H]⁺ | Route |
|---|---|---|---|---|
| 1.152 | | | 489 | E |
| 1.153 | | | 535 | E |
| 1.154 | | | 520 | E |
| 1.155 | | | 480 | E |
| 1.156 | | | 381 | F |
| 1.157 | | | 392 | F |

TABLE 1-continued
| Ex. | R³ | T | [M + H]⁺ | Route |
|---|---|---|---|---|
| 1.158 | 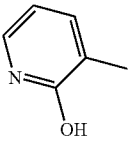 | 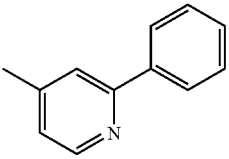 | 365 | H |
| 1.159 | 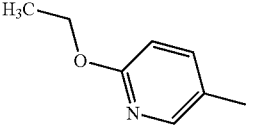 | 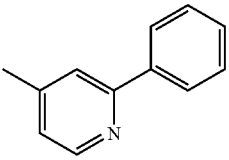 | 393 | I |
| 1.160 | 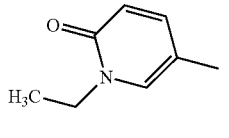 | 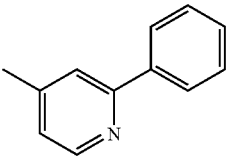 | 393 | I |
| 1.161 | 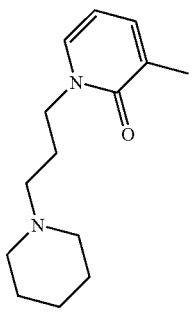 | 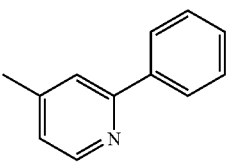 | 490 | I |
| 1.162 | 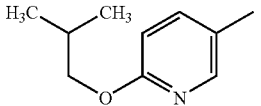 | 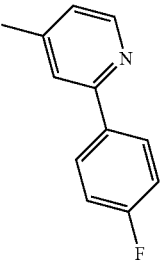 | 439 | I |
| 1.163 | 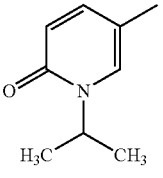 | 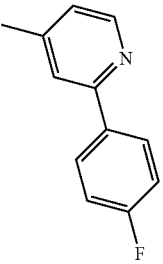 | 425 | I |

TABLE 1-continued
| Ex. | R³ | T | [M + H]⁺ | Route |
|---|---|---|---|---|
| 1.164 | 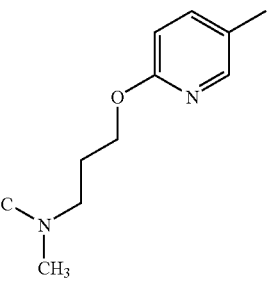 | 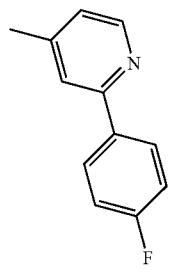 | 468 | I |
| 1.165 | 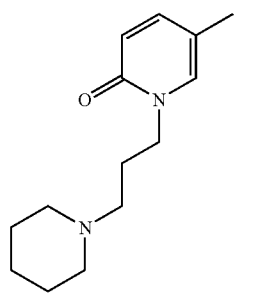 | 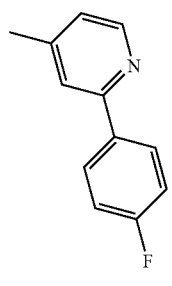 | 508 | I |
| 1.166 | 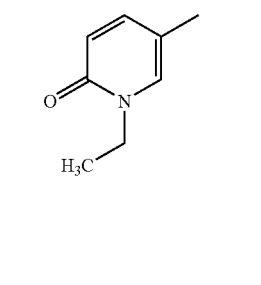 | 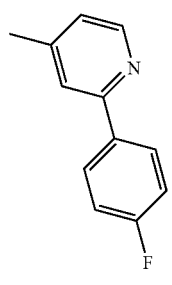 | 411 | I |
| 1.167 | 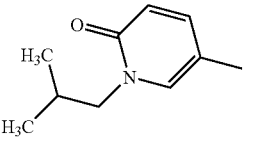 | 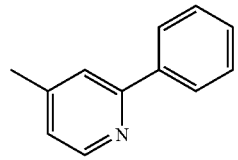 | 421 | I |
| 1.168 | 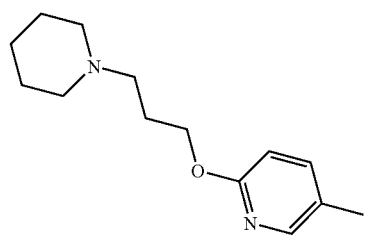 | 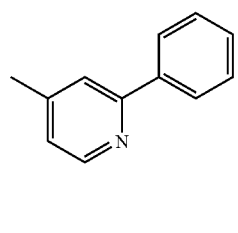 | 490 | I |
| 1.169 | 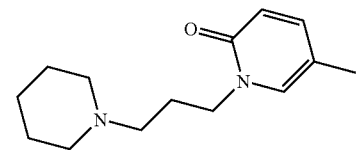 | 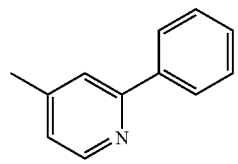 | 490 | I |
| 1.170 | 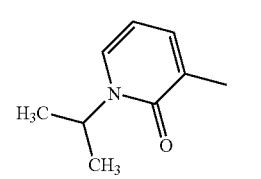 | 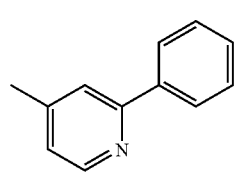 | 407 | I |

TABLE 1-continued
| Ex. | R³ | T | [M + H]⁺ | Route |
|---|---|---|---|---|
| 1.171 | 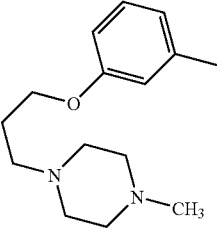 | 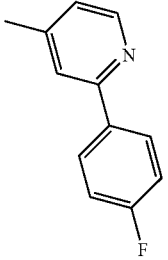 | 522 | I |
| 1.172 | 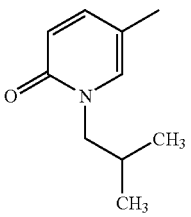 | 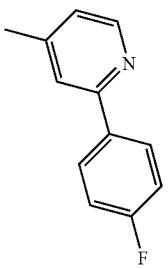 | 439 | I |
| 1.173 | 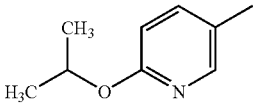 | 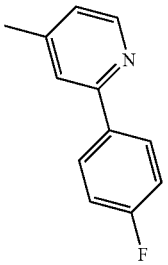 | 425 | I |
| 1.174 | 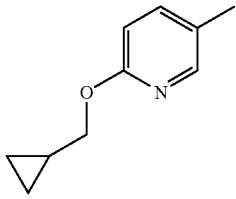 | 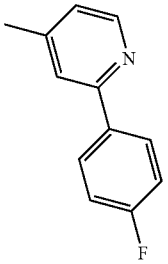 | 437 | I |
| 1.175 | 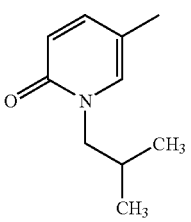 | 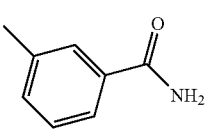 | 387 | I |
| 1.176 | 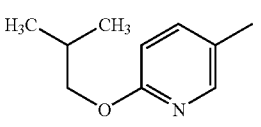 | 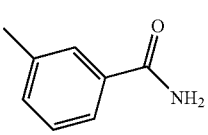 | 387 | I |

TABLE 1-continued

| Ex. | R³ | T | [M + H]⁺ | Route |
|---|---|---|---|---|
| 1.177 | | | 507 | J |
| 1.178 | | | 467 | J |
| 1.179 | | | 452 | K |
| 1.180 | | | 435 | K |
| 1.181 | | | 413 | K |

TABLE 1-continued

| Ex. | R³ | T | [M + H]⁺ | Route |
|---|---|---|---|---|
| 1.182 | phenyl | 4-methyl-6-phenyl-pyridin-2-yl(methyl)amine | 377 | K |
| 1.183 | 3-(N-methylcarbamoyl)phenyl | 4-methyl-6-phenyl-pyridin-2-yl(methyl)amine | 434 | K |
| 1.184 | 3-(N-methylcarbamoyl)phenyl | 4-methyl-6-phenyl-N-isopropylpyridin-2-amine | 462 | K |
| 1.185 | phenyl | 4-methyl-6-phenyl-N-isopropylpyridin-2-amine | 405 | K |
| 1.186 | 3-formylphenyl | 4-methyl-6-phenyl-N-isopropylpyridin-2-amine | 433 | K |

TABLE 1-continued

| Ex. | R³ | T | [M + H]⁺ | Route |
|---|---|---|---|---|
| 1.187 | 3-methyl-N-methylbenzamide | 4-methyl-6-phenyl-2-(cyclopropylamino)pyridine | 460 | K |
| 1.188 | toluene (methylphenyl) | 4-methyl-6-phenyl-2-(cyclopropylamino)pyridine | 403 | K |
| 1.189 | N-ethyl-3-methylbenzylamine | 4-methyl-6-phenyl-2-(isopropylamino)pyridine | 462 | L |
| 1.190 | 4-methyl-1,2,3,6-tetrahydropyridine | 4-methyl-2-phenylpyridine | 353 | M |
| 1.191 | 4-methyl-1,2,3,6-tetrahydropyridine | 4-methyl-2-(cyclopenten-1-yl)pyridine | 343 | M |
| 1.192 | 4-methyl-1,2,3,6-tetrahydropyridine | 3-methylbenzamide | 319 | M |
| 1.193 | 1-isopropyl-4-methyl-1,2,3,6-tetrahydropyridine | 4-methyl-2-phenylpyridine | 395 | N |

TABLE 1-continued
| Ex. | R³ | T | [M + H]⁺ | Route |
|---|---|---|---|---|
| 1.194 | 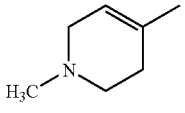 | 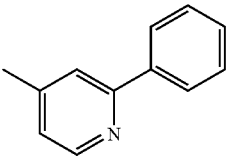 | 367 | N |
| 1.195 | 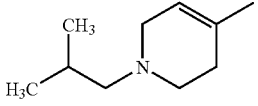 | 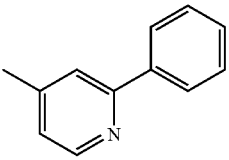 | 409 | N |
| 1.196 | 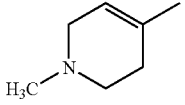 | 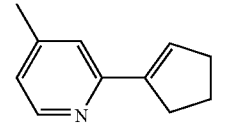 | 357 | N |
| 1.197 | 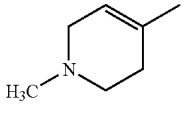 | 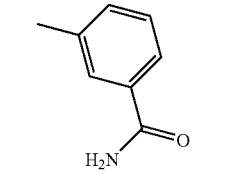 | 333 | N |
| 1.198 | 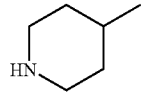 | 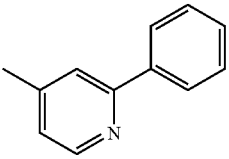 | 391 | O |
| 1.199 | 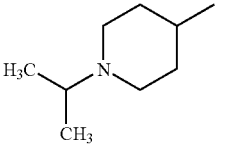 | 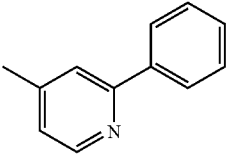 | 397 | P |
| 1.200 | 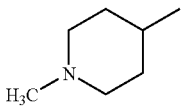 | 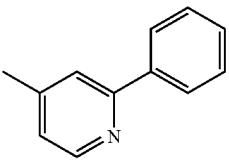 | 369 | P |
| 1.201 | 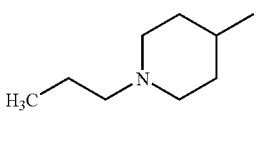 | 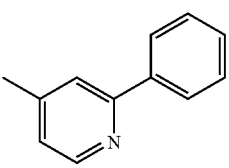 | 397 | P |
| 1.202 | 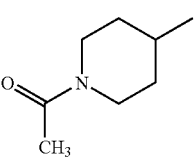 | 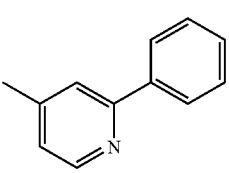 | 397 | Q |

TABLE 1-continued

| Ex. | R³ | T | [M + H]⁺ | Route |
|---|---|---|---|---|
| 1.203 | (CH₃)₂N-CH₂-C(O)-N(4-methylpiperidine) | 4-methyl-2-phenylpyridine | 440 | Q |
| 1.204 | CH₃NH-CH(CH₃)-C(O)-N(4-methylpiperidine) | 4-methyl-2-phenylpyridine | 440 | Q |
| 1.205 | pyrrolidine-2-C(O)-N(4-methylpiperidine) | 4-methyl-2-phenylpyridine | 452 | Q |
| 1.206 | 2-methylimidazol-1-yl-CH₂-C(O)-N(4-methylpiperidine) | 4-methyl-2-phenylpyridine | 477 | Q |
| 1.207 | imidazol-1-yl-CH₂-C(O)-N(4-methylpiperidine) | 4-methyl-2-phenylpyridine | 463 | Q |
| 1.208 | Cl | 4-methyl-2-phenylpyridine | 306 | Int D |
| 1.209 | Cl | 4-methyl-2-(2-fluorophenyl)pyridine | 324 | Int H |
| 1.210 | Cl | 4-methyl-2-(3-methylpyrazol-1-yl)pyridine | 310 | Int C |

TABLE 1-continued
| Ex. | R³ | T | [M + H]⁺ | Route |
|---|---|---|---|---|
| 1.211 | Cl | 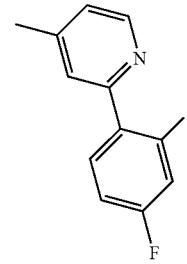 | 342 | Int O |
| 1.212 | Cl | 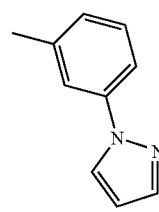 | 295 | Int A |
| 1.213 | Cl | 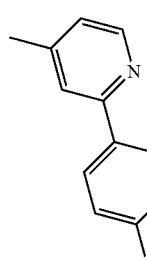 | 324 | Int E |
| 1.214 | Cl | 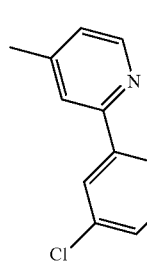 | 341 | Int S |
| 1.215 | Cl | 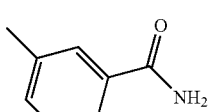 | 272 | Int B |
Yet further example compounds of the present invention include compounds of formula Y
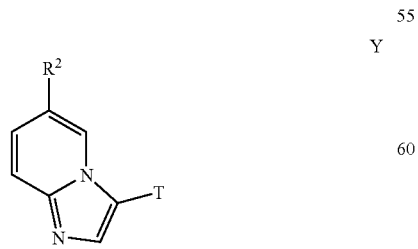
Y
where R² and T are as shown in Table 2 below. The method of preparation being described hereinafter.

TABLE 2
| Ex. | R² | T | [M + H]⁺ |
|---|---|---|---|
| 2.1 | 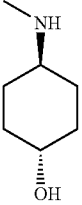 | 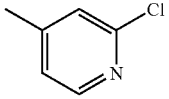 | 343(345) |
| 2.2 | 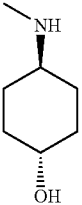 | 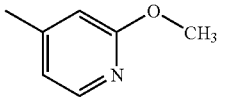 | 339 |
| 2.3 | 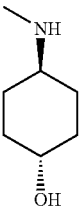 | 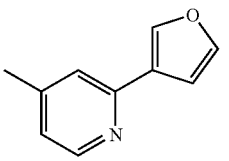 | 375 |
| 2.4 | 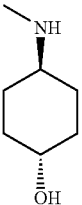 |  | 385 |
| 2.5 | 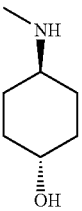 |  | 375 |
| 2.6 | 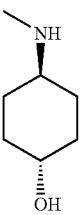 | 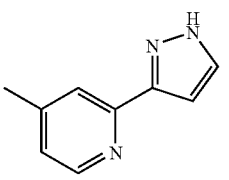 | 375 |
| 2.7 | 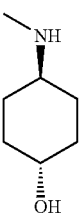 | 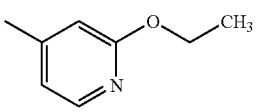 | 353 |

TABLE 2-continued

| Ex. | R² | T | [M + H]⁺ |
|---|---|---|---|
| 2.8 | 2-hydroxycyclohexyl-NH-CH₃ | 4-methyl-2-methoxypyridine | 339 |
| 2.9 | 4-methyl-2-methoxypyridine | 4-methyl-2-methoxypyridine | 333 |
| 2.10 | N-methyl-3-methylbenzamide | 4-methyl-2-(furan-3-yl)pyridine | 395 |
| 2.11 | 4-methyl-2-methoxypyridine (N-up) | 4-methyl-2-(furan-3-yl)pyridine | 369 |
| 2.12 | 3-methylfuran | 4-methyl-2-(furan-3-yl)pyridine | 328 |
| 2.13 | 3-methylpyridine | 4-methyl-2-(furan-3-yl)pyridine | 339 |
| 2.14 | 4-methylpyridine | 4-methyl-2-(furan-3-yl)pyridine | 339 |
| 2.15 | 3-methyl-2-methoxybenzene | 4-methyl-2-(furan-3-yl)pyridine | 368 |
| 2.16 | 4-methyl-2-methoxybenzene | 4-methyl-2-(furan-3-yl)pyridine | 368 |
| 2.17 | N-(3-methylphenyl)acetamide | 4-methyl-2-(furan-3-yl)pyridine | 395 |

TABLE 2-continued
| Ex. | R² | T | [M + H]⁺ |
|---|---|---|---|
| 2.18 | 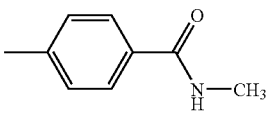 | 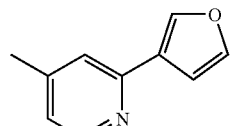 | 395 |
| 2.19 | 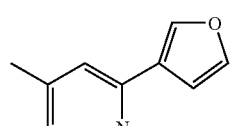 | 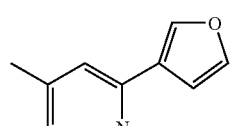 | 342 |
| 2.20 | 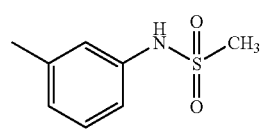 | 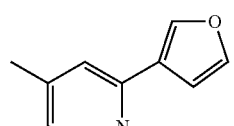 | 431 |
| 2.21 | 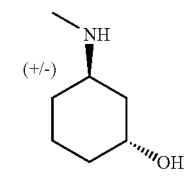 | 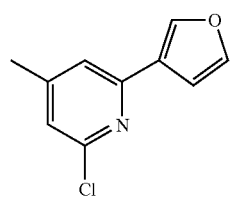 | 409 |
| 2.22 | 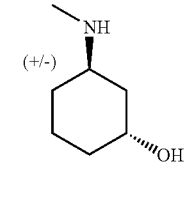 |  | 446 |
| 2.23 | 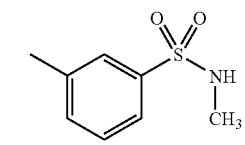 | 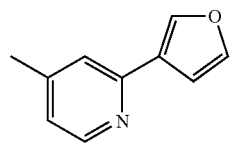 | 431 |
| 2.24 | 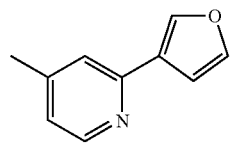 | 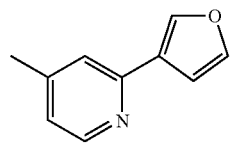 | 327 |
| 2.25 | 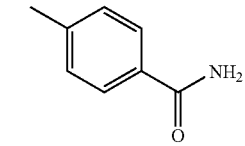 | 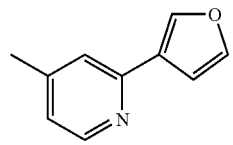 | 380 |
| 2.26 | 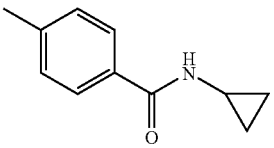 | 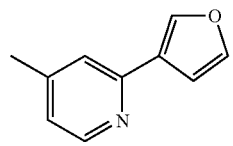 | 421 |

TABLE 2-continued
| Ex. | R² | T | [M + H]⁺ |
|---|---|---|---|
| 2.27 | 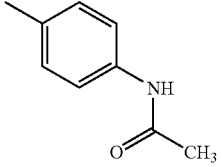 | 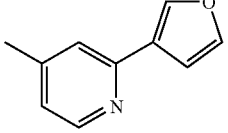 | 394 |
| 2.28 | 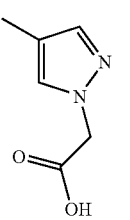 | 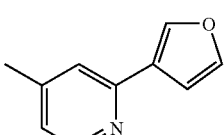 | 385 |
| 2.29 | 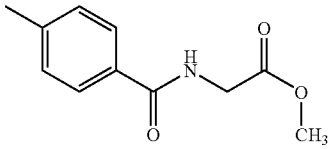 | 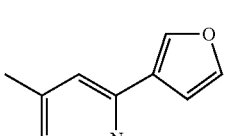 | 453 |
| 2.30 | 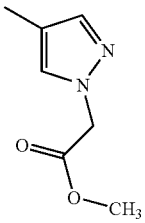 | 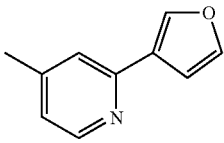 | 399 |
| 2.31 | 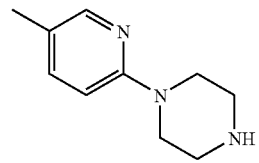 | 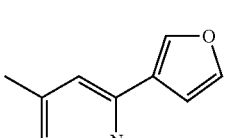 | 423 |
| 2.32 | 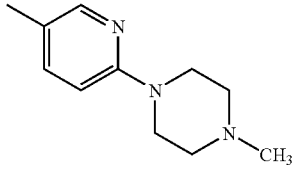 | 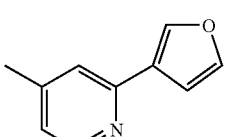 | 437 |
| 2.33 | 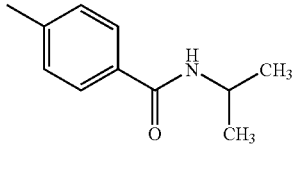 | 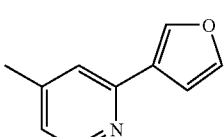 | 423 |
| 2.34 | 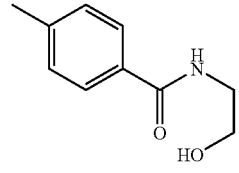 | 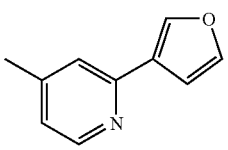 | 425 |

TABLE 2-continued
| Ex. | R² | T | [M + H]⁺ |
|---|---|---|---|
| 2.35 | 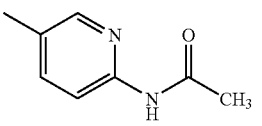 | 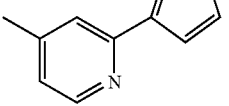 | 396 |
| 2.36 | 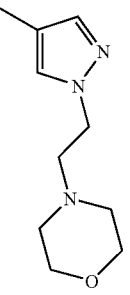 | 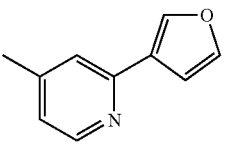 | 441 |
| 2.37 | 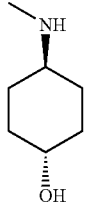 | 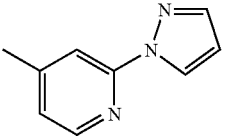 | 375 |
| 2.38 | 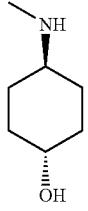 | 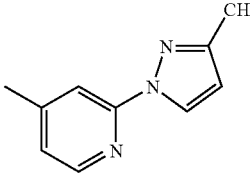 | 389 |
| 2.39 | 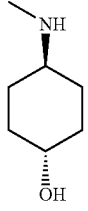 | 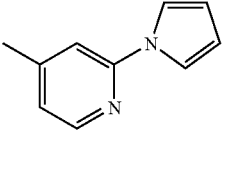 | 374 |
| 2.40 | 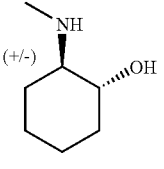 |  | 375 |
| 2.41 | CF₃ | 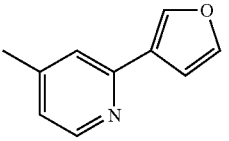 | 330 |
| 2.42 | 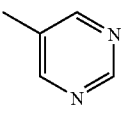 | 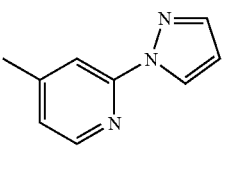 | 340 |

TABLE 2-continued
| Ex. | R² | T | [M + H]⁺ |
|---|---|---|---|
| 2.43 | 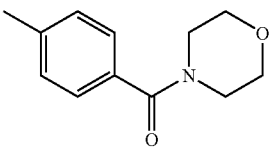 | 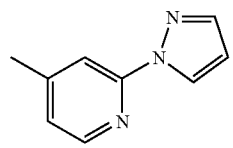 | 451 |
| 2.44 | 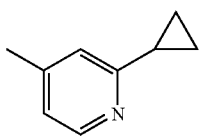 | 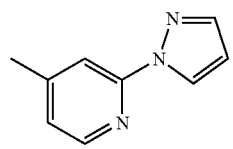 | 379 |
| 2.45 | 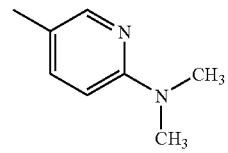 | 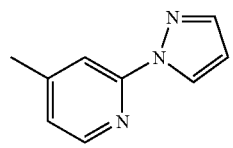 | 382 |
| 2.46 | 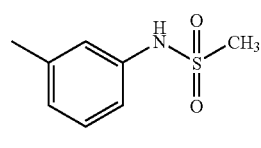 | 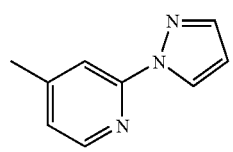 | 431 |
| 2.47 | 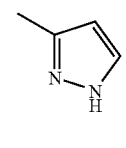 | 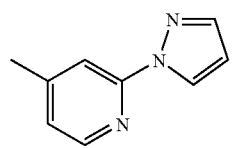 | 328 |
| 2.48 | 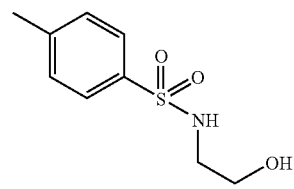 | 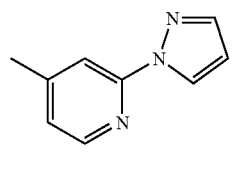 | 461 |
| 2.49 | 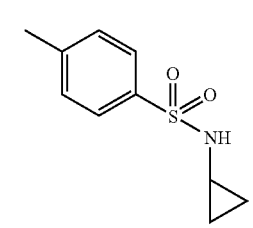 | 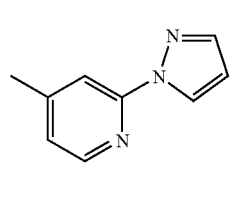 | 457 |
| 2.50 | 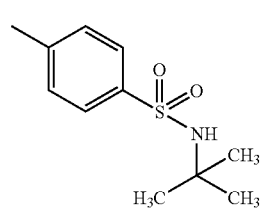 | 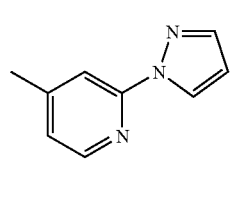 | 473 |
| 2.51 | 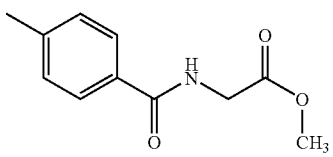 | 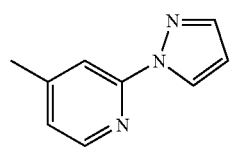 | 452 |

TABLE 2-continued
| Ex. | R² | T | [M + H]⁺ |
|---|---|---|---|
| 2.52 | 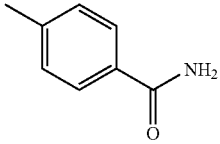 | 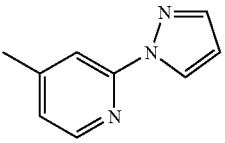 | 381 |
| 2.53 | 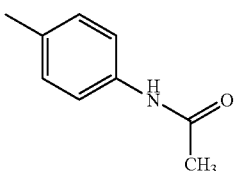 | 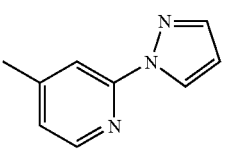 | 395 |
| 2.54 | 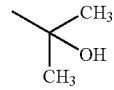 | 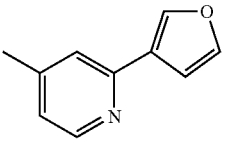 | 320 |
| 2.55 | 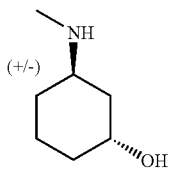 | 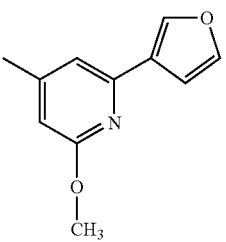 | 405 |
| 2.56 | 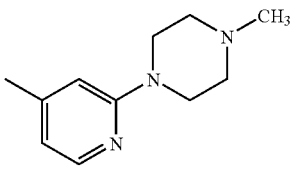 | 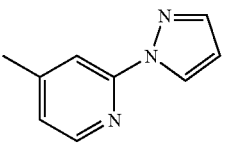 | 437 |
| 2.57 | 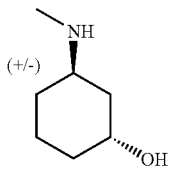 |  | 393 |
| 2.58 | 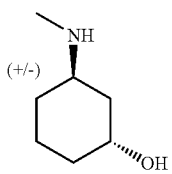 | 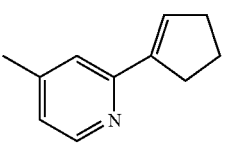 | 375 |
| 2.59 | 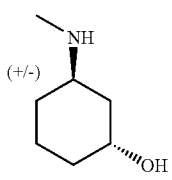 | 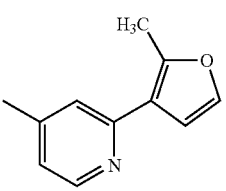 | 389 |

TABLE 2-continued

| Ex. | R² | T | [M + H]⁺ |
|---|---|---|---|
| 2.60 | (+/-) methylamino-cyclohexanol | 4-methylpyridin-2-yl-(5-methylfuran-3-yl) | 389 |
| 2.61 | (+/-) methylamino-cyclohexanol | 4-methylpyridin-2-yl-(3-trifluoromethylpyrazol-1-yl) | 443 |
| 2.62 | (+/-) methylamino-cyclohexanol | 4-methylpyridin-2-yl-(isoxazol-4-yl) | 376 |
| 2.63 | (+/-) methylamino-cyclohexanol | 4-methylpyridin-2-yl-(1H-pyrazol-5-yl) | 375 |
| 2.64 | (+/-) methylamino-cyclohexanol | 4-methylpyridin-2-yl-(1H-pyrazol-4-yl) | 375 |
| 2.65 | (+/-) methylamino-cyclohexanol | 4-methylpyridin-2-yl-(1-methylpyrazol-4-yl) | 389 |
| 2.66 | (+/-) methylamino-cyclohexanol | 4-methylpyridin-2-yl-(1-ethylpyrazol-4-yl) | 403 |
| 2.67 | (+/-) methylamino-cyclohexanol | 4-methylpyridin-2-yl-(1-methylpyrrol-2-yl) | 388 |

TABLE 2-continued

| Ex. | R² | T | [M + H]⁺ |
|---|---|---|---|
| 2.68 | (+/-) methylamino-cyclohexanol | 4-methyl-2-(2,5-dimethylthiophen-3-yl)pyridine | 419 |
| 2.69 | (+/-) methylamino-cyclohexanol | 4-methyl-2-(1H-pyrrol-2-yl)pyridine | 374 |
| 2.70 | (+/-) methylamino-cyclohexanol | 4-methyl-2-(1,3-dimethyl-1H-pyrazol-4-yl)pyridine | 403 |
| 2.71 | (+/-) methylamino-cyclohexanol | 4-methyl-2-(3-chloro-1H-pyrazol-1-yl)pyridine | 409(411) |
| 2.72 | (+/-) methylamino-cyclohexanol | 4-methyl-2-(2H-1,2,3-triazol-2-yl)pyridine | 375 |
| 2.73 | (+/-) methylamino-cyclohexanol | 4-methyl-2-(furan-3-yl)pyridine | 375 |
| 2.74 | (+/-) methylamino-cyclohexanol | 4-methyl-6-chloro-2-(furan-3-yl)pyridine | 409(411) |
| 2.75 | (+/-) methylamino-cyclohexanol | 4-methyl-6-fluoro-2-(furan-3-yl)pyridine | 393 |

TABLE 2-continued

| Ex. | R² | T | [M + H]⁺ |
|---|---|---|---|
| 2.76 | NH–cyclohexyl-OH (S,S) | 4-methylpyridin-2-yl-furan-3-yl | 375 |
| 2.77 | NH–cyclohexyl-OH (S,S) | 4-methylpyridin-2-yl-pyrazol-1-yl | 375 |
| 2.78 | NH–cyclohexyl-OH (S,S) | 4-methylpyridin-2-yl-(3-methyl-pyrazol-1-yl) | 389 |
| 2.79 | NH–cyclohexyl-OH (S,S) | 4-methylpyridin-2-yl-(3-cyclopropyl-pyrazol-1-yl) | 415 |
| 2.80 | NH–cyclohexyl-OH (S,S) | 4-methylpyridin-2-yl-(3,5-dimethyl-pyrazol-1-yl) | 403 |
| 2.81 | NH–cyclohexyl-OH (+/−) | 3-methylphenyl-pyrazol-1-yl | 373 |
| 2.82 | NH–cyclohexyl-OH (R,R) | 4-methylpyridin-2-yl-furan-3-yl | 375 |
| 2.83 | NH–cyclohexyl-OH (R,R) | 4-methylpyridin-2-yl-pyrazol-1-yl | 375 |

TABLE 2-continued

| Ex. | R² | T | [M + H]⁺ |
|---|---|---|---|
| 2.84 | NH, R,R cyclohexyl-OH | 4-methyl-2-(3-methyl-pyrazol-1-yl)pyridine | 389 |
| 2.85 | NH, R,R cyclohexyl-OH | 4-methyl-2-(3,5-dimethyl-pyrazol-1-yl)pyridine | 403 |
| 2.86 | NH, R,R cyclohexyl-OH | 4-methyl-2-(3-cyclopropyl-pyrazol-1-yl)pyridine | 415 |
| 2.87 | NH, (+/−) cyclohexyl-CH₃, OH | 4-methyl-2-(furan-3-yl)pyridine | 389 |
| 2.88 | NH, (+/−) cyclohexyl-CH₃, OH | 4-methyl-2-(pyrazol-1-yl)pyridine | 389 |
| 2.89 | NH, (+/−) cyclohexyl-CH₃, OH | 4-methyl-2-(3-trifluoromethyl-pyrazol-1-yl)pyridine | 457 |
| 2.90 | NH, (+/−) cyclohexyl-CH₃, OH | 4-methyl-2-phenylpyridine | 399 |
| 2.91 | NH, (+/−) cyclohexyl-CH₃, OH | 4-methyl-2-(3-cyclopropyl-pyrazol-1-yl)pyridine | 429 |

TABLE 2-continued

| Ex. | R² | T | [M + H]⁺ |
|---|---|---|---|
| 2.92 | (+/-) cyclohexane with NHMe and CH₃/OH | 4-methylpyridin-2-yl-(3,5-dimethylpyrazol-1-yl) | 417 |
| 2.93 | (S,S) cyclohexane with NHMe and CH₃/OH | 4-methylpyridin-2-yl-(pyrazol-1-yl) | 389 |
| 2.94 | (S,S) cyclohexane with NHMe and CH₃/OH | 4-methylpyridin-2-yl-(furan-3-yl) | 389 |
| 2.95 | (S,S) cyclohexane with NHMe and CH₃/OH | 4-methylpyridin-2-yl-(3-methylpyrazol-1-yl) | 403 |
| 2.96 | (R,R) cyclohexane with NHMe and CH₃/OH | 4-methylpyridin-2-yl-(furan-3-yl) | 389 |
| 2.97 | (R,R) cyclohexane with NHMe and CH₃/OH | 4-methylpyridin-2-yl-(pyrazol-1-yl) | 389 |
| 2.98 | (R,R) cyclohexane with NHMe and CH₃/OH | 4-methylpyridin-2-yl-(3-methylpyrazol-1-yl) | 403 |

General Conditions:

Mass spectra are run on an open access Agilent 1100 HPLC/Mass Spectrometer system using atmospheric pressure chemical ionisation or an open access Waters 600/ZQ HPLC/Mass Spectrometer system using electrospray ionization. [M+H]⁺ refers to mono-isotopic molecular weights.

Unless otherwise stated, all starting materials are obtained from commercial suppliers and used without further purification.

Abbreviations:

BOP is Benzotriazole-1-yl-oxy-tris-(dimethylamino)-phosphonium hexafluorophosphate, DCM is dichloromethane, DIBAL-H is diisobutylaluminum hydride, DIPEA is N,N-diisopropylethylamine, DME is dimethoxyethane, DMF is dimethylformamide, Et₃N is triethylamine, EtOAc is ethyl acetate, EtOH is ethanol, H₂O is water, HATU is O-(7-azabenzotriazol-1-yl)-N,N,N',N'-tetramethyluronium hexafluorophosphate, HPLC is high performance liquid chromatography, MgSO₄ is magnesium sulfate, MeOH is methanol, NaOH is sodium hydroxide, Na₂CO₃ is sodium carbonate, NBS is N-bromosuccinimide, NH₃(g) is ammonia (gas), NMP is N-methylpyrrolidinone, Pd₂(dba)₃ is Bis (dibenzylideneacetone) palladium(0), Pd is palladium, K₂CO₃ is potassium carbonate, and RT is room temperature.

Preparation of Example Compounds

Route A

Example 1.1

3-(3-Pyrazol-1-yl-phenyl)-7-pyridin-3-yl-imidazo[1,2-a]pyridine

7-Chloro-3-(3-pyrazol-1-yl-phenyl)-imidazo[1,2-a]pyridine (Intermediate AA) (1 eq, 0.214 mmol, 70 mg) and 3-pyridine boronic acid (1 eq, 0.214 mmol, 26.1 mg) are dissolved in DME (3 ml), EtOH (1 ml) and water (1.5 ml) and Na₂CO₃ (2 eq, 0.427 mmol, 53.0 mg) is added. Pd(PPh₃)₄ (0.06 eq, 0.01 mmol, 15 mg) is added and the reaction mixture is heated using microwave radiation at 120° C. for 15 min. At the completion of this time the solvent is removed in vacuo and the reaction mixture is purified by flash column chromatography eluting with 8:2 DCM/MeOH to yield 3-(3-pyrazol-1-yl-phenyl)-7-pyridin-3-yl-imidazo[1,2-a]pyridine as a light brown solid; [M+H]⁺=338
These examples namely,
3-[7-(3-Hydroxy-phenyl)-imidazo[1,2-a]pyridin-3-yl]-benzamide (Ex. 1.2),
7-(6-Morpholin-4-yl-pyridin-3-yl)-3-(3-pyrazol-1-yl-phenyl)-imidazo[1,2-a]pyridine (Ex. 1.3),
3-[7-(6-Morpholin-4-yl-pyridin-3-yl)-imidazo[1,2-a]pyridin-3-yl]-benzamide (Ex. 1.4),
7-(6-Morpholin-4-yl-pyridin-3-yl)-3-(2-phenyl-pyridin-4-yl)-imidazo[1,2-a]pyridine (Ex. 1.5)
7-[6-(4-Methyl-piperazin-1-yl)-pyridin-3-yl]-3-(3-pyrazol-1-yl-phenyl)-imidazo[1,2-a]pyridine (Ex. 1.6),
7-[6-(4-Methyl-piperazin-1-yl)-pyridin-3-yl]-3-(2-phenyl-pyridin-4-yl)-imidazo[1,2-a]pyridine (Ex. 1.7),
5-[3-(3-Pyrazol-1-yl-phenyl)-imidazo[1,2-a]pyridin-7-yl]-nicotinonitrile (Ex. 1.8
3-[3-(3-Pyrazol-1-yl-phenyl)-imidazo[1,2-a]pyridin-7-yl]-benzaldehyde (Ex. 1.9)
3-[3-(3-Pyrazol-1-yl-phenyl)-imidazo[1,2-a]pyridin-7-yl]-benzoic acid ethyl ester (Ex. 1.10),
4-[3-(3-Pyrazol-1-yl-phenyl)-imidazo[1,2-a]pyridin-7-yl]-benzoic acid ethyl ester (Ex. 1.11),
4-[3-(2-Phenyl-pyridin-4-yl)-imidazo[1,2-a]pyridin-7-yl]-benzoic acid ethyl ester (Ex. 1.12),
3-{3-[2-(3-Fluoro-phenyl)-pyridin-4-yl]-imidazo[1,2-a]pyridin-7-yl}-N-methyl-benzamide (Ex. 1.13),
N-Methyl-3-[3-(2-phenyl-pyridin-4-yl)-imidazo[1,2-a]pyridin-7-yl]-benzamide (Ex. 1.14),
N-Methyl-3-[3-(2-m-tolyl-pyridin-4-yl)-imidazo[1,2-a]pyridin-7-yl]-benzamide (Ex. 1.15)
3-{3-[2-(3-Fluoro-phenyl)-pyridin-4-yl]-imidazo[1,2-a]pyridin-7-yl}-phenylamine (Ex. 1.16),
3-[2-(3-Fluoro-phenyl)-pyridin-4-yl]-7-pyridin-3-yl-imidazo[1,2-a]pyridine (Ex. 1.17),
3-(2-Phenyl-pyridin-4-yl)-7-pyridin-3-yl-imidazo[1,2-a]pyridine (Ex. 1.18),
4-[3-(2-Phenyl-pyridin-4-yl)-imidazo[1,2-a]pyridin-7-yl]-benzaldehyde (Ex. 1.19),
3-[2-(3-Fluoro-phenyl)-pyridin-4-yl]-7-(6-methyl-pyridin-3-yl)-imidazo[1,2-a]pyridine (Ex. 1.20),
7-(6-Methyl-pyridin-3-yl)-3-(2-phenyl-pyridin-4-yl)-imidazo[1,2-a]pyridine (Ex. 1.21),
3-(2-Cyclopent-1-enyl-pyridin-4-yl)-7-(1-methyl-1H-pyrazol-4-yl)-imidazo[1,2-a]pyridine (Ex. 1.22),
N-Methyl-3-{3-[2-(3-methyl-pyrazol-1-yl)-pyridin-4-yl]-imidazo[1,2-a]pyridin-7-yl}-benzamide (Ex.1.23),
3-[2-(4-Fluoro-phenyl)-pyridin-4-yl]-7-pyridin-3-yl-imidazo[1,2-a]pyridine (Ex. 1.24),
3-[2-(4-Fluoro-phenyl)-pyridin-4-yl]-7-pyridin-4-yl-imidazo[1,2-a]pyridine (Ex. 1.25),
3-[2-(4-Fluoro-phenyl)-pyridin-4-yl]-7-(1-methyl-1H-pyrazol-4-yl)-imidazo[1,2-a]pyridine (Ex. 1.26),
3-[2-(2,4-Difluoro-phenyl)-pyridin-4-yl]-7-(1-methyl-1H-pyrazol-4-yl)-imididazol[1,2-a]pyridine (Ex. 1.27),
3-[2-(2-Fluoro-phenyl)-pyridin-4-yl]-7-(1-methyl-1H-pyrazol-4-yl)-imidazo[1,2-a]pyridine (Ex. 1.28),
7-(3-Fluoro-phenyl)-3-[2-(2-fluoro-phenyl)-pyridin-4-yl]-imidazo[1,2-a]pyridine (Ex. 1.29),
3-[2-(2-Fluoro-phenyl)-pyridin-4-yl]-7-pyridin-3-yl-imidazo[1,2-a]pyridine (Ex. 1.30),
3-{3-[2-(2-Fluoro-phenyl)-pyridin-4-yl]-imidazo[1,2-a]pyridin-7-yl}-N-methyl-benzamide (Ex. 1.31),
7-(1-Methyl-1H-pyrazol-4-yl)-3-(2-phenyl-pyridin-4-yl)-imidazo[1,2-a]pyridine (Ex. 1.32),
5-{3-[2-(4-Fluoro-phenyl)-pyridin-4-yl]-imidazo[1,2-a]pyridin-7-yl}-1H-pyridin-2-one (Ex. 1.33),
3-(2-Phenyl-pyridin-4-yl)-7-(1H-pyrazol-4-yl)-imidazo[1,2-a]pyridine (Ex. 1.34)
Dimethyl-{3-[3-(2-phenyl-pyridin-4-yl)-imidazo[1,2-a]pyridin-7-yl]-phenyl}-amine (Ex. 1.35),
7-(3-Fluoro-phenyl)-3-(2-phenyl-pyridin-4-yl)-imidazo[1,2-a]pyridine (Ex. 1.36),
5-[3-(2-Phenyl-pyridin-4-yl)-imidazo[1,2-a]pyridin-7-yl]-1H-pyridin-2-one (Ex. 1.37),
7-Phenyl-3-(2-phenyl-pyridin-4-yl)-imidazo[1,2-a]pyridine (Ex. 1.38),
7-(6-Fluoro-pyridin-3-yl)-3-(3-pyrazol-1-yl-phenyl)-imidazo[1,2-a]pyridine (Ex. 1.39),
3-{3-[2-(4-Fluoro-phenyl)-pyridin-4-yl]-imidazo[1,2-a]pyridin-7-yl}-N-methyl-benzamide (Ex. 1.40),
3-[3-(2-Cyclopent-1-enyl-pyridin-4-yl)-imidazo[1,2-a]pyridin-7-yl]-N-methyl-benzamide (Ex. 1.41),
3-(2-Cyclohex-1-enyl-pyridin-4-yl)-7-pyridin-3-yl-imidazo[1,2-a]pyridine (Ex. 1.42),
3-[3-(2-Phenyl-pyridin-4-yl)-imidazo[1,2-a]pyridin-7-yl]-phenylamine (Ex. 1.43),
Dimethyl-(5-{3-[2-(3-methyl-pyrazol-1-yl)-pyridin-4-yl]-imidazo[1,2-a]pyridin-7-yl}-pyridin-2-yl)-amine (Ex. 1.44),
N-Methyl-3-[3-(2-pyrrolidin-1-yl-pyridin-4-yl)-imidazo[1,2-a]pyridin-7-yl]-benzamide (Ex. 1.45),
3-[3-(2-Pyrrolidin-1-yl-pyridin-4-yl)-imidazo[1,2-a]pyridin-7-yl]-benzaldehyde (Ex. 1.46),
3-{3-[2-(3-Methyl-pyrazol-1-yl)-pyridin-4-yl]-imidazo[1,2-a]pyridin-7-yl}-benzaldehyde (Ex. 1.47),
3-[2-(4-Fluoro-phenyl)-pyridin-4-yl]-7-(6-methyl-pyridin-3-yl)-imidazo[1,2-a]pyridine (Ex. 1.48),
7-(3,5-Difluoro-phenyl)-3-(2-phenyl-pyridin-4-yl)-imidazo[1,2-a]pyridine (Ex. 1.49),
7-(6-Methyl-pyridin-3-yl)-3-(3-pyrazol-1-yl-phenyl)-imidazo[1,2-a]pyridine (Ex. 1.50 ),
3-(2-Cyclopent-1-enyl-pyridin-4-yl)-7-(6-methoxy-pyridin-3-yl)-imidazo[1,2-a]pyridine (Ex. 1.51),
7-[6-(4-Methyl-piperazin-1-yl)-pyridin-3-yl]-3-(2-phenyl-pyridin-4-yl)-imidazo[1,2-a]pyridine (Ex. 1.52),
3-[2-(1-Methyl-1H-pyrazol-4-yl)-pyridin-4-yl]-7-(6-morpholin-4-yl-pyridin-3-yl)-imidazo[1,2-a]pyridine (Ex. 1.53), 3-[3-(2-Cyclopent-1-enyl-pyridin-4-yl)-imidazo[1,2-a]pyridin-7-yl]-benzaldehyde (Ex. 1.54),
3-(2-Phenyl-pyridin-4-yl)-7-(3-piperidin-1-yl-phenyl)-imidazo[1,2-a]pyridine (Ex. 1.55),
3-[7-(6-Morpholin-4-yl-pyridin-3-yl)-imidazo[1,2-a]pyridin-3-yl]-benzamide (Ex. 1.56),
3-Fluoro-5-[3-(2-phenyl-pyridin-4-yl)-imidazo[1,2-a]pyridin-7-yl]-phenol (Ex. 1.57),
3-{3-[2-(2,4-Difluoro-phenyl)-pyridin-4-yl]-imidazo[1,2-a]pyridin-7-yl}-N-methyl-benzamide (Ex. 1.58),
3-[2-(2,4-Difluoro-phenyl)-pyridin-4-yl]-7-pyridin-3-yl-imidazo[1,2-a]pyridine (Ex. 1.59),
3-[2-(2-Methyl-pyrrolidin-1-yl)-pyridin-4-yl]-7-pyridin-3-yl-imidazo[1,2-a]pyridine (Ex. 1.60),
N-Methyl-3-{3-[2-(2-methyl-pyrrolidin-1-yl)-pyridin-4-yl]-imidazo[1,2-a]pyridin-7-yl}-benzamide (Ex. 1.61),
3-[2-(2-Fluoro-phenyl)-pyridin-4-yl]-7-(6-methyl-pyridin-3-yl)-imidazo[1,2-a]pyridine (Ex. 1.62),
(5-{3-[2-(2-Fluoro-phenyl)-pyridin-4-yl]-imidazo[1,2-a]pyridin-7-yl}-pyridin-2-yl)-dimethyl-amine (Ex. 1.63),
(3-{3-[2-(4-Fluoro-phenyl)-pyridin-4-yl]-imidazo[1,2-a]pyridin-7-yl}-benzyl)-dimethyl-amine (Ex. 1.64),
3-[2-(4-Fluoro-phenyl)-pyridin-4-yl]-7-(6-methoxy-pyridin-3-yl)-imidazo[1,2-a]pyridine (Ex. 1.65),
(3-{3-[2-(2-Fluoro-phenyl)-pyridin-4-yl]-imidazo[1,2-a]pyridin-7-yl}-benzyl)-dimethyl-amine (Ex. 1.66),
Methyl-{3-[3-(2-phenyl-pyridin-4-yl)-imidazo[1,2-a]pyridin-7-yl]-benzyl}-amine (Ex. 1.67),
{3-[3-(2-Cyclopent-1-enyl-pyridin-4-yl)-imidazo[1,2-a]pyridin-7-yl]-benzyl}-methyl-amine (Ex. 1.68),
(4-{3-[2-(4-Fluoro-phenyl)-pyridin-4-yl]-imidazo[1,2-a]pyridin-7-yl}-phenyl)-(4-methyl-piperazin-1-yl)-methanone (Ex. 1.69),
{4-[3-(2-Phenyl-pyridin-4-yl)-imidazo[1,2-a]pyridin-7-yl]-phenyl}-acetic acid (Ex. 1.70),
{4-[3-(2-Cyclopent-1-enyl-pyridin-4-yl)-imidazo[1,2-a]pyridin-7-yl]-phenyl}-acetic acid (Ex. 1.71),
3-(2-Cyclopent-1-enyl-pyridin-4-yl)-7-furan-3-yl-imidazo[1,2-a]pyridine (Ex. 1.72),
3-(2-Cyclopent-1-enyl-pyridin-4-yl)-7-(1H-pyrazol-4-yl)-imidazo[1,2-a]pyridine (Ex. 1.73),
3-(2-Cyclopent-1-enyl-pyridin-4-yl)-7-thiophen-3-yl-imidazo[1,2-a]pyridine (Ex. 1.74),
3-(2-Cyclopent-1-enyl-pyridin-4-yl)-7-(3-fluoro-phenyl)-imidazo[1,2-a]pyridine (Ex. 1.75),
3-Fluoro-N-methyl-5-[3-(2-phenyl-pyridin-4-yl)-imidazo[1,2-a]pyridin-7-yl]-benzamide (Ex. 1.76),
3-Fluoro-5-{3-[2-(4-fluoro-phenyl)-pyridin-4-yl]-imidazo[1,2-a]pyridin-7-yl}-N-methyl-benzamide (Ex. 1.77),
3-(2-Phenyl-pyridin-4-yl)-7-pyrimidin-5-yl-imidazo[1,2-a]pyridine (Ex. 1.78),
3-[2-(4-Fluoro-phenyl)-pyridin-4-yl]-7-(1,3,5-trimethyl-1H-pyrazol-4-yl)-imidazo[1,2-a]pyridine (Ex. 1.79),
(3-Fluoro-5-{3-[2-(4-fluoro-phenyl)-pyridin-4-yl]-imidazo[1,2-a]pyridin-7-yl}-phenyl)-methanol (Ex. 1.80),
3-Fluoro-5-{3-[2-(4-fluoro-phenyl)-pyridin-4-yl]-imidazo[1,2-a]pyridin-7-yl}-benzyl)-methyl-amine (Ex. 1.81),
3-[2-(4-Fluoro-phenyl)-pyridin-4-yl]-7-(1-piperidin-4-yl-1H-pyrazol-4-yl)-imidazo[1,2-a]pyridine (Ex. 1.82),
Methyl-{4-[3-(2-phenyl-pyridin-4-yl)-imidazo[1,2-a]pyridin-7-yl]-furan-2-ylmethyl}-amine (Ex. 1.83),
7-(3-Chloro-phenyl)-3-(2-phenyl-pyridin-4-yl)-imidazo[1,2-a]pyridine (Ex. 1.84),
7-(6-Fluoro-pyridin-3-yl)-3-(2-phenyl-pyridin-4-yl)-imidazo[1,2-a]pyridine (Ex. 1.85),
3-Fluoro-5-[3-(2-phenyl-pyridin-4-yl)-imidazo[1,2-a]pyridin-7-yl]-benzoic acid (Ex. 1.86),
7-(3,4-Difluoro-phenyl)-3-(2-phenyl-pyridin-4-yl)-imidazo[1,2-a]pyridine (Ex. 1.87),
7-(3-Fluoro-pyridin-4-yl)-3-(2-phenyl-pyridin-4-yl)-imidazo[1,2-a]pyridine (Ex. 1.88),
7-(2-Fluoro-pyridin-3-yl)-3-(2-phenyl-pyridin-4-yl)-imidazo[1,2-a]pyridine (Ex. 1.89),
7-(3,5-Dimethyl-1H-pyrazol-4-yl)-3-(2-phenyl-pyridin-4-yl)-imidazo[1,2-a]pyridine (Ex. 1.90),
3-(2-Cyclopent-1-enyl-pyridin-4-yl)-7-phenyl-imidazo[1,2-a]pyridine (Ex. 1.91),
3-(2-Phenyl-pyridin-4-yl)-7-(2-trifluoromethyl-pyridin-4-yl)-imidazo[1,2-a]pyridine (Ex. 1.92),
3-(2-Phenyl-pyridin-4-yl)-7-pyridin-2-yl-imidazo[1,2-a]pyridine (Ex. 1.93),
7-(2-Methyl-pyridin-4-yl)-3-(2-phenyl-pyridin-4-yl)-imidazo[1,2-a]pyridine (Ex. 1.94),
{2-Fluoro-4-[3-(2-phenyl-pyridin-4-yl)-imidazo[1,2-a]pyridin-7-yl]-phenyl}-acetic acid ethyl ester (Ex. 1.95),
N-Methyl-3-{3-[2-(3-methyl-cyclopent-1-enyl)-pyridin-4-yl]-imidazo[1,2-a]pyridin-7-yl}-benzamide (Ex. 1.96),
3-{3-[2-(4,4-Dimethyl-cyclopent-1-enyl)-pyridin-4-yl]-imidazo[1,2-a]pyridin-7-yl}-N-methyl-benzamide (Ex. 1.97),
Ethyl-{3-[3-(2-phenyl-pyridin-4-yl)-imidazo[1,2-a]pyridin-7-yl]-phenyl}-amine (Ex. 1.98),
5-[3-(2-Cyclopent-1-enyl-pyridin-4-yl)-imidazo[1,2-a]pyridin-7-yl]-1H-pyridin-2-one (Ex. 1.99),
7-(2-Methoxy-pyridin-3-yl)-3-(2-phenyl-pyridin-4-yl)-imidazo[1,2-a]pyridine (Ex. 1.100),
{2-Fluoro-4-[3-(2-phenyl-pyridin-4-yl)-imidazo[1,2-a]pyridin-7-yl]-phenyl}-acetic acid (Ex. 1.101),
3-{3-[2-(4-Fluoro-phenyl)-pyridin-4-yl]-imidazo[1,2-a]pyridin-7-yl}-phenol (Ex. 1.102),
4-[3-(2-Phenyl-pyridin-4-yl)-imidazo[1,2-a]pyridin-7-yl]-3,6-dihydro-2H-pyridine-1-carboxylic acid tert-butyl ester (Ex. 1.103) and
4-[3-(2-Cyclopent-1-enyl-pyridin-4-yl)-imidazo[1,2-a]pyridin-7-yl]-3,6-dihydro-2H-pyridine-1-carboxylic acid tert-butyl ester (Ex. 1.104)

are prepared by an analogous method to 3-(3-Pyrazol-1-yl-phenyl)-7-pyridin-3-yl-imidazo[1,2-a]pyridine (Ex. 1.1) starting from the appropriate intermediate and by replacing 3-pyridine boronic acid with the appropriate boronic acid.

Route B

Example 1.105

N-Methyl-3-[3-(3-pyrazol-1-yl-phenyl)-imidazo[1,2-a]pyridin-7-yl]-benzamide 3-(3-Bromo-imidazo[1,2-a]pyridine-7-yl)-N-methyl-benzamide (Intermediate EA) (1 eq, 0.303 mmol, 100 mg) and 3-(1H-pyrazolyl)-phenylboronic acid (1.3 eq, 0.394 mmol, 74 mg) are dissolved in DME (3 ml) and water (0.8 ml) and $Na_2CO_3$ (3 eq, 0.909 mmol, 96.3 mg) is added. $PdCl_2(PPh_3)_2$ (0.05 eq, 0.015 mmol, 10.6 mg) is added and the reaction mixture is heated using microwave radiation at 120° C. for 10 min. At the completion of this time the solvent is removed in vacuo and the reaction mixture is purified by flash column chromatography eluting with 9:1 DCM/MeOH to yield N-methyl-3-[3-(3-pyrazol-1-yl-phenyl)-imidazo[1,2-a]pyridin-7-yl]-benzamide as a light brown solid; $[M+H]^+$=395

These examples namely,
3-(3-Pyrazol-1-yl-phenyl)-7-pyridin-4-yl-imidazo[1,2-a]pyridine (Ex. 1.106), 3-(7-Pyridin-4-yl-imidazo[1,2-a]pyridin-3-yl]-benzamide (Ex. 1.107)

2-Methoxy-4-(7-pyridin-4-yl-imidazo [1,2-a]pyridin-3-yl]-phenol (Ex. 1.108) and 3-(2-Phenyl-pyridin-4-yl)-7-pyridin-4-yl-imidazo[1,2-a]pyridine (Ex. 1.109)

are prepared by an analogous method to N-methyl-3-[3-(3-pyrazol-1-yl-phenyl)-imidazo[1,2-a]pyridin-7-yl]-benzamide (Ex. 1.105) by using the appropriate intermediate and by replacing 3-(1H-pyrazolyl)-phenylboronic acid with the appropriate boronic acid Route C Example 1.110

7-[3-(4-Methyl-piperazine-1-ylmethyl)-phenyl]-3-(3-pyrazol-1-yl-phenyl)-imidazo-[1,2-a]pyridine To a solution of 3-[3-(3-pyrazol-1-yl-phenyl)-imidazo[1,2-a]pyridin-7-yl]-benzaldehyde (Ex. 1.9) (1 eq, 0.110 mmol, 40 mg) in DCM (2 ml) is added methyl piperazine (2 eq, 0.220, 0.24 ml) and the reaction mixture is stirred at room temperature for 2 h. After this time sodium triacetoxyborohydride (1.5 eq, 0.165 mmol, 36.7 mg) and acetic acid (0.1 ml) are added to the reaction mixture and this is stirred for a further one hour. The reaction is diluted with EtOAc and the organic phase is washed with NaHCO₃. The aqueous layer is further extracted with EtOAc. The combined organic layers are washed with brine, dried over MgSO₄, filtered and the solvent removed in vacuo. The reaction mixture is purified by flash column chromatography eluting with 8:2 DCM/MeOH to yield 7-[3-(4-methyl-piperazine-1-ylmethyl)-phenyl]-3-(3-pyrazol-1-yl-phenyl)-imidazo-[1,2-a]pyridine as a yellow solid; $[M+H]^+=449$ These examples namely, 7-[4-(4-Methyl-piperazine-1-ylmethyl)-phenyl]-3-(3-pyrazol-1-yl-phenyl)-imidazo-[1,2-a]pyridine (Ex. 1.111)

7-[3-(4-Methyl-piperazine-1-ylmethyl)-phenyl]-3-(2-phenyl-pyridin-4-yl)-imidazo-[1,2-a]pyridine (Ex. 1.112)

7-(3-Morpholin-4-ylmethyl-phenyl)-3-(2-phenyl-pyridin-4-yl)-imidazo-[1,2-a]pyridine (Ex. 1.113)

N,N-Dimethyl-N'-{3-[3-(2-phenyl-pyridin-4-yl)-imidazo-[1,2-a]pyridin-7-yl]-benzyl}-propane-1,3-diamine (Ex. 1.114)

N,N-Dimethyl-N'-{3-[3-(2-phenyl-pyridin-4-yl)-imidazo-[1,2-a]pyridin-7-yl]-benzyl}-ethane-1,2-diamine (Ex. 1.115)

7-(4-Morpholin-4-ylmethyl-phenyl)-3-(3-pyrazol-1-yl-phenyl)-imidazo-[1,2-a]pyridine (Ex. 1.116)

N'-(4-{3-[2-(3-Fluoro-phenyl)-pyiridin-4-yl]-imidazo-[1,2-a]pyridin-7-yl}-N,N-dimethyl-propane-1,3-diamine (Ex. 1.117)

N,N-Dimethyl-N'-{4-[3-(3-pyrazol-yl-phenyl)-imidazo-[1,2-a]pyridin-7-yl]-benzyl}-propane-1,3-diamine (Ex. 1.118)

N,N-Dimethyl-N'-{4-[3-(2-phenyl-pyiridin-4-yl)-imidazo-[1,2-a]pyridin-7-yl]-benzyl}-propane-1,3-diamine (Ex. 1.119)

[2-(4-Methyl-piperazine-1-yl)-ethyl]-{3-[3-(2-phenyl-pyridin-4-yl)-imidazo-[1,2-a]pyridin-7-yl]-benzyl}-amine (Ex. 1.120)

[2-(4-Methyl-piperazine-1-yl)-ethyl]-{4-[3-(3-pyrazol-1-yl-phenyl)-imidazo-[1,2-a]pyridin-7-yl]-benzyl}-amine (Ex. 1.121), {3-[3-(2-Cyclopent-1-enyl-pyridin-4-yl)-imidazo[1,2-a]pyridin-7-yl]-benzyl}-ethyl-amine (Ex. 1.122), {4-[3-(2-Phenyl-pyridin-4-yl)-imidazo[1,2-a]pyridin-7-yl]-benzyl}-propyl-amine (Ex. 1.123), {4-[3-(2-Phenyl-pyridin-4-yl)-imidazo[1,2-a]pyridin-7-yl]-benzyl}-(2-piperidin-1-yl-ethyl)-amine (Ex. 1.124), 3-[7-(3-Ethylaminomethyl-phenyl)-imidazo[1,2-a]pyridin-3-yl]-benzamide (Ex. 1.125), Ethyl-(3-{3-[2-(3-methyl-pyrazol-1-yl)-pyridin-4-yl]-imidazo[1,2-a]pyridin-7-yl}-benzyl)-amine (Ex. 1.126), 3-[2-(2-Fluoro-phenyl)-pyridin-4-yl]-7-[3-(4-methyl-piperazin-1-ylmethyl)-phenyl]-imidazo[1,2-a]pyridine (Ex. 1.127), Ethyl-(3-{3-[2-(2-fluoro-phenyl)-pyridin-4-yl]-imidazo[1,2-a]pyridin-7-yl}-benzyl)-amine (Ex. 1.128), (3-{3-[2-(2,4-Difluoro-phenyl)-pyridin-4-yl]-imidazo[1,2-a]pyridin-7-yl}-benzyl)-ethyl-amine (Ex. 1.129), Ethyl-(3-{3-[2-(4-fluoro-phenyl)-pyridin-4-yl]-imidazo[1,2-a]pyridin-7-yl}-benzyl)-amine (Ex. 1.130), (4-{3-[2-(3-Fluoro-phenyl)-pyridin-4-yl]-imidazo[1,2-a]pyridin-7-yl}-benzyl)-[2-4-methyl-piperazin-1-yl)-ethyl]-amine (Ex. 1.131), {3-[3-(2-Cyclopent-1-enyl-pyridin-4-yl)-imidazo[1,2-a]pyridin-7-yl]-benzyl}-isopropyl-amine (Ex. 1.132), N'-{3-[3-(2-Cyclopent-1-enyl-pyridin-4-yl)-imidazo[1,2-a]pyridin-7-yl]-benzyl}-N,N-dimethyl-ethane-1,2-diamine (Ex. 1.133), {3-[3-(2-Cyclohex-1-enyl-pyridin-4-yl)-imidazo[1,2-a]pyridin-7-yl]-benzyl}-ethyl-amine (Ex. 1.134), Ethyl-(3-{3-[2-(2-methyl-pyrrolidin-1-yl)-pyridin-4-yl]-imidazo[1,2-a]pyridin-7-yl}-benzyl)-amine (Ex. 1.135), 3-(2-Phenyl-pyridin-4-yl)-7-(4-piperidin-1-ylmethyl-phenyl)-imidazo[1,2-a]pyridine (Ex. 1.136), (3-{3-[2-(3,3-Difluoro-pyrrolidin-1-yl)-pyridin-4-yl]-imidazo[1,2-a]pyridin-7-yl}-benzyl)-ethyl-amine (Ex. 1.137), Isopropyl-{3-[3-(2-pyrrolidin-1-yl-pyridin-4-yl)-imidazo[1,2-a]pyridin-7-yl]-benzyl}-amine (Ex. 1.138), (3-Methyl-butyl)-{3-[3-(2-pyrrolidin-1-yl-pyridin-4-yl)-imidazo[1,2-a]pyridin-7-yl]-benzyl}-amine (Ex. 1.139), 3-(7-{3-[(3-Methyl-butylamino)-methyl]-phenyl}-imidazo[1,2-a]pyridin-3-yl)-benzamide (Ex. 1.140), (3-{3-[2-(2-Fluoro-phenyl)-pyridin-4-yl]-imidazo[1,2-a]pyridin-7-yl}-benzyl)-(3-methyl-butyl)-amine (Ex. 1.141), N'-(3-{3-[2-(2,4-Difluoro-phenyl)-pyridin-4-yl]-imidazo[1,2-a]pyridin-7-yl}-benzyl)-N,N-dimethyl-ethane-1,2-diamine (Ex. 1.142), 3-[7-(4-Propylaminomethyl-phenyl)-imidazo[1,2-a]pyridin-3-yl]-benzamide (Ex. 1.143), {3-Fluoro-5-[3-(2-phenyl-pyridin-4-yl)-imidazo[1,2-a]pyridin-7-yl]-benzyl}-methyl-amine (Ex. 1.144), 3-[7-(3-Ethylaminomethyl-phenyl)-imidazo[1,2-a]pyridin-3-yl]-N-methyl-benzamide (Ex. 1.145) and Ethyl-{4-[3-(2-phenyl-pyridin-4-yl)-imidazo[1,2-a]pyridin-7-yl]-furan-2-ylmethyl}-amine (Ex. 1.146)

are prepared by an analogous method to 7-[3-(4-methyl-piperazine-1-ylmethyl)-phenyl]-3-(3-pyrazol-1-yl-phenyl)-imidazo-[1,2-a]pyridine (Ex. 1.110) by using the appropriate intermediate and by replacing methyl piperazine with the appropriate amine.

Route D

Example 1.147

N-(2-Hydroxy-ethyl)-3-[3-(3-pyrazol-1-yl-phenyl)-imidazo-[1,2-a]-pyridin-7-yl]-benzamide 3-[3-(3-Pyrazol-1-yl-phenyl)-imidazo[1,2-a]pyridin-7-yl]-benzoic acid ethyl ester (Ex. 1.10) (1 eq, 0.098 mmol, 40 mg) and ethanol amine (10 eq, 0.98 mmol, 0.06 ml) are dissolved in EtOH (2 ml) and K$_2$CO$_3$ (1.5 eq, 0.147 mmol, 20.3 mg) is added. The reaction mixture is stirred for 5 h at 55° C. The solvent is removed in vacuo and the reaction is purified by flash column chromatography eluting with 9:1 DCM/MeOH to yield N-(2-hydroxy-ethyl)-3-[3-(3-pyrazol-1-yl-phenyl)-imidazo-[1,2-a]-pyridin-7-yl]-benzamide as a white solid; [M+H]$^+$=424

N-Ethyl-5-[3-(3-pyrazol-1-yl-phenyl)-imidazo[1,2-a]pyridin-7-yl]-nicotinamide (Ex. 1.148) is prepared by an analogous method to N-(2-hydroxy-ethyl)-4-[3-(3-pyrazol-1-yl-phenyl)-imidazo-[1,2-a]-pyridin-7-yl]-benzamide (Ex. 1.147) by using the appropriate ester compound and by replacing ethanol amine with the appropriate amine.

Route E

Example 1.149

N-(2-Hydroxy-ethyl)-4-[3-(3-pyrazol-1-yl-phenyl)-imidazo-[1,2-a]-pyridin-7-yl]-benzamide 4-[3-(3-Pyrazol-1-yl-phenyl)-imidazo[1,2-a]pyridin-7-yl]-benzoic acid ethyl ester (Ex. 1.11) (1 eq, 0.086 mmol, 35 mg) and ethanol amine (10 eq, 0.86 mmol, 0.05 ml) are dissolved in EtOH (2 ml) and K$_2$CO$_3$ (1.5 eq, 0.128 mmol, 17.7 mg) is added. The reaction mixture is stirred for 5 h at 55° C. The solvent is removed in vacuo and the reaction is purified by flash column chromatography eluting with 9:1 DCM/MeOH to yield N-(2-hydroxy-ethyl)-4-[3-(3-pyrazol-1-yl-phenyl)-imidazo-[1,2-a]-pyridin-7-yl]-benzamide as a white solid; [M+H]$^+$=424

These compounds namely,
N-(2-Dimethylamino-ethyl)-4-[3-(3-pyrazol-1-yl-phenyl)-imidazo-[1,2-a]-pyridin-7-yl]-benzamide (Ex. 1.150),
(4-Methyl-piperazine-1-yl)-{4-[3-(2-phenyl-pyridin-4-yl)-imidazo-[1,2-a]-pyridin-7-yl]-phenyl}-methanone (Ex. 1.151),
N-(4-Hydroxy-cyclohexyl)-4-[3-(2-phenyl-pyridin-4-yl)-imidazo-[1,2-a]-pyridin-7-yl]-benzamide (Ex. 1.152),
4-{3-[2-(4-Fluoro-phenyl)-pyridin-4-yl]-imidazo[1,2-a]pyridin-7-yl}-N-[2-(4-methyl-iperazin-1-yl)-ethyl]-benzamide (Ex. 1.153),
4-{3-[2-(4-Fluoro-phenyl)-pyridin-4-yl]-imidazo[1,2-a]pyridin-7-yl}-N-(2-piperidin-1-yl-ethyl)-benzamide (Ex. 1.154) and
N-(2-Dimethylamino-ethyl)-4-{3-[2-(4-fluoro-phenyl)-pyridin-4-yl]-imidazo[1,2-a]pyridin-7-yl}-benzamide (Ex. 1.155)
are prepared by an analogous method to N-(2-hydroxy-ethyl)-4-[3-(3-pyrazol-1-yl-phenyl)-imidazo-[1,2-a]-pyridin-7-yl]-benzamide (Ex. 1.149) by using the appropriate ester compound and by replacing ethanol amine with the appropriate amine.

Route F

Example 1.156

5-[3-(3-Pyrazol-1-yl-phenyl)-imidazo-[1,2-a]-pyridin-7-yl]-nicotinamide

5-[3-(3-pyrazol-1-yl-phenyl)-imidazo-[1,2-a]-pyridin-7-yl]-nicotinonitrile (Ex. 1.8) (1 eq, 0.099 mmol, 40 mg) and potassium hydroxide (10 eq, 0.99 mmol, 64.8 mg) are dissolved in tBuOH (2 ml) and the reaction mixture is heated at 85° C. for 1.5 h. At the completion of this time the solvent is removed in vacuo and the reaction mixture is diluted with NaHCO$_3$. The aqueous phase is extracted with EtOAc. The organic layer is washed with brine, dried over MgSO$_4$, filtered and evaporated to dryness. The reaction mixture is purified by flash chromatography on silica eluting with DCM/MeOH 9/1 to yield 5-[3-(3-pyrazol-1-yl-phenyl)-imidazo-[1,2-a]pyridin-7-yl]-nicotinamide as a yellow solid; [M+H]$^+$=381

5-[3-(2-Phenyl-pyridin-4-yl)-imidazo-[1,2-a]-pyridin-7-yl]-nicotin amide (Ex. 1.157), is prepared by an analogous method to 5-[3-(3-pyrazol-1-yl-phenyl)-imidazo-[1,2-a]-pyridin-7-yl]-nicotinamide (Ex. 1.156) by using the appropriate intermediate.

Route H

Example 1.158

3-[3-(2-Phenyl-pyridin-4-yl)-imidazo [1,2-a]pyridin-7-yl]-pyridin-2-ol 7-(2-Methoxy-pyridin-3-yl)-3-(2-phenyl-pyridin-4-y1)-imidazo[1,2-a]pyridine (Ex. 1.100) (1 eq, 0.38 mmol, 145 mg) is dissolved in EtOH (0.5 ml) and HCl (37% in H$_2$O, 0.04 eq, 0.015 mmol, 0.5 ml) is added. The reaction is heated at reflux for 3 h and is cooled down to rt before H$_2$O is added. The pH is adjusted to 7 with the addition of NaOH (4N) and the suspension is filtered. The solid is washed with a mixture H$_2$O/EtOH 4:1 and dried in vacuo to afford 3-[3-(2-Phenyl-pyridin-4-yl)-imidazo[1,2-a]pyridin-7-yl]-pyridin-2-ol as a light yellow oil; [M+H]$^+$=365

Route I

Examples 1.159 & 1.160

7-(6-Ethoxy-pyridin-3-yl)-3-(2-phenyl-pyridin-4-yl)-imidazo[1,2-a]pyridine and 1-Ethyl-5-[3-(2-phenyl-pyridin-4-yl)-imidazo [1,2-a]pyridin-7-yl]-1H-pyridin-2-one 5-[3-(2-Phenyl-pyridin-4-yl)-imidazo[1,2-a]pyridin-7-yl]-1H-pyridin-2-one (Ex. 1.37) (1 eq, 0.096 mmol, 35 mg), iodoethane (1.5 eq, 0.144 mmol, 22.5 mg), sodium iodide (1.5 eq, 0.155 mmol, 21.5 mg) and cesium carbonate (2.99 eq, 0.287 mmol, 93.6 mg) are dissolved in DMF (2 ml) and heated at 60° C. for 16 h. The reaction mixture is diluted with CH$_2$Cl$_2$ and washed with Na$_2$CO$_3$. The organic phase is dried over MgSO$_4$, filtered and evaporated to dryness. The reaction mixture is purified by flash chromatography on silica eluting with DCM/MeOH 8/2 to yield 7-(6-ethoxy-pyridin-3-yl)-3-(2-phenyl-pyridin-4-yl)-imidazo[1,2-a]pyridine as a yellow solid; [M+H]$^+$=393 and 1-ethyl-5-[3-(2-phenyl-pyridin-4-yl)-imidazo[1,2-a]pyridin-7-yl]-1H-pyridin-2-one as a yellow solid; [M+H]$^+$=393

These compounds namely,
3-[3-(2-Phenyl-pyridin-4-yl)-imidazo[1,2-a]pyridin-7-yl]-1-(3-piperidin-1-yl-propyl)-1H-pyridin-2-one (Ex. 1.161),
3-[2-(4-Fluoro-phenyl)-pyridin-4-yl]-7-(6-isobutoxy-pyridin-3-yl)-imidazo[1,2-a]pyridine (Ex. 1.162),
5-{3-[2-(4-Fluoro-phenyl)-pyridin-4-yl]-imidazo[1,2-a]pyridin-7-yl}-1-isopropyl-1H-pyridin-2-one (Ex. 1.163),
[3-(5-{3-[2-(4-Fluoro-phenyl)-pyridin-4-yl]-imidazo[1,2-a]pyridin-7-yl}-pyridin-2-loxy)-propyl]-dimethyl-amine (Ex. 1.164),
5-{3-[2-(4-Fluoro-phenyl)-pyridin-4-yl]-imidazo[1,2-a]pyridin-7-yl}-1-(3-piperidin-1-yl-propyl)-1H-pyridin-2-one (Ex. 1.165), 1-Ethyl-5-{3-[2-(4-fluoro-phenyl)-pyridin-4-yl]-imidazo[1,2-a]pyridin-7-yl}-1H-pyridin-2-one (Ex. 1.166),
1-Isobutyl-5-[3-(2-phenyl-pyridin-4-yl)-imidazo[1,2-a]pyridin-7-yl]-1H-pyridin-2-one (Ex. 1.167),
3-(2-Phenyl-pyridin-4-yl)-7-[6-(3-piperidin-1-yl-propoxy)-pyridin-3-yl]-imidazo[1,2-a]pyridine (Ex. 1.168),
5-[3-(2-Phenyl-pyridin-4-yl)-imidazo[1,2-a]pyridin-7-yl]-1-(3-piperidin-1-propyl)-1H-pyridin-2-one (Ex. 1.169),
1-Isopropyl-3-[3-(2-phenyl-pyridin-4-yl)-imidazo[1,2-a]pyridin-7-yl]-1H-pyridin-2-one (Ex. 1.170),
3-[2-(4-Fluoro-phenyl)-pyridin-4-yl]-7-{3-[3-(4-methyl-piperazin-1yl)-propoxy]-phenyl}-imidazo[1,2-a]pyridine (Ex. 1.171),
5-{3-[2-(4-Fluoro-phenyl)-pyridin-4-yl]-imidazo[1,2-a]pyridin-7-yl}-1-isobutyl-1H-pyridin-2-one (Ex. 1.172),
3-[2-(4-Fluoro-phenyl)-pyridin-4-yl]-7-(6-isopropoxy-pyridin-3-yl)-imidazo[1,2-a]pyridine (Ex. 1.173),
7-(6-Cyclopropylmethoxy-pyridin-3-yl)-3-[2-(4-fluoro-phenyl)-pyridin-4-yl]-imidazo[1,2-a]pyridine (Ex. 1.174),
3-[7-(1-Isobutyl-6-oxo-1,6-dihydro-pyridin-3-yl)-imidazo[1,2-a]pyridin-3-yl]-benzamide (Ex. 1.175) and
3-[7-(6-Isobutoxy-pyridin-3-yl)-imidazo[1,2-a]pyridin-3-yl]-benzamide (Ex. 1.176)

are prepared by an analogous method to 7-(6-ethoxy-pyridin-3-yl)-3-(2-phenyl-pyridin-4-yl)-imidazo[1,2-a]pyridine and 1-ethyl-5-[3-(2-phenyl-pyridin-4-yl)-imidazo[1,2-a]pyridin-7-yl]-1H-pyridin-2-one (Ex. 1.159 & Ex. 1.160) by using the appropriate intermediate and the appropriate alkyl halide.

Route J

Example 1.177

3-[2-(4-Fluoro-phenyl)-pyridin-4-yl]-7-[3-(3-piperidin-1-yl-propoxy)-phenyl]-imidazo[1,2-a]pyridine 3-{3-[2-(4-Fluoro-phenyl)-pyridin-4-yl]-imidazo[1,2-a]pyridin-7-yl}-phenol (Ex. 1.102) (1 eq, 0.131 mmol, 50 mg), 1-(3-chloropropyl)piperidine monohydrochloride (2.0 eq, 0.262 mmol, 53.7 mg) and potassium carbonate (3.0 eq, 0.394 mmol, 54.4 mg) are dissolved in DMF (4 ml) and heated at 60° C. for 16 h. The reaction mixture is diluted with $CH_2Cl_2$ and washed with $NaHCO_3$ and brine. The organic phase is dried over $MgSO_4$, filtered and evaporated to dryness. The reaction mixture is purified by flash chromatography on silica eluting with DCM/MeOH 7/3 to yield 3-[2-(4-fluoro-phenyl)-pyridin-4-yl]-7-[3-(3-piperidin-1-yl-propoxy)-phenyl]-imidazo[1,2-a]pyridine as a yellow solid; $[M+H]^+=507$

[3-(3-{3-[2-(4-Fluoro-phenyl)-pyridin-4-yl]-imidazo[1,2-a]pyridin-7-yl}-phenoxy)-propyl]-dimethyl-amine (Ex. 1.178)

is prepared by an analogous method to 3-[2-(4-fluoro-phenyl)-pyridin-4-yl]-7-[3-(3-piperidin-1-yl-propoxy)-phenyl]-imidazo[1,2-a]pyridine (Ex. 1.177) by using 3-dimethylamino-1-propylchloride.HCl instead of 1-(3-chloropropyl)piperidine monohydrochloride.

Route K

Example 1.179

3-{3-[2-(4-Fluoro-phenyl)-6-methylamino-pyridin-4-yl]-imidazo[1,2-a]pyridin-7-yl}-N-methyl-benzamide

[4-(7-Chloro-imidazo[1,2-a]pyridin-3-yl)-6-(4-fluoro-phenyl)-pyridin-2-yl]-methyl-amine (Intermediate YE) (1 eq, 0.093 mmol, 46 mg) and 3 methyl aminocarbonylphenyl boronic acid (1.1 eq, 0.103 mmol, 18.4 mg) are dissolved in dioxane (1 ml), EtOH (1 ml) and water (0.5 ml) and $K_2CO_3$ (2 eq, 0.187 mmol, 25.8 mg) is added. $Pd(PPh_3)_4$ (0.1 eq, 0.009 mmol, 10.8 mg) is added and the reaction mixture is heated using microwave radiation at 140° C. for 20 min. The solvent is removed in vacuo and the reaction mixture is purified by flash column chromatography eluting with 8:2 DCM/MeOH to yield 3-{3-[2-(4-fluoro-phenyl)-6-methylamino-pyridin-4-yl]-imidazo[1,2-a]pyridin-7-yl}-N-methyl-benzamide as a light yellow solid; $[M+H]^+=592$ These examples namely, {4-[3-(2-Methylamino-6-phenyl-pyridin-4-yl)-imidazo[1,2-a]pyridin-7-yl]-phenyl}-acetic acid (Ex. 1.180),
{6-(4-Fluoro-phenyl)-4-[7-(4-fluoro-phenyl)-imidazo[1,2-a]pyridin-3-yl]-pyridin-2-yl}-methyl-amine (Ex. 1.181),
Methyl-[6-phenyl-4-(7-phenyl-imidazo[1,2-a]pyridin-3-yl)-pyridin-2-yl]-amine (Ex. 1.182),
N-Methyl-3-[3-(2-methylamino-6-phenyl-pyridin-4-yl)-imidazo[1,2-a]pyridin-7-yl]-benzamide (Ex. 1.183),
3-[3-(2-Isopropylamino-6-phenyl-pyridin-4-yl)-imidazo[1,2-a]pyridin-7-yl]-N-methyl-benzamide (Ex. 1.184),
Isopropyl-[6-phenyl-4-(7-phenyl-imidazo[1,2-a]pyridin-3-yl)-pyridin-2-yl]-amine (Ex. 1.185),
3-[3-(2-Isopropylamino-6-phenyl-pyridin-4-yl)-imidazo[1,2-a]pyridin-7-yl]-benzaldehyde (Ex. 1.186),
3-[3-(2-Cyclopropylamino-6-phenyl-pyridin-4-yl)-imidazo[1,2-a]pyridin-7-yl]-N-methyl-benzamide (Ex. 1.187) and
Cyclopropyl-[6-phenyl-4-(7-phenyl-imidazo[1,2-a]pyridin-3-yl)-pyridin-2-yl]-amine (Ex. 1.188), are prepared by an analogous method to 3-{3-[2-(4-fluoro-phenyl)-6-methylamino-pyridin-4-yl]-thimidazo[1,2-a]pyridin-7-yl}-N-methyl-benzamide (Ex. 1.179) starting from the appropriate intermediate and by replacing 3 methyl aminocarbonylphenyl boronic acid with the appropriate boronic acid.

Route L

Example 1.189

{4-[7-(3-Ethylaminomethyl-phenyl)-imidazo[1,2-a]pyridin-3-yl]-6-phenyl-pyridin-2-yl}-isopropyl-amine To a solution of 3-[3-(2-isopropylamino-6-phenyl-pyridin-4-yl)-imidazo[1,2-a]pyridin-7-yl]-benzaldehyde (Ex. 1.186) (1 eq, 0.055 mmol, 30 mg) in MeOH (2 ml) is added ethyl amine (10 eq, 0.55, 0.27 ml) and acetic acid (2 eq, 0.11 mmol, 6.59 mg) and the reaction mixture is stirred at room temperature for 30 min. After this time sodium triacetoxyborohydride (5 eq, 0.27 mmol, 58.2 mg) is added to the reaction mixture and is stirred for a further 2 h. The reaction is diluted with $CH_2Cl_2$ and the organic phase is washed with $NaHCO_3$. The aqueous layer is further extracted with EtOAc. The combined organic layers are washed with brine, dried over $MgSO_4$, filtered and the solvent removed in vacuo. The reaction mixture is purified by flash column chromatography eluting with 8:2 DCM/MeOH to yield {4-[7-(3-ethylaminomethyl-phenyl)-imidazo[1,2-a]pyridin-3-yl]-6-phenyl-pyridin-2-yl}-isopropyl-amine as a light yellow solid; [M+H]$^+$=462

Route M

Example 1.190

3-(2-Phenyl-pyridin-4-yl)-7-(1,2,3,6-tetrahydro-pyridin-4-yl)-imidazo[1,2-a]pyridine 4-[3-(2-Phenyl-pyridin-4-yl)-imidazo[1,2-a]pyridin-7-yl]-3,6-dihydro-2H-pyridine-1-carboxylic acid tert-butyl ester (Ex. 1.103) (1.0 eq, 0.2 mmol, 90 mg) is dissolved in dioxane/MeOH (1 ml, 1 ml) and HCl (4M in dioxane, 10.0 eq, 2.0 mmol, 0.5 ml) is added. The reaction is stirred at room temperature for 16 h. The solvent is removed in vacuo to yield 3-(2-phenyl-pyridin-4-yl)-7-(1,2,3,6-tetrahydro-pyridin-4-yl)-imidazo[1,2-a]pyridine as a yellow solid; [M+H]$^+$=353

These examples namely,
3-(2-Cyclopent-1-enyl-pyridin-4-yl)-7-(1,2,3,6-tetrahydro-pyridin-4-yl)-imidazo[1,2-a]pyridine (Ex. 1.191) and
3-[7-(1,2,3,6-Tetrahydro-pyridin-4-yl)-imidazo[1,2-a]pyridin-3-yl]-benzamide (Ex. 1.192)
are prepared by an analogous method to 3-(2-phenyl-pyridin-4-yl)-7-(1,2,3,6-tetrahydro-pyridin-4-yl)-imidazo[1,2-a]pyridine (Ex. 1.190) starting from the appropriate intermediate.

Route N

Example 1.193

7-(1-Isopropyl-1,2,3,6-tetrahydro-pyridin-4-yl)-3-(2-phenyl-pyridin-4-yl)-imidazo[1,2-a]pyridine To a solution of 3-(2-Phenyl-pyridin-4-yl)-7-(1,2,3,6-tetrahydro-pyridin-4-yl)-imidazo[1,2-a]pyridine (Ex. 1.190) (1.0 eq, 0.2 mmol, 90 mg) in MeOH (2 ml) is added acetone (10 eq, 1.04, 0.76 ml) and acetic acid (2 eq, 0.21 mmol, 0.1 ml) and the reaction mixture is stirred at room temperature for 30 min. After this time sodium triacetoxyborohydride (5 eq, 0.52 mmol, 116 mg) is added to the reaction mixture and is stirred for a further 2 h. The reaction is diluted with CH$_2$Cl$_2$ and the organic phase is washed with NaHCO$_3$. The aqueous layer is further extracted with EtOAc. The combined organic layers are washed with brine, dried over MgSO$_4$, filtered and the solvent removed in vacuo. The reaction mixture is purified by flash column chromatography eluting with 8:2 DCM/MeOH to yield 7-(1-isopropyl-1,2,3,6-tetrahydro-pyridin-4-yl)-3-(2-phenyl-pyridin-4-yl)-imidazo[1,2-a]pyridine as a light yellow solid; [M+H]$^+$=395

These examples namely,
7-(1-Methyl-1,2,3,6-tetrahydro-pyridin-4-yl)-3-(2-phenyl-pyridin-4-yl)-imidazo[1,2-a]pyridine (Ex. 1.194),
7-(1-Isobutyl-1,2,3,6-tetrahydro-pyridin-4-yl)-3-(2-phenyl-pyridin-4-yl)-imidazo[1,2-a]pyridine (Ex. 1.195),
3-(2-Cyclopent-1-enyl-pyridin-4-yl)-7-(1-methyl-1,2,3,6-tetrahydro-pyridin-4-yl)-imidazo[1,2-a]pyridine (Ex. 1.196) and
3-[7-(1-Methyl-1,2,3,6-tetrahydro-pyridin-4-yl)-imidazo[1,2-a]pyridin-3-yl]-benzamide (Ex. 1.197)
are prepared by an analogous method to 7-(1-isopropyl-1,2,3,6-tetrahydro-pyridin-4-yl)-3-(2-phenyl-pyridin-4-yl)-imidazo[1,2-a]pyridine (Ex. 1.193) starting from the appropriate intermediate and replacing acetone with the appropriate reagent.

Route O

Example 1.198

3-(2-Phenyl-pyridin-4-yl)-7-piperidin-4-yl-imidazo[1,2-a]pyridine 3-(2-Phenyl-pyridin-4-yl)-7-(1,2,3,6-tetrahydro-pyridin-4-yl)-imidazo[1,2-a]pyridine (Ex. 1.190) (1.0 eq, 1.15 mmol, 0.51 g) in dissolved in MeOH (20 ml) and Pd/C (10%, 1.15 eq, 1.32 mmol, 140 mg) and the reaction mixture is hydrogenated at rt for 16 h (4 bar pressure). The solid is removed by filtration and the solvent is evaporated to dryness to yield 3-(2-phenyl-pyridin-4-yl)-7-piperidin-4-yl-imidazo[1,2-a]pyridine as a light yellow solid which did not require any further purification; [M+H]$^+$=391

Route P

Example 1.199

7-(1-Isopropyl-piperidin-4-yl)-3-(2-phenyl-pyridin-4-yl)-imidazo[1,2-a]pyridine

To a solution of 3-(2-phenyl-pyridin-4-yl)-7-piperidin-4-yl-imidazo[1,2-a]pyridine (Ex. 1.198) (1.0 eq, 0.16 mmol, 80 mg) in MeOH (2 ml) is added acetone (10 eq, 1.6 mmol, 0.12 ml) and acetic acid (2 eq, 0.33 mmol, 0.19 ml) and the reaction mixture is stirred at room temperature for 30min. After this time sodium triacetoxyborohydride (5 eq, 0.82 mmol, 183 mg) is added to the reaction mixture and is stirred for a further 2 h. The reaction is diluted with CH$_2$C$_{12}$ and the organic phase is washed with NaHCO$_3$. The aqueous layer is further extracted with EtOAc. The combined organic layers are washed with brine, dried over MgSO$_4$, filtered and the solvent removed in vacuo. The reaction mixture is purified by flash column chromatography eluting with 8:2 DCM/MeOH to yield 7-(1-Isopropyl-piperidin-4-yl)-3-(2-phenyl-pyridin-4-yl)-imidazo[1,2-a]pyridine as a light yellow solid; [M+H]$^+$=397

These examples namely,
7-(1-Methyl-piperidin-4-yl)-3-(2-phenyl-pyridin-4-yl)-imidazo[1,2-a]pyridine (Ex. 1.200) and
3-(2-Phenyl-pyridin-4-yl)-7-(1-propyl-piperidin-4-yl)-imidazo[1,2-a]pyridine (Ex. 1.201),
are prepared by an analogous method to 7-(1-Isopropyl-piperidin-4-yl)-3-(2-phenyl-pyridin-4-yl)-imidazo[1,2-a]pyridine (Ex. 1.199) starting from the appropriate intermediate and replacing acetone with the appropriate reagent.

Route Q

Example 1.202

1-{4-[3-(2-Phenyl-pyridin-4-yl)-imidazo[1,2-a]pyridin-7-yl]-piperidin-1-yl}-ethanone To a solution of 3-(2-phenyl-pyridin-4-yl)-7-piperidin-4-yl-imidazo[1,2-a]pyridine (Ex. 1.198) (1.0 eq, 0.20 mmol, 80 mg) in CH$_2$Cl$_2$ (2 ml) is added triethylamine (3 eq, 0.61 mmol, 0.09 ml) and acetyl chloride (1.5 eq, 0.31 mmol, 0.02 ml) and the reaction mixture is stirred at room temperature for 2 h. The reaction is poured into NaHCO$_3$ (50 ml) and the organic phase is extracted with CH$_2$Cl$_2$. The combined organic layers are washed with brine, dried over MgSO$_4$, filtered and the solvent removed in vacuo. The reaction mixture is purified by flash column chromatography eluting with 9:1 DCM/MeOH to yield 1-{4-[3-(2-phenyl-pyridin-4-yl)-imidazo[1,2-a]pyridin-7-yl]-piperidin-1-yl}-ethanone as a white solid; [M+H]⁺=397

These examples namely,
2-Dimethylamino-1-{4-[3-(2-phenyl-pyridin-4-yl)-imidazo[1,2-a]pyridin-7-yl]-piperidin-1-yl}-ethanone (Ex. 1.203),
(S)-2-Methylamino-1-{4-[3-(2-phenyl-pyridin-4-yl)-imidazo[1,2-a]pyridin-7-yl]-piperidin-1-yl}-propan-1-one (Ex. 1.204),
{4-[3-(2-Phenyl-pyridin-4-yl)-imidazo[1,2-a]pyridin-7-yl]-piperidin-1-yl}-pyrrolidin-2-yl-methanone (Ex. 1.205),
2-(2-Methyl-imidazol-1-yl)-1-{4-[3-(2-phenyl-pyridin-4-yl)-imidazo[1,2-a]pyridin-7-yl]-piperidin-1-yl}-ethanone (Ex. 1.206) and
2-Imidazol-1-yl-1-{4-[3-(2-phenyl-pyridin-4-yl)-imidazo[1,2-a]pyridin-7-yl]-piperidin-1-yl}-ethanone (Ex. 1.207)
are prepared by an analogous method to 1-{4-[3-(2-phenyl-pyridin-4-yl)-imidazo[1,2-a]pyridin-7-yl]-piperidin-1-yl}-ethanone (Ex. 1.202) by replacing acetyl chloride with the appropriate acyl chloride.

Examples 1.208-1.215

These compounds namely,
7-Chloro-3-(2-phenyl-pyridin-4-yl)-imidazo[1,2-a]pyridine (Ex. 1.208=Intermediate DA),
7-Chloro-3-[2-(2-fluoro-phenyl)-pyridin-4-yl]-imidazo[1,2-a]pyridine (Ex. 1.209=Intermediate DD),
7-Chloro-3-[3-(3-methyl-pyrazol-1-yl)-phenyl]-imidazo[1,2-a]pyridine (Ex. 1.210=Intermediate AC),
7-Chloro-3-[2-(2,4-difluoro-phenyl)-pyridin-4-yl]-imidazo[1,2-a]pyridine (Ex. 1.211=Intermediate DK),
7-Chloro-3-(3-pyrazol-1-yl-phenyl)-imidazo[1,2-a]pyridine (Ex. 1.212=Intermediate AA),
7-Chloro-3-[2-(4-fluoro-phenyl)-pyridin-4-yl]-imidazo[1,2-a]pyridine (Ex. 1.213=Intermediate DB),
7-Chloro-3-[2-(3-chloro-phenyl)-pyridin-4-yl]-imidazo[1,2-a]pyridine (Ex. 1.214=Intermediate DN) and
3-(7-Chloro-imidazo[1,2-a]pyridin-3-yl)-benzamide (Ex. 1.215=Intermediate AB)
are prepared according to the methods described in the intermediates section.

Example 2.1

[4-[3-(2-Chloro-pyridin-4-yl)-imidazo[1,2-a]pyridin-6-ylamino]-cyclohexanol

Step 1: 4-(3-Bromo-imidazo[1,2-a]pyridin-6-ylamino)-cyclohexanol

Copper (I) iodide (0.1 eq, 1.45 g, 7.68 mmol) and potassium phosphate tribasic (2 eq, 0.153 mol, 32.5 g) are stirred at RT under an atmosphere of argon during the addition of 3-bromo-6-iodo-imidazo[1,2-a]pyridine (Intermediate F) (25 g, 77 mmol, 1 eq) in isopropyl alcohol (200 ml), ethylene glycol (2 eq, 0.153 mol, 8.5 ml) and finally trans-4-aminocyclohexanol (2 eq, 17.5 g, 153 mmol) The reaction is heated at 80° C. for 40 hours. The majority of the solvent is removed in vacuo and the residue is diluted with water (500 ml) and extracted with EtOAc (3×500 ml). The combined organic portions are dried (MgSO₄) and concentrated in vacuo. Purification by flash chromatography on silica eluting with 0-15% MeOH in EtOAc gives 4-(3-bromo-imidazo[1,2-a]pyridin-6-ylamino)-cyclohexanol; [M+H]⁺=310 (312)

Step 2: [4-[3-(2-Chloro-pyridin-4-yl)-imidazo[1,2-a]pyridin-6-ylamino]-cyclohexanol To a solution of 4-(3-bromo-imidazo[1,2-a]pyridin-6-ylamino)-cyclohexanol (1 eq, 9.6 mmol, 3 g), 3-chloropyrid-4-yl boronic acid (1.05 eq, 10.1 mmol, 1.6 g), Na₂CO₃ (2 eq, 19 mmol, 2 g) in dioxane (45 ml) and water (13.5 ml), under an inert atmosphere of argon is added bis(triphenylphosphine)palladium II chloride (0.1 eq, 0.96 mmol, 679 mg). The reaction mixture is heated at 95° C. for 16 hours. The mixture is diluted with H₂O (50 ml) and extracted with EtOAc. The combined organic portions are washed with brine, dried (MgSO₄) and concentrated in vacuo. The residue is purified by chromatography on silica eluting with 0-10% MeOH in EtOAc to afford the title compound; [M+H]⁺=343/345

Example 2.2

[4-[3-(2-Methoxy-pyridin-4-yl)-imidazo[1,2-a]pyridin-6-ylamino]-cyclohexanol

This compound is prepared analogously to Example 2.1 by replacing 3-chloropyrid-4-yl boronic acid (Step 2) with the appropriate boronic acid.

Example 2.3

4-(3-(2-Furan-3-yl-pyridin-4-yl)-imidazo[1,2-a]pyridin-6-ylamino)-cyclohexanol

To [4-[3-(2-chloro-pyridin-4-yl)-imidazo[1,2-a]pyridin-6-ylamino]-cyclohexanol (Example 2.1) (1 eq, 100 mg, 0.29 mmol), 3-furyl boronic acid (1.05 eq, 0.3 mmol, 34 mg), Na₂CO₃ (2 eq, 0.58 mmol, 62 mg) in ethanol (2 ml) and H₂O (0.7 ml), under inert atmosphere is added tetakis(triphenylphosphine)palladium (0.1 eq, 0.029 mmol, 21 mg). The reaction is heated in using microwave radiation at 80° C. for 2 hours. The mixture is diluted with H₂O (5 ml) and extracted with EtOAc. The combined organic portions are washed with brine, dried (MgSO₄) and concentrated in vacuo. The residue is purified by flash chromatography on silica eluting with 0-2.5% methanol in EtOAc to afford the title compound; [M+H]+375

Examples 2.4-2.6

These examples namely,
4-(3-(2-Phenyl-pyridin-4-yl)-imidazo[1,2-a]pyridin-6-ylamino)-cyclohexanol (Ex. 2.4),
4-(3-(2-Furanyl-pyridin-4-yl)-imidazo[1,2-a]pyridin-6-ylamino)-cyclohexanol (Ex 2.5) and
4-{3-[2-(1H-Pyrazol-3-yl)-pyridin-4-yl]-imidazo[1,2-a]pyridin-6-ylamino}-cyclohexanol (Ex 2.6)
are prepared analogously to Example 2.3 by replacing 3-furyl boronic acid with the appropriate boronic acid.

Example 2.7

[4-[3-(2-Ethoxy-pyridin-4-yl)-imidazo[1,2-a]pyridin-6-ylamino]-cyclohexanol

Cs₂CO₃ (5 eq, 1.45 mmol, 480 mg) and 4A molecular sieves (400 mg) are stirred in a mixture of DMSO (5 ml) and ethanol (5 eq 0.8 ml). To this suspension is added [4-[3-(2-chloro-pyridin-4-yl)-imidazo[1,2-a]pyridin-6-ylamino]-cyclohexanol (Example 2.1) (1 eq, 100 mg, 0.29 mmol). The reaction is heated at 120° C. for 16 hours. The mixture is diluted with H₂O (20 ml) and extracted with EtOAc. The combined organic portions are washed with brine, dried (MgSO₄) and concentrated in vacuo to give a blue oil. The residue is purified by flash chromatography on silica eluting with 0-10% methanol in EtOAc The resulting residue is loaded onto a SCX-2 cartridge (resin loading 0.67 mmol/g) eluting with MeOH followed by 2M NH₃ in MeOH. The methanolic ammonia fractions are concentrated in vacuo and dried under vacuum to afford the title compound; $[M+H]^+=$ 353

Example 2.8

[2-[3-(2-Methoxy-pyridin-4-yl)-imidazo[1,2-a]pyridin-6-ylamino]-cyclohexanol

6-Chloro-3-(2-methoxy-pyridin-4-yl)-imidazo[1,2-a]pyridine (Intermediate G) (1 eq, 200 mg, 0.769 mmol), sodium tert-butoxide (2.4 eq, 1.8 mmol, 177 mg), palladium acetate (17 mg, 0.1 eq), (R)-1-[(1S)-2-(diphenylphosphino)ferrocenyl]ethyldicyclohexylphosphine (43 mg, 0.1 eq) are stirred at RT under an inert atmosphere of argon in DME (3 ml) and degassed thoroughly before adding 2-aminocyclohexanol (2 eq, 1.53 mmol, 176 mg) The reaction is heated using microwave radiation at 100° C. for 2 hours. The majority of the solvent is removed in vacuo and the resulting residue is loaded onto a SCX-2 cartridge (resin loading 0.67 mmol/g) eluting with MeOH followed by 2M NH₃ in MeOH. The methanolic ammonia fractions are concentrated in vacuo and further purified by flash chromatography (10% MeOH/ EtOAc) to afford the title compound; $[M+H]^+$=339

Example 2.9

3,6-Bis-(2-methoxy-pyridin-4-yl)-imidazo[1,2-a]pyridine

To a solution of 3-bromo-6-bromo-imidazo[1,2-a]pyridine (Intermediate H) (1 eq, 0.72 mmol, 0.2 g), 3-methoxypyrid-4-yl boronic acid (1.0 eq, 0.72 mmol, 0.11 g), Na₂CO₃ (2 eq, 1.44 mmol, 152 mg) in dioxane (45 ml) and water (13.5 ml) under inert atmosphere of argon is added bis(triphenylphosphine)palladium II chloride (0.1 eq, 0.07 mmol, 50 mg). The reaction mixture is heated at 100° C. for 2 hours. The mixture is diluted with H₂O (50 ml) and extracted with EtOAc. The combined organic portions are washed with brine, dried (MgSO₄) and concentrated in vacuo. The residue is purified by flash chromatography on silica eluting with 25-75% ethyl acetate in iso-hexane to afford the title compound; $[M+H]^+=$ 333

Example 2.10

3-[3-(2-Furan-3-yl-pyridin-4-yl)-imidazo[1,2-a]pyridin-6-yl-N-metylbenzamide

6-Chloro-3-(2-furanyl-3-yl-pyridin-4-yl)-imidazo[1,2-a] pyridine (Intermediate I) (50 mg, 0.169 mmol, 1 eq), 3-(N-Methylaminocarbonyl) phenyl boronic acid (91 mg, 0.51 mmol, 3 eq), Pd₂(dba)₃ (15 mg, 0.0169 mmol, 0.1 eq) and tri-tertbutylphosphoniumtetrafluoroborate (9.8 mg, 0.0338 mmol, 0.2 eq) are dissolved in ethanol (1.5 ml) and 2M aqueous sodium carbonate (0.4 ml) under an inert atmosphere of argon. The mixture is heated using microwave radiation at 100° C. for 30 mins. The mixture is diluted with water (1.5 ml) and ethyl acetate (1.5 ml). The organic phase is separated and loaded onto a SCX-2 cartridge (1 g resin 0.67 mmol/g) eluting with MeOH followed by 2M NH₃ in MeOH. The methanolic ammonia fractions are concentrated in vacuo and dried under vacuum to afford the title compound; $[M+H]^+=$ 395

Examples 2.11-2.20 and 2.23-2.36

These examples namely,
3-(2-Furan-3-yl-pyridin-4-yl)-6-(2-methoxy-pyridin-4-yl)-imidazo[1,2-a]pyridine (Ex 2.11),
6-Furan-3-yl-3-(2-Furan-3-yl-pyridin-4-yl)-imidazo[1,2-a]pyridine (Ex 2.12),
3-(2-Furan-3-yl-pyridin-4-yl)-6-pyridin-3-yl)-imidazo[1,2-a]pyridine (Ex 2.13),
3-(2-Furan-3-yl-pyridin-4-yl)-6-pyridin-4-yl)-imidazo[1,2-a]pyridine (Ex 2.14),
3-(2-Furan-3-yl-pyridin-4-yl)-6-(3-methoxyphenyl)-imidazo[1,2-a]pyridine (Ex 2.15),
3-(2-Furan-3-yl-pyridin-4-yl)-6-(4-methoxyphenyl)-imidazo[1,2-a]pyridine (Ex 2.16),
N-{3-[3-(2-Furan-3-yl-pyridin-4-yl)-imidazo[1,2-a]pyridin-6-yl]-phenyl}-acetamide (Ex 2.17),
4-[3-(2-Furan-3-yl-pyridin-4-yl)-imidazo[1,2-a]pyridin-6-yl]-N-methyl-benzamide (Ex 2.18),
3-(2-Furan-3-yl-pyridin-4-yl)-6-(methyl-1H-pyrazole-4-yl)-imidazo[1,2-a]pyridine (Ex 2.19) and
N-{3-[3-(2-Furan-3-yl-pyridin-4-yl)-imidazo[1,2-a]pyridin-6-yl]-phenyl}-methanesulfonamide (Ex 2.20)
3-[3-(2-Furan-3-yl)-pyridin-4-yl)-imidazo[1,2-a]pyridin-6-yl]-N-methyl-benzenesulfonamide (Ex 2.23),
3-(2-Furan-3-yl-pyridin-4-yl)-6-(1H-pyrazol-3-yl)-imidazo[1,2-a]pyridine (Ex 2.24),
4-[3-(2-Furan-3-yl-pyridin-4-yl)-imidazo[1,2-a]pyridin-6-yl]-benzamide (Ex 2.25),
N-cyclopropyl-4-[3-(2-Furan-3-yl-pyridin-4-yl)-imidazo[1,2-a]pyridin-6-yl]-benzamide (Ex 2.26),
N-{4-[3-(2-Furan-3-yl-pyridin-4-yl)-imidazo[1,2-a]pyridin-6-yl]-phenyl}-acetamide (Ex 2.27),
{4-[3-(2-Furan-3-yl-pyridin-4-yl)-imidazo[1,2-a]pyridin-6-yl]-pyrazol-1-yl}-acetic acid (Ex 2.28),
{4-[3-(2-Furan-3-yl-pyridin-4-yl)-imidazo[1,2-a]pyridin-6-yl]-benzoylamino}-acetic acid methyl ester (Ex 2.29),
{4-[3-(2-Furan-3-yl-pyridin-4-yl)-imidazo[1,2-a]pyridin-6-yl]-pyrazol-1-yl}-acetic acid methyl ester (Ex 2.30),
3-(2-Furan-3-yl-pyridin-4-yl)-6-(6-piperazin-1-yl-pyridin-3-yl)-imidazo[1,2-a]pyridine (Ex 2.31),
3-(2-Furan-3-yl-pyridin-4-yl)-6-[6-(4-methyl-piperazin-1-yl)-pyridin-3-yl]-imidazo[1,2-a]pyridine (Ex 2.32),
4-[3-(2-Furan-3-yl-pyridin-4-yl)-imidazo[1,2-a]pyridin-6-yl]-N-isopropyl-benzamide (Ex 2.33),
4-[3-(2-Furan-3-yl-pyridin-4-yl)-imidazo[1,2-a]pyridin-6-yl]-N-(2-hydroxy-ethyl)-benzamide (Ex 2.34),
N-{5-[3-(2-Furan-3-yl-pyridin-4-yl)-imidazo[1,2-a]pyridin-6-yl]-pyridin-2-yl}pyridin-2-yl}acetamide (Ex 2.35),
[3-(2-Furan-3-yl-pyridin-4-yl)-6-[1-(2-morpholin-4-yl-ethyl)-1H-pyrazol-4-yl]-imidazo[1,2-a]pyridine (Ex 2.36),
are prepared by an analogous method to 3-[3-(2-Furan-3-yl-pyridin-4-yl)-imidazo[1,2-a]pyridin-6-yl-N-metylbenzamide (Ex. 2.10) by replacing 3-(N-Methylaminocarbonyl) phenyl boronic acid with the appropriate boronic acid.

Example 2.21

(1RS,3RS)-3-[3-(2-Chloro-6-furan-3-yl-pyridin-4-yl)-imidazo[1,2-a]pyridin-6-ylamino]-cyclohexanol This compound is prepared analogously to 4-(3-(2-furan-3-yl-pyridin-4-yl)-imidazo[1,2-a]pyridin-6-ylamino)-cyclohexanol (Example 2.3) by replacing [4-[3-(2-chloro-pyridin-4-yl)-imidazo[1,2-a]pyridin-6-ylamino]-cyclohexanol (Example 2.1) with 1-(RS/RS)-3-(2,6-dichloro-pyridin-4-yl)-imidazo[1,2-a]pyridin-6-ylamino)-cyclohexanol (Intermediate J); [M+H]$^+$ 409

Example 2.22

(1RS,3RS)-3-[3-(2-tert-Butylamino-6-furan-3-yl-pyridinin-4-yl)-imidazo[1,2-a]pyridin-6-ylamino]-cyclohexanol Step 1: (1RS,3RS)-3-[3-(2-tert-Butylamino-6-chloro-pyridinin-4-yl)-imidazo[1,2-a]pyridin-6-ylamino]-cyclohexanol A solution of 1-(RS/RS)-3-(2,6-dichloro-pyridin-4-yl)-imidazo[1,2-a]pyridin-6-ylamino)-cyclohexanol (Intermediate J) (34 mg) in t-butylamine (2 ml) is heated using microwave radiation at 180° C. for 60 hrs. The resulting mixture is diluted with EtOAc and washed with water. The organic layer is separated and concentrated in vacuo to yield the title compound.

Step 2: (1RS, 3RS)-3-[3-(2-tert-Butylamino-6-furan-3-yl-pyridinin-4-yl)-imidazo[1,2-a]pyridin-6-ylamino]-cyclohexanol The title compound is prepared analogously to 4-(3-(2-furan-3-yl-pyridin-4-yl)-imidazo [1,2-a]pyridin-6-ylamino)-cyclohexanol (Example 2.3) by replacing [4-[3-(2-chloro-pyridin-4-yl)-imidazo[1,2-a]pyridin-6-ylamino]-cyclohexanol (Example 2.1) with (1RS,3RS)-3-[3-(2-tert-Butylamino-6-chloro-pyridinin-4-yl)-imidazo[1,2-a]pyridin-6-ylamino]-cyclohexanol (step 1);[M+H]$^+$ 446.

Example 2.37

[4-[3-(2-Pyrazol-1-yl-pyridin-4-yl)-imidazo[1,2-a]pyridin-6-ylamino]-cyclohexanol A mixture comprising [4-[3-(2-Chloro-pyridin-4-yl)-imidazo[1,2-a]pyridin-6-ylamino]-cyclohexanol (Example 2.1) (1 eq, 0.29 mmol, 100 mg), pyrazole (5 eq, 1.45 mmol, 99 mg) and cesium carbonate (3 eq, 0.87 mmol, 284 mg) in DMF (25 ml) is heated using microwave radiation at 145° C. for 6 hours. After cooling to room temperature, the mixture is loaded onto a SCX-2 cartridge eluting with MeOH followed by 2M NH$_3$ in MeOH. The solvent is removed in vacuo and the crude product is triturated with ethyl acetate to afford the title compound; [M+H]$^+$=375

Examples 2.38-2.39

These examples namely,
4-{3-[2-(3-Methyl-pyrazol-1-yl)-pyridin-4-yl]-imidazo[1,2-a]pyridin-6-ylamino}-cyclohexanol (Ex 2.38)
and [4-[3-(2-Pyrrol-1-yl-pyridin-4-yl)-imidazo[1,2-a]pyridin-6-ylamino]-cyclohexanol (Ex. 2.39)
are prepared by an analogous method to [4-[3-(2-Pyrazol-1-yl-pyridin-4-yl)-imidazo[1,2-a]pyridin-6-ylamino]-cyclohexanol (Ex. 2.37) by replacing pyrazole with the appropriate heterocycle.

Example 2.40

(1SR,2SR)-2-[3-(2-Furan-3-yl-pyridin-4-yl)-imidazo[1,2-a]pyridin-6-ylamino]-cyclohexanol The title compound is prepared from (1SR,2SR)-2-[3-(2-Chloro-pyridin-4-yl)-imidazo[1,2-a]pyridin-6-ylamino]-cyclohexanol (Intermediate K) and 3-furyl boronic acid using a procedure analogous to that described in Example 2.3.

Example 2.41

3-(2-Furan-3-yl-pyridin-4-yl)-6-trifluoromethyl-imidazo[1,2-a]pyridine

The title compound is prepared from 3-(2-Chloro-pyridinyl)-6-trifluoromethyl-imidazo[1,2-a]pyridine (Intermediate L) and 3-furyl boronic acid using a procedure analogous to that described in Example 2.3.

Example 2.42

3-(2-Pyrazol-1-yl-pyridin-4-yl-6-pyrimidin-5-yl-imidazo[1,2-a]pyridine

The title compound is prepared from 6-Chloro-3-(2-pyrazolyl-1-yl-pyridin-4-yl)-imidazo[1,2-a]pyridine (Intermediate M) and 5-pyrimidyl boronic acid using a procedure analogous to that described in Example 2.10.

Examples 2.43-2.53 and 2.56

The following compounds namely,
Morpholin-4-yl-{4-[3-(2-pyrazol-1-yl-pyridin-4-yl)-imidazo[1,2-a]pyridin-6-yl-phenyl}methanone (Ex. 2.43),
6-(2-Cyclopropyl-pyridin-4-yl)-3-(2-pyrazol-1-yl-pyridin-4-yl)-imidazo[1,2-a]pyridine (Ex. 2.44),
Dimethyl-{5-[3-(2-pyrazol-1-yl-pyridin-4-yl)-imidazo[1,2-a]pyridin-6-yl]-pyridin-2-yl}-amine (Ex. 2.45),
N-{3-[3-(2-Pyrazol-1-yl-pyridin-4-yl)-imidazo[1,2-a]pyridin-6-yl]-phenyl}-methanesulfonamide (Ex 2.46),
6-(1H-pyrazol-3-yl)-3-(2-pyrazol-1-yl-pyridin-4-yl)-imidazo[1,2-a]pyridine (2.47),
N-(2-hydroxyethyl)-4-[3-(2-Pyrazol-1-yl-pyridin-4-yl)-imidazo[1,2-a]pyridin-6-yl]-benzenesulfonamide (Ex 2.48),
N-(Cyclopropyl)-4-[3-(2-Pyrazol-1-yl-pyridin-4-yl)-imidazo[1,2-a]pyridin-6-yl]-benzenesulfonamide (Ex 2.49),
N-(tert-Butyl)-4-[3-(2-Pyrazol-1-yl-pyridin-4-yl)-imidazo[1,2-a]pyridin-6-yl]-benzenesulfonamide (Ex 2.50),
{4-[3-(2-Pyrazol-1-yl-pyridin-4-yl)-imidazo[1,2-a]pyridin-6-yl]-benzoylamino}-acetic acid methyl ester (Ex 2.51),
4-[3-(2-Pyrazol-1-yl-pyridin-4-yl)-imidazo[1,2-a]pyridin-6-yl]-benzamide (Ex 2.52),
N-{4-[3-(2-Pyrazol-1-yl-pyridin-4-yl)-imidazo[1,2-a]pyridin-6-yl]-phenyl}-acetamide (Ex 2.53) and
6-[2-(4-Methyl-piperazin-1-yl)-pyridin-4-yl]-3-(2-pyrazol-1-yl-pyridin-4-yl)-imidazo[1,2-a]pyridine (Ex 2.56),
are prepared by an analogous method to 3-(2-Pyrazol-1-yl-pyridin-4-yl-6-pyrimidin-5-yl-imidazo[1,2-a]pyridine (Ex. 2.42) by replacing 5-pyrimidyl boronic acid with the appropriate boronic acid

Example 2.54

2-[3-(2-Furan-3-yl-pyridin-4-yl)-imidazo[1,2-a]pyridin-6-yl]-propanol-2-ol 3-(2-Furan-3-yl-pyridin-4-yl)-imidazo[1,2-a]pyridine-6-carboyxlic acid methyl ester (Intermediate N) (20 mg, 0.063 mmol) is dissolved in THF (6 ml) and treated with 3.0M methyl magnesium bromide in ether (0.2 ml, 10 eq). After stirring at room temperature overnight, the reaction is quenched by the addition of aqueous ammonium chloride and diluted with ether. The organic portion is dried (MgSO$_4$) and evaporated to afford the title compound.

Example 2.55

(1SR,3SR)-3-[3-(2-Furan-3-yl-6-methoxy-pyridin-4-yl)-imidazo[1,2-a]pyridin-6-ylamino)-cyclohexanol The title compound is prepared from (1SR,3SR)-3-[3-(2-Chloro-6-methoxy-pyridin-4-yl)-imidazo[1,2-a]pyridin-6-ylamino)-cyclohexanol (Intermediate O) and 3-furyl boronic acid using a procedure analogous to that described in Example 2.3.

Example 2.57

(1SR,3SR)-3-[3-(2-Fluoro-6-furan-3-yl-pyridin-4-yl)-imidazo[1,2-a]pyridin-6-ylamino]-cyclohexanol The title compound is prepared from (1SR,3SR)-3-[3-(2-Chloro-6-methoxy-pyridin-4-yl)-imidazo[1,2-a]pyridin-6-ylamino)-cyclohexanol (Intermediate P) and 3-furyl boronic acid using a procedure analogous to that described in Example 2.3.

Example 2.58

(1SR,3SR)-3-[3-(2-Cyclopent-1-enyl-pyridin-4-yl)-imidazo[1,2-a]pyridin-6-ylamino)-cyclohexanol The title compound is prepared from (1SR,3SR)-3-[3-(2-Chloro-pyridin-4-yl)-imidazo[1,2-a]pyridin-6-ylamino)-cyclohexanol (Intermediate Q) and Cyclopent-1-enyl boronic acid using a procedure analogous to that described in Example 2.3.

Examples 2.59-2.60 and 2.62-2.70

The following compounds namely,
(1SR,3SR)-3-{3-{2-(2-Methyl-furan-3-yl-pyridin-4-yl]-imidazo[1,2-a]pyridin-6-ylamino}-cyclohexanol (Ex. 2.59),
(1SR,3SR)-3-{3-{2-(5-Methyl-furan-3-yl-pyridin-4-yl]-imidazo[1,2-a]pyridin-6-ylamino}-cyclohexanol (Ex. 2.60),
(1SR,3SR)-3-[3-(2-Isoxazol-4-yl-pyridin-4-yl)-imidazo[1,2-a]pyridin-6-ylamino]-cyclohexanol (Ex. 2.62),
(1SR,3SR)-3-{3-{2-(2H-Pyrazol-3-yl)-pyridin-4-yl]-imidazo[1,2-a]pyridin-6-ylamino}-cyclohexanol (Ex. 2.63),
(1SR,3SR)-3-{3-{2-(1H-pyrazol-4-yl)-pyridin-4-yl]-imidazo[1,2-a]pyridin-6-ylamino}-cyclohexanol (Ex. 2.64),
(1SR,3SR)-3-{3-{2-(1-Methyl-1H-pyrazol-4-yl)-pyridin-4-yl]-imidazo[1,2-a]pyridin-6-ylamino}-cyclohexanol (Ex. 2.65),
(1SR,3SR)-3-{3-{2-(1-Ethyl-1H-pyrazol-4-yl)-pyridin-4-yl]-imidazo[1,2-a]pyridin-6-ylamino}-cyclohexanol (Ex. 2.66),
(1SR,3SR)-3-{3-{2-(1-Methyl-1H-pyrrol-2-yl)-pyridin-4-yl]-imidazo[1,2-a]pyridin-6-ylamino}-cyclohexanol (Ex. 2.67),
(1SR,3SR)-3-{3-{2-(2,5-Dimethyl-thiophen-3-yl)-pyridin-4-yl]-imidazo[1,2-a]pyridin-6-ylamino}-cyclohexanol (Ex. 2.68),
(1SR,3SR)-3-{3-{2-(1H-pyrrol-2-yl)-pyridin-4-yl]-imidazo[1,2-a]pyridin-6-ylamino}-cyclohexanol (Ex. 2.69) and
(1SR,3SR)-3-{3-{2-(1,3-Dimethyl-1H-pyrazol-4-yl)-pyridin-4-yl]-imidazo[1,2-a]pyridin-6-ylamino}-cyclohexanol (Ex. 2.70)
are prepared by an analogous method to (1SR,3SR)-3-[3-(2-Cyclopent-1-enyl-pyridin-4-yl)-imidazo[1,2-a]pyridin-6-ylamino)-cyclohexanol (Ex. 2.58) by replacing cyclopent-1-enyl boronic acid with the appropriate boronic acid.

Example 2.61

(1SR,3SR)-3-{3-{2-(3-Trifluoromethyl-pyrazol-1-yl)-pyridin-4-yl]-imidazo[1,2-a]pyridin-6-ylamino}-cyclohexanol The title compound is prepared from (1SR,3SR)-3-[3-(2-Chloro-pyridin-4-yl)-imidazo[1,2-a]pyridin-6-ylamino)-cyclohexanol (Intermediate Q) and 3 trifluoromethylpyrazole using a procedure analogous to that described in example 2.37.

Examples 2.71 and 2.72

The following compounds namely,
(1SR,3SR)-3-{3-{2-(3-Chloro-pyrazol-1-yl)-pyridin-4-yl]-imidazo[1,2-a]pyridin-6-ylamino}-cyclohexanol (Ex. 2.71) and
(1SR,3SR)-3-[3-(2-[1,2,3]-Triazol-2-yl-pyridin-4-yl)-imidazo[1,2-a]pyridin-6-ylamino]-cyclohexanol (Ex. 2.72)
are prepared by an analogous method to (1SR,3SR)-3-{2-(3-Trifluoromethyl-pyrazol-1-yl)-pyridin-4-yl]-imidazo[1,2-a]pyridin-6-ylamino}-cyclohexanol (Ex. 2.61) by replacing 3-trifluoromethylpyrazole with the appropriate heterocycle.

Example 2.73

(1SR,3RS)-3-[3-(2-Furan-3-yl-pyridin-4-yl)-imidazo[1,2-a]pyridin-6-ylamino]-cyclohexanol The title compound is prepared from (1SR,3RS)-3-[3-(2-Chloro-pyridin-4-yl)-imidazo[1,2-a]pyridin-6-ylamino)-cyclohexanol (Intermediate R) and 3-furyl boronic acid using a procedure analogous to that described in Example 2.3.

Example 2.74

(1SR,3RS)-3-[3-(2-Chloro-6-furan-3-yl-pyridin-4-yl)-imidazo[1,2-a]pyridin-6-ylamino]-cyclohexanol The title compound is prepared from (1SR,3RS)-3-[3-(2,6-dichloro-pyridin-4-yl)-imidazo[1,2-a]pyridin-6-ylamino)-cyclohexanol (Intermediate S) and 3-furyl boronic acid using a procedure analogous to that described in Example 2.3.

Example 2.75

(1SR,3RS)-3-[3-(2-Fluoro-6-furan-3-yl-pyridin-4-yl)-imidazo[1,2-a]pyridin-6-ylamino]-cyclohexanol The title compound is prepared from (1SR,3RS)-3-[3-(2-Chloro-6-fluoro-pyridin-4-yl)-imidazo[1,2-a]pyridin-6-ylamino)-cyclohexanol (Intermediate T) and 3-furyl boronic acid using a procedure analogous to that described in Example 2.3.

Example 2.76

(1S,3S)-3-[3-(2-Furan-3-yl-pyridin-4-yl)-imidazo[1,2-a]pyridin-6-ylamino]-cyclohexanol The title compound is prepared from (S/S)-3-(2-Chloro-pyridin-4-yl)-imidazo[1,2-a]pyridin-6-ylamino)-cyclohexanol (Intermediate U) and 3-furyl boronic acid using a procedure analogous to that described in Example 2.3.

Example 2.77

(1S,3S)-3-[3-(2-Pyrazol-1-yl-pyridin-4-yl)-imidazo[1,2-a]pyridin-6-ylamino]-cyclohexanol The title compound is prepared from (S/S)-3-(2-Chloro-pyridin-4-yl)-imidazo[1,2-a]pyridin-6-ylamino)-cyclohexanol (Intermediate U) and pyrazole using a procedure analogous to that described in example 2.37.

Examples 2.78-2.80

The following compounds namely,
(1S,3S)-3-{3-[2-(3-Methyl-pyrazol-1-yl-pyridin-4-yl]-imidazo[1,2-a]pyridin-6-ylamino}-cyclohexanol (Ex. 2.78),
(1S,3S)-3-{3-[2-(3-Cyclopropyl-pyrazol-1-yl-pyridin-4-yl]-imidazo[1,2-a]pyridin-6-ylamino}-cyclohexanol (Ex. 2.79) and
(1S,3S)-3-{3-[2-(3,5-Dimethyl-pyrazol-1-yl-pyridin-4-yl]-imidazo[1,2-a]pyridin-6-ylamino}-cyclohexanol (Ex. 2.80)
are prepared by an analogous method to (1S,3S)-3-[3-(2-Pyrazol-1-yl-pyridin-4-yl)-imidazo[1,2-a]pyridin-6-ylamino]-cyclohexanol (Ex. 2.77) by replacing pyrazole with the appropriate heterocycle.

Example 2.81

(1RS,3RS)-3-[3-(3-Pyrazol-1-yl-phenyl)-imidazo[1,2-a]pyridin-6-ylamino]-cyclohexanol This compound is prepared from (1RS,3RS)-3-(3-Bromo-imidazo[1,2-a]pyridin-6-ylamino)-cyclohexanol (Intermediate J [step 1]) and 3-(1H-pyrazol-1-yl)-phenylboronic acid analogously to Example 2.1 (step 2)

Example 2.82

(1R,3R)-3-[3-(2-Furan-3-yl-pyridin-4-yl)-imidazo[1,2-a]pyridin-6-ylamino]-cyclohexanol The title compound is prepared from (R/R)-3-(2-Chloro-pyridin-4-yl)-imidazo[1,2-a]pyridin-6-ylamino)-cyclohexanol (Intermediate V) and 3-furyl boronic acid using a procedure analogous to that described in Example 2.3.

Example 2.83

(1R,3R)-3-[3-(2-Pyrazol-1-yl-pyridin-4-yl)-imidazo[1,2-a]pyridin-6-ylamino]-cyclohexanol The title compound is prepared from —(R/R)-3-(2-Chloro-pyridin-4-yl)-imidazo[1,2-a]pyridin-6-ylamino)-cyclohexanol (Intermediate V) and pyrazole using a procedure analogous to that described in Example 2.37.

Examples 2.84-2.86

The following compounds namely
(1R,3R)-3-{3-[2-(3-Methyl-pyrazol-1-yl-pyridin-4-yl]-imidazo[1,2-a]pyridin-6-ylamino}-cyclohexanol (Ex. 2.84),
(1R,3R)-3-{3-[2-(3,5-Dimethyl-pyrazol-1-yl-pyridin-4-yl]-imidazo[1,2-a]pyridin-6-ylamino}-cyclohexanol (Ex. 2.85) and
(1R,3R)-3-{3-[2-(3-Cyclopropyl-pyrazol-1-yl-pyridin-4-yl]-imidazo[1,2-a]pyridin-6-ylamino}-cyclohexanol (Ex. 2.86)
are prepared by an analogous method to (1S,3S)-3-[3-(2-Pyrazol-1-yl-pyridin-4-yl)-imidazo[1,2-a]pyridin-6-ylamino]-cyclohexanol (Ex. 2.77) by replacing pyrazole with the appropriate heterocycle.

Example 2.87

(1SR,3RS)-3-[3-(2-Furan-3-yl-pyridin-4-yl)-imidazo[1,2-a]pyridin-6-ylamino]-1-methyl-cyclohexanol The title compound is prepared from (RS/SR)-3-[3-(2-Chloro-pyridin-4-yl)-imidazo[1,2-a]pyridin-6-ylamino]-1-methyl-cyclohexanol (Intermediate W) and 3-furyl boronic acid using a procedure analogous to that described in Example 2.3.

Example 2.88

(1SR,3RS)-1-Methyl-3-[3-(2-pyrazol-1-yl-pyridin-4-yl)-imidazo[1,2-a]pyridin-6-ylamino]-cyclohexanol The title compound is prepared from (RS/SR)-3-[3-(2-Chloro-pyridin-4-yl)-imidazo[1,2-a]pyridin-6-ylamino]-1-methyl-cyclohexanol (Intermediate W) and pyrazole using a procedure analogous to that described in Example 2.37.

Example 2.89

(1SR,3RS)-1-Methyl-3-{3-[2-(3-trifluoromethylpyrazol-1-yl)-pyridin-4-yl]-imidazo[1,2-a]pyridin-6-ylamino}-cyclohexanol The title compound is prepared from (RS/SR)-3-[3-(2-Chloro-pyridin-4-yl)-imidazo[1,2-a]pyridin-6-ylamino]-1-methyl-cyclohexanol (Intermediate W) and 3-trifluoromethyl pyrazole using a procedure analogous to that described in Example 2.37.

Example 2.90

(1SR,3RS)-1-Methyl-3-[3-(2-Phenyl-pyridin-4-yl)-imidazo[1,2-a]pyridin-6-ylamino]-cyclohexanol The title compound is prepared from (RS/SR)-3-[3-(2-Chloro-pyridin-4-yl)-imidazo[1,2-a]pyridin-6-ylamino]-1-methyl-cyclohexanol (Intermediate W) and phenyl boronic acid using a procedure analogous to that described in Example 2.3.

Example 2.91

(1RS,3RS)-3-{3-[2-(3-Cyclopropyl-pyrazol-1-yl)-pyridin-4-yl]-imidazo[1,2-a]pyridin-6-ylamino}-1-methyl-cyclohexanol The title compound is prepared from (RS/RS)-3-[3-(2-Chloro-pyridin-4-yl) -imidazo[1,2-a]pyridin-6-ylamino]-1-methyl-cyclohexanol (Intermediate X) and 3-cyclopropyl pyrazole using a procedure analogous to that described in Example 2.37.

Example 2.92

(1RS,3RS)-3-{3-[2-(3,5-Dimethyl-pyrazol-1-yl)-pyridin-4-yl]-imidazo[1,2-a]pyridin-6-ylamino}-1-methyl-cyclohexanol The title compound is prepared from (RS/RS)-3-[3-(2-Chloro-pyridin-4-yl) -imidazo[1,2-a]pyridin-6-ylamino]-1-methyl-cyclohexanol (Intermediate X) and 3,5-Dimethyl pyrazole using a procedure analogous to that described in Example 2.37.

Example 2.93 and 2.97

(1S,3S)-1-Methyl-3-[3-(2-pyrazol-1-yl-pyridin-4-yl)-imidazo[1,2-a]pyridin-6-ylamino]-cyclohexanol (Ex. 2.93) and (1R,3R)-1-Methyl-3-[3-(2-pyrazol-1-yl-pyridin-4-yl)-imidazo[1,2-a]pyridin-6-ylamino]-cyclohexanol (Ex. 2.97)

(1RS,3RS)-1-Methyl-3-[3-(2-pyrazol-1-yl-pyridin-4-yl)-imidazo[1,2-a]pyridin -6-ylamino]-cyclohexanol is prepared from (RS/RS)-3-[3-(2-Chloro-pyridin-4-yl) -imidazo[1,2-a]pyridin-6-ylamino]-1-methyl-cyclohexanol (Intermediate X) and pyrazole using a procedure analogous to that described in Example 2.37 and subsequently separated by chiral chromatography {Mobile Phase:40% methanol+0.1% DEA/60% $CO_2$:Column: Chiralpak AD-H, 250×10 mm id, 5 μm} to yield (1S,3S)-1-Methyl-3-[3-(2-pyrazol-1-yl-pyridin-4-yl)-imidazo[1,2-a]pyridin-6-ylamino]-cyclohexanol (Ex. 2.93) and (1R,3R)-1-Methyl-3-[3-(2-pyrazol-1-yl-pyridin-4-yl)-imidazo[1,2-a]pyridin-6-ylamino]-cyclohexanol (Ex. 2.97).

Example 2.94 and 2.96

(1S,3S)-3-[3-(2-Furan-3-yl-pyridin-4-yl)-imidazo[1,2-a]pyridin-6-ylamino]-1-methyl-cyclohexanol (Ex. 2.94) and (1R,3R)-3-[3-(2-Furan-3-yl-pyridin-4-yl)-imidazo[1,2-a]pyridin-6-ylamino]-1-methyl-cyclohexanol (Ex. 2.96)

(1RS,3RS)-3-[3-(2-Furan-3-yl-pyridin-4-yl)-imidazo[1,2-a]pyridin-6-ylamino]-1-methyl-cyclohexanol is prepared from (RS/RS)-3-[3-(2-Chloro-pyridin-4-yl)-imidazo[1,2-a]pyridin-6-ylamino]-1-methyl-cyclohexanol (Intermediate X) and 3-furyl boronic acid using a procedure analogous to that described in Example 2.3 and subsequently separated by chiral chromatography {Mobile Phase:40% methanol+0.1% DEA/60% $CO_2$:Column: Chiralpak AD-H, 250×10 mm id, 5 μm} to yield (1S,3S)-3-[3-(2-Furan-3-yl-pyridin-4-yl)-imidazo[1,2-a]pyridin-6-ylamino]-1-methyl-cyclohexanol (Ex. 2.94) and (1R,3R)-3-[3-(2-Furan-3-yl-pyridin-4-yl)-imidazo[1,2-a]pyridin-6-ylamino]-1-methyl-cyclohexanol (Ex. 2.96)

Example 2.95 and 2.98

(1S,3S)-1-Methyl-3-{3-[2-(3-methyl-pyrazol-1-yl-pyridin-4-yl]-imidazo[1,2-a]pyridin-6-ylamino]-cyclohexanol (Ex. 2.95) and (1R,3R)-1-Methyl-3-{3-[3-(3-methyl-pyrazol-1-yl-pyridin-4-yl)-imidazo[1,2-a]pyridin-6-ylamino]-cyclohexanol (Ex. 2.98)

(1RS,3RS)-1-Methyl-3-{3-[2-(3-methyl-pyrazol-1-yl-pyridin-4-yl]-imidazo[1,2-a]pyridin-6-ylamino]-cyclohexanol is prepared from (RS/RS)-3-[3-(2-Chloro-pyridin-4-yl)-imidazo[1,2-a]pyridin-6-ylamino]-1-methyl-cyclohexanol (Intermediate X) and 3-methylpyrazole using a procedure analogous to that described in example 2.37, and subsequently separated by chiral chromatography {Mobile Phase:40% methanol+0.1% DEA/60% $CO_2$:Column: Chiralpak AD-H, 250×10 mm id, 5 μm} to yield (1S,3S)-1-Methyl-3-[3-(2-pyrazol-1-yl-pyridin-4-yl)-imidazo[1,2-a]pyridin-6-ylamino]-cyclohexanol (Ex. 2.95) and (1R,3R)-1-Methyl-3-[3-(2-pyrazol-1-yl-pyridin-4-yl)-imidazo[1,2-a]pyridin-6-ylamino]-cyclohexanol (Ex. 2.98).

Preparation of Intermediate Compounds

Intermediate AA

7-Chloro-3-(3-Pyrazol-1-yl-phenyl)-imidazo[1,2-a]pyridine

Step AA1: 7-chloro-imidazo-[1,2-a]-pyridine

4-Chloro-pyridin-2-ylamine (1 eq, 38.9 mmol, 5 g) is added to a solution of chloroacetic aldehyde (3 eq, 117 mmol, 15.1 ml) in EtOH (60 ml). $NaHCO_3$ (2 eq, 77.8 mmol, 6.53 g) is added and the reaction mixture is heated at reflux for 17 h. The solvent is removed in vacuo and the product is purified by flash column chromatography eluting with 8:2 DCM/MeOH to afford 7-chloro-imidazo-[1,2-a]-pyridine as a red solid; $[M+H]^+=153$ Step AA2: 3-Bromo-7-chloro-imidazo-[1,2-a]-pyridine 7-Chloro-imidazo-[1,2-a]-pyridine (1 eq, 38.9 mmol, 5.93 g) is dissolved in DMF (20 ml) at 0° C. and NBS (1.1 eq, 42.8 mmol, 7.61 g) is added. The reaction mixture is stirred for 1 h at 0° C. and is diluted with EtOAc. The reaction mixture is washed with $NaHCO_3$ and brine, dried over $MgSO_4$, filtered and evaporated. The product is purified by flash column chromatography eluting with 8:2 DCM/MeOH to afford 3-bromo-7-chloro-imidazo-[1,2-a]-pyridine as a brown solid; $[M+H]^+=232$ Step AA3: 7-Chloro-3-(3-pyrazol-1-yl-phenyl)-imidazo[1,2-a]pyridine 3-Bromo-7-chloro-imidazo-[1,2-a]-pyridine (1 eq, 2.59 mmol, 600 mg) and 3-(1H-pyrazolyl)-phenylboronic acid (1.2 eq, 1.04 mmol, 195 mg) are dissolved in DME (5 ml) and water (1.5 ml) and $Na_2CO_3$ (0.65 eq, 1.68 mmol, 209 mg) is added. $PdCl_2(PPh_3)_2$ (0.04 eq, 0.104 mmol, 72.8 mg) is added and the reaction mixture is heated using microwave radiation at 120° C. for 10 min. At the completion of this time the solvent is removed in vacuo and the reaction mixture is purified by flash column chromatography eluting with 9:1 DCM/MeOH to yield 7-chloro-3-(3-pyrazol-1-yl -phenyl)-imidazo[1,2-a]pyridine as a brown solid; $[M+H]^+=295$ These examples namely,
3-(7-Chloro-imidazo[1,2-a]pyridine-3-yl)-benzamide (Intermediate AB)
7-Chloro-3-[3-(3-methyl-pyrazol-1-yl)-phenyl]-imidazo[1,2-a]pyridine (Intermediate AC) and
7-Chloro-3-[2-(1-methyl-1H-pyrazol-4-yl)-pyridin-4-yl]-imidazo[1,2-a]pyridine (Intermediate AD)
are prepared analogously to 7-Chloro-3-(3-pyrazol-1-yl-phenyl)-imidazo[1,2-a]pyridine (Intermediate AA) by replacing 3-1H-pyrazolyl-phenylboronic acid (step AA3) with the appropriate boronic acid.

Intermediate DA

7-Chloro-3-(2-phenyl-pyridin-4-yl)-imidazo[1,2-a]pyridine

Step DA1: 7-Chloro-3-(2-chloro-pyridin-4-yl)-imidazo[1,2-a]pyridine

3-Bromo-7-chloro-imidazo-[1,2-a]-pyridine (1 eq, 6.48 mmol, 1.5 g) and 2-chloro-pyridine-4-boronic acid (1 eq, 6.48 mmol, 1.02 g) are dissolved in DME (6 ml) and water (2 ml) and $Na_2CO_3$ (2 eq, 13.0 mmol, 1.61 g) is added. $PdCl_2(PPh_3)_2$ (0.06 eq, 0.389 mmol, 273 mg) is added and the reaction mixture is heated using microwave radiation at 120° C. for 10 min. At the completion of this time the solvent is removed in vacuo and the reaction mixture is purified by flash column chromatography eluting with 8:2 DCM/MeOH to yield 7-chloro-3-(2-chloro-pyridin-4-yl)-imidazo[1,2-a]pyridine as an orange solid; $[M+H]^+=265$ Step DA2: 7-Chloro-3-(2-phenyl-pyridin-4-yl)-imidazo[1,2-a]pyridine 7-Chloro-3-(2-chloro-pyridin-4-yl)-imidazo[1,2-a]pyridine (1 eq, 1.136 mmol, 300 mg) and phenyl boronic acid (1 eq, 1.136 mmol, 138 mg) are dissolved in DME (3 ml) and water (1 ml) and $Na_2CO_3$ (2 eq, 2.27 mmol, 282 mg) is added. $PdCl_2(PPh_3)_2$ (0.1 eq, 0.114 mmol, 79.7 mg) is added and the reaction mixture is heated using microwave radiation at 120° C. for 10 min. At the completion of this time the solvent is removed in vacuo and the reaction mixture is purified by flash column chromatography eluting with 8:2 DCM/MeOH to yield 7-chloro-3-(2-phenyl-pyridin-4-yl)-imidazo[1,2-a]pyridine as a yellow solid; $[M+H]^+=306$ These examples namely,
7-Chloro-3-[2-(4-fluoro-phenyl)-pyridin-4-yl]-imidazo[1,2-a]pyridine (Intermediate DB),
7-Chloro-3-(2-m-tolyl-pyridin-4-yl)-imidazo[1,2-a]pyridine (Intermediate DC),
7-Chloro-3-[2-(2-fluoro-phenyl)-pyridin-4-yl]-imidazo[1,2-a]pyridine (Intermediate DD),
7-Chloro-3-(2-cyclohex-1-enyl-pyridin-4-yl)-imidazo[1,2-a]pyridine (Intermediate DE),
7-Chloro-3-[3-(2-methyl-pyrrolidin-1-yl)-phenyl]-imidazo[1,2-a]pyridine (Intermediate DF),
7-Chloro-3-[2-(4,4-dimethyl-cyclopent-1-enyl)-pyridin-4-yl]-imidazo[1,2-a]pyridin (Intermediate DG),
7-Chloro-3-[2-(3-chloro-phenyl)-pyridin-4-yl]-imidazo[1,2-a]pyridine (Intermediate DH),
7-Chloro-3-[2-(3-fluoro-phenyl)-pyridin-4-yl]-imidazo[1,2-a]pyridine (Intermediate DI),
7-Chloro-3-(2-cyclopent-1-enyl-pyridin-4-yl)-imidazo[1,2-a]pyridine (Intermediate DJ),
7-Chloro-3-[2-(2,4-difluoro-phenyl)-pyridin-4-yl]-imidazo[1,2-a]pyridine (Intermediate DK),
7-Chloro-3-(3-pyrrolidin-1-yl-phenyl)-imidazo[1,2-a]pyridine (Intermediate DL),
7-Chloro-3-[2-(3-methyl-cyclopent-1-enyl)-pyridin-4-yl]-imidazo[1,2-a]pyridine (Intermediate DM) and
7-Chloro-3-[2-(3-chloro-phenyl)-pyridin-4-yl]-imidazo[1,2-a]pyridine (Intermediate DN)
are prepared analogously to 7-chloro-3-(2-phenyl-pyridin-4-yl)-imidazo[1,2-a]pyridine (Intermediate DA) by replacing phenylboronic acid with the appropriate boronic acid.

Intermediate EA 3-(3-Bromo-imidazo[1,2-a]pyridin-7-yl)-N-methyl-benzamide

Step EA1: 7-Bromo-imidazo-[1,2-a]-pyridine

4-Bromo-pyridin-2-ylamine (1 eq, 5.78 mmol, 1 g) is added to a solution of chloroacetic aldehyde (5 eq, 28.9 mmol, 5 ml) in EtOH (25 ml). $NaHCO_3$ (2 eq, 11.6 mmol, 971 g) is then added and the reaction mixture is heated at reflux for 17 h. The solvent is then removed in vacuo and the product is purified by flash column chromatography eluting with 9:1 DCM/MeOH to afford 7-bromo-imidazo-[1,2-a]-pyridine as a brown solid; $[M+H]^+=198$ Step EA2: 3-Imidazo[1,2-a]pyridine-7-yl-N-methyl-benzamide 7-Bromo-imidazo-[1,2-a]-pyridine (1 eq, 0.5 mmol, 100 mg) and (3-methylamino carbonylphenyl)boronic acid (1.1 eq, 0.558 mmol, 99.9 mg) are dissolved in DME (3 ml) and water (0.8 ml) and $Na_2CO_3$ (3 eq, 1.52 mmol, 161 mg) is added. $PdCl_2(PPh_3)_2$ (0.05 eq, 0.025 mmol, 17.8 mg) is then added and the reaction mixture is heated using microwave radiation at 120° C. for 10 min. At the completion of this time the solvent is removed in vacuo and the reaction mixture is purified by flash column chromatography eluting with 9:1 DCM/MeOH to yield 3-imidazo[1,2-a]pyridine-7-yl-N-methyl-benzamide as a brown solid; $[M+H]^+=252$ Step EA3: 3-(3-Bromo-imidazo[1,2-a]pyridin-7-yl)-N-methyl-benzamide 3-Imidazo[1,2-a]pyridine-7-yl-N-methyl-benzamide (1 eq, 0.398 mmol, 100 mg) is dissolved in DMF (4 ml) at 0° C. and NBS (1.1 eq, 0.438 mmol, 77.9 mg) is added. The reaction mixture is stirred for 1 h at 0° C. and then is diluted with EtOAc. The reaction mixture is washed with $NaHCO_3$ and brine, dried over $MgSO_4$, filtered and evaporated. The product is purified by flash column chromatography eluting with 8:2 DCM/MeOH to afford 3-(3-bromo-imidazo[1,2-a]pyridin-7-yl)-N-methyl-benzamide as a brown solid; $[M+H]^+=331$ Intermediate EB 3-Bromo-7-pyridin-4-yl-imidazo[1,2-a]pyridine This compound is prepared analogously to 3-(3-Bromo-imidazo[1,2-a]pyridin-7-yl)-N-methyl-benzamide (Intermediate EA) by replacing (3-methylaminocarbonylphenyl)boronic acid (step EA2) with 4-pyridine boronic acid.

Intermediate F

3-Bromo-6-iodo-imidazo[1,2-a]pyridine

Step F1: 6-Iodo-imidazo[1,2-a]pyridine

To a solution of 50% aq. chloroacetaldehyde (1.5 eq, 125 mmol, 16 ml) in ethanol (625 ml) is added 2-amino-5-iodo-pyridine (1 eq, 113 mmol, 25 g) at room temperature. The reaction mixture is heated at reflux for 18 hours. The solvent is removed in vacuo and the crude product is dissolved in water (400 ml). The aqueous solution is treated with sodium bicarbonate to pH=8 and extracted with DCM (3×250 ml). The organic portion is dried (MgSO$_4$) and evaporated to give a beige solid of the title compound. $^1$H nmr (CDCl$_3$) 8.44 (1H, s), 7.60 (1H, s), 7.53 (1H, s), 7.42 (1H, d, J=9.4 Hz), and 7.33 (1H, d, J=9.58 Hz).

Step F2: 3-Bromo-6-iodo-imidazo[1,2-a]pyridine

To a mixture comprising 6-iodo-imidazo[1,2-a]pyridine (1 eq, 95 mmol, 23.3 g) in acetic acid (220 ml) under an inert atmosphere of argon is added dropwise bromine (1 eq, 95 mmol, 4.8 ml). After stirring at room temperature for 1 hour, the reaction mixture is filtered. The resulting solid is suspended in DCM (1% MeOH) (500 ml) and washed with 4N sodium hydroxide (100 ml). When the solid dissolves, the organic layer is separated, dried (MgSO$_4$) and evaporated to give a beige solid; [M+H]$^+$323 (325).

Intermediate G

6-Chloro-3-(2-methoxy-pyridin-4-yl)-imidazo[1,2-a]pyridine

Step G1: 6-chloro-imidazo[1,2-a]pyridine

To a solution of 50% aq. chloroacetaldehyde (1.1 eq, 291 mmol, 37 ml) in ethanol (700 ml) is added 3-amino-6-chloro-pyridine (1 eq, 264 mmol, 34 g) at room temperature. The reaction mixture is refluxed for 3 hours. The solvent is removed in vacuo and the crude product is dissolved in water (400 ml). The aqueous solution is treated with sodium bicarbonate to pH=8 and extracted with dcm (3×250 ml), the organic layer is dried (MgSO$_4$) and evaporated to give a brown solid (39.2 g) 6-chloro-imidazo[1,2-a]pyridine; [M+H]$^+$153(155)

Step G2: 3-Bromo-6-chloro-imidazo[1,2-a]pyridine

To 6-chloro-imidazo[1,2-a]pyridine (1 eq, 253 mmol, 39 g) in acetic acid (500 ml) under inert atmosphere, is added dropwise bromine (1 eq, 253 mmol, 13 ml). After 1 hour stirring at room temperature, the reaction mixture is filtered and to give a beige solid (64 g) 3-Bromo-6-chloro-imidazo[1,2-a]pyridine hydrobromide; [M+H]$^+$232 (234)

Step G3: 6-Chloro-3-(2-methoxy-pyridin-4-yl)-imidazo[1,2-a]pyridine

To a solution of 3-bromo-6-chloro-imidazo[1,2-a]pyridine (1 eq, 0.72 mmol, 0.2 g), 2-methoxypyrid-4-yl boronic acid (1.0 eq, 0.72 mmol, 0.11 g), Na$_2$CO$_3$ (2 eq, 1.44 mmol, 0.152 g) in dioxane (0.6 ml) and water (0.2 ml), under an inert atmosphere of argon is added bis(triphenylphosphine)palladium II chloride (50 mg). The reaction mixture is heated using microwave radiation at 100° C. for 2 hours. The mixture is diluted with H$_2$O (50 ml) and extracted with EtOAc. The combined organic portions are washed with brine, dried (MgSO$_4$) and concentrated in vacuo. The residue is purified by flash chromatography on silica eluting with 0-25% EtOAc in iso-hexane to afford the title compound; [M+H]$^+$=260 (262).

Intermediate H

3-Bromo-6-bromo-imidazo[1,2-a]pyridine

Step H1: 6-bromo-imidazo[1,2-a]pyridine

To a solution of 50% aq. chloroacetaldehyde (1.1 eq, 158 mmol, 20 ml) in ethanol (625 ml) is added 3-amino-6-bromo-pyridine (1 eq, 143 mmol, 25 g) at room temperature. The reaction mixture is heated at reflux for 18 hours. The solvent is removed in vacuo and the crude product is dissolved in water (400 ml). The aqueous solution is treated with sodium bicarbonate to pH=8 and extracted with DCM (3×250 ml). The organic layer is dried (MgSO$_4$) and evaporated to give the title compound as a beige solid.

Step H2: 3-Bromo-6-bromo-imidazo[1,2-a]pyridine

To 6-bromo-imidazo[1,2-a]pyridine (1 eq, 96 mmol, 19 g) in acetic acid (200 ml) under an inert atmosphere of argon is added dropwise bromine (1 eq, 96 mmol, 4.9 ml). After stirring at room temperature for 1 hour, the reaction mixture is filtered to afford the title compound as a beige solid; [M+H]$^+$=275/277/278

Intermediate I

6-Chloro-3-(2-furanyl-3-yl-pyridin-4-yl)-imidazo[1,2-a]pyridine

Step I1: 6-Chloro-3-(2-chloro-pyridin-4-yl)-imidazo[1,2-a]pyridine

To a solution of 3-bromo-6-chloro-imidazo[1,2-a]pyridine (1 eq, 18.1 mmol, 4.2 g), 2-chloropyridin-4-yl boronic acid (1.05 eq, 19 mmol, 3 g), Na$_2$CO$_3$ (2 eq, 36.2 mmol, 3.84 g) in dioxane (30 ml) and water (10 ml), under an inert atmosphere of argon is added bis(triphenylphosphine)palladium II chloride (1.23 g). The reaction mixture is heated at 100° C. for 16 hours. The mixture is diluted with H$_2$O (50 ml) and extracted with EtOAc. The combined organic portions are washed with brine, dried (MgSO$_4$) and concentrated in vacuo. The residue is purified by flash chromatography on silica eluting with 0-50% EtOAc in iso-hexane to afford the title compound; [M+H]$^+$=264 (266).

Step I2: 6-Chloro-3-(2-furanyl-3-yl-pyridin-4yl)-imidazo[1,2-a]pyridine

To a solution of 6-Chloro-3-(2-chloro-pyridin-4-yl)-imidazo[1,2-a]pyridine_(1 eq, 8.75 mmol, 2.31 g), 3-furyl boronic acid (1.05 eq, 9.1 mmol, 1.02 g), Na$_2$CO$_3$ (2 eq, 17.5 mmol, 1.84 g) in dioxane (25 ml) and water (9 ml), under an inert atmosphere of argon is added bis(triphenylphosphine)palladium II chloride (614 mg). The reaction mixture is heated at 100° C. for 16 hours. The mixture is diluted with H$_2$O (50 ml) and extracted with EtOAc. The combined organic portions are purified by passing through an SCX-2 cartridge (20 g resin 0.67 mmol/g) and eluting the basic fraction with 2M ammonia in methanol. The basic fractions are purified by flash chromatography on silica eluting with 50% iso-hexane in EtOAc to afford the title compound; [M+H]$^+$=295 (297).

Intermediate J 1-(RS/RS)-3-(2,6-Dichloro-pyridin-4-yl)-imidazo[1,2-a]pyridin-6-ylamino)-cyclohexanol

Step J1: (1SR,3SR)-3-(3-Bromo-imidazo[1,2-a]pyridin-6-ylamino)-cyclohexanol

Copper (I) iodide (0.1 eq, 0.8 g, 0.43 mmol) and potassium phosphate tribasic (2 eq, 43.4 mmol, 9.2 g) are stirred at RT under an atmosphere of argon during the addition of 3-bromo-6-iodo-imidazo[1,2-a]pyridine (Intermediate F) (7 g, 21.7 mmol, 1 eq) in isopropyl alcohol (75 ml), ethylene glycol (2 eq, 43.4 mmol, 2.4 ml) and finally trans-(RS/RS)-3-aminocyclohexanol (2 eq, 5 g, 43.4 mmol). The reaction is heated at 95° C. for 40 hours. The majority of the solvent is removed in vacuo and the residue is diluted with water (500 ml) and extracted with (9:1) EtOAc: Methanol (3×500 ml). The combined organic portions are passed through SCX (solid-supported sulfonic acid) resin (95 g) eluting with MeOH followed by 2M NH$_3$ in MeOH (250 ml). The basic ammonia wash is concentrated in vacuo and purification of the residue by flash chromatography on silica eluting with EtOAc affords the title compound; [M+H]$^+$=310 (312).

Step J2: 1-(RS/RS)-3-(2,6-Dichloro-pyridin-4-yl)-imidazo[1,2-a]pyridin-6-ylamino)-cyclohexanol To a solution of 3-trans-RS/RS(3-bromo-imidazo[1,2-a]pyridin-6-ylamino)-cyclohexanol (1 eq, 10.1 mmol, 3.4 g), 2,6-dichloro-4-(4,4,5,5-tetramethyl-[1,3,2]dioxaboroloan-2-yl)-pyridinepyrid-4-yl (1.05 eq, 10.1 mmol, 2.9 g), Na$_2$CO$_3$ (2 eq, 19 mmol, 2 g) in dioxane (45 ml) and water (13.5 ml), under an inert atmosphere of argon is added bis(triphenylphosphine)palladium II chloride (0.1 eq, 0.96 mmol, 679 mg). The reaction mixture is heated at 95° C. for 16 hours. The mixture is diluted with H$_2$O (50 ml) and extracted with EtOAc. The combined organic portions are washed with brine, dried (MgSO$_4$) and concentrated in vacuo. The residue is purified by chromatography on silica eluting with 0-10% MeOH in EtOAc to afford the title compound; [M+H]$^+$=343/345.

Intermediate K (1SR,2SR)-2-[3-(2-Chloro-pyridin-4-yl)-imidazo[1,2-a]pyridin-6-ylamino]-cyclohexanol The title compound is prepared in a manner analogous to that of 1-(RS/RS)-3-(2,6-Dichloro-pyridin-4-yl)-imidazo[1,2-a]pyridin-6-ylamino)-cyclohexanol (Intermediate J) by substituting trans-(RS/RS)-3-aminocyclohexanol with trans-(SR/SR)-2- aminocyclohexanol in step 1.

Intermediate L 3-(2-Chloro-pyridinyl)-6-trifluoromethyl-imidazo[1,2-a]pyridine

Step L1: 6-trifluoromethyl-imidazo[1,2-a]pyridine

To a solution of 50% aq. chloroacetaldehyde (1.1 eq, 6.8 mmol, 0.862 ml) in ethanol (30 ml) is added 3-amino-6-trifluoromethyl-pyridine (1 eq, 6.2 mmol, 1 g) at room temperature. The reaction mixture is heated at reflux for 18 hours. The solvent is removed in vacuo and the crude product is dissolved in water (10 ml). The aqueous solution is treated with sodium bicarbonate to pH=8 and extracted with DCM (3×25 ml). The organic layer is dried (MgSO$_4$) and evaporated to give the title compound as a beige solid.

Step L2: 3-Bromo-6-trifluoromethyl-imidazo[1,2-a]pyridine

To 6-trifluoromethyl-imidazo[1,2-a]pyridine (1 eq, 6.2 mmol, 1.1 g) in acetic acid (15 ml) under an inert atmosphere of argon is added dropwise bromine (1 eq, 6.2 mmol, 0.313 ml). After stirring at room temperature for 1 hour, the reaction mixture is filtered to afford the title compound as a beige solid; [M+H]$^+$=266(268)

Step L3: 3-(2-Chloro-pyridinyl)-6-trifluoromethyl-imidazo[1,2-a]pyridine

To a solution of 3-Bromo-6-trifluoromethyl-imidazo[1,2-a]pyridine (1 eq, 2.9 mmol, 0.77 g), 2-chloropyrid-4-yl boronic acid (1.05 eq, 3.05 mmol, 0.478 g), Na$_2$CO$_3$ (2 eq, 5.81 mmol, 0.616 g) in dioxane (45 ml) and water (13.5 ml), under an inert atmosphere of argon is added bis(triphenylphosphine)palladium II chloride (0.1 eq, 0.03 mmol, 200 mg). The reaction mixture is heated at 95° C. for 16 hours. The mixture is diluted with H$_2$O (50 ml) and extracted with EtOAc. The combined organic portions are washed with brine, dried (MgSO$_4$) and concentrated in vacuo. The residue is purified by chromatography on silica eluting with 0-10% MeOH in EtOAc to afford the title compound; [M+H]$^+$=297/299.

Intermediate M

6-Chloro-3-(2-pyrazolyl-1-yl-pyridin-4-yl)-imidazo[1,2-a]pyridine

A mixture comprising [6-Chloro-3-(2-chloro-pyridin-4-yl)-imidazo[1,2-a]pyridine (Intermediate I, step 1) (1 eq, 10 mmol, 2.67 g), pyrazole (5 eq, 50 mmol, 3.44 g) and cesium carbonate (3 eq, 30 mmol, 9.9 g) in DMF (25 ml) is heated using microwave radiation at 145° C. for 3 hours. After cooling to room temperature, the mixture is loaded onto a SCX-2 cartridge eluting with MeOH followed by 2M NH$_3$ in MeOH. The solvent is removed in vacuo and the crude product is triturated with ethyl acetate to afford the title compound; [M+H]$^+$=296/298.

Intermediate N 3-(2-Furan-3-yl-pyridin-4-yl)-imidazo[1,2-a]pyridine-6-carboyxlic acid methyl ester

Step N1: Imidazo[1,2-a]pyridine-6-carboxylic acid methyl ester

To a solution of 50% aq. chloroacetaldehyde (1.1 eq, 36 mmol, 4.6 ml) in ethanol (120 ml) is added 6-amino-nicotinic acid methyl ester (1 eq, 33 mmol, 5 g) at room temperature. The reaction mixture is heated at reflux for 18 hours. The solvent is removed in vacuo and the crude product is dissolved in water (400 ml). The aqueous solution is treated with sodium bicarbonate to pH=8 and extracted with DCM (3×250 ml). The organic layer is dried (MgSO₄) and evaporated to give the title compound as a beige solid.

Step N2:
3-Bromo-imidazo[1,2-a]pyridine-6-carboxylic acid methyl ester

To Imidazo[1,2-a]pyridine-6-carboxylic acid methyl ester (1 eq, 33 mmol, 5.8 g) in acetic acid (60 ml) under an inert atmosphere of argon is added dropwise bromine (1 eq, 33 mmol, 1.7 ml). After stirring at room temperature for 1 hour, the reaction mixture is filtered to afford the title compound as a beige solid; $[M+H]^+=255/257$ Step N3: 3-(2-Chloro-pyridin-4-yl)-imidazo[1,2-a]pyridine-6-carboyxlic acid methyl ester To a solution of 3-Bromo-imidazo[1,2-a]pyridine-6-carboxylic acid methyl ester (1 eq, 23 mmol, 5.9 g), 2-chloropyrid-4-yl boronic acid (1.05 eq, 24 mmol, 3.8 g), Na₂CO₃ (2 eq, 46 mmol, 4.9 g) in dioxane (40 ml) and water (15 ml), under an inert atmosphere of argon is added bis(triphenylphosphine)palladium II chloride (0.1 eq, 2.4 mmol, 1.6 g). The reaction mixture is heated at 95° C. for 16 hours. The mixture is diluted with H₂O (50 ml) and extracted with EtOAc. The combined organic portions are washed with brine, dried (MgSO₄) and concentrated in vacuo. The residue is purified by chromatography on silica eluting with 0-10% MeOH in EtOAc to afford the title compound; $[M+H]^+=287/289$.

Step N4: 3-(2-Furan-3-yl-pyridin-4-yl)-imidazo[1,2-a]pyridine-6-carboyxlic acid methyl ester To 3-(2-Chloro-pyridin-4-yl)-imidazo[1,2-a]pyridine-6-carboyxlic acid methyl ester (1 eq, 800 mg, 2.8 mmol), 3-furyl boronic acid (1.05 eq, 3 mmol, 0.325 mg), Na₂CO₃ (2 eq, 5.6 mmol, 590 mg) in dioxane (6 ml) and H₂O (3 ml), under inert atmosphere is added tetakis(triphenylphosphine)palladium (0.1 eq, 195 mg). The reaction is heated in using microwave radiation at 80° C. for 2 hours. The mixture is diluted with H₂O (5 ml) and extracted with EtOAc. The combined organic portions are washed with brine, dried (MgSO₄) and concentrated in vacuo. The residue is purified by flash chromatography on silica eluting with 0-2.5% methanol in EtOAc to afford the title compound; [M+H]+320

Intermediate O (1SR,3SR)-3-[3-(2-Chloro-6-methoxy-pyridin-4-yl)-imidazo[1,2-a]pyridin-6-ylamino)-cyclohexanol To a solution of 3-trans-RS/RS(3-bromo-imidazo[1,2-a]pyridin-6-ylamino)-cyclohexanol [intermediate J step 2] (1 eq, 10.1 mmol, 3.4 g), 2-Chloro-6-methoxy-4-(4,4,5,5-tetramethyl-[1,3,2]dioxaborolan-2-yl)-pyridine (1.05 eq, 10.1 mmol, 2.9 g), Na₂CO₃ (2 eq, 19 mmol, 2 g) in dioxane (45 ml) and water (13.5 ml), under an inert atmosphere of argon is added bis(triphenylphosphine)palladium II chloride (0.1 eq, 0.96 mmol, 224 mg). The reaction mixture is heated at 95° C. for 16 hours. The mixture is diluted with H₂O (50 ml) and extracted with EtOAc. The combined organic portions are washed with brine, dried (MgSO₄) and concentrated in vacuo. The residue is purified by chromatography on silica eluting with 0-10% MeOH in EtOAc to afford the title compound; $[M+H]^+=343/345$.

Intermediate P (1SR,3SR)-3-[3-(2-Chloro-6-Fluoro-pyridin-4-yl)-imidazo[1,2-a]pyridin-6-ylamino)-cyclohexanol To a solution of 3-trans-RS/RS (3-bromo-imidazo[1,2-a]pyridin-6-ylamino)-cyclohexanol [intermediate J step 2] (1 eq, 0.1 g), 2-Chloro-6-fluoro-4-(4,4,5,5-tetramethyl-[1,3,2]dioxaborolan-2-yl)-pyridine (1.05 eq,82 mg), Na₂CO₃ (2 eq, 68 mg) in ethanol (2 ml) and water (0.2 ml), under an inert atmosphere of argon is added bis(triphenylphosphine)palladium II chloride (0.1 eq, 0.96 mmol, 22 mg). The reaction mixture is heated at 95° C. for 16 hours. The mixture is diluted with H₂O (50 ml) and extracted with EtOAc. The combined organic portions are washed with brine, dried (MgSO₄) and concentrated in vacuo. The residue is purified by chromatography on silica eluting with 0-10% MeOH in EtOAc to afford the title compound; $[M+H]^+=360$.

Intermediate Q (1SR,3SR)-3-[3-(2-Chloro-pyridin-4-yl)-imidazo[1,2-a]pyridin-6-ylamino)-cyclohexanol To a solution of 3-trans-RS/RS(3-bromo-imidazo[1,2-a]pyridin-6-ylamino)-cyclohexanol [intermediate J step 2] (1 eq, 13.7 mmol, 4.25 g), 3-chloropyridin-4-yl boronic acid (1.05 eq, 15 mmol, 2.37 g), Na₂CO₃ (1 eq, 13.7 mmol, 1.4 g) in dioxane (125 ml) and water (22 ml), under an inert atmosphere of argon is added bis(triphenylphosphine)palladium II chloride (0.1 eq, 560 mg). The reaction mixture is heated at 95° C. for 16 hours. The mixture is diluted with H₂O (50 ml) and extracted with EtOAc. The combined organic portions are washed with brine, dried (MgSO₄) and concentrated in vacuo. The residue is purified by chromatography on silica eluting with 0-10% MeOH in EtOAc to afford the title compound; $[M+H]^+=343/345$.

Intermediate R (1SR,3RS)-3-[3-(2-Chloro-pyridin-4-yl)-imidazo[1,2-a]pyridin-6-ylamino)-cyclohexanol Step R1: (1SR,3RS)-3-(3-Bromo-imidazo[1,2-a]pyridin-6-ylamino)-cyclohexanol The title compound is prepared from 3-bromo-6-iodo-imidazo[1,2-a]pyridine (Intermediate F) and cis-(RS/SR)-3-aminocyclohexanol (2 eq, 5 g, 43.4 mmol) by a procedure analogous to that described for (Intermediate J step 1).

Step R2: (1SR,3RS)-3-[3-(2-Chloro-pyridin-4-yl)-imidazo[1,2-a]pyridin-6-ylamino)-cyclohexanol To a solution of (1SR,3RS)-3-(3-Bromo-imidazo[1,2-a]pyridin-6-ylamino)-cyclohexanol (1 eq, 1 mmol, 0.34 g), 3-chloropyridin-4-yl boronic acid (1.05 eq, 1.05 mmol, 0.29 g), Na₂CO₃ (2 eq, 1.9 mmol, 0.2 g) in dioxane (5 ml) and water (1 ml), under an inert atmosphere of argon is added bis(triphenylphosphine)palladium II chloride (0.1 eq, 70 mg). The reaction mixture is heated at 95° C. for 16 hours. The mixture is diluted with H₂O (50 ml) and extracted with EtOAc. The combined organic portions are washed with brine, dried (MgSO₄) and concentrated in vacuo. The residue is purified by chromatography on silica eluting with 0-10% MeOH in EtOAc to afford the title compound; $[M+H]^+=343/345$.

Intermediate S (1SR,3RS)-3-[3-(2,6-Dichloro-pyridin-4-yl)-imidazo[1,2-a]pyridin-6-ylamino)-cyclohexanol The title compound is prepared from 2,6-dichloro-4-(4,4,5,5-tetramethyl-[1,3,2]dioxaborolan-2-yl)-pyridinel and (1SR,3RS)-3-(3-Bromo-imidazo[1,2-a]pyridin-6-ylamino)-cyclohexanol [Intermediate R (step 1)] by a procedure analogous to Intermediate J (step 2)

Intermediate T (1SR,3RS)-3-[3-(2-Chloro-6-fluoro-pyridin-4-yl)-imidazo[1,2-a]pyridin-6-ylamino)-cyclohexanol The title compound is prepared from 2-Chloro-6-fluoro-4-(4,4,5,5-tetramethyl-[1,3,2]dioxaborolan-2-yl)-pyridine and (1SR,3RS)-3-(3-Bromo-imidazo[1,2-a]pyridin-6-ylamino)-cyclohexanol [Intermediate R (step 1)] by a procedure analogous to [Intermediate J (step 2)]

Intermediate U (S/S)-3-(2-Chloro-pyridin-4-yl)-imidazo[1,2-a]pyridin-6-ylamino)-cyclohexanol Step U1: (1S,3S)-3-(3-Bromo-imidazo[1,2-a]pyridin-6-ylamino)-cyclohexanol 3-Bromo-6-iodo-imidazo[1,2-a]pyridine (Intermediate F) (1.5 eq, 59.0 mmol, 19 g), ethylene glycol (2 eq, 79 mmol, 4.39 ml) and potassium phosphate tribasic (2 eq, 79 mmol, 16.7 g) in isopropyl alcohol (262 ml) are stirred at RT under an atmosphere of argon during. Trans-(S/S)-3-aminocyclohexanol (1.0 eq, 39 mmol, 4.5 g) is added followed by copper (I) iodide (0.1 eq, 3.93 mmol, 0.8 g). The reaction is heated at 85° C. for 40 hours. The majority of the solvent is removed in vacuo and the residue is diluted with water (500 ml) and EtOAc (500 ml). The biphasic mixture is passed through a pad of Celite® 521. The combined organic portions are washed with brine, dried (MgSO$_4$) and concentrated in vacuo. The residue is purified by flash chromatography on silica eluting with 50-100% EtOAc in iso-hexane to afford the title compound; [M+H]$^+$=310 (312).

Step U2: (S/S)-3-(2-Chloro-pyridin-4-yl)-imidazo[1,2-a]pyridin-6-ylamino)-cyclohexanol The title compound is prepared from 3-trans-S/S (3-bromo-imidazo[1,2-a]pyridin-6-ylamino)-cyclohexanol and 3-chloropyrid-4-yl boronic acid in a manner analogous to that described for Intermediate Q [M+H]$^+$=343/345.

Intermediate V (R/R)-3-(2-Chloro-pyridin-4-yl)-imidazo[1,2-a]pyridin-6-ylamino)-cyclohexanol Step V1: (1R,3R)-3-(3-Bromo-imidazo[1,2-a]pyridin-6-ylamino)-cyclohexanol The title compound is prepared analogously to [Intermediate U (step 1)] replacing trans-(S/S)-3-aminocyclohexanol with trans-(R/R)-3-aminocyclohexanol.

Step V2: —(R/R)-3-(2-Chloro-pyridin-4-yl)-imidazo[1,2-a]pyridin-6-ylamino)-cyclohexanol The title compound is prepared from 3-trans-R/R (3-bromo-imidazo[1,2-a]pyridin-6-ylamino)-cyclohexanol and 3-chloropyrid-4-yl boronic acid in a manner analogous to that described for Intermediate Q [M+H]$^+$=343/345.

Intermediate W (RS/SR)-3-[3-(2-Chloro-pyridin-4-yl)-imidazo[1,2-a]pyridin-6-ylamino]-1-methyl-cyclohexanol Step W1: (1RS,3SR)-3-(3-Bromo-imidazo[1,2-a]pyridin-6-ylamino)-1-methyl-cyclohexanol The title compound is prepared analogously to [Intermediate U (step 1)] replacing trans-(S/S)-3-aminocyclohexanol with cis-(1RS/3SR)-3-amino-1-methyl-cyclohexanol.

Step W2: (RS/SR)-3-[3-(2-Chloro-pyridin-4-yl)-imidazo[1,2-a]pyridin-6-ylamino]-1-methyl-cyclohexanol The title compound is prepared from (1RS, 3SR)-3-(3-Bromo-imidazo[1,2-a]pyridin-6-ylamino)-1-methyl-cyclohexanol and 3-chloropyridin-4-yl boronic acid in a manner analogous to that described for Intermediate Q [M+H]$^+$=343/345.

Intermediate X (RS/RS)-3-[3-(2-Chloro-pyridin-4-yl)-imidazo[1,2-a]pyridin-6-ylamino]-1-methyl-cyclohexanol Step X1: (1RS,3RS)-3-(3-Bromo-imidazo[1,2-a]pyridin-6-ylamino)-1-methyl-cyclohexanol The title compound is prepared analogously to [Intermediate U (step 1)] replacing trans-(S/S)-3-aminocyclohexanol with trans-(1RS/RS)-3-amino-1-methyl-cyclohexanol.

Step X2: (RS/RS)-3-[3-(2-Chloro-pyridin-4-yl)-imidazo[1,2-a]pyridin-6-ylamino]-1-methyl-cyclohexanol The title compound is prepared from (1RS,3RS)-3-(3-Bromo-imidazo[1,2-a]pyridin-6-ylamino)-1-methyl-cyclohexanol and 3-chloropyrid-4-yl boronic acid in a manner analogous to that described for intermediate Q [M+H]$^+$=343/345.

Intermediate YA

[4-(7-Chloro-imidazo[1,2-a]pyridin-3-yl)-6-phenyl-pyridin-2-yl]methyl-amine

Step YA1: 7-Chloro-3-(2,6-dichloro-pyridin-4-yl)-imidazo[1,2-a]pyridine

3-Bromo-7-chloro-imidazo[1,2-a]pyridine (1 eq, 3.02 mmol, 700 mg) and 2,6-dichloro-4-(4,4,5,5-tetramethyl-[1,3,2]dioxaborolan-2-yl)-pyridine (1.1 eq, 3.32 mmol, 1.01 g) are dissolved in DME (4 ml) and water (1 ml) and Na$_2$CO$_3$ (1.5 eq, 5.53 mmol, 562 mg) is added. PdCl$_2$(PPh$_3$)$_2$ (0.1 eq, 0.3 mmol, 212 mg) is added and the reaction mixture is heated using microwave radiation at 120° C. for 15 min. At the completion of this time the solvent is removed in vacuo and the reaction mixture is purified by flash column chromatography eluting with 9:1 DCM/MeOH to yield 7-chloro-3-(2, 6-dichloro-pyridin-4-yl)-imidazo[1,2-a]pyridine as a yellow solid; [M+H]⁺=299

Step YA2: [6-Chloro-4-(7-chloro-imidazo[1,2-a] pyridin-3-yl)-pyridin-2-yl]-methyl-amine 7-Chloro-3-(2,6-dichloro-pyridin-4-yl)-imidazo[1,2-a] pyridine (1.0 eq, 0.64 mmol, 190 mg), methyl amine (8M in EtOH, 3.5 eq, 2.2 mmol, 0.28 ml) and $Cs_2CO_3$ (2.5 eq, 1.59 mmol, 518 mg) are dissolved in DMF (2 ml) and the reaction mixture is heated using microwave radiation at 160° C. for 30 min, it is diluted with $CH_2Cl_2$. The reaction mixture is washed with $NaHCO_3$ and brine, dried over $MgSO_4$, filtered and evaporated. The product is purified by flash column chromatography eluting with 8:2 DCM/MeOH to afford [6-chloro-4-(7-chloro-imidazo[1,2-a]pyridin-3-yl)-pyridin-2-yl]-methyl-amine as a brown solid; [M+H]⁺=294

Step YA3: [4-(7-Chloro-imidazo[1,2-a]pyridin-3-yl)-6-phenyl-pyridin-2-yl]-methyl-amine

[6-Chloro-4-(7-chloro-imidazo[1,2-a]pyridin-3-yl)-pyridin-2-yl]-methyl-amine (1 eq, 0.19 mmol, 56 mg) and phenylboronic acid (1.1 eq, 0.21 mmol, 25.6 mg) are dissolved in DME (2 ml) and water (0.5 ml) and $Na_2CO_3$ (1.5 eq, 0.29 mmol, 35.5 mg) is added. $PdCl_2(PPh_3)_2$ (0.1 eq, 0.019 mmol, 13.4 mg) is added and the reaction mixture is heated using microwave radiation at 120° C. for 10 min. At the completion of this time the solvent is removed in vacuo and the reaction mixture is purified by flash column chromatography eluting with 9:1 DCM/MeOH to yield [4-(7-chloro-imidazo[1,2-a] pyridin-3-yl)-6-phenyl-pyridin-2-yl]-methyl-amine as a brown solid; [M+H]⁺=335

These examples namely,
Isopropyl-[6-phenyl-4-(7-phenyl-imidazo[1,2-a]pyridin-3-yl)-pyridin-2-yl]amine (Intermediate YB),
Cyclopropyl-[6-phenyl-4-(7-phenyl-imidazo[1,2-a]pyridin-3-yl)-pyridin-2-yl]amine (Intermediate YC)
{6-(4-Fluoro-phenyl)-4-[7-(4-fluoro-phenyl)-imidazo[1,2-a]pyridin-3-yl]-pyridin-2-yl}-methyl-amine (Intermediate YD) and
[4-(7-Chloro-imidazo[1,2-a]pyridin-3-yl)-6-(4-fluoro-phenyl)-pyridin-2-yl]-methyl-amine (Intermediate YE)
are prepared by an analogous method to [4-(7-chloro-imidazo [1,2-a]pyridin-3-yl)-6-phenyl-pyridin-2-yl]-methyl-amine (Intermediate YA) by replacing methyl amine with the appropriate amine (Step YA2) and phenyl boronic acid with the appropriate boronic acid (Step YA3).

The invention claimed is:
1. A compound of Formula I,

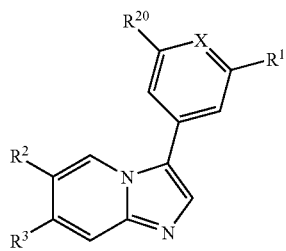

wherein
X is N;
$R^1$ is selected from aryl, heterocyclyl, $C_1$-$C_7$ alkyl, $C_3$-$C_{10}$-cycloalkyl, $C_5$-$C_{10}$ cycloalkenyl, $C(O)NR^5R^6$, halo, $C_1$-$C_7$ alkoxy, alkylthio, hydroxyl, $C_1$-$C_7$ alkylcarbonyl, carboxy, carbonyl, cyano and sulfonamide, wherein the alkyl, cycloalkyl, cycloalkenyl, aryl and heterocyclyl groups are optionally substituted by one or more substituents each independently selected from halogen, $C_1$-$C_6$ alkyl, $C_1$-$C_6$ haloalkyl, $C_1$-$C_6$ hydroxyalkyl, $C_3$-$C_8$ cycloalkyl and $C_1$-$C_6$ alkoxy;
$R^2$ is independently selected from H, halogen, OH, $C_1$-$C_6$ alkyl, $C_1$-$C_6$ hydroxyalkyl, $C_1$-$C_6$ alkoxy, $C_3$-$C_6$ cycloalkyl, $NR^7R^8$ and Z;
$R^3$ is independently selected from H, halogen, $C_2$-$C_7$ alkynyl, aryl and heterocyclyl, wherein the alkynyl group is optionally substituted by one or more groups independently selected from hydroxy, cyano, amino, $C_1$-$C_7$ alkylamino and halogen, and wherein the aryl and heterocyclyl groups are optionally substituted by one or more $R^x$ groups and each $R^x$ is independently selected from $C_1$-$C_7$ alkyl; hydroxyl; carbonyl; aminocarbonyl; $C_1$-$C_7$ alkylaminocarbonyl; amino; $C_1$-$C_7$ alkylamino; $C_1$-$C_7$ alkylthio; sulfonylamino; carbonylamino; $C_1$-$C_7$ alkylcarbonylamino; $C_1$-$C_7$ alkylaminocarbonyl; $C_1$-$C_7$ alkylcarbonyl; halogen; oxo; carboxyl; $C_1$-$C_7$ alkoxy; benzyloxy; $C_1$-$C_7$ alkoxycarbonyl; aminosulfonyl; cyano; sulfonyl; sulfanyl; sulfoxide; -L-$C_3$-$C_{10}$-cycloalkyl, -L- $C_5$-$C_{10}$ cycloalkenyl; -L-aryl; -L-het; carbonyloxy; $C_1$-$C_7$ aminoalkyl; $C_1$-$C_7$ alkylamino-$C_1$-$C_7$ alkyl; $C_1$-$C_7$ alkylamino-$C_1$-$C_7$ alkoxy; $C_1$-$C_7$ alkylamino- $C_1$-$C_7$ alkylcarbonyl; and a group of the formula: P—NH-Q-T, wherein each $R^x$ group itself is optionally substituted by one or more groups each independently selected from OH, COOH, halogen, $C_1$-$C_7$ alkyl, aryl, amino, $C_1$-$C_7$ alkylamino, het, cyano, sulfonyl, sulfanyl, sulfoxide, hydroxy-$C_1$-$C_7$ alkyl, $C_1$-$C_7$ alkoxy, $C_1$-$C_7$ alkoxycarbonyl and $C_1$-$C_7$ alkylamino-$C_1$-$C_7$ alkyl; or
when two $R^x$ groups are present, they may be joined together to form a ring system fused to $R^3$, the ring system being optionally substituted by one or more groups eachindependently selected from hydroxyl, $C_1$-$C_7$ alkyl, aryl, amino, $C_1$-$C_7$ alkylamino, heterocyclyl, cyano, halo, sulfonyl, sulfanyl, sulfoxide, hydroxy-$C_1$-$C_7$ alkyl, $C_1$-$C_7$ alkoxy and $C_1$-$C_7$ alkylamino-$C_1$-$C_7$ alkyl;
each L is independently a bond, —C(O)—, —C(O)NH—, a $C_1$-$C_6$ alkylene linker, a $C_1$-$C_6$ alkylenecarbonyl linker or a $C_1$-$C_6$ alkyleneoxy linker;
P is —C(O)—, a $C_1$-$C_6$ alkylene linker, a $C_1$-$C_6$ alkylenecarbonyl linker or a $C_1$-$C_6$ alkyleneoxy linker;
Q is —C(O)—, a $C_1$-$C_6$ alkylene linker or a $C_1$-$C_6$ alkylenecarbonyl linker;
T is aryl, het, $NR^aR^b$ or $C_3$-$C_8$ cycloalkyl;
$R^a$ and $R^b$ are each independently selected from H and $C_1$-$C_6$ alkyl;
$R^5$, $R^6$ and $R^7$ are each independently selected from H and $C_1$-$C_6$ alkyl;
$R^8$ is selected from $C_5$-$C_7$ cycloalkyl and a 5- or 6-membered heterocyclic group, each optionally substituted by one or more groups independently selected from $C_1$-$C_6$ alkyl, $C_1$-$C_6$ alkoxy and OH;
Z is selected from 5- or 6-membered heteroaryl and aryl, each being optionally substituted by one or more groups independently selected from $C_1$-$C_6$ alkyl, $C_1$-$C_6$ alkoxy, $C_3$-$C_8$ cycloalkyl, OH, CN, halo, —C(O)H, —C(O)

$OC_1$-$C_6$ alkyl, —$C(O)NR^9R^{10}$, —$(CH_2)_pNR^{11}R^{12}$, —$(CH_2)_n$het, —$NR^{13}C(O)C_1$-$C_6$ alkyl, —$S(O)_2NHR^{14}$ and —$NR^{14}S(O)_2C_1$-$C_6$ alkyl, wherein each alkyl group is optionally substituted by OH, $COOR^c$ and halogen;

each het is independently a 5- or 6-membered heterocyclic group optionally substituted by one or more groups each independently selected from OH, $C_1$-$C_6$ alkyl and $C_1$-$C_6$ alkoxy;

$R^c$ is H or $C_1$-$C_6$ alkyl;

n and p are each independently 0, 1 or 2;

$R^9$, $R^{11}$, $R^{13}$ and $R^{14}$ are each independently selected from H, $C_1$-$C_6$ alkyl, $C_1$-$C_6$ haloalkyl, $C_1$-$C_6$ hydroxyalkyl and $C_3$-$C_8$ cycloalkyl;

$R^{10}$ is selected from H, $C_1$-$C_6$ alkyl, $C_1$-$C_6$ hydroxyalkyl, —$(CH_2)_mNR^{15}R^{16}$, —$(CH_2)_tCOOR^d$ and $C_5$-$C_7$ cycloalkyl optionally substituted by one or more groups independently selected from OH, $C_1$-$C_3$ alkyl and $C_1$-$C_3$ alkoxy; or $R^9$ and $R^{10}$, together with the nitrogen atom to which they are attached, form a 5- or 6-membered heterocyclic group which optionally contains one or more further heteroatoms selected from N, O and S, the heterocyclic group being optionally substituted by one or more groups independently selected from OH, $C_1$-$C_3$ alkyl and $C_1$-$C_3$ alkoxy;

m is 2 or 3;

t is 1, 2 or 3;

$R^d$ is H or $C_1$-$C_6$ alkyl;

$R^{12}$ is selected from H, $C_1$-$C_6$ alkyl and $(CH_2)_qNR^{17}R^{18}$;

q is 2, 3 or 4;

$R^{15}$, $R^{16}$, $R^{17}$ and $R^{18}$ are each independently selected from H and $C_1$-$C_3$ alkyl; or $R^{15}$ and $R^{16}$, together with the nitrogen atom to which they are attached, form a 5- or 6-membered heterocyclic group which optionally contains one or more further heteroatoms selected from N, O and S, the heterocyclic group being optionally substituted by one or more groups independently selected from OH, $C_1$-$C_3$ alkyl and $C_1$-$C_3$ alkoxy; or $R^{17}$ and $R^{18}$, together with the nitrogen atom to which they are attached, form a 5-or 6-membered heterocyclic group which optionally contains one or more further heteroatoms selected from N, O and S, the heterocyclic group being optionally substituted by one or more groups independently selected from OH, $C_1$-$C_3$ alkyl and $C_1$-$C_3$ alkoxy;

$R^{20}$ is selected from H, halo, $NR^{21}R^{22}$ and $OR^{23}$; and $R^{21}$, $R^{22}$ and $R^{23}$ are each independently selected from H, $C_1$-$C_6$ alkyl and $C_3$-$C_6$ cyclolkyl; or $R^{21}$ and $R^{22}$, together with the nitrogen atom to which they are attached form a 4-, 5- or 6-membered N-containing heterocyclic group;

provided that when $R^3$ is other than H, $R^2$ is H, halo, OH, $C_1$-$C_6$ alkyl, $C_1$-$C_6$ alkoxy or $C_3$-$C_6$ cyclolkyl; and when $R^3$ is H, $R^2$ is halogen, $NR^7R^8$ or Z.

2. A compound according to claim 1, wherein $R^1$ is selected from $C(O)NR^5R^6$, $C_1$-$C_6$ alkoxy, $C_5$-$C_6$ cycloalkenyl, halogen, 5- or 6-membered heteroaryl and aryl, wherein the cycloalkenyl, heteroaryl and aryl groups are optionally substituted by one or more groups independently selected from halogen, $C_1$-$C_6$ alkyl and $C_1$-$C_6$ alkoxy.

3. A compound according to claim 1, wherein $R^3$ is H, optionally substituted phenyl or optionally substituted pyridinyl.

4. A compound according to claim 3, wherein $R^3$ is H, phenyl or pyridinyl, wherein the phenyl and pyridinyl groups are optionally substituted by one or more groups independently selected from $C_1$-$C_6$ alkyl, $C_1$-$C_6$ alkoxy, OH, CN, halo, —$C(O)H$, —$C(O)OC_1$-$C_6$ alkyl, —$C(O)NR^9R^{10}$, —$(CH_2)_pNR^{11}R^{12}$, —$(CH_2)_n$het, —$NR^{13}C(O)C_1$-$C_6$ alkyl and —$NR^{14}S(O)_2C_1$-$C_6$ alkyl;

$R^9$, $R^{11}$, $R^{13}$ and $R^{14}$ are each independently selected from H and $C_1$-$C_3$ alkyl;

$R^{10}$ is selected from H, $C_1$-$C_6$ alkyl, $C_1$-$C_6$ hydroxyalkyl, —$(CH_2)_mNR^{15}R^{16}$ and $C_5$-$C_7$ cycloalkyl optionally substituted by one or more groups independently selected from OH, $C_1$-$C_3$ alkyl and $C_1$-$C_3$ alkoxy; or $R^9$ and $R^{10}$, together with the nitrogen atom to which they are attached, form a 5- or 6-membered heterocyclic group which optionally contains one or more further heteroatoms selected from N, O and S, the heterocyclic group being optionally substituted by one or more groups independently selected from OH, $C_1$-$C_3$ alkyl and $C_1$-$C_3$ alkoxy; and m is 2 or 3.

5. A compound according to claim 1 which is a compound of Formula X

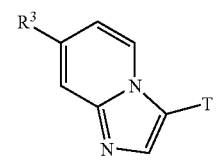

where $R^3$ and T are as shown below:

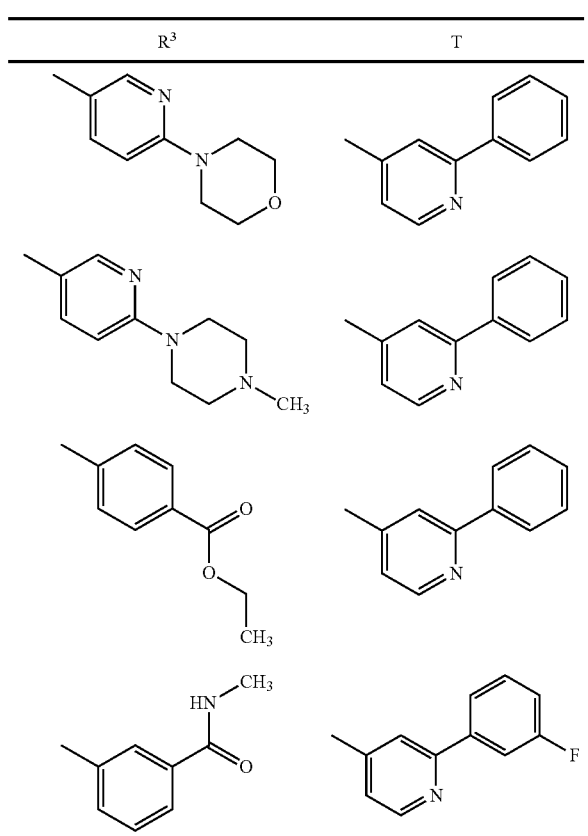

| R³ | T |
|---|---|
| 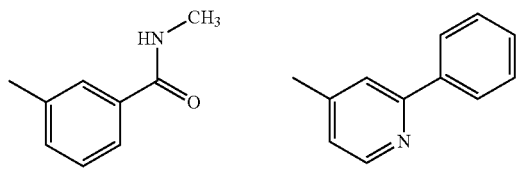 | |
| 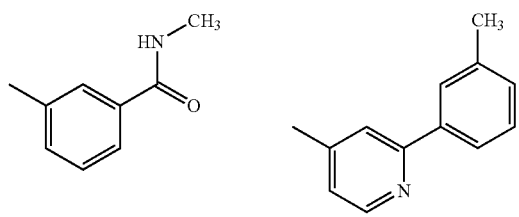 | |
| 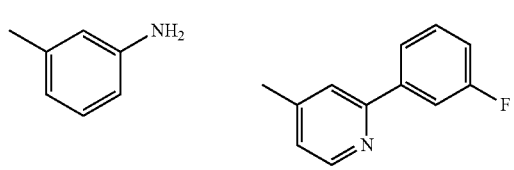 | |
| 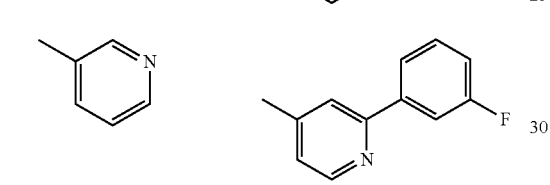 | |
| 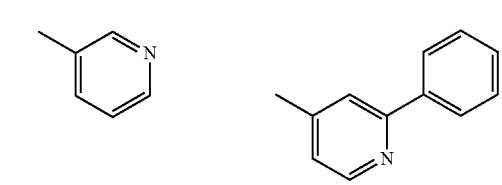 | |
| 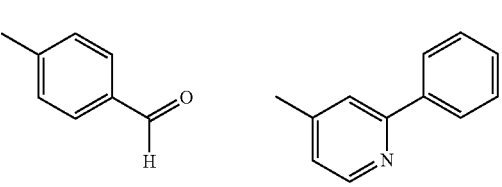 | |
| 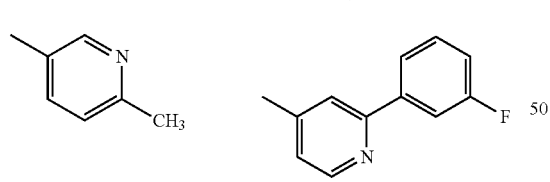 | |
| 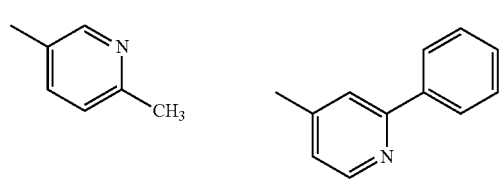 | |
| 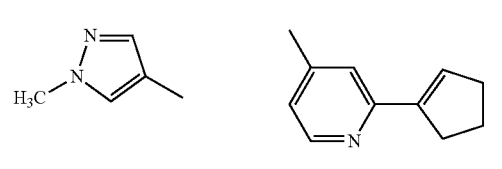 | |
| R³ | T |
|---|---|
| 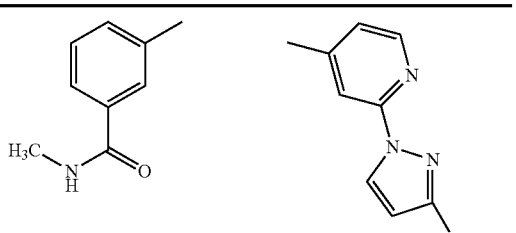 | |
| 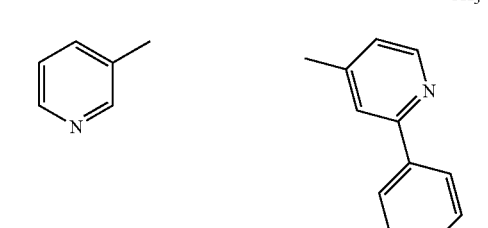 | |
| 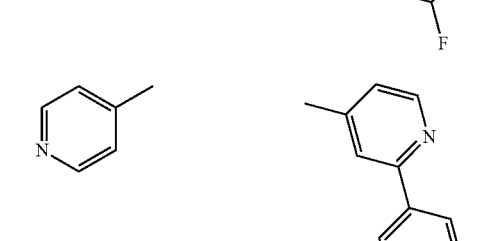 | |
| 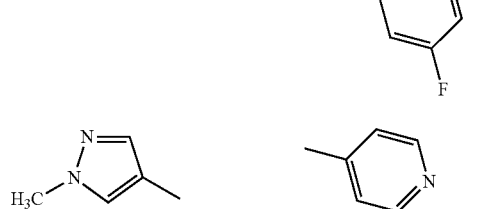 | |
|  | |
| 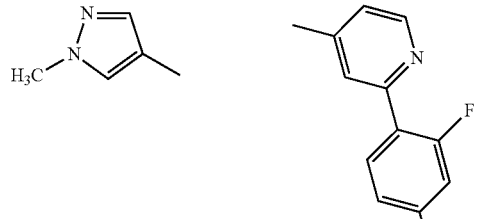 | |
| 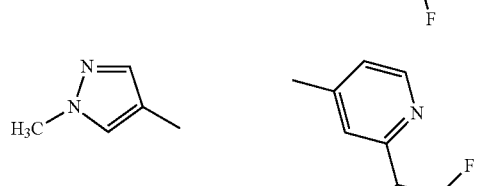 | |
|  | |

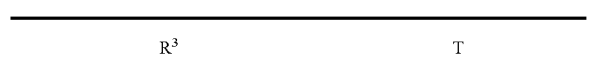
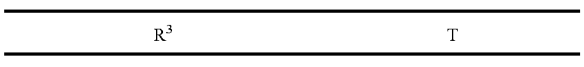

| R³ | T |
|---|---|
| 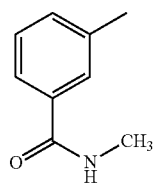 | 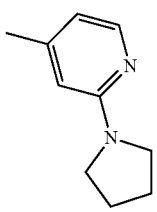 |
| 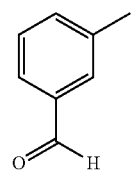 | 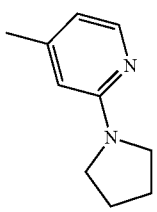 |
| 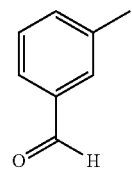 | 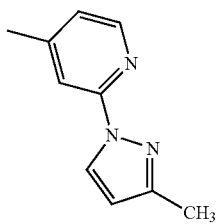 |
| 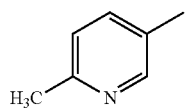 | 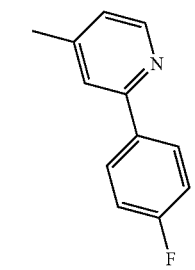 |
| 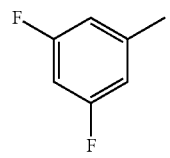 | 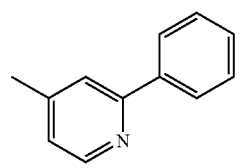 |
| 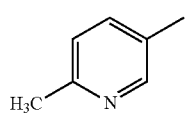 | 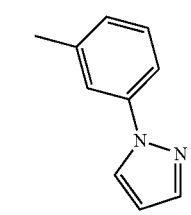 |
| 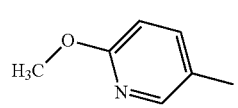 | 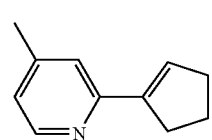 |
| R³ | T |
|---|---|
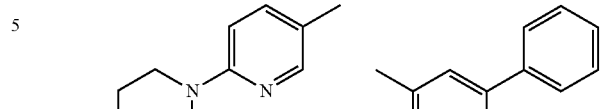
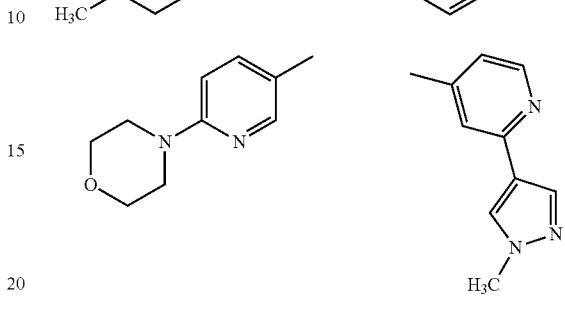
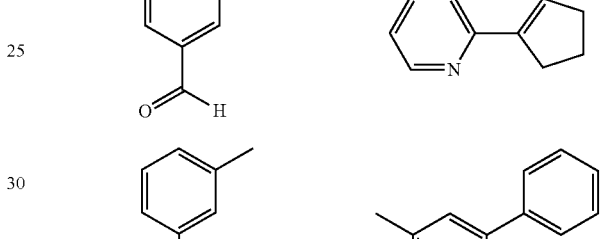
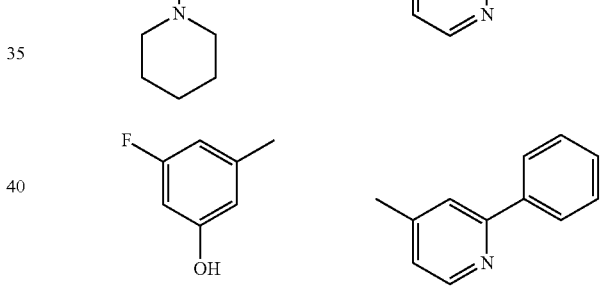
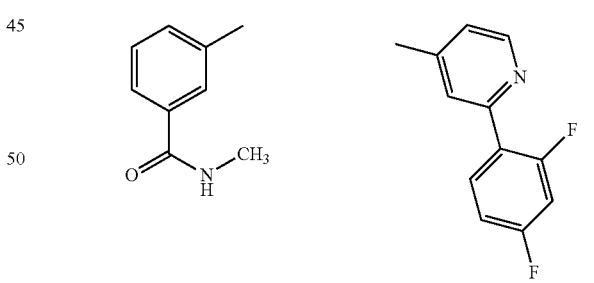
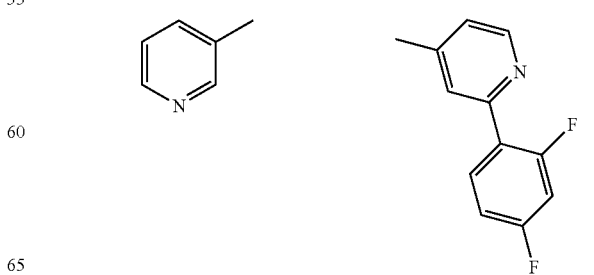

| R³ | T |
|---|---|
| 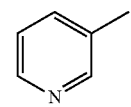 | 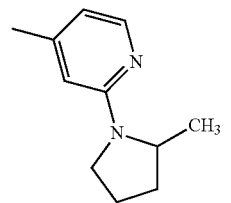 |
| 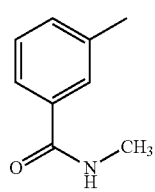 | 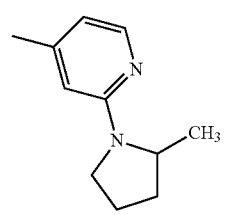 |
| 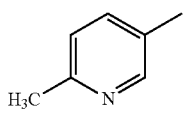 | 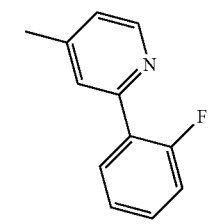 |
| 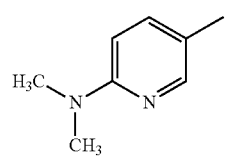 | 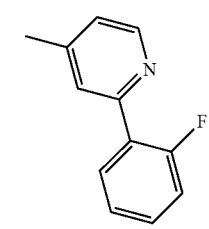 |
| 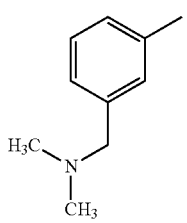 | 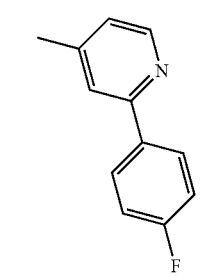 |
| 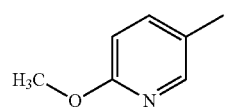 | 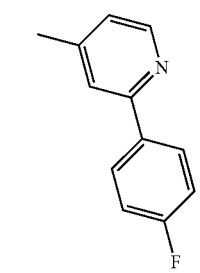 |
| R³ | T |
|---|---|
| 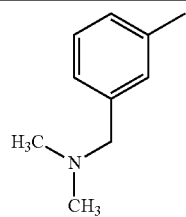 | 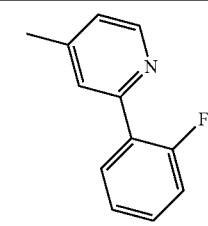 |
| 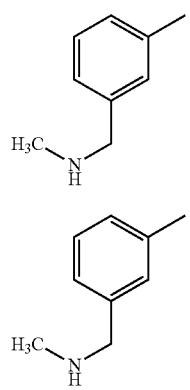 | 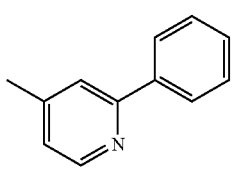 |
| 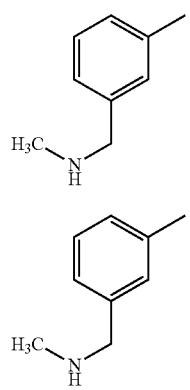 | 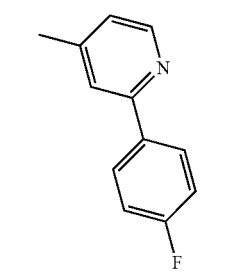 |
| 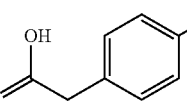 | 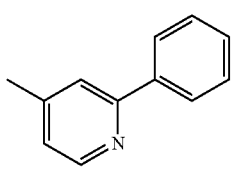 |
| 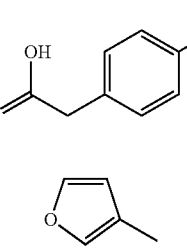 | 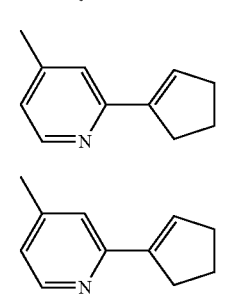 |
| 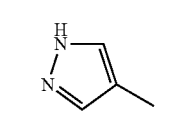 | 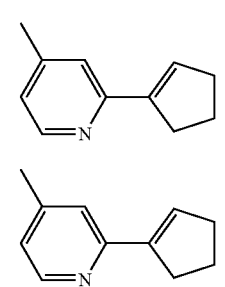 |
| 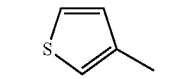 | 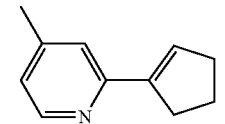 |
| 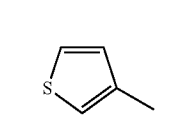 | 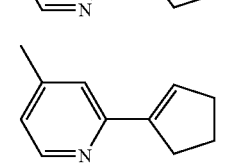 |

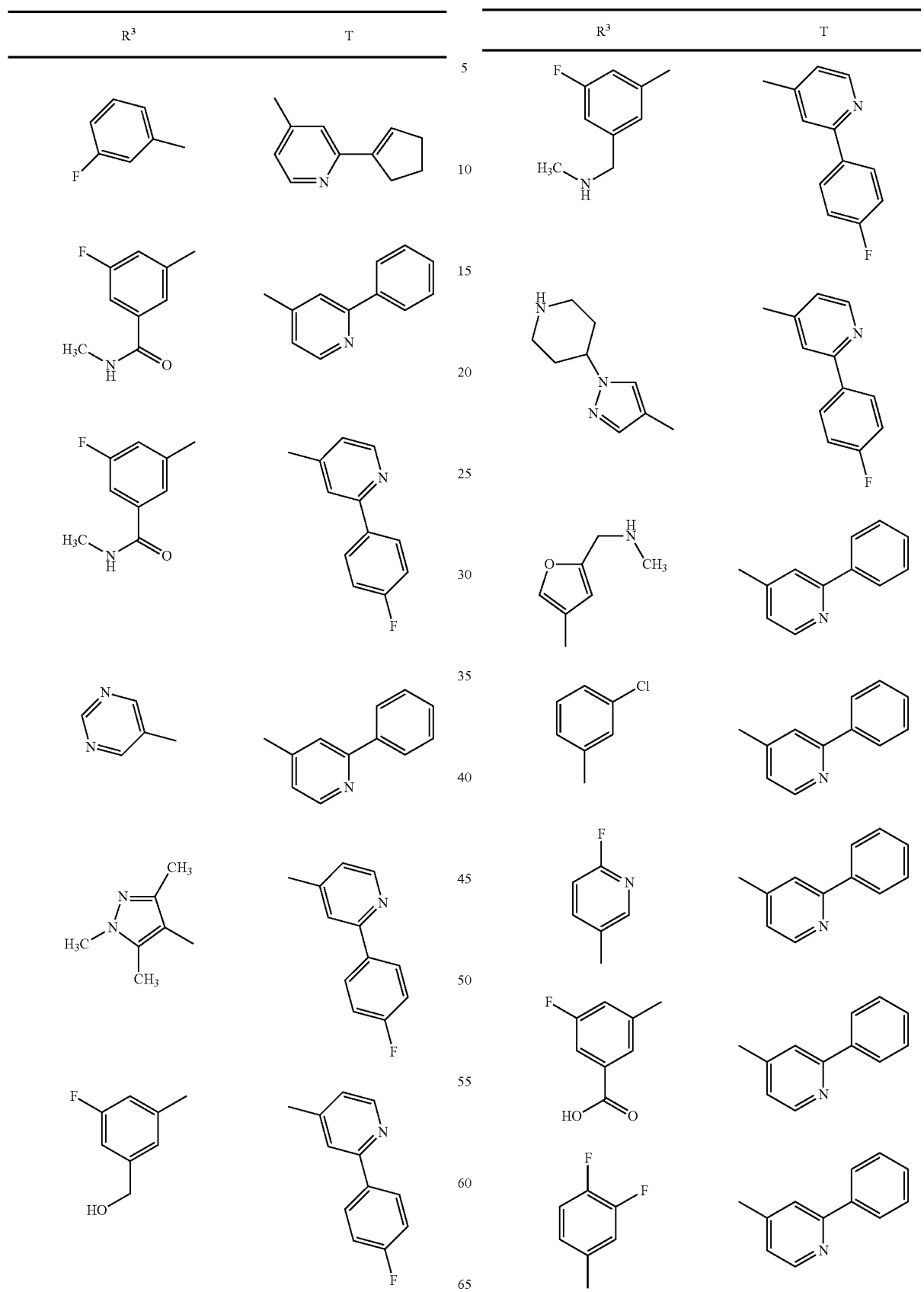

-continued
| R³ | T |
|---|---|
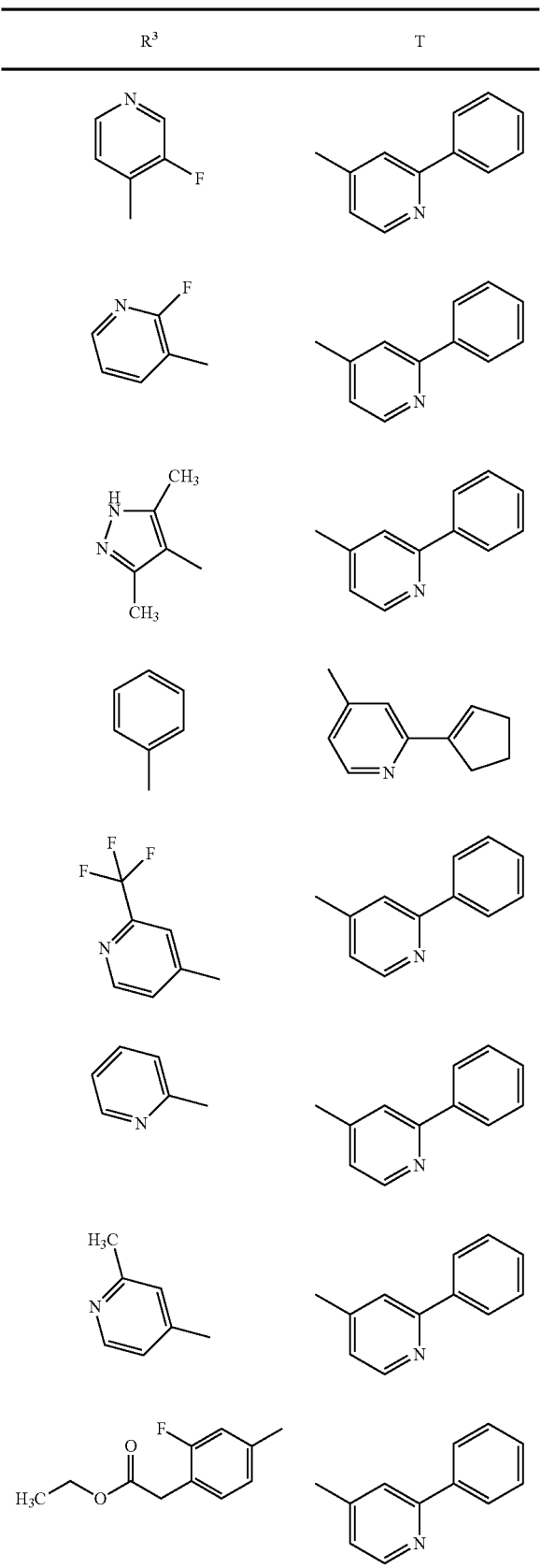
-continued
| R³ | T |
|---|---|
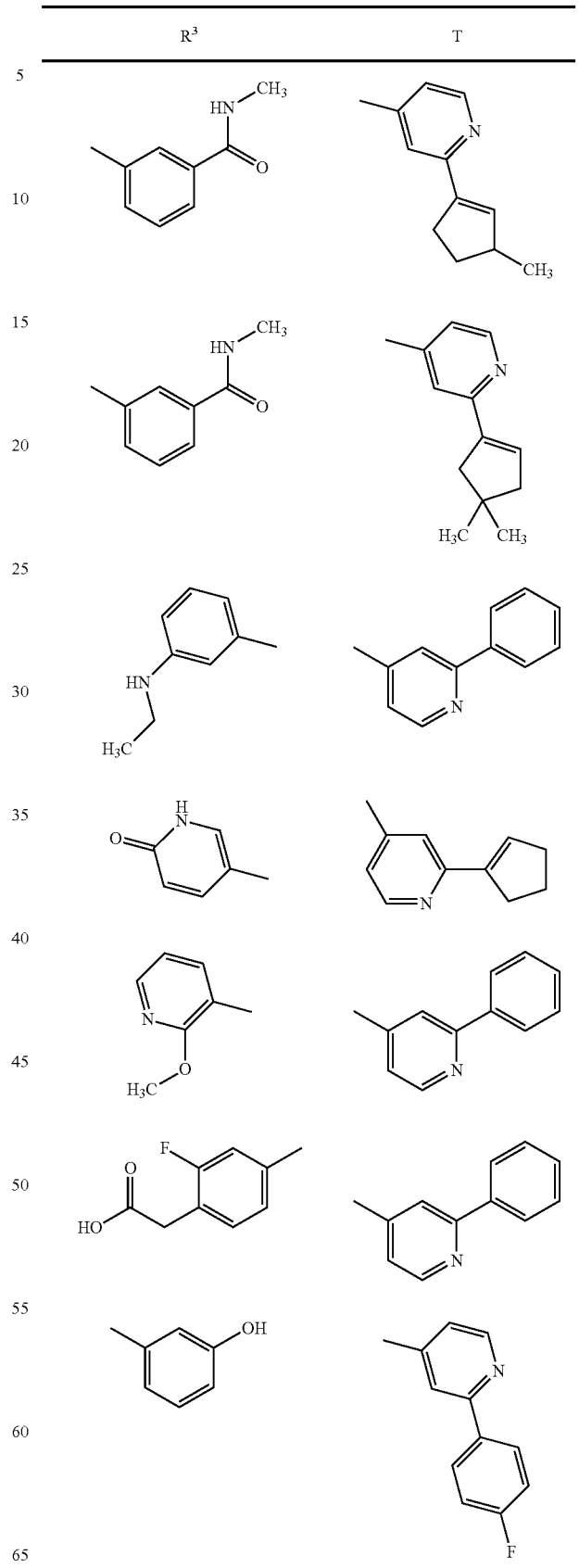

163
-continued
| R³ | T |
|---|---|
| 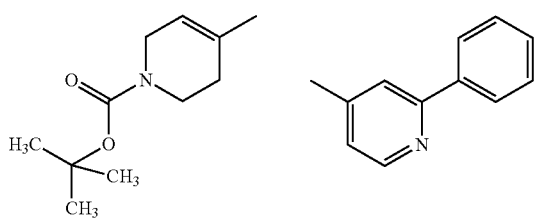 | |
| 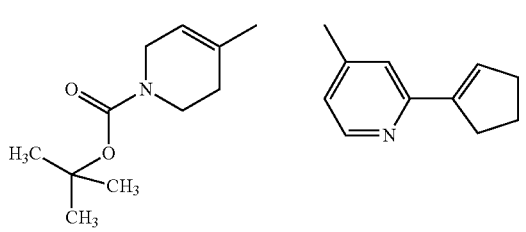 | |
| 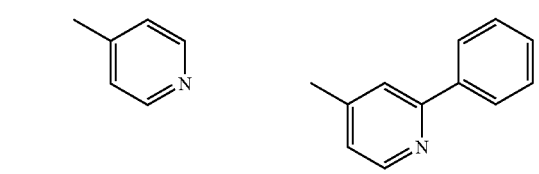 | |
| 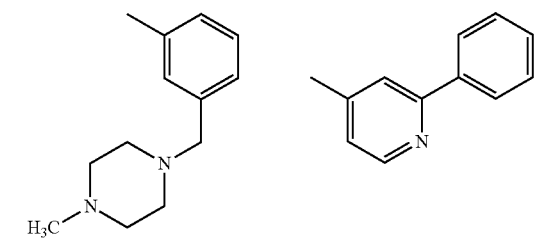 | |
| 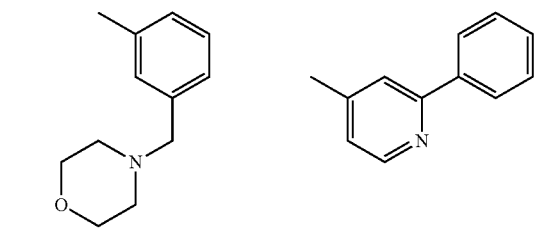 | |
| 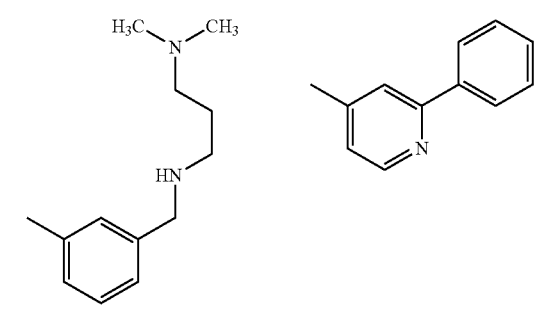 | |
164
-continued
| R³ | T |
|---|---|
| 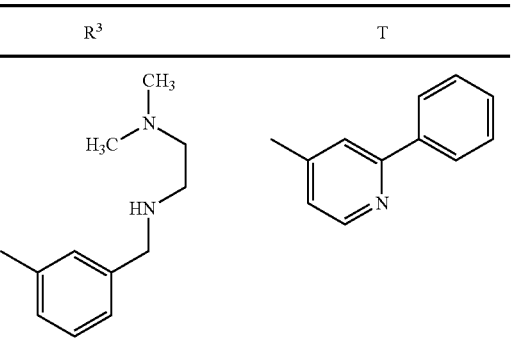 | |
| 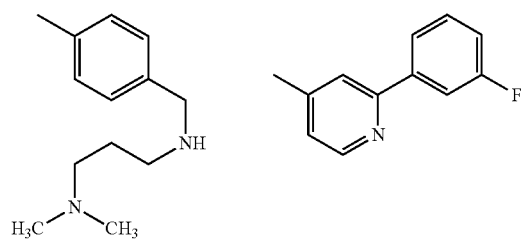 | |
| 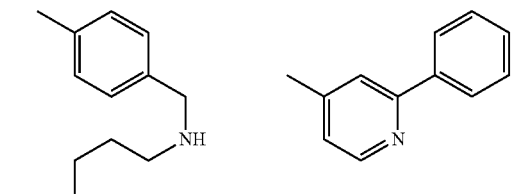 | |
| 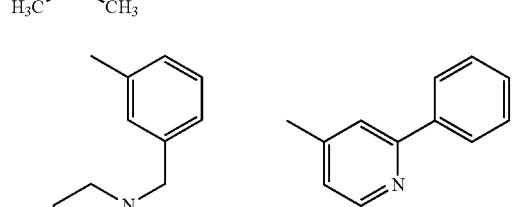 | |
|  | |
| 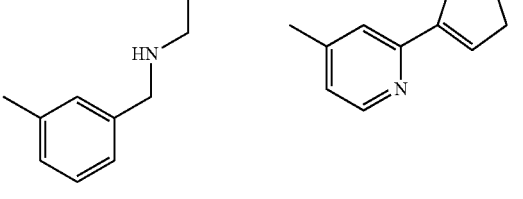 | |
| 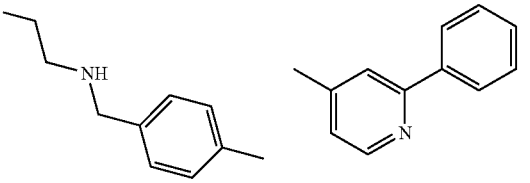 | |

| R³ | T |
|---|---|
| 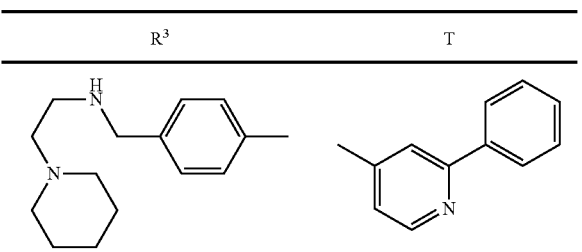 | |
| 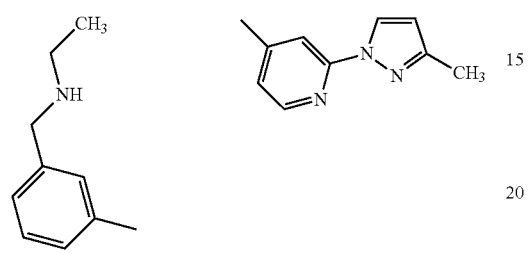 | |
| 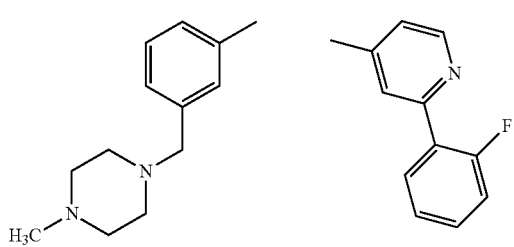 | |
| 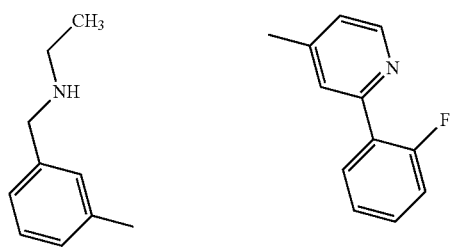 | |
| 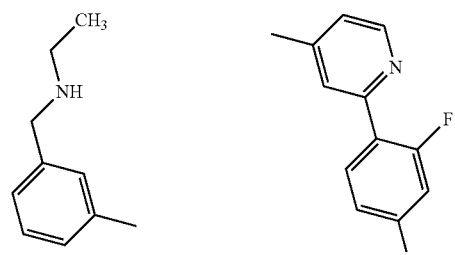 | |
| 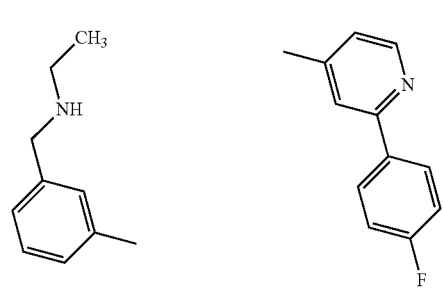 | |
| R³ | T |
|---|---|
| 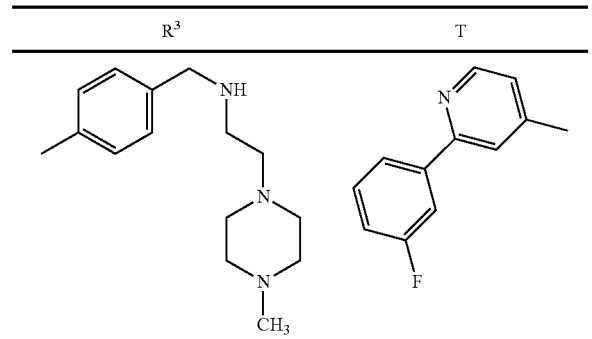 | |
| 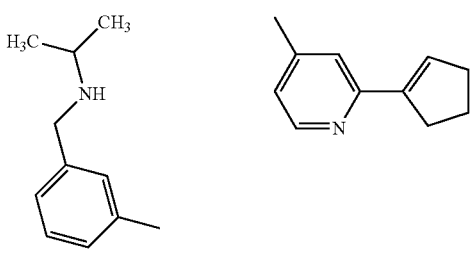 | |
| 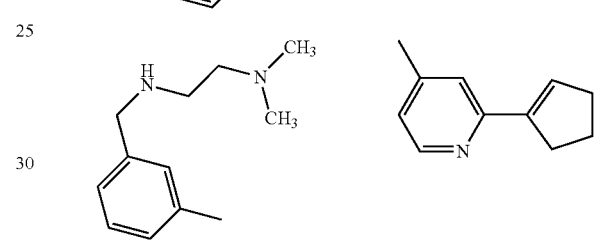 | |
| 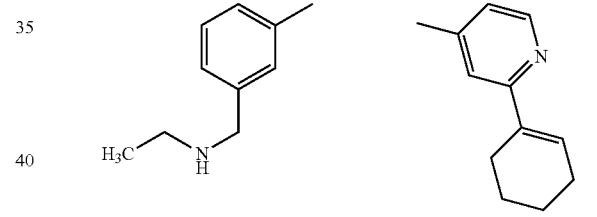 | |
| 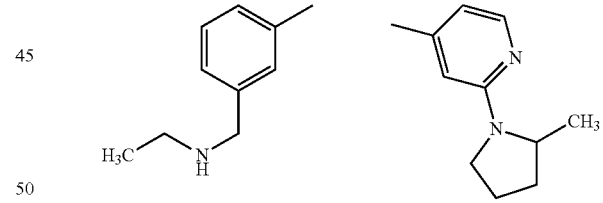 | |
| 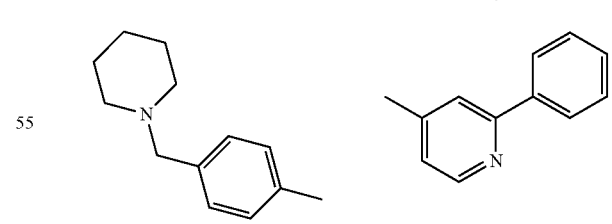 | |
| 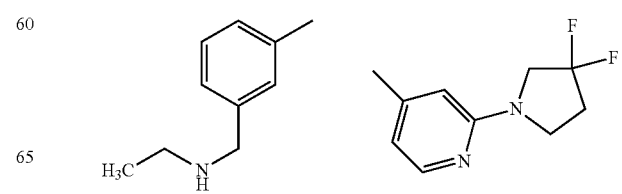 | |

167
-continued
| R³ | T |
|---|---|
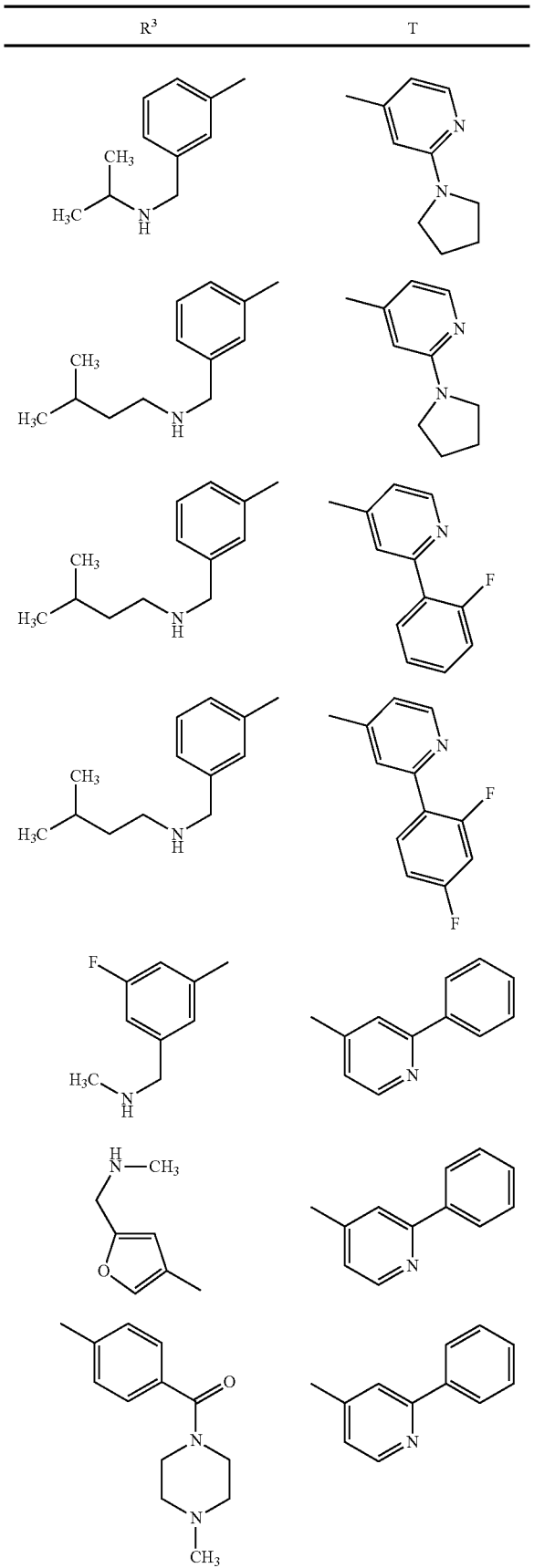
168
-continued
| R³ | T |
|---|---|
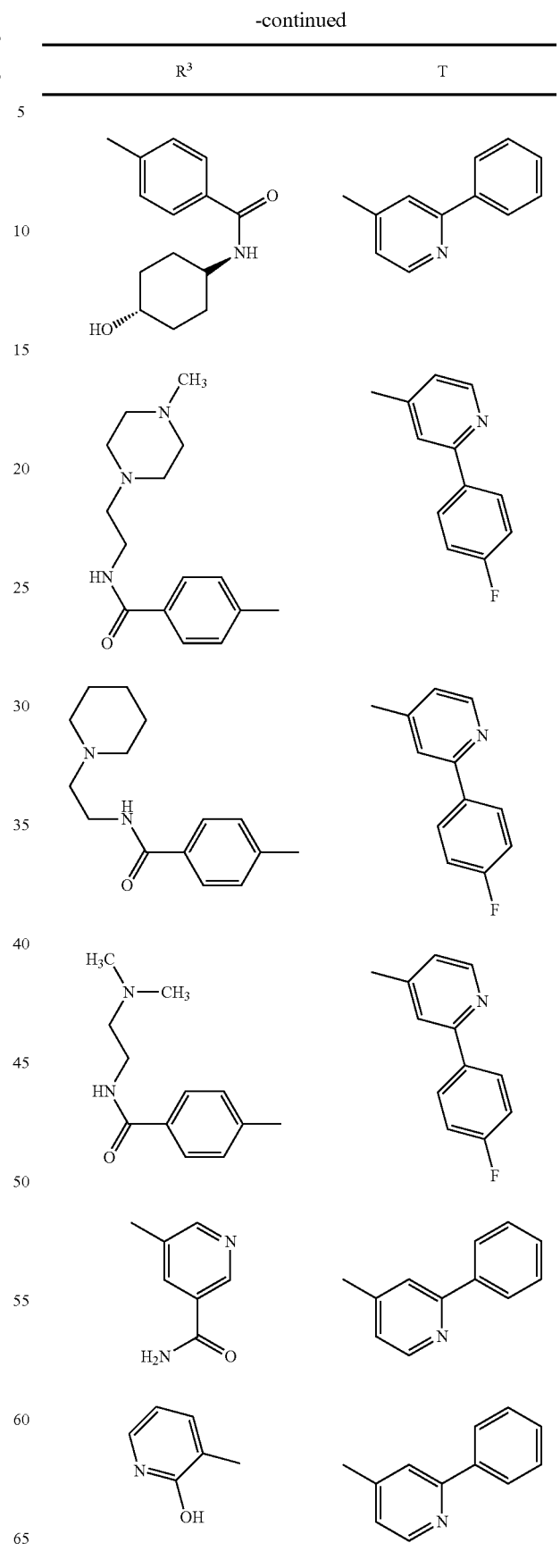

| 169 -continued | | | 170 -continued | |
|---|---|---|---|---|
| R³ | T | | R³ | T |
| 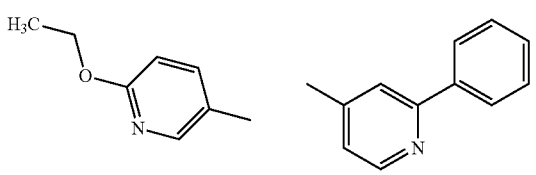 | | | 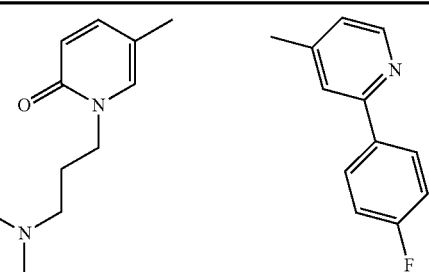 | |
| 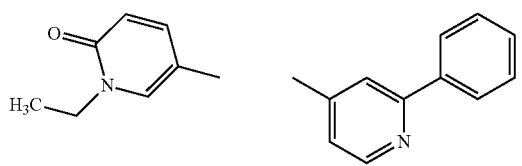 | | | | |
| 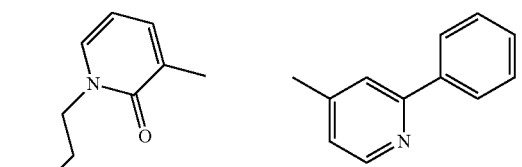 | | | 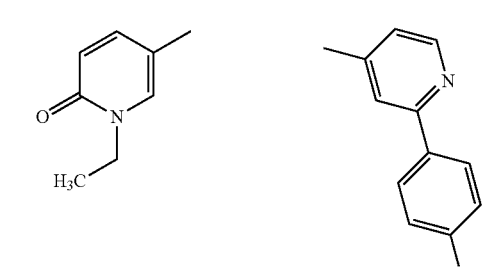 | |
|  | | | 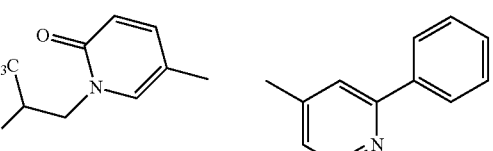 | |
| 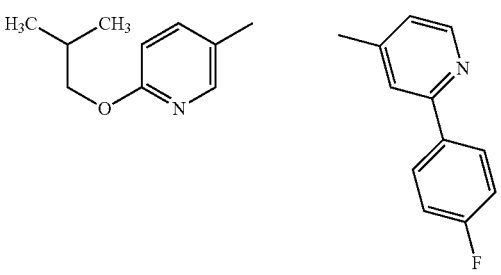 | | | 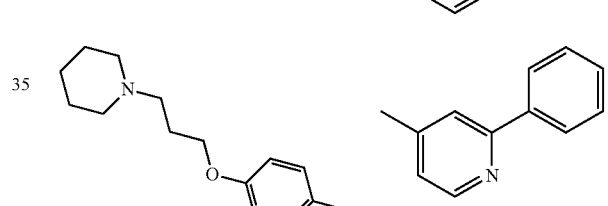 | |
| 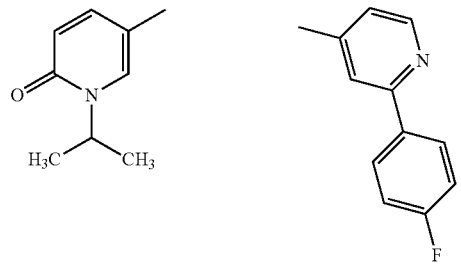 | | | 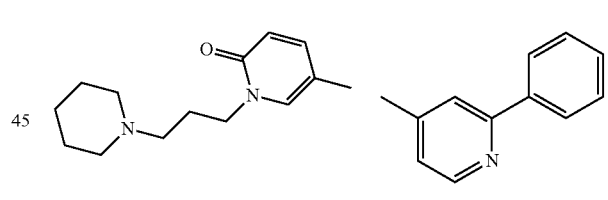 | |
| | | | 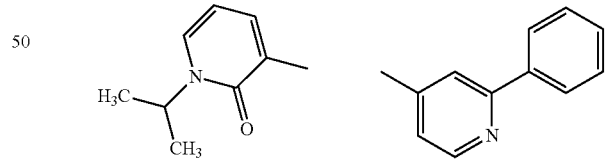 | |
| 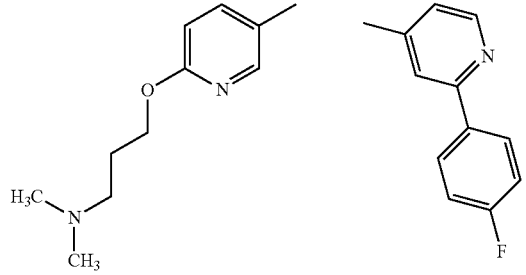 | | | 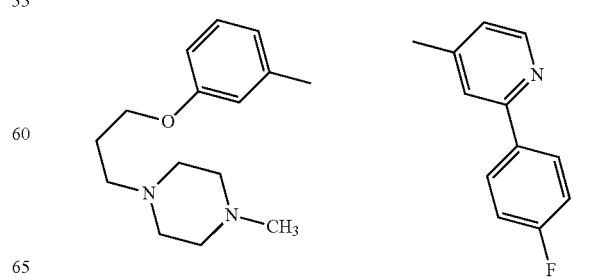 | |

| R³ | T | R³ | T |
|---|---|---|---|
| 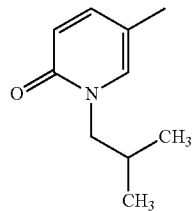 | 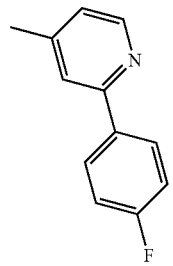 | 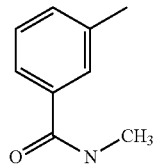 | 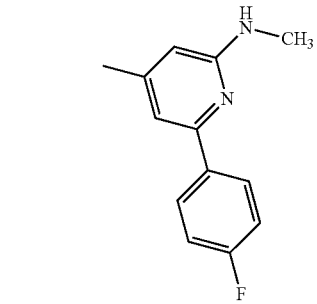 |
| 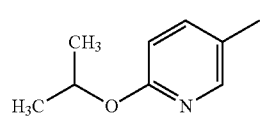 | 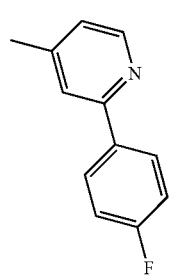 | 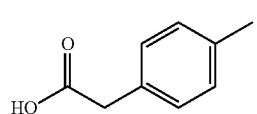 | 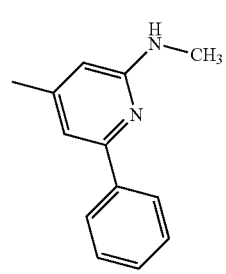 |
| 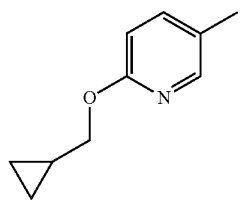 | 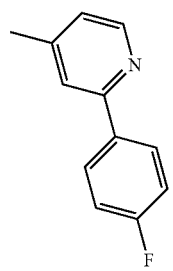 | 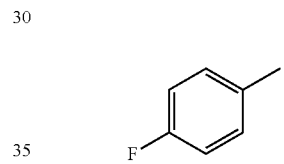 | 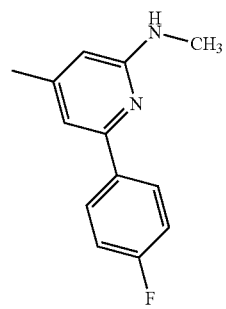 |
| 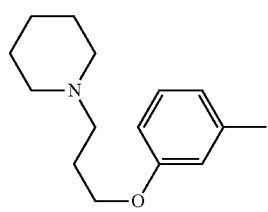 | 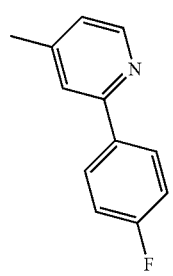 | 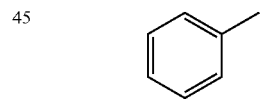 | 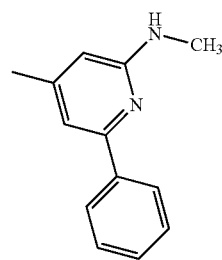 |
| 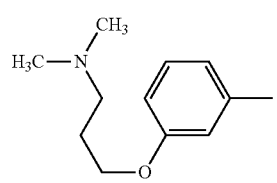 | 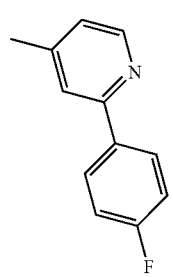 | 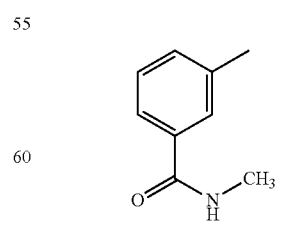 | 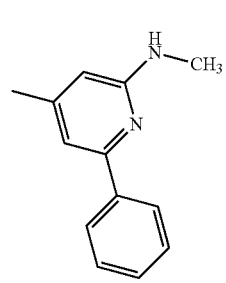 |

| R³ | T |
|---|---|
| 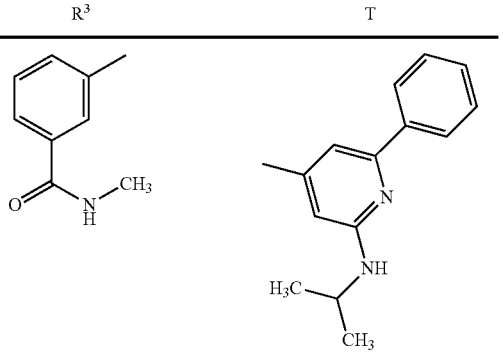 | 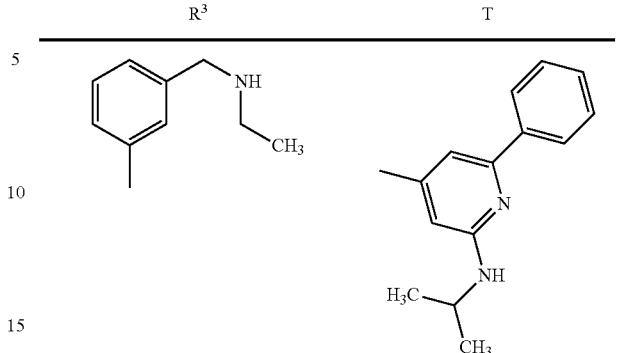 |
| 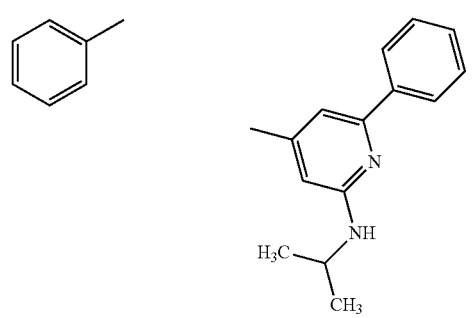 | 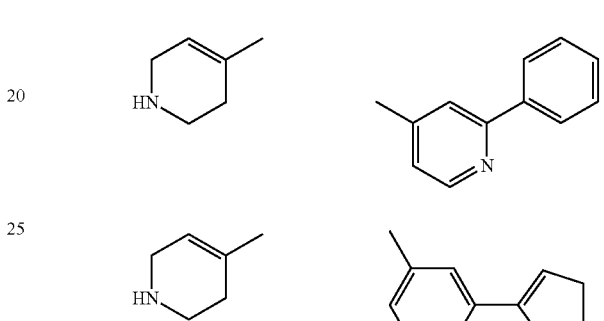 |
| 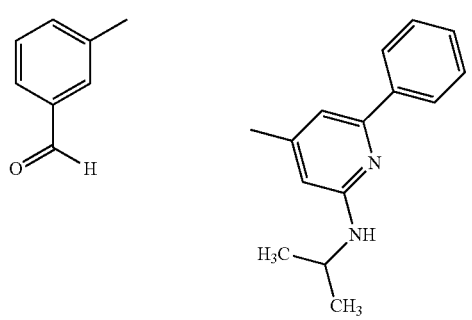 | 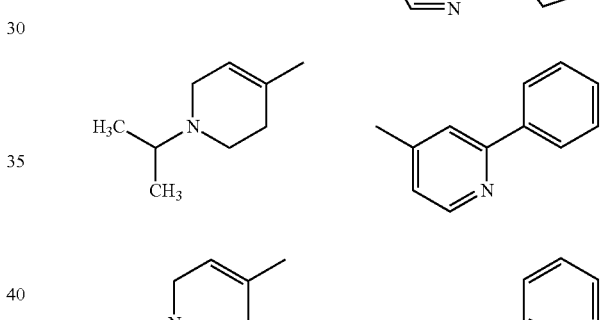 |
| 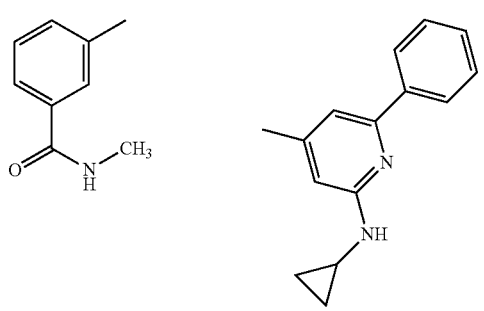 | 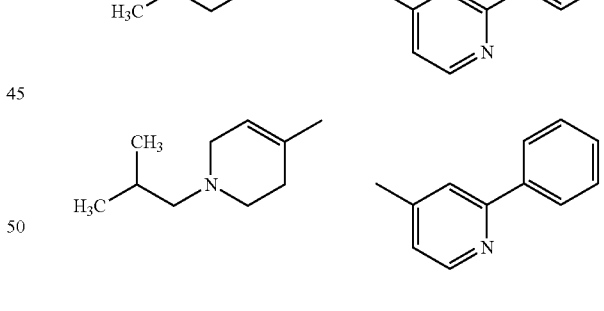 |
| 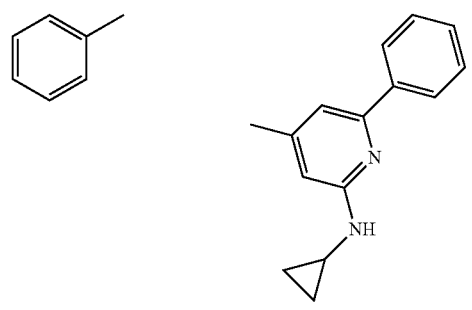 | 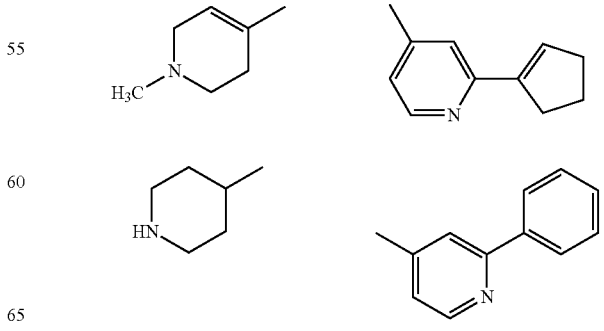 |

-continued
| R³ | T |
|---|---|
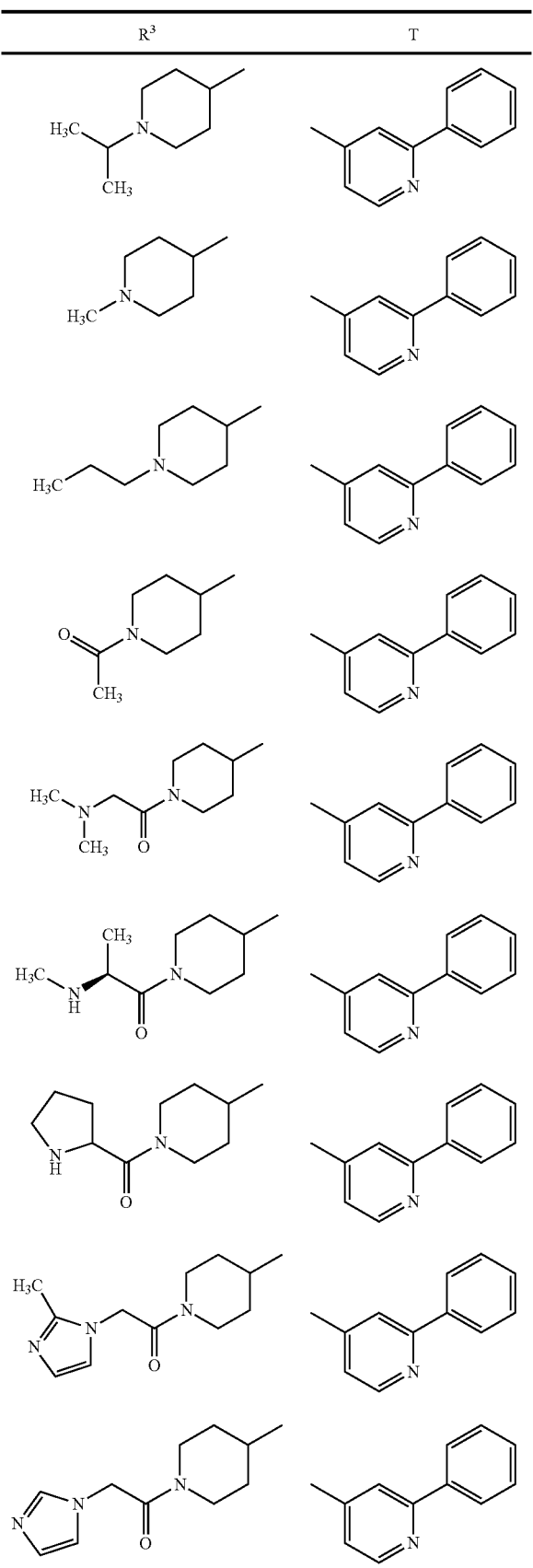
-continued
| R³ | T |
|---|---|
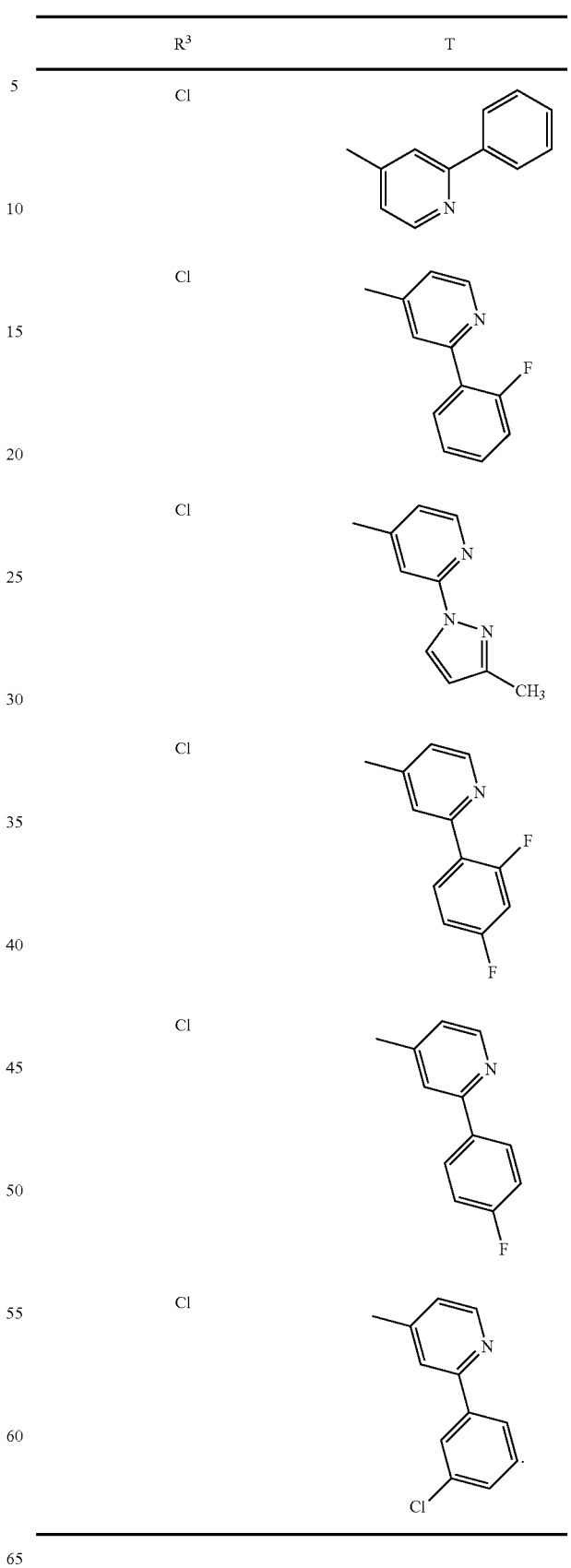
6. A compound according to claim 1 which is a compound of Formula Y

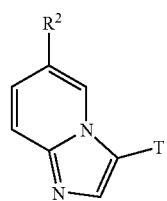
where R² and T are as shown below:
| R² | T |
|---|---|
| NH-cyclohexyl-OH (trans) | 2-chloro-4-methylpyridine |
| NH-cyclohexyl-OH (trans) | 2-methoxy-4-methylpyridine |
| NH-cyclohexyl-OH (trans) | 2-(furan-3-yl)-4-methylpyridine |
| NH-cyclohexyl-OH (trans) | 4-methyl-2-phenylpyridine |
| NH-cyclohexyl-OH (trans) | 2-(furan-2-yl)-4-methylpyridine |
| NH-cyclohexyl-OH (trans) | 4-methyl-2-(1H-pyrazol-3-yl)pyridine |

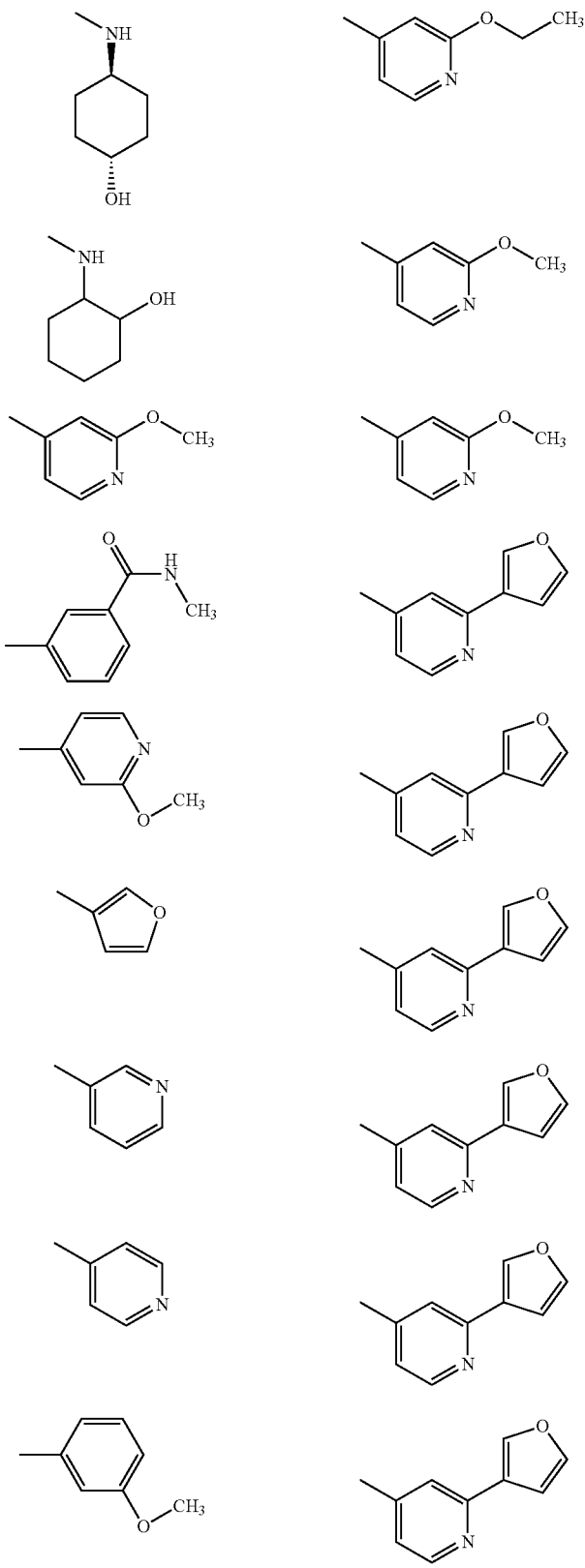

-continued
| R² | T |
|---|---|
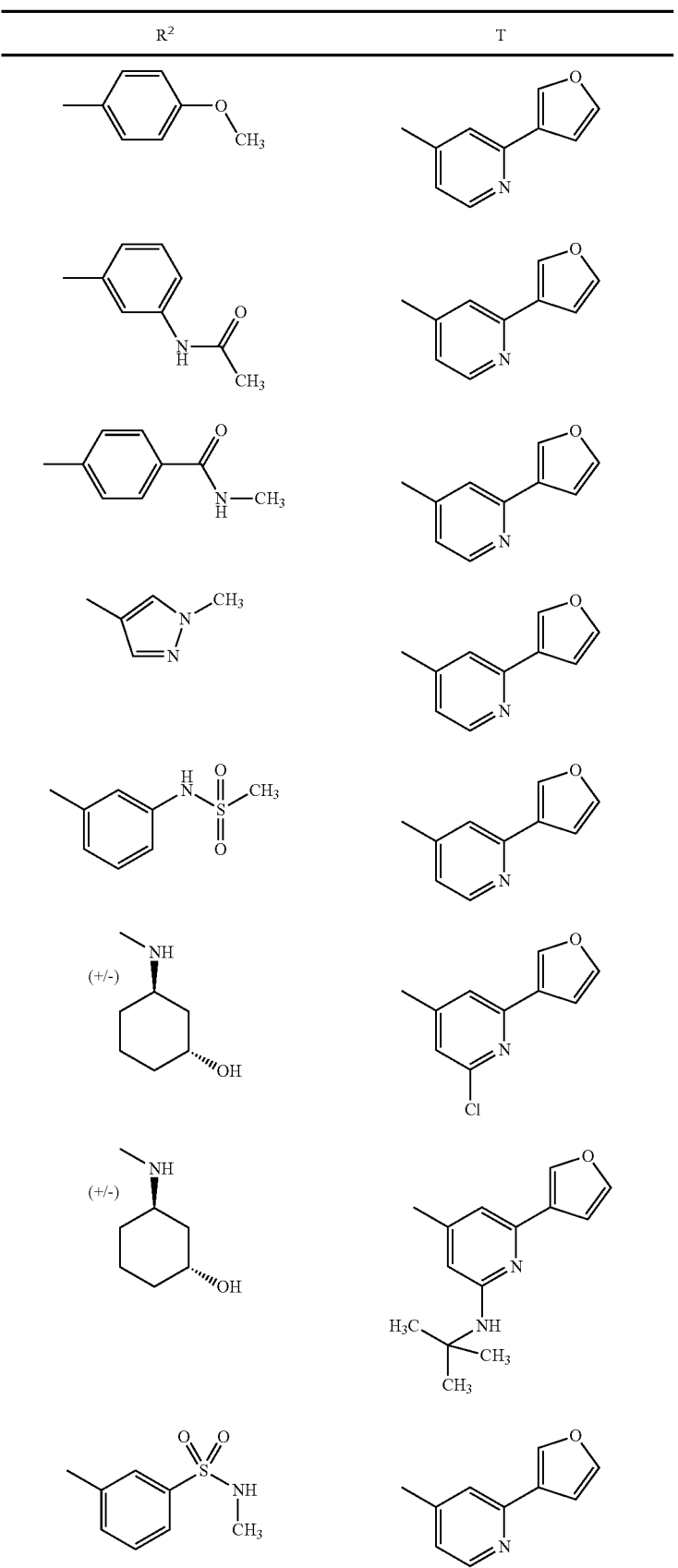

-continued
| R² | T |
|---|---|
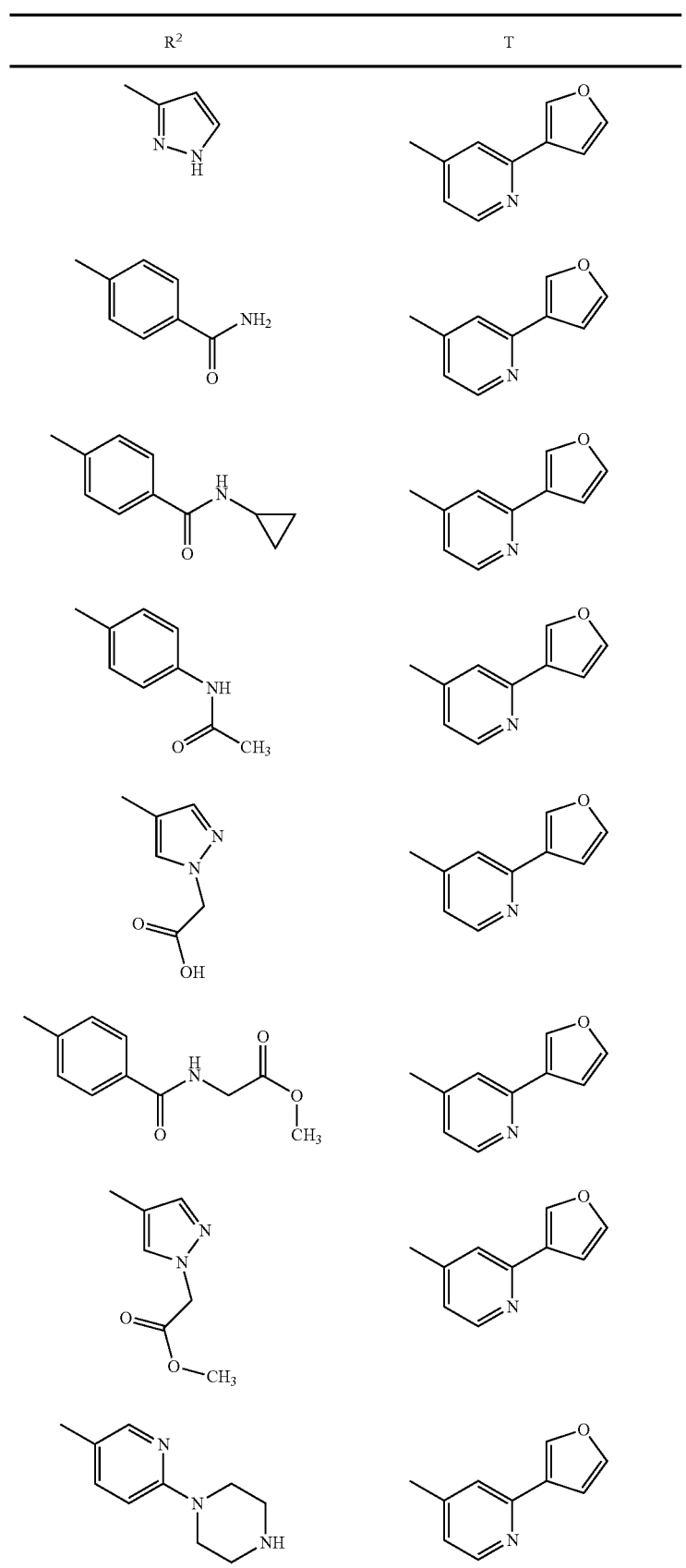

| R² | T |
|---|---|
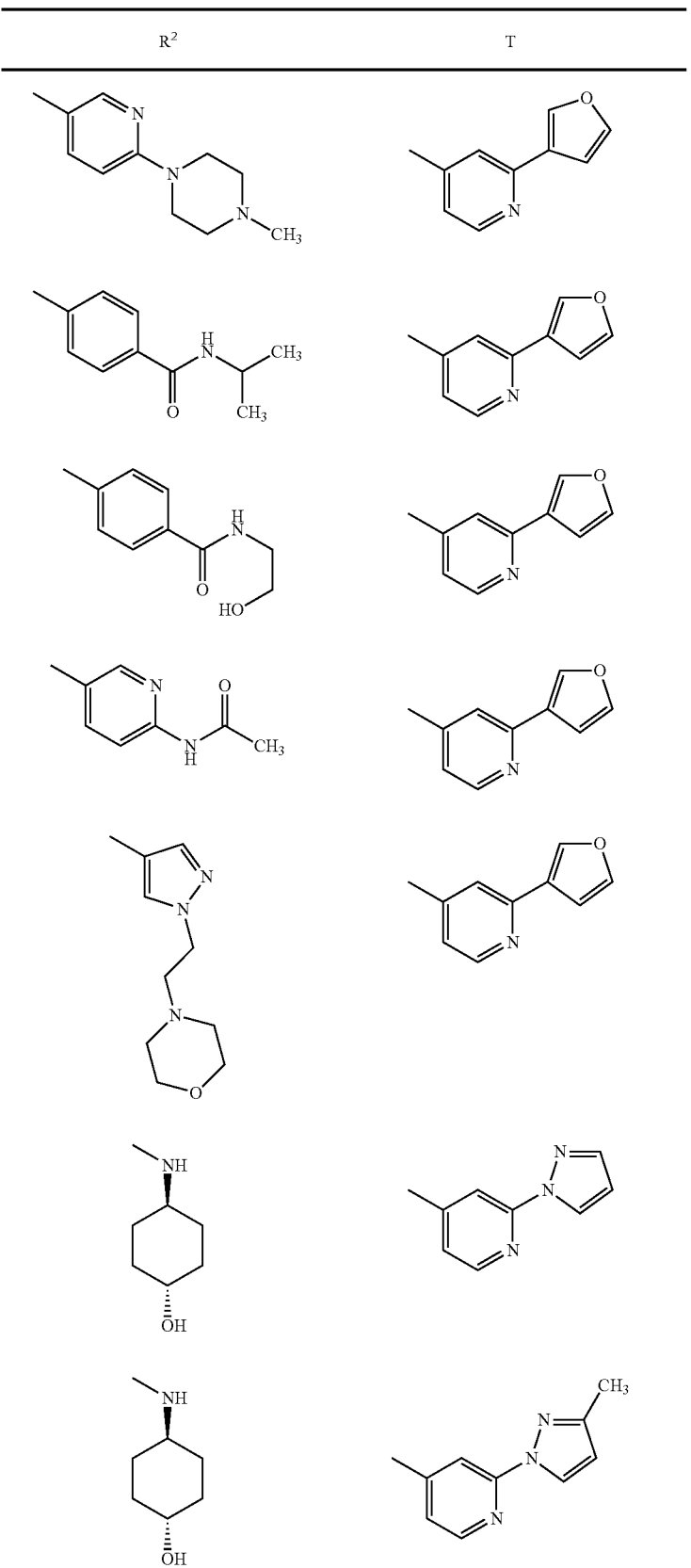

-continued
| R² | T |
|---|---|
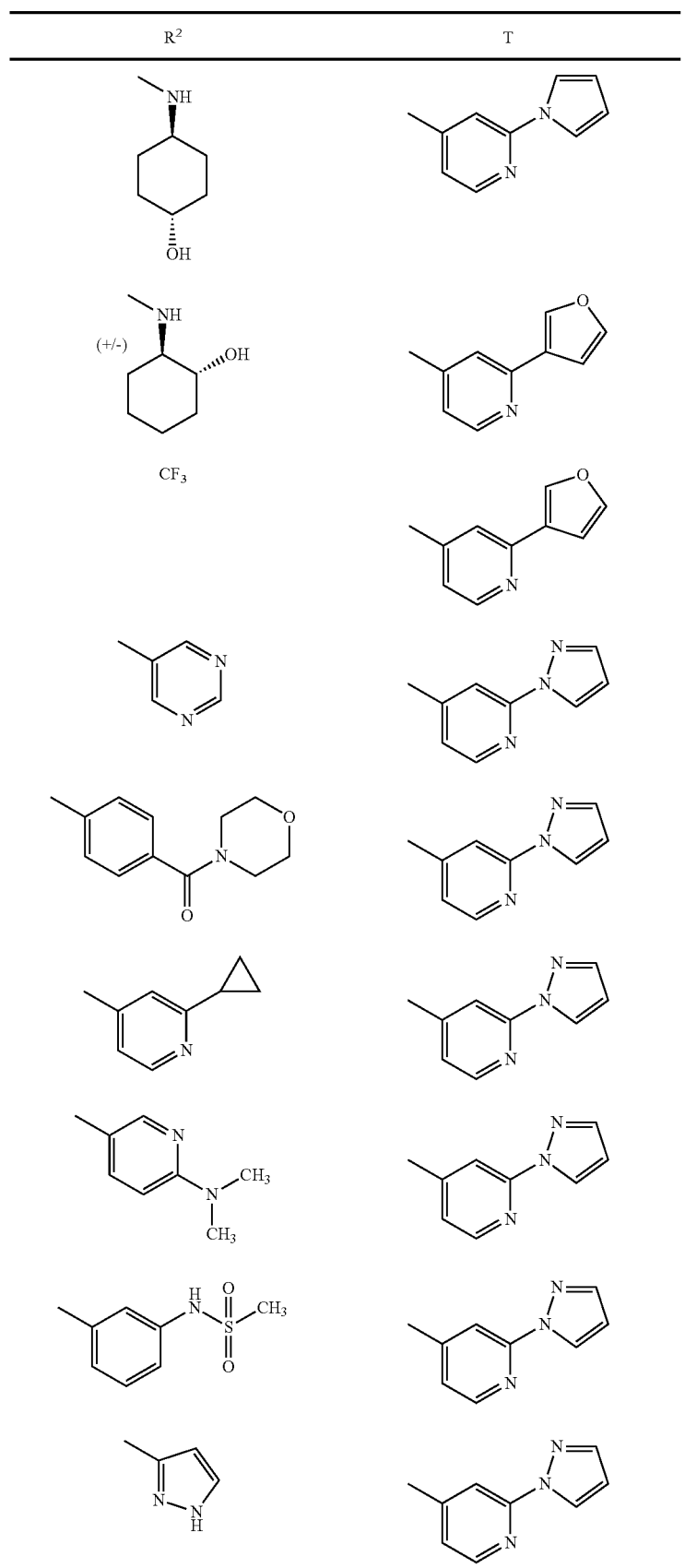

-continued
| R² | T |
|---|---|
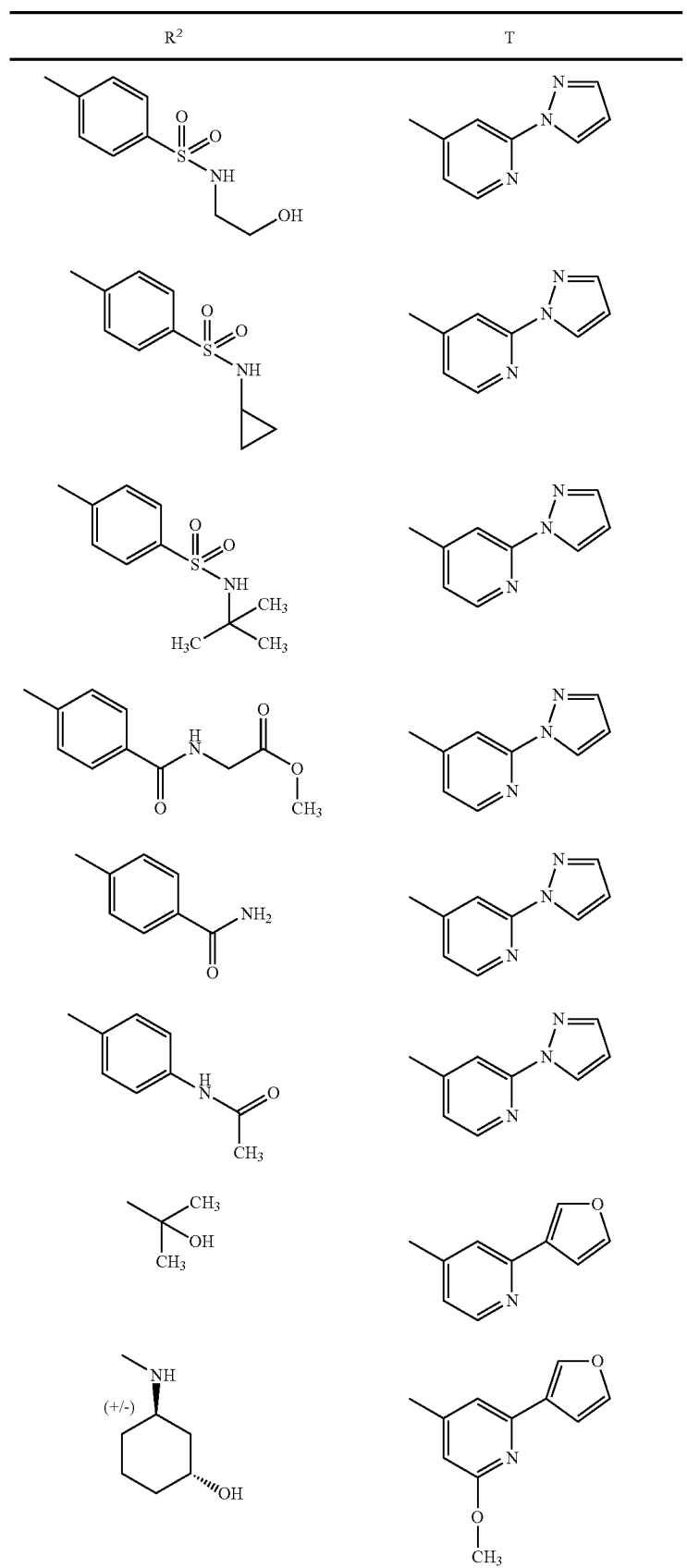

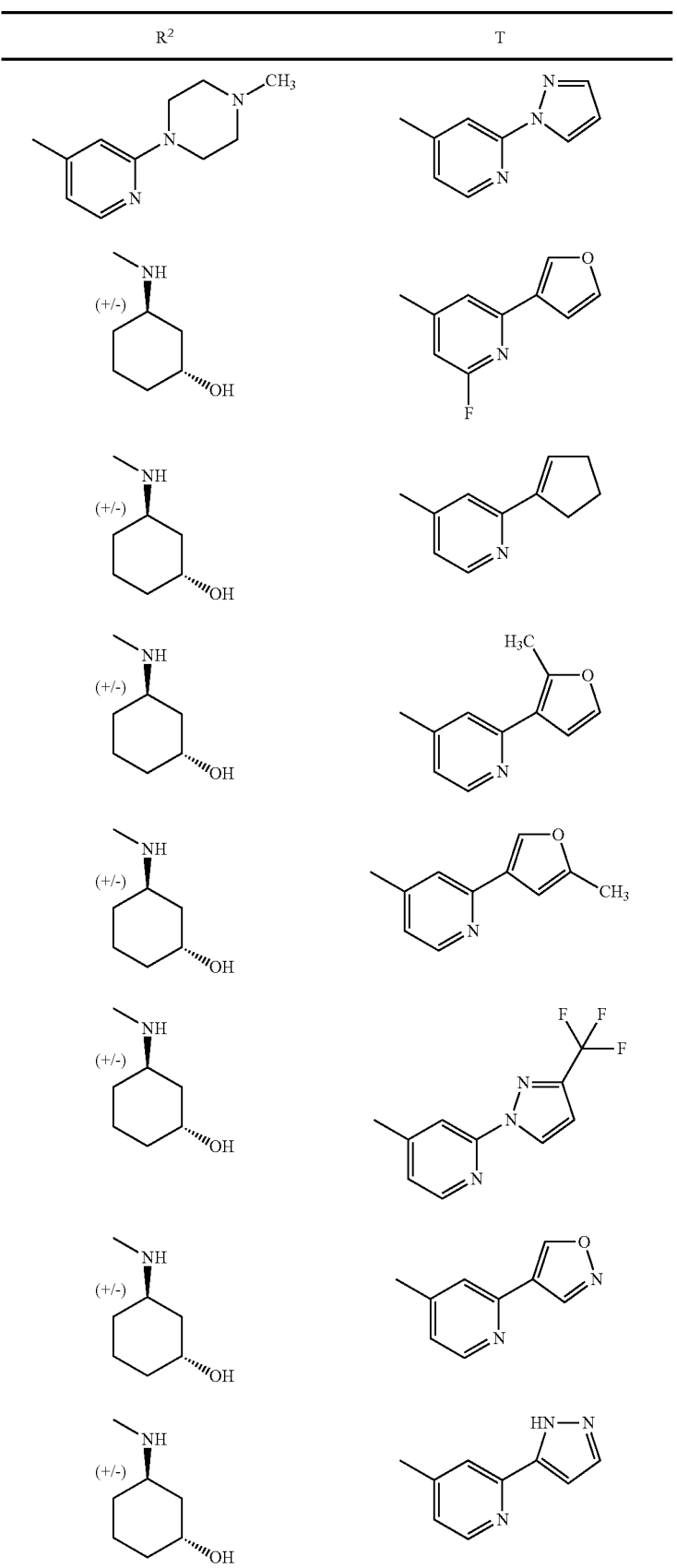

-continued
| R² | T |
|---|---|
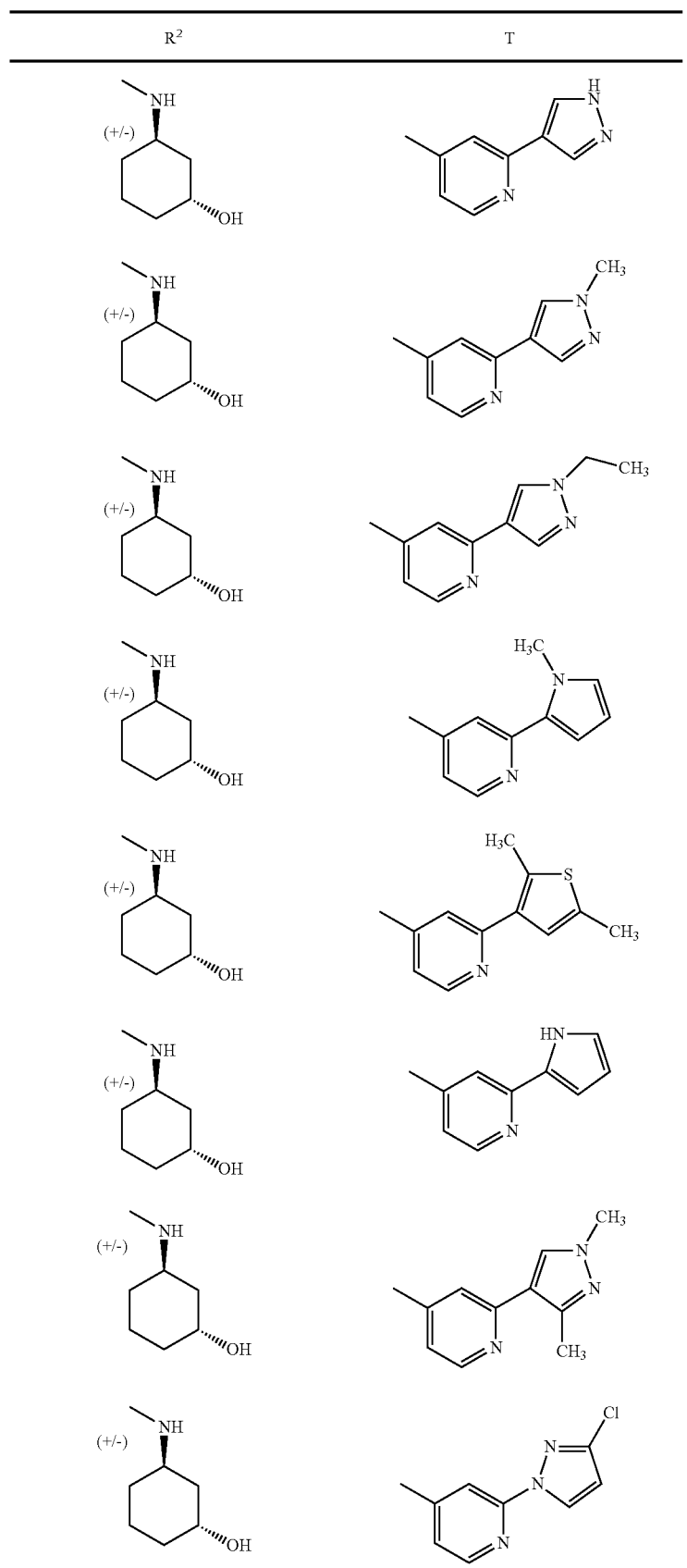

-continued
| R² | T |
|---|---|
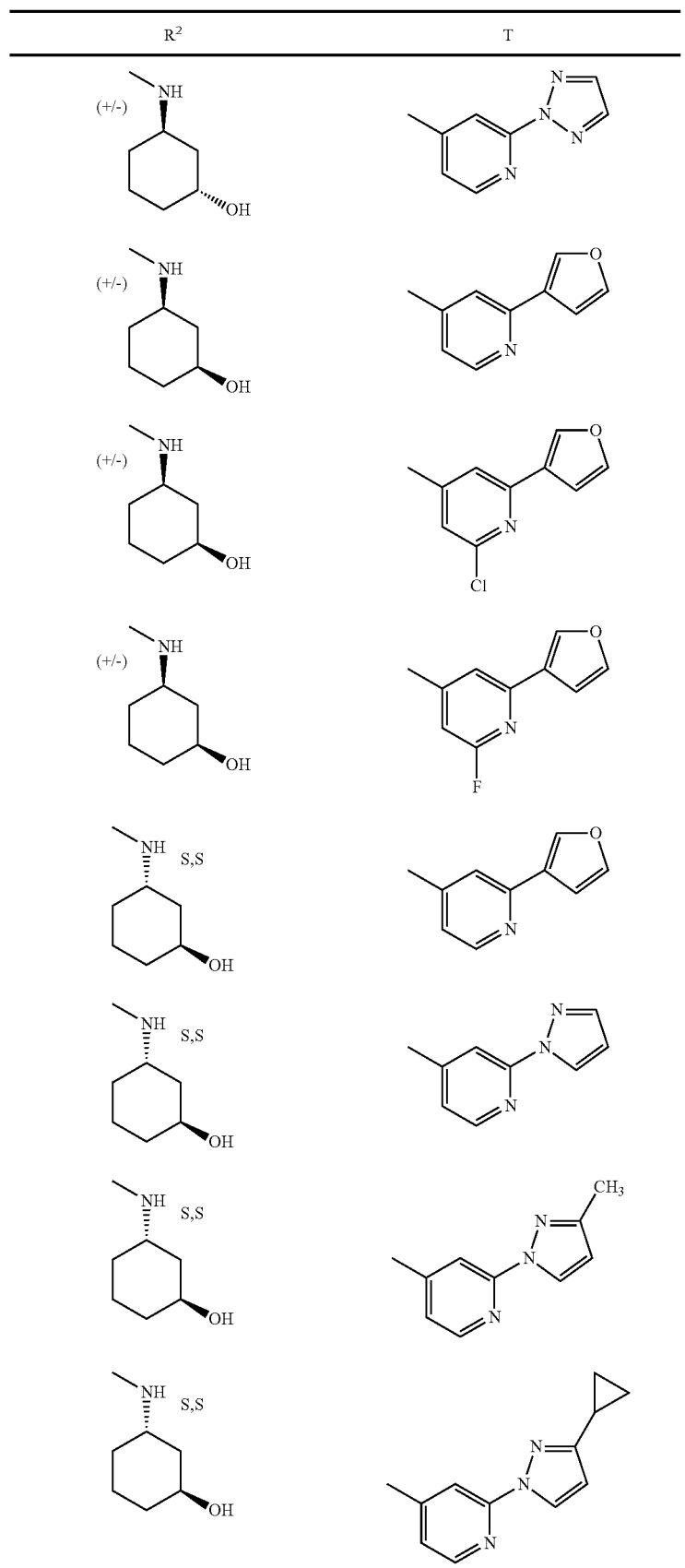

-continued
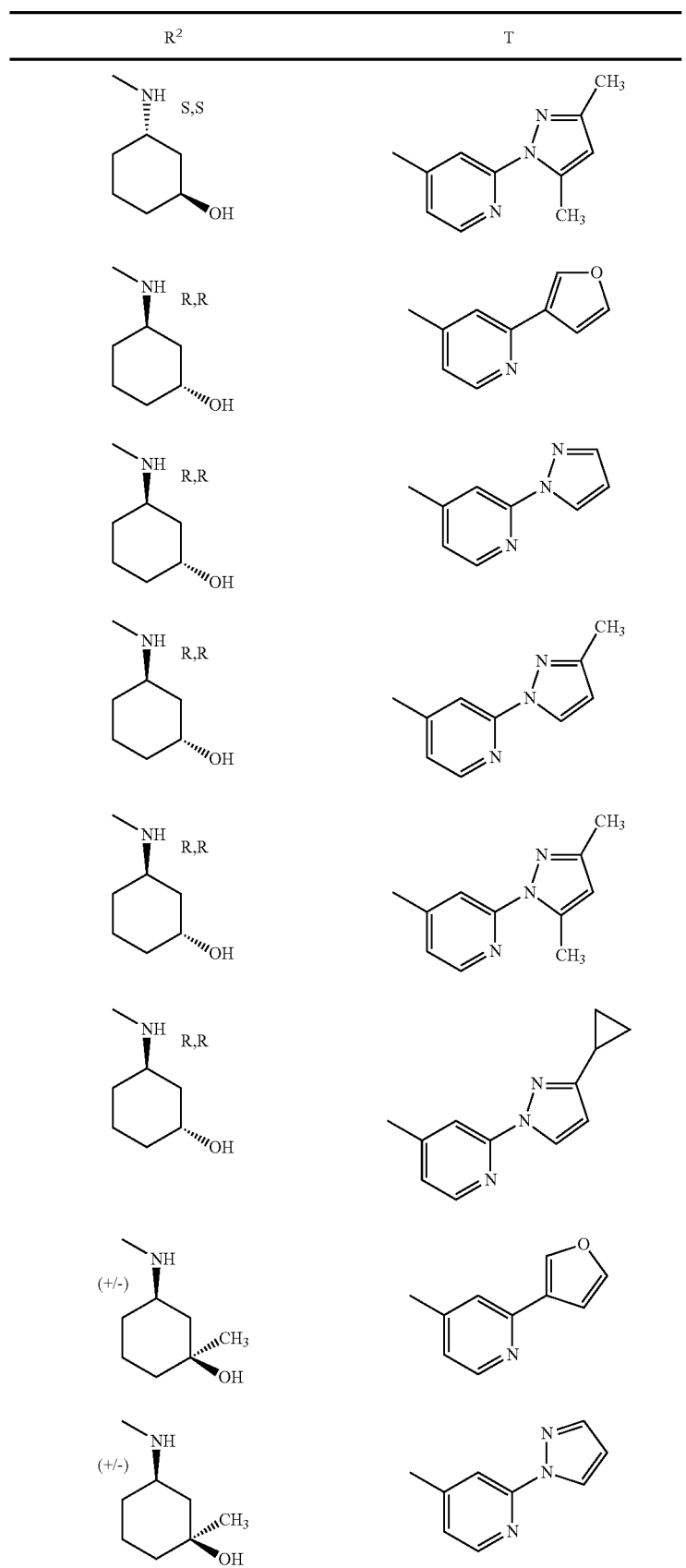

-continued
| R² | T |
|---|---|
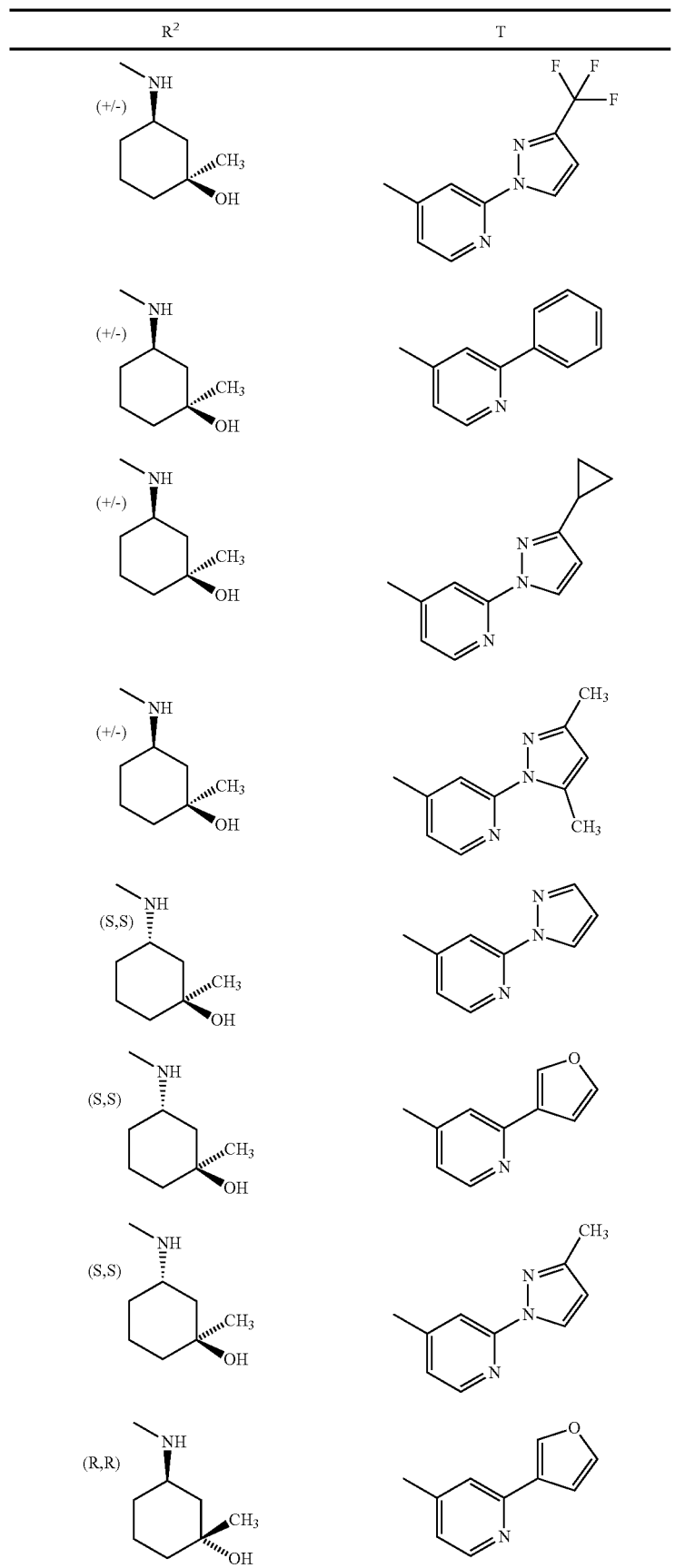

-continued

| R² | T |
|---|---|
| 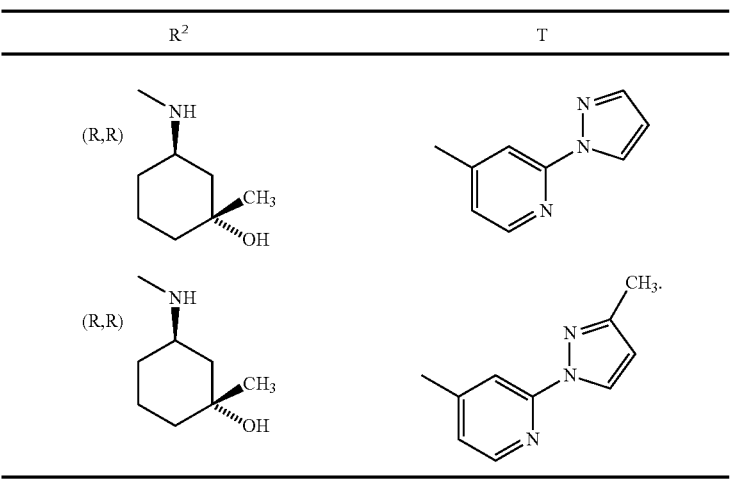 | |

7. A pharmaceutical composition including a compound according to any of claim 1 and one or more pharmaceutically acceptable excipients, diluents and/or carriers.

8. A process for preparing a compound of Formula I comprising the step of:

(a) reacting a compound of Formula II

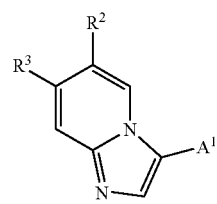

II where $R^2$ and $R^3$ are as defined in claim 1 and $A^1$ is a halogen atom, with a compound of Formula III

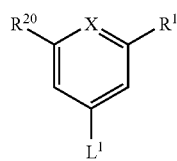

III where X, $R^1$ and $R^{20}$ are as defined in claim 1 and $L^1$ is a boronic acid or boronic anhydride group; or (b) reacting a compound of Formula IV

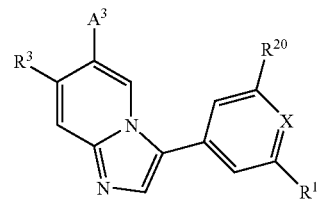

IV where X, $R^1$, $R^3$ and $R^{20}$ are as defined in claim 1 and $A^3$ is a halogen atom, with a compound having the formula $R^2L^2$, where $R^2$ is as defined in claim 1 and $L^2$ is a boronic acid or boronic anhydride group; or (c) reacting a compound of Formula V

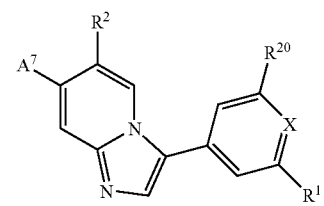

V where X, $R^1$, $R^2$ and $R^{20}$ are as defined in claim 1 and $A^7$ is a halogen atom, with a compound having the formula $R^3L^3$, where $R^3$ is as defined in claim 1 and $L^3$ is a boronic acid or boronic anhydride group.

* * * * *